United States Patent [19]

Takaya et al.

[11] Patent Number: 4,493,833

[45] Date of Patent: Jan. 15, 1985

[54] SYN-ISOMER OF 3,7-DISUBSTITUTED-3-CEPHEM-4-CARBOXYLIC ACID COMPOUNDS

[75] Inventors: Takao Takaya, Kawanishi; Takashi Masugi, Toyonaka; Hisashi Takasugi, Osaka; Hiromu Kochi, Sakai, all of Japan

[73] Assignee: Fujisawa Pharmaceutical Co., Ltd., Osaka, Japan

[21] Appl. No.: 296,117

[22] Filed: Aug. 25, 1981

Related U.S. Application Data

[60] Division of Ser. No. 77,557, Sep. 21, 1979, Pat. No. 4,304,770, which is a continuation of Ser. No. 941,541, Sep. 12, 1978, abandoned, which is a continuation-in-part of Ser. No. 767,700, Feb. 11, 1977, Pat. No. 4,166,115.

[30] Foreign Application Priority Data

| Apr. 12, 1976 | [GB] | United Kingdom | 14916/76 |
| Jun. 7, 1976 | [GB] | United Kingdom | 23490/76 |
| Oct. 19, 1976 | [JP] | Japan | 51-125826 |
| Aug. 31, 1978 | [GB] | United Kingdom | 35195/78 |
| Sep. 4, 1978 | [GB] | United Kingdom | 35435/78 |
| Aug. 24, 1979 | [BE] | Belgium | 6/46.924 |
| Aug. 30, 1979 | [BE] | Belgium | 0/196.949 |

[51] Int. Cl.$^3$ .................. A61K 31/545; C07D 501/56
[52] U.S. Cl. ..................................... 424/246; 544/27
[58] Field of Search ......................... 544/27; 424/246

[56] References Cited

U.S. PATENT DOCUMENTS

| 4,098,888 | 7/1978 | Ochiai et al. | 424/246 |
| 4,152,432 | 5/1979 | Heymes et al. | 544/19 |
| 4,166,115 | 8/1979 | Takaya et al. | 544/26 |
| 4,196,205 | 4/1980 | Heymes et al. | 544/28 |
| 4,278,793 | 7/1981 | Durckheimer et al. | 544/22 |

*Primary Examiner*—Paul M. Coughlan, Jr.
*Attorney, Agent, or Firm*—Dayton R. Stemple

[57] ABSTRACT

Preparation of pharmaceutical composition comprising, treatment of human and animal diseases with, and compound of, 3,7-disubstituted-3-cephem-4-carboxylic acid.

7 Claims, No Drawings

SYN-ISOMER OF 3,7-DISUBSTITUTED-3-CEPHEM-4-CARBOXYLIC ACID COMPOUNDS

This is a division of application Ser. No. 77,557, filed Sept. 21, 1979, now U.S. Pat. No. 4,304,770, which is a continuation of application, Ser. No. 941,541, filed Sept. 12, 1978, now abandoned, which in turn was a continuation-in-part of application, Ser. No. 767,700, filed Feb. 11, 1977, now U.S. Pat. No. 4,166,115.

The present invention relates to new syn-isomer of 3,7-disubstituted-3-cephem-4-carboxylic acid compounds and pharmaceutically acceptable salts thereof. More particularly, it relates to new syn-isomer of 3,7-disubstituted-3-cephem-4-carboxylic acid compounds and pharmaceutically acceptable salts thereof which have antibacterial activities and to processes for the preparation thereof, to pharmaceutical composition comprising the same, and to a method of using the same therapeutically in the treatment of infectious diseases in human being and animals.

Accordingly, it is one object of the present invention to provide syn-isomer of 3,7-disubstituted-3-cephem-4-carboxylic acid compounds and pharmaceutically acceptable salts thereof, which are highly active against a number of pathogenic bacteria.

Another object of the present invention is to provide processes for the preparation of syn-isomer of 3,7-disubstituted-3-cephem-4-carboxylic acid compounds and pharmaceutically acceptable salts thereof.

A further object of the present invention is to provide pharmaceutical composition comprising, as active ingredients, said syn-isomer of 3,7-disubstituted-3-cephem-4-carboxylic acid compounds and pharmaceutically acceptable salts thereof.

Still further object of the present invention is to provide a method for the treatment of infectious diseases caused by pathogenic bacteria in human being and animals.

The object syn-isomer of 3,7-disubstituted-3-cephem-4-carboxylic acid compounds are novel and can be represented by the following formula (I):

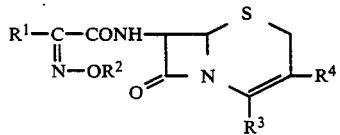

(I)

in which
$R^1$ is a group of the formula:

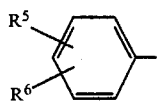

wherein $R^5$ is hydrogen, halogen, nitro, hydroxy, lower alkoxy or acyloxy and $R^6$ is hydroxy, lower alkoxy, acyloxy, acylamino or di(lower)alkylamino;

a group of the formula:

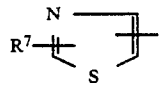

wherein $R^7$ is amino, protected amino, hydroxy or lower alkyl; or
a group of the formula:

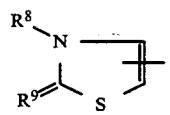

wherein $R^8$ is lower alkyl and $R^9$ is imino, protected imino or oxo;

$R^2$ is an aliphatic hydrocarbon group which may have suitable substituent(s);

$R^3$ is carboxy or protected carboxy; and $R^4$ is acyloxymethyl, hydroxymethyl, formyl, methyl or heterocyclicthiomethyl group which may have suitable substituent(s); or $R^3$ and $R^4$ are linked together to form —COOCH$_2$—.

With regard to the present invention, it is to be noted that this invention is characterized by providing syn-isomer of 3,7-disubstituted-3-cephem-4-carboxylic acid compounds, which is represented by the formula (I), and the said syn-isomer can be represented by the partial structure of the formula:

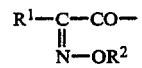

in their molecules, while the corresponding anti-isomer is represented by the partial structure of the formula:

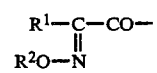

Accordingly, in the following detailed explanations of this invention in this specification and claims, it is to be understood that the syn-isomers of the object compounds as well as the starting compounds of this invention are represented by the partial structure of the formula:

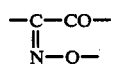

in their molecules, provided that, in case that it is convenient for the explanation of this invention to express both of the syn-isomer and anti-isomer by one general formula, they are represented by the partial structure of the formula:

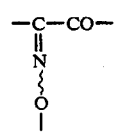

The object compounds of the present invention (I) are novel compounds and can be prepared by the Processes 1 to 8 as mentioned below.

Process 1

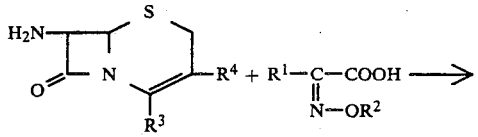

(II)
or its reactive derivative at the amino group or a salt thereof (III)
or its reactive derivative at the carboxy group or a salt thereof

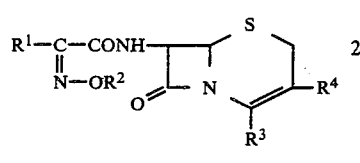

(I)
or a salt thereof

Process 2

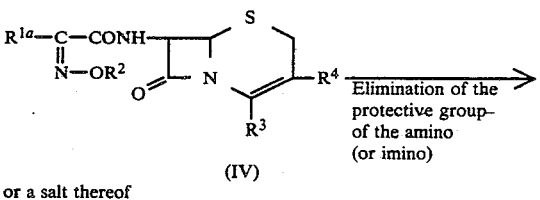

(IV)
or a salt thereof $\xrightarrow{\text{Elimination of the protective group of the amino (or imino)}}$

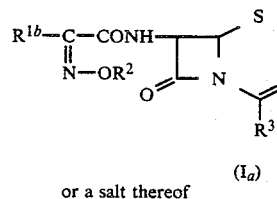

($I_a$)
or a salt thereof

Process 3

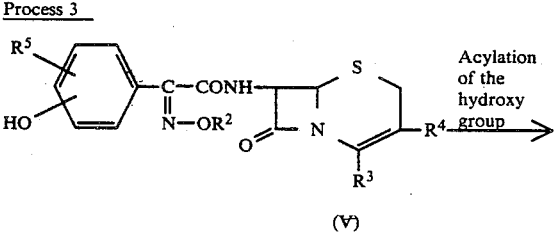

(V)
or a salt thereof $\xrightarrow{\text{Acylation of the hydroxy group}}$

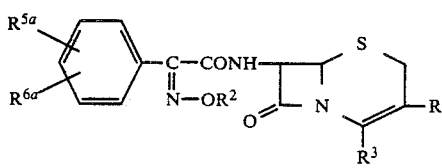

($I_b$)
or a salt thereof

Process 4

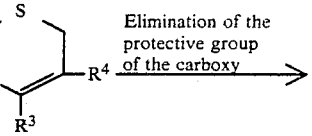

($V_a$)
or a salt thereof $\xrightarrow{\text{Elimination of the protective group of the carboxy}}$

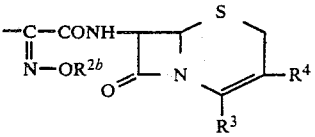

($I_c$)
or a salt thereof

Process 5

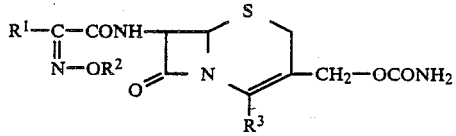

($V_b$)
or a salt thereof $\xrightarrow{\text{Elimination of the protective group of the amino}}$

($I_d$)
or a salt thereof

Process 6

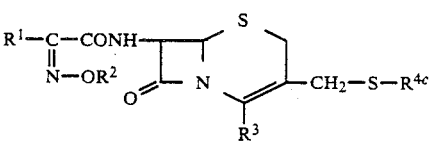

($V_c$)
or a salt thereof $R^{4c}$—SH ($V_d$)
or its reactive derivative at the mercapto group $\longrightarrow$ ($I_e$)
or a salt thereof Process 7

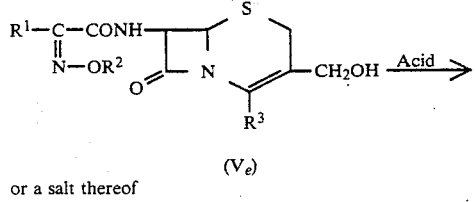

(V_e)

or a salt thereof

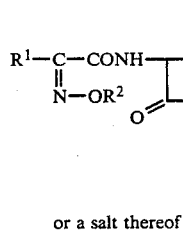

(I_f)

or a salt thereof

Process 8

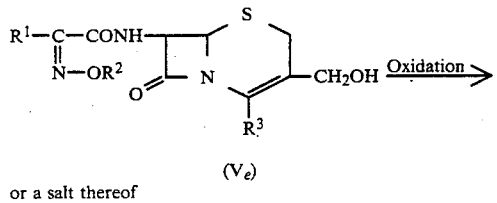

(V_e)

or a salt thereof

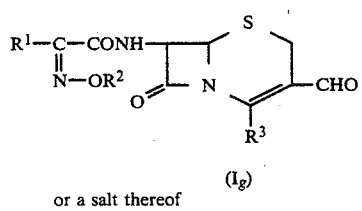

(I_g)

or a salt thereof wherein $R^1$, $R^2$, $R^3$, $R^4$ and $R^5$ are each as defined above;

$R^{1a}$ is a group of the formula:

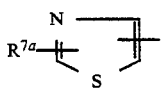

in which $R^{7a}$ is protected amino; or
a group of the formula

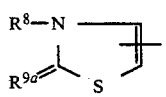

in which $R^8$ is as defined above and $R^{9a}$ is protected imino;

$R^{1b}$ is a group of the formula:

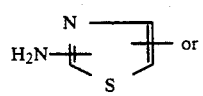

or
a group of the formula:

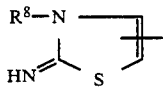

in which $R^8$ is as defined above;

$R^{5a}$ is hydrogen, halogen, nitro, lower alkoxy or acyloxy;

$R^{6a}$ is acyloxy;

$R^{2a}$ is protected carboxy(lower)alkyl;

$R^{2b}$ is carboxy(lower)alkyl; $R^{4a}$ is a protective group of amino;

$R^{4b}$ is a group which can be substituted by a group $R^{4c}$—S— wherein $R^{4c}$ is a heterocyclic group which may have suitable substituent(s); and $R^{4c}$ is as defined above.

Among the starting compounds, the starting compound (III), including the corresponding anti-isomer are novel and can be prepared by the processes which are illustrated by the following scheme.

(i)                                                                                           (1)

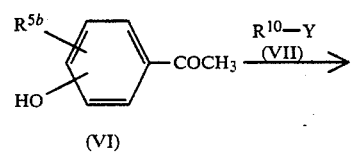

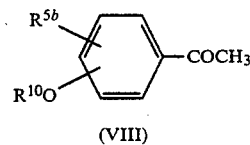

(ii)

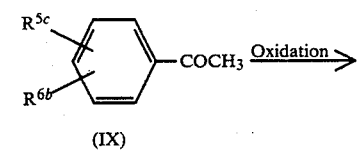

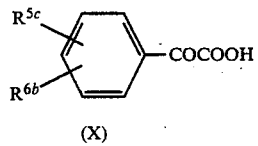

(iii)

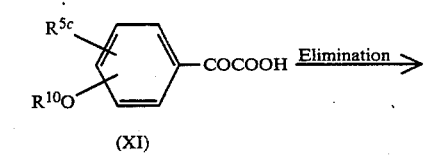

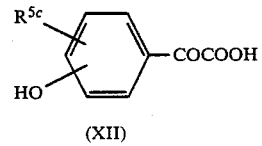

4,493,833
-continued
(iv)
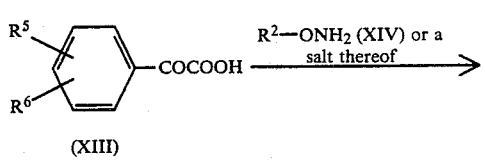
(XIII)
→ R²—ONH₂ (XIV) or a salt thereof →
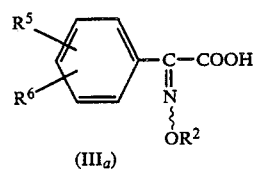
(IIIₐ)
(i) (2)
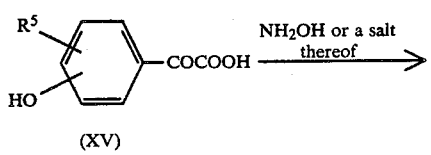
(XV)
→ NH₂OH or a salt thereof →
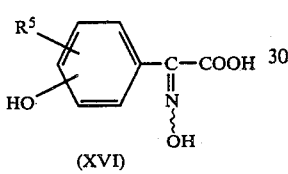
(XVI)
(ii)
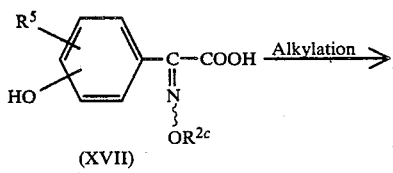
(XVII)
Alkylation →
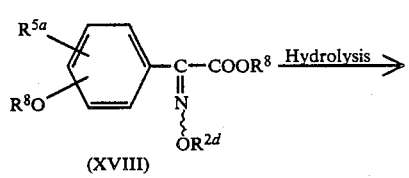
(XVIII)
Hydrolysis →
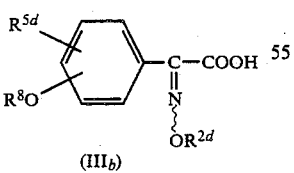
(III_b)
(3)
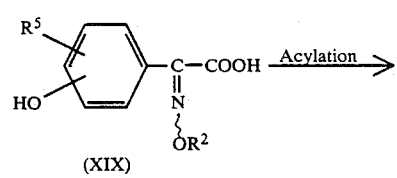
(XIX)
Acylation →
-continued
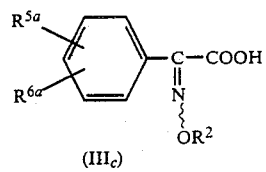
(III_c)
(i) (4)
X—CH₂—CO—CH₂—Z (XX) Nitrosation →
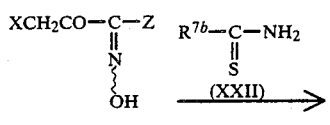
(XXI)
R^{7b}—C—NH₂ ‖ S (XXII) →
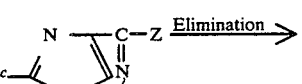
(XXIII)
Elimination →
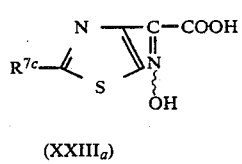
(XXIIIₐ)
(ii)
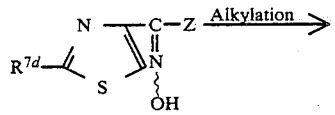
(XXIV)
Alkylation →
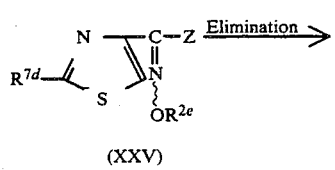
(XXV)
Elimination →
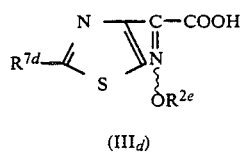
(III_d)
(5)
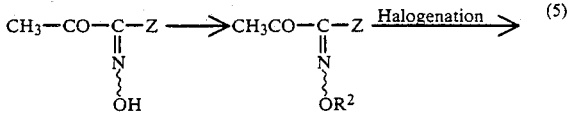
(XXVI) (XXVII)
Halogenation →

-continued

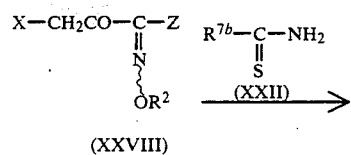
(XXVIII)

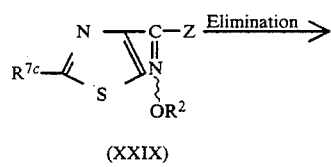
(XXIX)

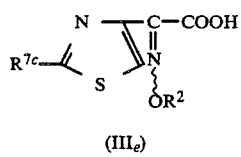
(III$_e$)

(i)

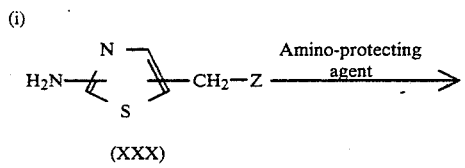
(XXX)

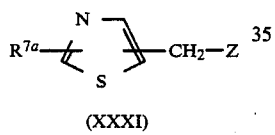
(XXXI)

(ii)

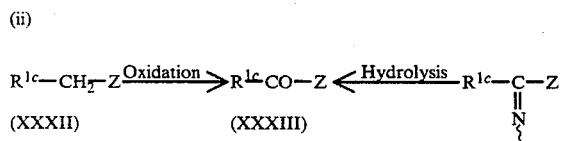
(XXXII) (XXXIII) (XXIII$_b$)

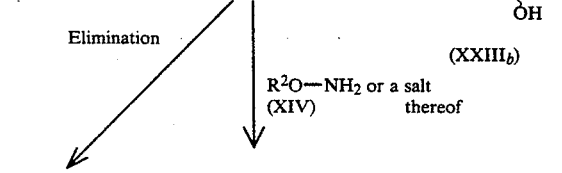

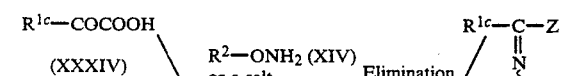
(XXXIV)

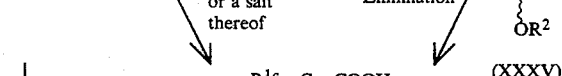

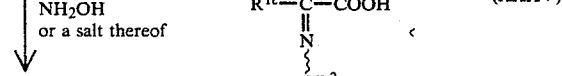

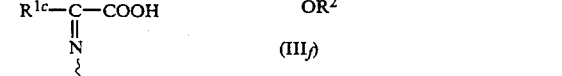
(III$_f$)

(XXXVI)

(iii)

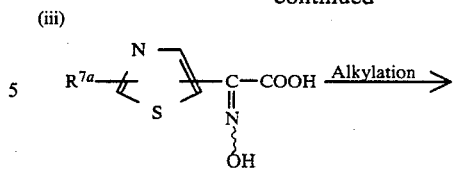
(XXXVII)

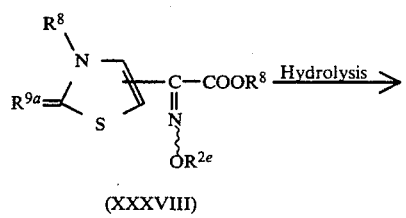
(XXXVIII)

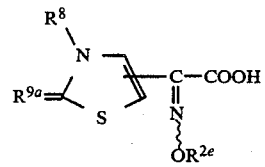
(III$_g$)

(6)

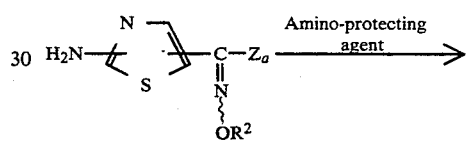
(XXXIX)

(7)

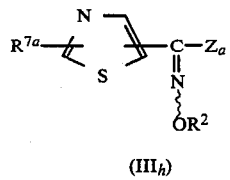
(III$_h$)

in which
$R^2$, $R^5$, $R^6$, $R^{5a}$, $R^{6a}$, $R^{7a}$, $R^8$ and $R^{9a}$ are each as defined above;
$R^{5b}$ is halogen;
Y is an acid residue;
$R^{10}$ is ar(lower)alkyl;
$R^{5c}$ is hydrogen, halogen or nitro;
$R^{6b}$ is lower alkoxy, ar(lower)alkoxy or acylamino;
$R^{2c}$ is hydrogen, lower alkyl or lower alkenyl;
$R^{5d}$ is hydrogen, halogen, nitro, hydroxy or lower alkoxy;
X is halogen;
Z is protected carboxy;
$R^{7b}$ is lower alkyl, amino or lower alkoxy;
$R^{7c}$ is lower alkyl, amino or hydroxy;
$R^{7d}$ is lower alkyl;
$R^{2e}$ is lower alkyl;
$R^{1c}$ is a group of the formula:

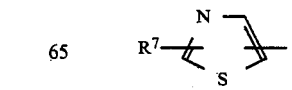

in which $R^7$ is as defined above, or a group of the formula:

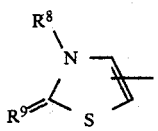

in which $R^8$ and $R^9$ are each as defined above;
$R^{2d}$ is lower alkyl or lower alkenyl; and
$Z_a$ is carboxy or protected carboxy.

The other starting compounds (IV), (V), $(V_a)$-$(V_c)$ and $(V_e)$ are all novel compounds and can be prepared by the aforesaid Processes 1 to 8.

Regarding the object compounds of the formulae (I), $(I_a)$ and $(I_c)$-$(I_g)$, and the starting compounds of the formulae (III), $(III_e)$, $(III_f)$, $(III_h)$, (IV), $(V_a)$-$(V_c)$, $(V_e)$, (XXIII)-$(XXIII_b)$, (XXIX)-(XXXVII) and (XXXIX), it is to be understood that said object and starting compounds include tautomeric isomers relating to their thiazole groups. That is, in case that the group represented by the formula:

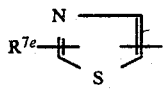

(wherein $R^{7e}$ is amino, protected amino or hydroxy) in the formula of said object and starting compounds take the formula:

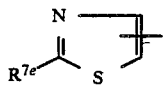

(A) ($R^{7e}$ is as defined above), said group of the formula:

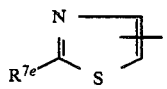

can be also alternatively represented by its tautomeric formula:

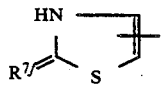

(B) (wherein $R^{7f}$ is imino, protected imino or oxo). That is, both of the said groups (A) and (B) are in the state of equilibrium as so-colled tautomeric forms which can be represented by the following equilibrium:

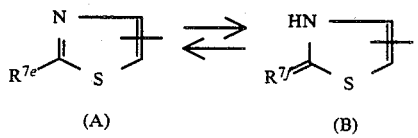

(wherein $R^{7e}$ and $R^{7f}$ are each as defined above).

These types of tautomerism between 2-amino- and 2-hydroxythiazole compounds and 2-imino- or 2-oxothiazoline compounds as stated above have been well known in the literature, and it is obvious to a person skilled in arts that both of the tautomeric isomers are equilibrated and easily convertible reciprocally, and accordingly it is to be understood that such isomers are included within the same category of the compound per se. Accordingly, the both of the tautomeric forms of the object compounds (I), $(I_a)$ and $(I_c)$-$(I_g)$, and the starting compounds (III), $(III_e)$, $(III_f)$, $(III_h)$, (IV), $(V_a)$-$(V_c)$, $(V_e)$, (XXIII)-$(XXIII_b)$, (XXIX)-(XXXVII) and (XXXIX) are clearly included within the scope of the present invention. In the present specification, claims and examples, the object and starting compounds including the group of such tautomeric isomers are represented by using one of the expressions therefor, that is the formula:

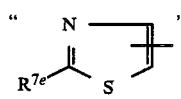

(A)

only for the convenient sake.

Furthermore, regarding the object compounds (I), $(I_a)$-$(I_e)$ and $(I_g)$, and the starting compounds (II), (IV), (V) and $(V_a)$, the compounds wherein $R^3$ is carboxy and $R^4$ is formyl can be also regarded as substantially same compounds as the compounds wherein $R^3$ and $R^4$ are linked together to form a group of the formula: —COOCH(OH)—, i.e. so-called intramolecular hemiacylal type compounds, and accordingly both of them are understood to be included within the same category of the compound per se and therefore within the scope of the present invention.

Suitable pharmaceutically acceptable salt of the object syn-isomer of 3,7-disubstituted-3-cephem-4-carboxylic acid compounds (I) are conventional non-toxic salts and may include an inorganic salt, for example, a metal salt such as an alkali metal salt (e.g., sodium salt, potassium salt, etc.) and an alkaline earth metal salt (e.g., calcium salt, magnesium salt, etc.), ammonium salt etc., an organic salt, for example, an organic amine salt (e.g., trimethylamine salt, triethylamine salt, ethanolamine salt, diethanolamine salt, pyridine salt, picoline salt, dicyclohexylamine salt, N,N'-dibenzylethylenediamine salt, etc.) etc., an organic acid salt (e.g., acetate, maleate, tartrate, methanesulfonate, benzenesulfonate, toluenesulfonate, etc.), an inorganic acid salt (e.g., hydrochloride, hydrobromide, sulfate, phosphate, etc.), or a salt with an amino acid (e.g., arginine, aspartic acid, glutamic acid, etc.), and the like.

In the above and subsequent descriptions of the present specification, suitable examples and illustrations of the various definitions which the present invention intend to include within the scope thereof are explained in details as follows.

The term "lower" is intended to mean 1 to 6 carbon atom(s), unless otherwise provided.

Aliphatic hydrocarbon group is intended to mean straight branched or cyclic aliphatic hydrocarbon having 1 to 6 carbon atom(s) and may include lower alkyl, cyclo(lower)alkyl, lower alkenyl, lower alkynyl and the like. And said aliphatic hydrocarbon group may have 1 to 2 suitable substituent(s) such as carboxy, protected carboxy, arylthio, lower alkylthio, aryl, acyloxy, lower alkoxy, aryloxy, a heterocyclic group or the like.

Suitable cyclo(lower)alkyl is one having 3 to 6 carbon atoms and may include cyclopropyl, cyclobutyl, cyclopentyl, cyclohexyl and the like, and preferably one having 5 to 6 carbon atoms.

Suitable lower alkynyl is one having 2 to 6 carbon atoms and may include ethynyl, 2-propynyl, 2-butynyl, 3-pentynyl, 3-hexynyl and the like, and preferably one having 2 to 4 carbon atoms, and more preferably one having 2 to 3 carbon atoms.

Suitable halogen may include chlorine, bromine, fluorine and iodine.

Suitable lower alkoxy and lower alkoxy moiety in the term "ar(lower)alkoxy" may include one which may be branched, for example, methoxy, ethoxy, propoxy, isopropoxy, butoxy, isobutoxy, tert-butoxy, pentyloxy, hexyloxy and the like, and preferably one having 1 to 4 carbon atom(s), and more preferably one having 1 to 2 carbon atom(s).

Suitable protected amino may include an acylamino and amino group substituted by a conventional protective group other than the acyl group such as benzyl or the like.

Suitable lower alkyl and lower alkyl moiety in the terms "lower alkylthio", "carboxy(lower)alkyl", "protected carboxy(lower)alkyl", "ar(lower)alkyl" and "di(lower)alkylamino" may include one which may be branched, for example, methyl, ethyl, propyl, isopropyl, butyl, isobutyl, tert-butyl, pentyl, hexyl and the like, wherein lower alkyl moiety may preferably be one having 1 to 4 carbon atom(s), and more preferably one having 1 to 2 carbon atom(s).

Suitable protected imino may include an acylimino and imino group substituted by a conventional protective group other than the acyl group such as benzyl and the like.

Suitable protected carboxy and protected carboxy moiety in the term "protected carboxy(lower)alkyl" may include esterified carboxy in which said ester moiety may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g., mesylmethyl ester, 2-mesylethyl ester etc.); ar(lower)alkyl ester, for example, mono- or di- or triphenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g., phenyl ester, tolyl ester, tertiarybutylphenyl ester, xylyl ester, mesityl ester, cumenyl ester, etc.), and the like. Preferable example of protected carboxy may be lower alkoxycarbonyl (e.g., methoxycarbonyl, ethoxycarbonyl, propoxycarbonyl, butoxycarbonyl, t-butoxycarbonyl, t-pentyloxycarbonyl, hexyloxycarbonyl, etc.) having 2 to 7 carbon atoms, preferably one having 2 to 5 carbon atoms; lower alkanoyloxy(lower)alkoxycarbonyl having 3 to 13 carbon atoms (e.g., acetoxymethoxycarbonyl, pivaloyloxymethoxycarbonyl, hexanoyloxymethoxycarbonyl, etc.), preferably one having 6 to 8 carbon atoms; or ar(lower)alkoxycarbonyl having 8 to 20 carbon atoms (e.g., benzyloxycarbonyl, phenethyloxycarbonyl, benzhydryloxycarbonyl, trityloxycarbonyl, etc.), preferably one having 12 to 14 carbon atoms.

Suitable aryl and aryl moiety in the terms "ar(lower)alkyl", "ar(lower)alkoxy", "arylthio" and "aryloxy" may include phenyl, tolyl, xylyl, mesityl, cumenyl, naphthyl and the like, wherein said aryl group may have 1 to 3 suitable substituent(s) such as halogen (e.g. chlorine, bromine, iodine or fluorine), hydroxy, amino(lower)alkyl (e.g.,aminomethyl, aminoethyl, aminopropyl, aminobutyl, etc.), protected amino(lower)alkyl wherein protected amino is as defined above, preferably lower alkoxycarbonylamino(lower)alkyl (e.g., methoxycarbonylaminomethyl, ethoxycarbonylaminomethyl, t-butoxycarbonylaminomethyl, etc.), or the like.

Suitable heterocyclic group and heterocyclic moiety in the term "a heterocyclicthiomethyl group which may have suitable substituent(s)" means saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (preferably 5 to 6 membered) heteromonocyclic group containing 1 to 4 nitrogen atom(s), for example, pyrrolyl, pyrrolinyl, imidazolyl, pyrazolyl, pyridyl and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc; saturated 3 to 8-membered (preferably 5 to 6 membered) heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, tetrazolopyridazinyl, etc.; unsaturated 3- to 8-membered (preferably 5 to 6 membered) heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.; saturated 3 to 8-membered (preferably 5 to 6 membered) heteromonocyclic group containing 1 to 2 oxygen atom(s) and 1 to 3 nitrogen atom(s), for example, morpholinyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (preferably 5 to 6 membered) heteromonocyclic group containing 1 to 2 sulfur atom(s) and 1 to 3 nitrogen atom(s), for example, thiazolyl, thiadiazolyl (e.g., 1,2,4-thiadiazolyl, 1,3,4-thiadiazolyl, 1,2,5-thiadiazolyl, etc.), etc; saturated 3 to 8-membered (preferably 5 to 6 membered) heteromonocyclic group containing 1 to 2 sulfur atom(s) and 1 to 3 nitrogen atom(s), for example, thiazolidinyl, etc.; unsaturated 3 to 8 membered (preferably 5 to 6 membered) heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzo-thiadiazolyl, etc. and the like; wherein said heterocyclic group may have 1 to 2 suitable substituent(s) such as lower alkyl (e.g., methyl, ethyl, propyl, isopropyl, butyl, isobutyl, pentyl, cyclopentyl, hexyl, cyclohexyl, etc.); lower alkenyl (e.g., vinyl, allyl, 1-propenyl, 2-butenyl, etc.), preferably one having 2 to 4 carbon atoms; aryl (e.g., phenyl, tolyl, etc.); halogen (e.g., chlorine, bromine, iodine or fluorine); amino; di(lower)alkylamino(lower)alkyl (e.g. dimethylaminomethyl, dimethylaminoethyl, diethylaminopropyl, diethylaminobutyl, etc.), preferably one having 3 to 6 carbon atoms; or the like.

Suitable lower alkenyl is one having 2 to 6 carbon atoms and may include, for example, vinyl, allyl, isopropenyl, 1-propenyl, 2-butenyl, 3-pentenyl and the like, and preferably one having 2 to 4 carbon atoms.

Suitable acyl moiety in the terms "acylamino", "acylimino", "acyloxy" and "acyloxymethyl" as mentioned above may include carbamoyl, aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, hexanoyl, etc.), preferably one having 1 to 5 carbon atom(s); cyclo(lower)alkanecarbonyl having 4 to 7 carbon atoms (e.g., cyclopropanecarbonyl, cyclohexanecarbonyl, etc.), preferably one having 6 to 7 carbon atoms; lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl t-pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.); aryloxy(lower)alkanoyl (e.g., phenoxyacetyl, phenoxypropionyl, phenoxyhexanoyl, etc.); heterocyclicarbonyl (e.g., thenoyl, furoyl, nicotinoyl, etc.); and the like.

The acyl moiety as stated above may have 1 to 3 suitable substituent(s) such as halogen (e.g., chlorine, bromine, iodine or fluorine), hydroxy, cyano, nitro, amino, lower alkoxy (e.g., methoxy, ethoxy, propoxy, isopropoxy, etc.), preferably one having 1 to 2 carbon atom(s), lower alkyl (e.g., methyl, ethyl, propyl, isopropyl, butyl, etc.), lower alkenyl (e.g., vinyl, allyl etc.), aryl (e.g., phenyl, tolyl, etc.) which may have halogen, or the like.

Preferable example of acyl having said substituent(s) may be N-aryl- or N-halogen substituted aryl-carbamoyl, aryloxy(lower)alkanoyl having lower alkoxy, or aroyl having nitro or amino.

Preferable example of acylamino may be lower alkanoylamino or ar(lower)alkanoylamino [more preferably phenyl(lower)alkanoylamino]; and preferable example of acyloxy may be lower alkanoyloxy; carbamoyloxy which may have aryl (more preferably phenyl) or halogen substituted aryl(more preferably phenyl); aryloxy(lower)alkanoyloxy [more preferably phenoxy(lower)alkanoyloxy] having lower alkoxy; thenoyloxy; cyclo(lower)alkanecarbonyloxy; or aroyloxy(more preferably benzoyloxy) having nitro or amino.

Suitable protective group of amino for $R^{4a}$ may include acyl such as halo(lower)alkanoyl (e.g., chloroacetyl, dichloroacetyl, trichloroacetyl, trifluoroacetyl, etc.), preferably one having 2 to 3 carbon atoms, or the like.

Suitable acid residue may include a residue of an acid such as an inorganic acid (e.g., hydrochloric acid, hydrobromic acid, hydriodic acid, sulfuric acid, etc.) or an organic acid (e.g., methanesulfonic acid, benzenesulfonic acid, p-toluenesulfonic acid, etc.).

Suitable example of a group which can be substituted by a group $R^{4c}$—S— may include an acid residue such as halogen, azido or acyloxy wherein said halogen and acyl moiety of said acyloxy are the same ones as aforementioned.

Among the suitable examples of each of the groups of the object compounds as explained and illustrated above, the preferred examples thereof are illustrated as follows.

Preferable example of $R^5$ may be hydrogen halogen (preferably chlorine) or nitro; preferable example of $R^6$ may be hydroxy, lower alkoxy (preferably $C_1$-$C_4$, more preferably $C_1$-$C_2$), acyloxy[preferably lower alkanoyloxy (preferably $C_1$-$C_4$, more preferably $C_1$-$C_2$) or carbamoyloxy], acylamino [preferably lower alkanesulfonylamino (preferably $C_1$-$C_4$, more preferably ($C_1$-$C_2$)] or di(lower)alkylamino (wherein the alkyl moiety is preferably $C_1$-$C_4$, more preferably $C_1$-$C_2$); preferable example of $R^7$ may be amino, protected amino such as acylamino [preferably lower alkanesulfonylamino (preferably $C_1$-$C_4$, more preferably $C_1$-$C_2$), trihalo(lower)alkanoylamino (preferably $C_1$-$C_4$, more preferably $C_1$-$C_2$) lower alkoxycarbonylamino (preferably $C_2$-$C_7$, more preferably $C_3$-$C_6$) or lower alkanoylamino (preferably $C_1$-$C_4$, more preferably $C_1$-$C_2$)], hydroxy or lower alkyl (preferably $C_1$-$C_4$, more preferably $C_1$-$C_2$); preferable example of $R^8$ is $C_1$-$C_4$ lower alkyl, more preferably $C_1$-$C_2$ lower alkyl; preferable example of $R^9$ may be protected imino such as acylimino [preferably lower alkanesulfonylimino (preferably $C_1$-$C_4$, more preferably $C_1$-$C_2$)]; preferable example of $R^2$ may be lower alkyl, cyclo(lower)alkyl, lower alkenyl, lower alkynyl, ar(lower)alkenyl [more preferably phenyl(lower)alkenyl], carboxy(lower)alkyl, protected carboxy(lower)alkyl [more preferably lower alkoxycarbonyl (preferably $C_3$-$C_6$) (lower)alkyl], arylthio(lower)alkyl [more preferably phenylthio(lower)alkyl], ar(lower)alkyl [more preferably phenyl(lower)alkyl] which may have halogen, amino(lower)alkyl, protected amino(lower)alkyl or halogen (preferably bromine) and hydroxy, thienyl(lower)alkyl, aryloxy(lower)alkyl [more preferably phenoxy(lower)alkyl] which may have hydroxy, in which alkenyl and alkenyl moiety is $C_2$-$C_6$, preferably $C_2$-$C_4$, and alkyl moiety is preferably $C_1$-$C_4$, more preferably $C_1$-$C_2$, lower alkylthio(lower)alkyl, ar(lower)alkyl [more preferably phenyl(lower)alkyl], acyloxy(lower)alkyl [more preferably lower alkanoyloxy(lower)alkyl], carboxy(lower)alkyl, lower alkoxy(lower)alkyl or isoxazolyl(lower)alkyl; preferable example of $R^3$ may be carboxy, lower alkanoyloxy(lower)alkoxycarbonyl or ar(lower)alkoxycarbonyl[more preferably diphenyl(lower)alkoxycarbonyl]; preferable example of $R^4$ may be acyloxymethyl[preferably lower alkanoyloxymethyl (in which alkanoyl moiety is preferably $C_1$-$C_4$, more preferably $C_1$-$C_2$, most preferably $C_2$, i.e. acetyl) or carbamoyloxymethyl which may have trihalo(lower)alkanoyl (in which trihalo moiety is preferably trichloro and alkanoyl moiety is preferably $C_2$-$C_3$)], hydroxymethyl, formyl, tetrazolylthiomethyl which may have lower alkyl, lower alkenyl (preferably $C_2$-$C_4$) or di(lower)alkylamino(lower)alkyl (in which alkyl moiety is preferably C$_1$-C$_4$, more preferably C$_1$-C$_2$), triazolylthiomethyl which may have lower alkyl (preferably C$_1$-C$_4$, more preferably C$_1$-C$_2$), thiadiazolylthiomethyl which may have lower alkyl (preferably C$_1$-C$_4$, more preferably C$_1$-C$_2$), methyl, carbamoyloxymethyl having aryl(more preferably phenyl) or halogen substituted aryl(more preferably phenyl), aryloxy(lower)alkanoyloxy[more preferably phenoxy(lower)alkanoyloxy] having lower alkoxy, thenoyloxy, cyclo(lower)alkanecarbonyloxy, aroyloxy (more preferably benzoyloxy) having nitro or amino, triazolylthiomethyl having lower alkenyl, or tetrazolopyridazinylthiomethyl; or R$^3$ and R$^4$ are linked together to form —COOCH$_2$—.

The various processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof, which is a fundamental method for preparing the object compound (I).

Suitable reactive derivative at the amino group of the compound (II) may include conventional reactive derivative used in amidation, for example, a silyl derivative formed by the reaction of the compound (II) with a silyl compound such as bis(trimethylsilyl)acetamide, trimethylsilylacetamide or the like.

Suitable salt of the compound (II) may include: an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a salt with an inorganic base such as an alkali metal salt (e.g., sodium salt, potassium salt, etc.), an alkaline earth metal salt (e.g., calcium salt, magnesium salt, etc.) or ammonium salt; a salt with an organic base (e.g., triethylamine salt, pyridine salt, etc.); and the like.

Suitable reactive derivative at the carboxy group of the compound (III) may include conventional one used in amidation.

The salts of the compound (III) may be salts with an inorganic base such as an alkali metal salts (e.g., sodium or potassium salt), or an alkaline earth metal salt (e.g., calcium or magnesium salt), a salt with an organic base such as trimethylamine, triethylamine, pyridine, a salt with an acid (e.g., hydrochloric acid or hydrobromic acid) or the like.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction. Among these solvents, hydrophilic solvents may be used in a mixture with water.

The present reaction is preferably carried out in the presence of a condensing agent such as so-called Vilsmeier reagent, for example, (chloromethylene)-dimethylammonium chloride produced by the reaction of dimethylformamide with thionyl chloride or phosgene, a compound produced by the reaction of dimethylformamide with phosphorus oxychloride, etc., or the like.

The reaction may be also carried out in the presence of an inorganic or an organic base such as an alkali metal hydroxide, an alkali metal bicarbonate, alkali metal carbonate, alkali metal acetate, tri(lower)alkylamine, pyridine, N-(lower)alkylmorphorine, N,N-di(lower)alkylbenzylamine, N,N-di(lower)alkylaniline as exemplified below, or the like. When the base or the condensing agent is in liquid, it can be used also as a solvent. The reaction temperature is not critical, and the reaction is usually carried out under cooling or at ambient temperature.

In the present reaction, it is to be noted that, in case that the starting compound (III) is reacted with the compound (II) or its reactive derivative at the amino group or a salt thereof in the presence of, for example, phosphorus pentachloride, thionyl chloride, etc., only the corresponding anti-isomer to the object compund (I) or a mixture of the corresponding anti-isomer and syn-isomer is always given as an object compound even if the compound (III), i.e., syn-isomer is used as a starting compound. It is of course to be noted that the reaction of the corresponding anti-isomer to the starting compound (III) with the compound (II) can never produce the object compound (I) of the present invention, i.e. syn-isomer. It may be understood that such tendency and singularity of the reaction as mentioned above is due to the fact that the less stable syn-isomer tends to isomerize partially or wholly to the corresponding more stable anti-isomer in the course of the reaction, for example, in so-called activation step of the compound (III) so that the isomerized compound, i.e. the anti-isomer corresponding to the object compound (I) can be produced as an object compound.

Accordingly, in order to obtain the object compound (I), i.e., syn-isomer selectively and in high yield, it is necessary to use the starting compound (III), i.e., syn-isomer and to select a suitable reaction condition. That is, the object compound (I), i.e., syn-isomer can be obtained selectively and in high yield by conducting the reaction, for example, in the presence of a Vilsmeier reagent as mentioned above etc. and under around neutral condition.

Especially, in case that the starting compound (III) wherein R$^1$ is a group of the formula:

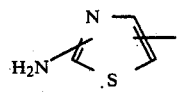

is used, the object compound (I), i.e., syn-isomer can be obtained selectively and in high yield by conducting the present reaction of the corresponding starting compound (III), i.e., syn-isomer with the compound (II), for example, in the presence of a Vilsmeier reagent produced by the reaction of dimethylformamide with phosphorus oxychloride and under around neutral condition. And, in this case, it is to be noted that particularly good results can be achieved by conducting the reaction in the presence of more than two molar equivalents of phosphorus oxychloride to each amount of the said starting compound (III), i.e., syn-isomer and dimethylformamide as shown in the working examples. Further, in this case, it is to be also noted that good results can be achieved by conducting an activation step of the starting compound (III), i.e., syn-isomer in the presence of a silyl compound [e.g. bis(trimethylsilyl)acetamide, trimethylsilylacetamide, etc.] and the like.

With regard to the reaction of the compound (II) with the compound (III), it is to be noted that; when the compound (II) wherein $R^4$ is carbamoyloxymethyl group having acyl group is used as a starting compound, there may be obtained occasionally either the object compound (I) wherein $R^4$ is carbamoyloxymethyl group having acyl group or free carbamoyloxymethyl group according to reaction conditions; when the compound (II) wherein $R^4$ is hydroxymethyl group is used as a starting compound, there may be obtained occasionally the object compound (I) wherein $R^3$ and $R^4$ are linked together to form —COOCH$_2$—; and further the protected carboxy group or salts in the compound (II) may be converted into free carboxy group; in the course of the reaction or in post-treatment. These cases are also included within the scope of the present invention.

As clear from the explanation as stated above, it is to be understood that the Process 1 is a fundamental and the most advantageous method for preparing the object compound (I), i.e. syn-isomer.

Process 2

The object compound (I$_a$) or a salt thereof can be prepared by subjecting the compound (IV) or a salt thereof to elimination reaction of the protective group of the amino or imino.

Suitable salt of the compound (IV) may include a metal salt, ammonium salt, an organic amine salt and the like as aforementioned.

The present elimination reaction is carried out in accordance with a conventional method such as hydrolysis; reduction; a method by reacting the compound (IV) wherein the protective group is acyl group with iminohalogenating agent and then with iminoetherifying agent, and, if necessary, subjecting the resulting compound to hydrolysis; or the like. The hydrolysis may include a method using an acid or base or hydrazine and the like. These methods may be selected depending on the kind of the protective groups to be eliminated.

Among these methods, hydrolysis using an acid is one of the common and preferable method for eliminating the protective groups such as substituted or unsubstituted alkoxycarbonyl (e.g., t-pentyloxycarbonyl, etc.), alkanoyl (e.g., formyl, etc.), cycloalkoxycarbonyl, substituted or unsubstituted aralkoxycarbonyl (e.g., benzyloxycarbonyl, substituted benzyloxycarbonyl, etc.), substituted phenylthio, substituted aralkylidene, substituted alkylidene, substituted cycloalkylidene, or the like. Suitable acid may include an organic or an inorganic acid, for example, formic acid, trifluoroacetic acid, benzenesulfonic acid, p-toluenesulfonic acid, hydrochloric acid and the like, and preferable acid is an acid which can be easily removed from the reaction mixture by a conventional manner such as distillation under reduced pressure, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include an organic solvent, water or a mixed solvent thereof. When trifluoroacetic acid is used, the elimination reaction may be preferably carried out in the presence of anisole.

The hydrolysis using hydrazine is commonly applied for eliminating the protective group, for example, succinyl or phthaloyl.

The hydrolysis with a base is preferably applied for eliminating acyl group, for example, haloalkanoyl (e.g., trifluoroacetyl, etc.) etc. Suitable base may include, for example, an inorganic base such as alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective groups, the acyl group can be generally eliminated by hydrolysis as mentioned above or by the other conventional hydrolysis. In case that the acyl group is halogen substituted-alkoxycarbonyl or 8-quinolyloxycarbonyl, they are eliminated by treating with a heavy metal such as copper, zinc or the like.

The reductive elimination is generally applied for eliminating the protective group, for example, haloalkoxycarbonyl (e.g., trichloroethoxycarbonyl etc.), substituted or unsubstituted aralkoxycarbonyl (e.g., benzyloxycarbonyl, substituted benzyloxycarbonyl etc.), 2-pyridylmethoxycarbonyl, etc. Suitable reduction may include, for example, reduction with an alkali metal borohydride (e.g., sodium borohydride, etc.) and the like.

Suitable iminohalogenating agent used in a method as mentioned above may include phosphorus trichloride, phosphorus pentachloride, phosphorus tribromide, phosphorus pentabromide, phosphorus oxychloride, thionyl chloride, phosgene and the like. The reaction temperature is not critical, and the reaction is usually carried out at ambient temperature or under cooling. Suitable iminoetherifying agent reacted with thus obtained reaction product may include an alcohol, metal alkoxide and the like. Suitable alcohol may include alkanol (e.g., methanol, ethanol, propanol, isopropanol, butanol, t-butanol, etc.) which may be substituted with alkoxy (e.g., methoxy, ethoxy, propoxy, isopropoxy, butoxy, etc.). Suitable metal alkoxide may include alkali metal alkoxide (e.g., sodium alkoxide, potassium alkoxide, etc.), alkaline earth metal alkoxide (e.g., calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can be readily carried out by pouring the reaction mixture obtained above into water, but there may be previously added a hydrophilic solvent (e.g., methanol, ethanol, etc.), a base (e.g., alkali metal bicarbonate, trialkylamine, etc.) or an acid (e.g., diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the cases that the protected carboxy is transformed into the free carboxy group; that when the compound (IV) wherein $R^4$ is carbamoyloxymethyl group having acyl grup is used as the starting compound, there may be obtained occasionally either the object compound $(I_a)$ wherein $R^4$ is carbamoyloxymethyl group having acyl group or free carbamoyloxymethyl group according to reaction conditions; and that when the compound (IV) wherein $R^4$ is acyloxymethyl group is used as the starting compound, there may be obtained occasionally the object compound $(I_a)$ wherein $R^3$ and $R^4$ are linked together to form —COOCH$_2$— according to reaction conditions; in the course of the reaction or in post-treatment.

Process 3

The object compound $(I_b)$ or a salt thereof can be prepared by acylating the hydroxy group of the compound (V) or a salt thereof.

Suitable salt of the compound (V) can also be referred to the ones exemplified for the compound (IV).

The acylating agent to be used for the present reaction may include an aliphatic, aromatic and heterocyclic carboxylic acid, and the corresponding sulfonic acid and thio acid which have aforesaid acyl group as their acyl moieties, and reactive derivatives of the above-mentioned acids. Suitable reactive derivative of the above-mentioned acids may include an acid halide, an acid anhydride, an activated amide, an activated ester, and the like. Suitable example may be an acid chloride; an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; or an activated ester [e.g., cyanomethyl ester, methoxymethyl ester, dimethyliminomethyl ((CH$_3$)$_2$N$^+$=CH—) ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester], or an ester with N,N-dimethylhydroxylamine, 1-hydroxy-2-(1H)-pyridone, N-hydroxysuccinimide, N-hydroxyphthalimide or 1-hydroxy-6-chloro-1H-benzotriazole, and the like. These reactive derivatives can be optionally selected from them according to the kind of the acylating agent to be used.

The acylating agent may further include aliphatic, aromatic or heterocyclic isocyanate or isothiocyanate (e.g., methyl isocyanate, phenyl isocyanate, trichloroacetyl isocyanate, methyl isothiocyanate, etc.) and haloformate (e.g., ethyl chloroformate, benzyl chloroformate, etc.). In this case, for example, when trichloroacetyl isocyanate is used as an acylating agent, trichloroacetylcarbamoyl group is introduced as acyl group and said group may be converted to carbamoyl group by treating with base, and when ethyl chloroformate is used as an acylating agent, ethoxycarbonyl group is introduced as acyl group.

The present reaction is carried out according to similar reaction conditions to those of aforesaid reaction of the compound (II) with the compound (III), and is preferably carried out in the presence of a base. In the reaction of the compound (V) with an acylating agent, the protected carboxy group or salts in the compound (V) may be converted into free carboxy group in the course of the reaction or in post-treatment; and when the compound (V) wherein $R^4$ is carbamoyloxymethyl group having acyl group is used as the starting compound, there may be obtained occasionally either the object compound $(I_b)$ wherein $R^4$ is carbamoyloxymethyl group having acyl group or free carbamoyloxymethyl group according to reaction conditions in the course of the reaction or in post-treatment. These cases are also included in the scope of the present invention.

Process 4

The object compound $(I_c)$ or a salt thereof can be prepared by subjecting the compound $(V_a)$ or a salt thereof to elimination reaction of the protective group of the carboxy.

Suitable salt of the compound $(V_a)$ can be referred to the ones exemplified for the compound (IV).

The present elimination reaction is carried out in accordance with a conventional method such as hydrolysis or the like. The hydrolysis may include a method using an acid or base and the like. These methods may be selected depending on kind of the protective groups to be eliminated.

The hydrolysis using an acid is one of the most common and preferable methods for eliminating the protective groups such as phenyl(lower)alkyl, substituted phenyl(lower)alkyl, lower alkyl, substituted lower alkyl, or the like. Suitable acid may include inorganic or organic acid, for example, formic acid, trifluoroacetic acid, benzenesulfonic acid, p-toluenesulfonic acid, hydrochloric acid, and the like. The present reaction may be carried out in the presence of anisole. The acid suitable for the reaction can be selected according to the protective group to be eliminated and other factors. The hydrolysis using an acid may be carried out in the presence of a solvent, such as an organic solvent, water or a mixed solvent thereof.

The reaction temperature is not critical and may be suitably selected in accordance with the kind of the protective group and the elimination method, and the present reaction is preferably carried out under a mild condition such as under cooling, at ambient temperature or slightly warming.

The present invention includes, within its scope, the cases that the protected carboxy group for $R^3$ is transformed into the free carboxy group; that the protected amino group is transformed into the free amino group; that the protected imino group is transformed into the free imino group; that the acyloxy group is transformed into the hydroxy group; and/or that the carbamoyloxymethyl group having acyl group is transformed into the free carbamoyloxymethyl group; during the reaction or post-treating in the present reaction.

Process 5

The object compound $(I_d)$ or a salt thereof can be prepared by subjecting the compound $(V_b)$ or a salt thereof to elimination reaction of the protective group of the amino.

Suitable salt of the compound ($V_b$) can be referred to the ones exemplified for the compound (IV).

The present elimination reaction may include an elimination method using a base, for example, an inorganic base such as an alkali metal hydroxide (e.g., sodium hydroxide, potassium hydroxide, etc.), an alkali metal bicarbonate (e.g., sodium bicarbonate, potassium bicarbonate, etc.) or alkali metal carbonate (e.g., sodium carbonate, potassium carbonate, etc.), an organic base such as an alkali metal alkoxide (e.g., sodium methoxide, sodium ethoxide, etc.), a trialkylamine (e.g., trimethylamine, triethylamine, etc.), triethanolamine, N,N-dimethylaniline, N,N-dimethylbenzylamine, N-methylmorpholine or pyridine; and an elimination reaction using basic alumina, basic ion exchange resin, acid (e.g., trifluoroacetic acid, trifluoroacetic acid.anisole, etc.). The present elimination reaction is usually carried out in water, hydrophilic solvent or a mixture thereof. The reaction temperature is not critical and the reaction is preferably carried out at ambient temperature or under cooling.

The present invention includes, within its scope, the cases that the protected carboxy group or salts in the compound ($V_b$) may be converted into free carboxy group, and that the protected amino and/or imino group may be converted into the free amino and/or imino group, respectively in the course of the reaction or in post-treatment.

Process 6

The object compound ($I_e$) or a salt thereof can be prepared by reacting the compound ($V_c$) or a salt thereof with the compound ($V_d$) or its reactive derivative at the mercapto group.

Suitable salt of the compound ($V_c$) can be referred to the ones exemplified for the compound (IV).

The suitable reactive derivative at the mercapto group of the compound ($V_d$) may include a metal salt such as alkali metal salts (e.g., sodium salt, potassium salt, etc.) or the like.

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other solvent which does not adversely affect the reaction, preferably in ones having strong polarities. Among the solvents, hydrophilic solvents may be used in a mixture with water. The reaction is preferably carried out in weekly basic or around neutral condition. When the compound ($V_c$) and or the thiol compound ($V_d$) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming. The reaction product can be isolated from the reaction mixture by conventional methods.

The reaction of the compound ($V_c$) with the compound ($V_d$) includes, within its scope, the cases that the protected carboxy group or salts in the compound ($V_c$) may be converted into free carboxy group; that the protected amino and/or imino group may be converted into free amino and/or imino group; and that the acyloxy group may be converted into hydroxy group; respectively in the course of the reaction or in post-treatment.

Process 7

The object compound ($I_f$) or a salt thereof can be prepared by treating the compound ($V_e$) or a salt thereof with an acid.

Suitable salt of the compound ($V_e$) can be referred to the ones exemplified for the compound (IV).

Suitable acid to be used in the present reaction may include an inorganic acid (e.g., hydrochloric acid, hydrobromic acid, sulfuric acid, etc.) or an organic acid (e.g., formic acid, acetic acid, etc.).

The present reaction is usually carried out in a solvent such as water, acetone, acetic acid or any other solvent which does not adversely influence the reaction. Among these solvents hydrophilic solvents can be used as a mixture with water.

The reaction temperature is not critical and the reaction is preferably carried out under cooling to warming.

Process 8

The object compound ($I_g$) or a salt thereof can be prepared by oxidizing the compound ($V_e$) or a salt thereof.

Suitable oxidizing agent used in the present reaction may include Jones reagent being used by a combination of sulfuric acid and chromium trioxide, manganese dioxide, a reagent being used by a combination of dimethylsulfoxide and N,N'-dicyclohexylcarbodiimide etc., and the like.

The present reaction is usually carried out in a solvent such as water, acetone, dimethylformamide or any other solvent which does not adversely affect the reaction. These solvents may be used as a mixture thereof.

The reaction temperature is not critical and the reaction is preferably carried out under cooling or around ambient temperature.

Processes for preparing the starting compound (III) i.e., syn-isomer and anti-isomer thereof used for References are explained in details as follows.

(A) Process of (VI)+(VII)→(VIII) [Scheme (1)(i)]

The compound (VIII) can be prepared by reacting the compound (VI) with the compound (VII).

The present reaction is usually carried out in a solvent such as water, ethanol, acetone, ether, dimethylformamide or any other solvent which does not adversely influence the present reaction. The reaction is preferably carried out in the presence of a base such as an inorgnic base or an organic base as aforementioned. The reaction temperature is not critical and the reaction is usually carried out under cooling to under heating of boiling point of the solvent.

(B) Processes of (IX)→(X) [Scheme (1)(ii)] and (XXXII)→(XXXIII) [Scheme (6)(ii)]

The compounds (X) and (XXXIII) can be prepared by oxidizing the compounds (IX) and (XXXII), respectively.

The present oxidation reaction is conducted by a conventional method which is applied for the transformation of so-called activated methylene group into carbonyl group. That is, the present oxidation is conducted by a conventional method such as oxidation by using a conventional oxidizing agent such as selenium dioxide, potassium permanganate or the like. The present oxidation is usually carried out in a solvent which does not adversely influence the reaction, for example, water, dioxane, pyridine, tetrahydrofuran, and the like.

The reaction temperature is not critical and the reaction is preferably carried out under warming to heating.

(C) Process of (XI)→(XIII) [Scheme (1)(iii)]

The compound (XII) can be prepared by subjecting the compound (XI) to elimination reaction of the ar(-lower)alkyl group.

The present elimination method may include all conventional methods used in the elimination reaction of the ar(lower)alkyl group, for example, hydrolysis, reduction, etc.

The hydrolysis using acid is one of the most preferable method and the acid to be used may include an inorganic acid (e.g., hydrochloric acid, hydrobromic acid, etc.), an organic acid (e.g., formic acid, acetic acid, trifluoroacetic acid, etc.) and a mixture thereof. The present reaction can be carried out in a solvent such as water, an organic solvent or a mixture thereof or without solvent. The reaction temperature is not critical and the reaction is preferably carried out under warming to heating.

(D) Processes of (XIII)+(XIV)→(IIIa) [Scheme (1)(iv)], (XXXIII)+(XIV)→(XXXV) [Scheme (6)(ii)] and (XXXIV)+(XIV)→(III$_f$) [Scheme (6)(ii)]

The compounds (III$_a$), (XXXV) and (III$_f$) can be prepared by reacting the compounds (XIII), (XXXIII) and (XXXIV) with the compound (XIV) or a salt thereof, respectively.

Suitable salt of the compound (XIV) may include an inorganic acid salt (e.g., hydrochloride, hydrobromide, sulfate, etc.), an organic acid salt (e.g., acetate, p-toluenesulfonate, etc.) and the like.

The present reaction is usually carried out in a solvent such as water, an alcohol (e.g., methanol, ethanol, etc.), a mixture thereof or any other solvent which does not adversely influence the present reaction.

The present reaction, in case that the compound (XIV) is used in its salt form, is preferably carried out in the presence of a base, for example, an inorganic base such as alkali metal (e.g., sodium, potassium, etc.), alkaline earth metal (e.g., magnesium, calcium, etc.), the hydroxide or carbonate or bicarbonate thereof or the like, and an organic base such as alkali metal alkoxide (e.g., sodium methoxide, sodium ethoxide, etc.), trialkylamine (e.g., trimethylamine, triethylamine, etc.), N,N-dialkylamine (e.g., N,N-dimethylaniline, etc.), N,N-dialkylbenzylamine (e.g., N,N-dimethylbenzylamine, etc.), pyridine or the like.

The reaction temperature is not critical and the reaction is usually carried out under cooling to heating.

In the present reaction, the mixture of syn- and anti-isomers of the compound (III$_a$), (XXXV) or (III$_f$) may be obtained according to reaction conditions etc., and in such case, both isomers may be resolved by conventional manners from the mixture. For example, the mixture is firstly esterified and the resulting esters are resolved, for example, by chromatography into each isomer. The resolved each isomer of esters is hydrolyzed by a conventional method to give the corresponding syn- or anti-carboxylic acid.

In order to obtain syn-isomer of the compound (III$_a$), (XXXV) or (III$_f$) selectively and in high yield the present reaction is preferably carried out around neutral condition.

(E) Processes of (XV)→(XVI) [Scheme (2)(i)] and, (XXXIV)→(XXXVI) [Scheme (6)(ii)]

The compounds (XVI) and (XXXVI) can be prepared by reacting the compounds (XV) and (XXXIV) with hydroxylamine or a salt thereof, respectively.

Suitable salt of hydroxylamine can be referred to the ones exemplified for the compound (XIV).

The reaction conditions of the present reaction can also be referred to the ones exemplified for the processes of (XIII)+(XIV)→(III$_a$), (XXXIII)+(XIV)→(XXXV) and (XXXIV)+(XIV)→(III$_f$) as mentioned in aforementioned (D).

(F) Processes of (XVII)→(XVIII) [Scheme (2)(ii)], (XXIV)→(XXV) [Scheme (4)(ii)] (XXVI)→(XXVII) [Scheme (5)] and (XXXVII)→(XXXVIII) [Scheme (6)(iii)]

The compounds (XVIII), (XXV), (XXVII) and (XXXVIII) can be prepared by alkylating the compounds (XVII), (XXIV), (XXVI) and (XXXVII), respectively.

The alkylating agent to be used in the present alkylation reaction may include di(lower)alkyl sulfate (e.g., dimethyl sulfate, diethyl sulfate, etc.), diazo(lower)alkane (e.g., diazomethane, diazoethane, etc.), lower alkyl halide (e.g., methyl iodide, ethyl iodide, etc.), lower alkyl sulfonate (e.g., methyl p-toluenesulfonate, etc.), and the like.

The reaction using di(lower)alkyl sulfate, lower alkyl halide or lower alkyl sulfonate is usually carried out in a solvent such as water, acetone, ethanol, ether, dimethylformamide or any other solvent which does not adversely influence the reaction.

The present reaction is preferably carried out in the presence of a base such as an inorganic base or an organic base as aforementioned.

The reaction temperature is not critical and the reaction is usually carried out under cooling to heating around boiling point of the solvent.

The reaction using diazoalkane is usually carried out in a solvent such as ether, tetrahydrofuran or the like.

The reaction temperature is not critical and the reaction is usually carried out under cooling or at ambient temperature.

(G) Processes of (XVIII)→(III$_b$) [Scheme (2)(ii)] and (XXXVIII)→(III$_g$) [Scheme (6)(iii)]

The compounds (III$_b$) and (III$_g$) can be prepared by subjecting the compounds (XVIII) and (XXXVIII) to hydrolysis, respectively.

The hydrolysis is preferably carried out in the presence of a base or an acid. Suitable base may include an inorganic base and an organic base such as an alkali metal (e.g., sodium, potassium, etc.), an alkaline earth metal (e.g., magnesium, calcium, etc.), the hydroxide or carbonate or bicarbonate thereof, trialkylamine (e.g., trimethylamine, triethylamine, etc.), picoline, 1,5-diazabicyclo[4,3,0]non-5-ene, 1,4-diazabicyclo[2,2,2]octane, 1,5-diazabicyclo[5,4,0]undecene-5, or the like.

Suitable acid may include an organic acid (e.g., formic acid, acetic acid, propionic acid, trifluoroacetic acid, etc.) and an inorganic acid (e.g., hydrochloric acid, hydrobromic acid, sulfuric acid, etc.).

The reaction is usually carried out in a solvent such as water, an alcohol (e.g., methanol, ethanol, etc.), a mixture thereof or any other solvent which does not adversely influence the reaction. A liquid base or acid can also be used as the solvent.

The reaction temperature is not critical and the reaction is usually carried out under cooling to warming.

(H) Process of (XIX)→(III$_c$) [Scheme (3)]

The compound (III$_c$) can be prepared by subjecting the compound (XIX) to acylation.

The acylating agent to be used for the present reaction and the reaction conditions of the present reaction can be referred to the ones exemplified for Process 3.

(I) Process of (XX)→(XXI) [Scheme (4)(i)]

The compound (XXI) can be prepared by subjecting the compound (XX) to nitrosation.

The nitrosating agent to be used for the present reaction may include conventional agent which give C-nitroso compound by reacting with activated methylene group, such as nitrous acid, alkali metal nitrite (e.g., sodium nitrite, etc.), lower alkyl nitrite (e.g., isopentyl nitrite, t-butyl nitrite, etc.) or the like.

In case that salt of nitrous acid is used as nitrosating agent, the present reaction is usually carried out in the presence of an acid such as an inorganic acid or an organic acid (e.g., hydrochloric acid, acetic acid, etc.) In case that ester of nitrous acid is used, the present reaction is preferably carried out in the presence of a strong base such as alkali metal alkoxide or the like.

The present reaction is usually carried out in a solvent such as water, acetic acid, benzene, alcohol (e.g., ethanol, methanol, etc.) or any other solvent which does not adversely influence the reaction.

The reaction temperature is not critical and the reaction is usually carried out under cooling or at ambient temperature.

(J) Processes of (XXI)+(XXII)→(XXIII) [Scheme (4)(i)] and (XXVIII)+(XXII)→(XXIX) [Scheme (5)]

The compounds (XXIII) and (XXIX) can be prepared by reacting the compounds (XXI) and (XXVIII) with the compound (XXII), respectively.

The present reaction is usually carried out in a solvent such as water, an alcohol (e.g., methanol, ethanol, etc.), benzene, dimethylacetamide, dimethylformamide, tetrahydrofuran, a mixture thereof or any other solvent which does not adversely influence the reaction.

The reaction temperature is not critical and the reaction is usually carried out from ambient temperature to under heating around the boiling point of the solvent.

In order to obtain syn-isomer of the compound (XXIII) or (XXIX) selectively and in high yield, it is necessary to use syn-isomer of the starting compound (XXI) or (XXVIII) and the present reaction is preferably carried out around neutral condition in the presence of a base as aforementioned. Preferable example of base may be week base such as alkali metal acetate (e.g., sodium acetate, potassium acetate, etc.), alkali metal bicarbonate (e.g., sodium bicarbonate, potassium bicarbonate, etc.), alkali metal carbonate (e.g., sodium carbonate, potassium carbonate, etc.) or the like.

(K) Processes of (XXIII)→(XXIII$_a$) [Scheme (4)(i)], (XXV)→(III$_d$) [Scheme (4)(ii)], (XXIX)→(III$_e$) [Scheme (5)], (XXXIII)→(XXXIV) [Scheme (6)(ii)] and (XXXV)→(III$_f$) [Scheme (6)(ii)]

The compounds (XXIII$_a$), (III$_d$), (III$_e$), (XXXIV) and (III$_f$) can be prepared by subjecting the compounds (XXIII), (XXV), (XXIX), (XXXIII) and (XXV) to elimination reaction of the protective group of the carboxy, respectively.

In the present elimination reaction, conventional methods used in the elimination reaction of the protected carboxy, for example, hydrolysis etc. can be applicable. When the protective group is an ester, it can be eliminated by hydrolysis.

The present hydrolysis is carried out according to similar manners to those of processes (XVIII)→(III$_b$) and (XXXVIII)→(III$_g$) as mentioned in aforesaid (G).

(L) Process of (XXVII)→(XXVIII) [Scheme (5)]

The compound (XXVIII) can be prepared by halogenating the compound (XXVII).

The halogenating agent to be used in the present reaction may include a conventional halogenating agent used in halogenation of so-called activated methylene group such as halogen (e.g., bromine, chlorine, etc.), sulfuryl halide (e.g., sulfuryl chloride, etc.), hypohalite (e.g., hypochlorous acid, hypobromous acid, sodium hypochlorite, etc.), N-halogenated-imide (e.g., N-bromosuccinimide, N-bromophthalimide, N-chlorosuccinimide, etc.) and the like.

The present reaction is usually carried out in a solvent such as an organic acid (e.g., formic acid, acetic acid, propionic acid, etc.), carbon tetrachloride or any other solvent which does not adversely influence the reaction.

The reaction temperature is not critical and the reaction is usually carried out under cooling, at ambient temperature, under warming or heating.

(M) Processes of (XXX)→(XXXI) [Scheme (6)(i)] and (XXXIX)→(III$_h$) [Scheme (7)]

The compound (XXXI) can be prepared by reacting the compound (XXX) or its reactive derivative at the amino group or a salt thereof with an amino-protecting agent and the compound (III$_h$) can be prepared by reacting the compound (XXXIX) or its reactive derivative at the amino group or a salt thereof with an amino-protecting agent. Suitable reactive derivative at the amino group of the compound (XXX) or (XXXIX) and suitable salt of the compound (XXX) or (XXXIX) may include the same ones as illustrated in the explanations of the reactive derivative at the amino group of the compound (II) and salt of the compound (II), respectively.

Suitable amino-protecting agent may include acylating agent which may include an aliphatic, aromatic and heterocyclic carboxylic acid, and the corresponding sulfonic acid, haloformic acid ester, isocyanic acid ester and carbamic acid, and the corresponding thio acid thereof, and the reactive derivative of the above acids.

Suitable reactive derivatives of the above acids may include the same ones as illustrated in the explanation of Process 3. The example of the protective group (e.g. acyl group) to be introduced into the amino group in the compound (XXX) or (XXXIX) by the above amino-protecting agent (e.g. acylating agent) may be the same protecting group (e.g., acyl group) as illustrated in the explanation of the protective group moiety (e.g., acyl moiety) in the term "acylamino".

The present invention amino-protecting reaction is carried out in a similar manner as illustrated in the reaction of the compound (II) with the compound (III) (Process 1).

(N) Process of (XXIII$_b$)→(XXXIII) [Scheme (6) (ii)]

The compound (XXXIII) can be prepared by subjecting the compound (XXIII$_b$) to hydrolysis.

The present hydrolysis is carried out in the presence of alkali metal bisulfite (e.g., sodium bisulfite, etc.) titanium trichloride, inorganic or organic acid such as hydrohalogenic acid (e.g., hydrochloric acid, hydrobromic acid, etc.), formic acid, nitrous acid or the like. Hydrohalogenic acid is preferably used in a combination of aldehyde (e.g., formaldehyde, etc.).

The present reaction is usually carried out in a solvent such as water, aqueous alcohol (e.g., aqueous methanol, aqueous ethanol, etc.), water.acetic acid or any other solvent which does not adversely influence the reaction.

The reaction temperature is not critical and the reaction is usually carried out at ambient temperature, under warming or heating.

In the present reaction, protected carboxy group may be occasionally transformed into free carboxy group. This case is also included in the scope of the present invention.

In the aforementioned reactions and/or the post-treating of the reactions of the present invention, the aforementioned tautomeric isomers may be occasionally transformed into the other tautomeric isomers and such case is also included in the scope of the present invention.

In case that the object compound (I) is obtained in a form of the free acid at 4 position and/or in case that the object compound (I) has free amino group, it may be transformed into its pharmaceutically acceptable salt as aforementioned by a conventional method.

The object compound (I) and pharmaceutically acceptable salt thereof of the present invention are all novel compounds which exhibit high antibacterial activity, inhibiting the growth of a wide variety of pathogenic microorganisms including Gram-positive and Gram-negative bacteria and are useful as antibacterial agents. Particularly, it is to be noted that the object compound (I), i.e., syn-isomer has much higher antibacterial activities than the corresponding anti-isomer to the compound (I), and accordingly the object compound (I), i.e., syn-isomer is characterized by having much superiority to the corresponding anti-isomer in the therapeutic value.

Now, in order to show the utility of the object compound (I), with regard to some representative compounds of this invention, there are shown the test data on the in vitro anti-bacterial activity, the test data on in vivo, i.e. the protecting effect against experimental infections and the acute toxicity in the following. Additionally, there are also shown the comparative test data on in vitro antibacterial activities relating to the corresponding anti-isomer to the object compound (I) for the reference's sake in the following.

Test compounds (1) 7-[2-Methoxyimino-2-(3-hydroxyphenyl)acetamido]-3-carbamoyloxymethyl-3-cephem-4-carboxylic acid (syn isomer)

(2) 7-[2-Methoxyimino-2-(3-hydroxyphenyl)acetamido]-3-(1-methyl-1H-tetrazol-5-yl)thiomethyl-3-cephem-4-carboxylic acid (syn isomer)

(3) 7-[2-Methoxyimino-2-(3-hydroxyphenyl)acetamido]-3-(1-methyl-1H-tetrazol-5-yl)thiomethyl-3-cephem-4-carboxylic acid (anti isomer)

(4) 7-[2-Methoxyimino-2-(3-hydroxyphenyl)acetamido]-3-(1,3,4-thiadiazol-2-yl)thiomethyl-3-cephem-4-carboxylic acid (syn isomer)

(5) 7-[2-Methoxyimino-2-(3-acetoxyphenyl)acetamido]-3-(1,3,4-thiadiazol-2-yl)thiomethyl-3-cephem-4-carboxylic acid (syn isomer)

(6) 7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer)

(7) 7-[2-Methoxyimino-2-(2-amino-1,3-thiazol-4-yl)acetamido]-3-(1-methyl-1H-tetrazol-5-yl)thiomethyl-3-cephem-4-carboxylic acid (anti isomer)

(8) 7-[2-Methoxyimino-2-(2-amino-1,3-thiazol-4-yl)acetamido]cephalosporanic acid (syn isomer)

(9) 7-[2-Methoxyimino-2-(2-amino-1,3-thiazol-4-yl)acetamido]cephalosporanic acid (anti isomer)

(10) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer)

(11) 7-[2-Methoxyimino-2-(2-formamido-1,3-thiazol-4-yl)acetamido]-3-(1,3,4-thiadiazol-2-yl)thiomethyl-3-cephem-4-carboxylic acid (anti isomer)

(12) 7-[2-Methoxyimino-2-(2-formamido-1,3-thiazol-4-yl)acetamido]cephalosporanic acid (syn isomer)

(13) 7-[2-Methoxyimino-2-(2-amino-1,3-thiazol-4-yl)acetamido]-3-carbamoyloxymethyl-3-cephem-4-carboxylic acid (syn isomer)

(14) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer)

(15) 7-[2-Methoxyimino-2-(2-amino-1,3-thiazol-4-yl)acetamido]-3-hydroxymethyl-3-cephem-4-carboxylic acid (syn isomer)

(16) 7-[2-Methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer)

(17) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer)

(18) 7-[2-Methoxyimino-2-{2-(2,2,2-trifluoroacetamido)-1,3-thiazol-4-yl}acetamido]-3-carbamoyloxymethyl-3-cephem-4-carboxylic acid (syn isomer)

(19) 7-[2-(2-Propynyl)oxyimino-2-(2-amino-1,3-thiazol-4-yl)acetamido]cephalosporanic acid (syn isomer)

(20) 7-[2-Isopropoxyimino-2-(2-amino-1,3-thiazol-4-yl)acetamido]-3-carbamoyloxymethyl-3-cephem-4-carboxylic acid (syn isomer)

(21) 7-[2-Isopropoxyimino-2-(2-amino-1,3-thiazol-4-yl)acetamido]-3-(1-allyl-1H-tetrazol-5-yl)thiomethyl-3-cephem-4-carboxylic acid (syn isomer)

1. In vitro antibacterial activity

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml. after incubation at 37° C. for 20 hours.

Test Results
MIC (µg/ml)
Test Bacteria     Test Compounds suspension. A solution containing each test compounds was given subcutaneously to the mice in various dosage one hour after challenge. The $ED_{50}$ values were calculated from the number of surviving mice for each dosage after one week of observation.

Test Results
Protecting Effect against Experimental Infections in Mice

| Test Bacteria | Challenge cells/mouse | MIC of used strain (µg/ml) | | | | | | $ED_{50}$ (S.C.) (mg/mouse) | | | | |
|---|---|---|---|---|---|---|---|---|---|---|---|---|
| | | viable cells/ml | Test Compounds | | | | | Test Compounds | | | | |
| | | | (8) | (14) | (5) | (4) | CET* | (8) | (14) | (5) | (4) | CET |
| *Escherichia coli* 29 | 6 × 10$^6$ | 10$^8$ | 0.2 | ≦0.03 | 0.78 | 0.78 | 12.5 | <0.005 | <0.005 | 0.081 | 0.111 | 1.402 |
| | | 10$^6$ | ≦0.03 | ≦0.03 | 0.39 | 0.78 | 3.13 | | | | | |

*CET: 7-(2-Thienyl)acetamidocephalosporanic acid

| | | viable cells/ml | Test Compounds | | | Test Compounds | | |
|---|---|---|---|---|---|---|---|---|
| | | | (13) | (12) | Cefuroxime* | (13) | (12) | Cefuroxime |
| *Serratia marcesens* 4 | 1.0 × 10$^6$ | 10$^8$ | 25 | 200 | 400 | <0.156 | 0.018 | 4.329 |
| | | 10$^6$ | ≦0.025 | 6.25 | 50 | | | |

*Cefuroxime: 7-[2-Methoxyimino-2(2-furyl)acetamido]-3-carbamoyloxymethyl-3-cephem-4-carboxylic acid (syn isomer)

| | | viable cells/ml | Test Compounds | | Test Compounds | |
|---|---|---|---|---|---|---|
| | | | (6) | Cefuroxime | (6) | Cefuroxime |
| *Escherichia coli* 100 | 3.5 × 10$^4$ | 10$^8$ | 1.56 | 12.5 | 0.023 | 1.158 |
| | | 10$^6$ | 0.2 | 12.5 | | |

| | | viable cells/ml | Test Compounds | | Test Compounds | |
|---|---|---|---|---|---|---|
| | | | (2) | (1) | CEZ Na* | (2) | (1) | CEZ Na |
| *Escherichia coli* 29 | 5.5 × 10$^5$ | 10$^8$ | 0.78 | 0.39 | 3.13 | 0.386 | 0.079 | 0.182 |
| | | 10$^6$ | ≦0.1 | 0.2 | 0.78 | | | |

*CEZ Na: Sodium 7-[2-(1H—tetrazol-1-yl)acetamido]-3-(5-methyl-1,3,4-thiadiazol-2-yl)thiomethyl-3-cephem-4-carboxylate

| | (1) | (2) | (3) | (4) | (5) | (6) |
|---|---|---|---|---|---|---|
| *Escherichia coli* NIHJ JC-2 | 1.56 | 1.56 | 50 | 3.13 | 12.5 | 0.20 |
| *Klebsiella pneumoniae* 417 | 0.39 | 0.39 | 6.25 | 0.78 | 0.78 | 0.10 |
| *Proteus mirabilis* 525 | 0.78 | 0.78 | 25 | 0.78 | 1.56 | 0.10 |

| | (7) | (8) | (9) | (10) | (11) | (12) |
|---|---|---|---|---|---|---|
| *Escherichia coli* NIHJ JC-2 | 12.5 | 0.10 | 3.13 | 0.78 | 12.5 | 1.56 |
| *Klebsiella pneumoniae* 417 | 6.25 | 0.10 | 1.56 | 1.56 | 3.13 | 1.56 |
| *Proteus mirabilis* 525 | 3.13 | 0.05 | 0.78 | 0.39 | 3.13 | 0.78 |

| | (13) | (14) | (15) | (16) | (17) | (18) |
|---|---|---|---|---|---|---|
| *Escherichia coli* NIHJ JC-2 | 1.56 | 0.10 | 0.78 | 0.39 | 0.20 | 3.13 |
| *Klebsiella pneumoniae* 417 | 0.50 | 0.20 | 0.05 | 0.10 | 0.20 | 0.05 |
| *Proteus mirabilis* 525 | 0.025 | 0.10 | 0.10 | 0.39 | 0.39 | 0.025 |

| | (19) | (20) | (21) |
|---|---|---|---|
| *Bacillus subtilis* ATCC 6633 | 3.13 | 1.56 | 0.78 |
| *Proteus vulgaris* IAM-1025 | 0.78 | 0.2 | 0.78 |
| *Proteus vulgaris* 1 | 0.78 | 0.2 | 0.78 |

As clearly seen from the above test results, the object compounds (I) of the present invention, i.e., syn-isomers have much higher antibacterial activity as compared with the corresponding anti-isomers thereof.

2. Protecting effect against experimental infections in mice

Test Method

Male ICR strain mice aged 4 weeks, each weighing 20–23 g were used in groups of 8 mice. The test bacteria were cultured overnight at 37° C. on HI-agar and then suspended in 2.5–5% mucin solution to obtain the suspension corresponding to each challenge cells. Mice were inoculated intraperitoneally with 0.5 ml of the

3. Acute Toxicity in Mice

The same strain mice as aforesaid protecting test against experimental infections were used in groups of 10 mice. Test compound (8) (2 g) was administered intravenously to said mice. All mice survived without showing any disorder after one week observation.

For therapeutic administration, the object compound (I) of the present invention is used in the form of conventional pharmaceutical preparation which contains said compound, as an active ingredient, in admixture with a pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age, conditions of the patient, a kind of disease, a kind of the compound (I) to be applied, etc., an average single dose of about 50 mg., 100 mg., 250 mg., and 500 mg. of the object compound (I) of the present invention has proved to be effective in treating diseases infected by pathogenic bacteria.

In general, daily dose between 1 mg/body and about 6,000 mg/body or even more may be administered to a patient.

Now, in order to show the utility of the object compound (I), with regard to some representative compounds of this invention, there are shown the test data on the in vitro anti-bacterial activity in the following.

Test Compounds (1) 7-[2-Methoxyimino-2-(2-aminothiazol-4-yl)acetamido]-3-(1-allyl-1H-tetrazol-5-yl)thiomethyl-3-cephem-4-carboxylic acid (syn isomer)
(2) 7-[2-Ethoxyimino-2-(2-aminothiazol-4-yl)acetamido]-3-(1-allyl-1H-tetrazol-5-yl)thiomethyl-3-cephem-4-carboxylic acid (syn isomer)
(3) 7-[2-Allyloxyimino-2-(2-aminothiazol-4-yl)acetamido]-3-(1-allyl-1H-tetrazol-5-yl)thiomethyl-3-cephem-4-carboxylic acid (syn isomer)
(4) 7-[2-(2-Propynyl)oxyimino-2-(2-aminothiazol-4-yl)acetamido]-3-(1-allyl-1H-tetrazol-5-yl)thiomethyl-3-cephem-4-carboxylic acid (syn isomer)
(5) 7-[2-Methylthiomethoxyimino-2-(2-aminothiazol-4-yl)acetamido]-3-(1-allyl-1H-tetrazol-5-yl)thiomethyl-3-cephem-4-carboxylic acid (syn isomer)

In vitro antibacterial activity

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of test compounds, and the minimal inhibitory concentration (MIC) was expressed in terms of $\mu$g/ml. after incubation at 37° C. for 20 hours.

| | Test Results | | | | |
|---|---|---|---|---|---|
| | MIC ($\mu$g/ml.) Test Compounds | | | | |
| Test Bacteria | (1) | (2) | (3) | (4) | (5) |
| Bacillus subtilis ATCC 6633 | 1.56 | 0.78 | 0.78 | 1.56 | 1.56 |
| Pseudomonas aeruginosa NCTC-10490 | 3.13 | 12.50 | 6.25 | 12.50 | 12.50 |

Test Compounds (1) 7-[2-Methylthiomethoxyimino-2-(2-aminothiazol-4-yl)acetamido]-3-(1,3,4-thiadiazol-2-yl)thiomethyl-3-cephem-4-carboxylic acid (syn isomer)
(2) 7-[2-Carboxymethoxyimino-2-(2-aminothiazol-4-yl)acetamido]-3-(1,3,4-thiadiazol-2-yl)thiomethyl-3-cephem-4-carboxylic acid (syn isomer)

In vitro antibacterial activity

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentration of test compounds, and the minimal inhibitory concentration (MIC) was expressed in terms of $\mu$g/ml after incubation at 37° C. for 20 hours.

| | Test Results | |
|---|---|---|
| | MIC ($\mu$g/ml) Test Compounds | |
| Test Bacteria | (1) | (2) |
| Proteus vulgaris IAM-1025 | 3.13 | 0.39 |

Test Compounds (1) 7-[2-Ethoxyimino-2-(2-aminothiazol-4-yl)acetamido]-3-(1,3,4-thiadiazol-2-yl)thiomethyl-3-cephem-4-carboxylic acid (syn isomer).
(2) 7-[2-(2-Propynyloxyimino)-2-(2-aminothiazol-4-yl)acetamido]-3-(1,3,4-thiadiazol-2-yl)thiomethyl-3-cephem-4-carboxylic acid (syn isomer).
(3) 7-[2-Methoxyimino-2-(2-aminothiazol-4-yl)acetamido]-3-(3-methyl-1,2,4-thiadiazol-5-yl)thiomethyl-3-cephem-4-carboxylic acid (syn isomer).
(4) 7-[2-Methoxyimino-2-(2-aminothiazol-4-yl)acetamido]-3-(1-hexyl-1H-tetrazol-5-yl)thiomethyl-3-cephem-4-carboxylic acid (syn isomer).

In vitro antibacterial activity

Test Method

In vitro antibacterial activity was determined by the two-fold agar-plate dilution method as described below.

One loopful of an overnight culture of each test strain in Trypticase-soy broth ($10^8$ viable cells per ml.) was streaked on heart infusion agar (HI-agar) containing graded concentrations of test compounds, and the minimal inhibitory concentration (MIC) was expressed in terms of $\mu$g/ml. after incubation at 37° C. for 20 hours.

| | Test Results | | | |
|---|---|---|---|---|
| | MIC ($\mu$g/ml.) Test Compounds | | | |
| Test Bacteria | (1) | (2) | (3) | (4) |
| Bacillus subtilis ATCC-6633 | 0.78 | 0.39 | 1.56 | 1.56 |

Among the starting compounds, some of the compound (III) is novel and can be prepared by the processes which are illustrated by the following scheme.

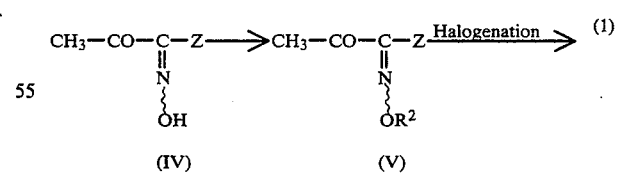

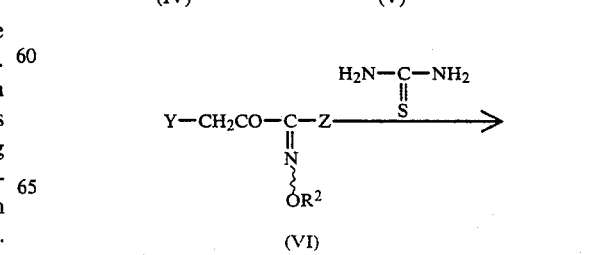

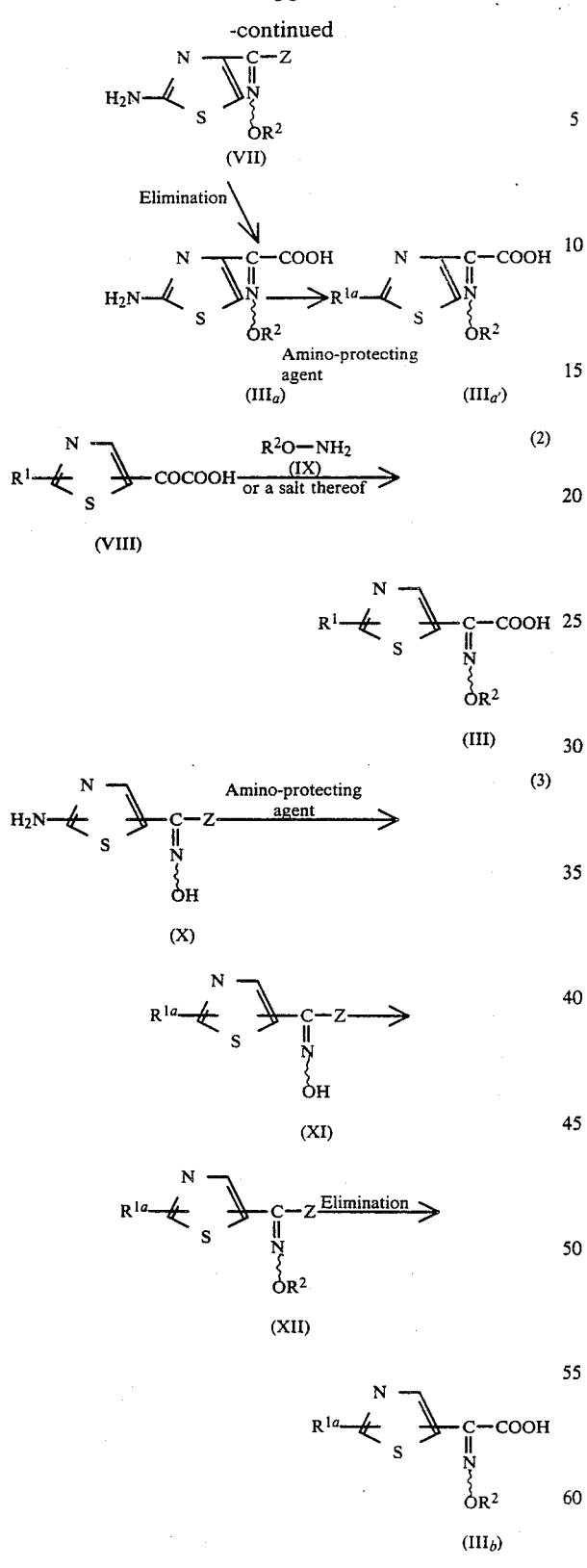
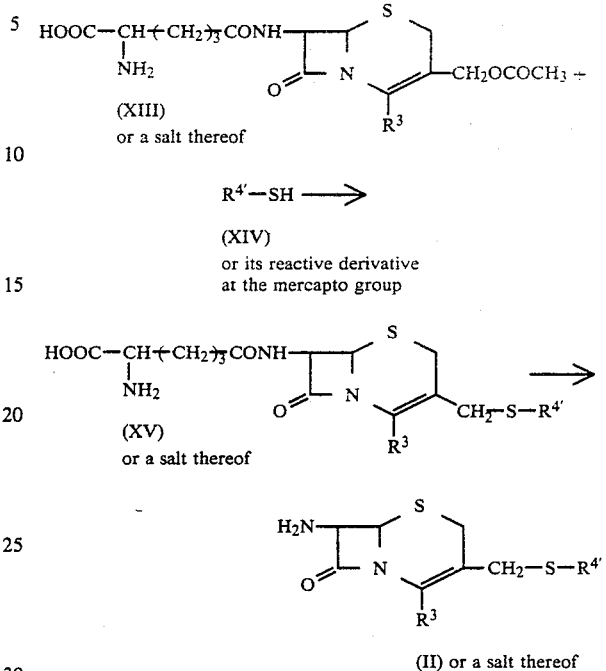

wherein
R¹ is amino or a protected amino, R¹ᵃ is a protected amino, R² is as defined above,
Z is a protected carboxy, and
Y is halogen.

The other starting compound (II) can be prepared by the processes as illustrated below.

wherein
R³ is carboxy or a protected carboxy, and
R⁴' is N-containing 5-membered heteromonocyclic group having lower alkenyl group.

Suitable N-containing 5-membered heteromonocyclic group means saturated or unsaturated 5-membered heteromonocyclic group containing at least one nitrogen atom(s) such as unsaturated 5-membered heteromonocyclic group containing 1 to 4 nitrogen atom(s), for example, pyrrolyl, pyrrolinyl, imidazolyl, pyrazolyl, triazolyl (e.g., 4H-1,2,4-triazolyl, 1H-1,2,3-triazolyl, 2H-1,2,3-triazolyl, etc.), tetrazolyl (e.g., 1H-tetrazolyl or 2H-tetrazolyl) etc.; or saturated 5-membered heteromonocyclic group containing 1 to 4 nitrogen atom(s), for example, pyrrolidinyl, imidazolidinyl, etc. And said N-containing 5-membered heteromonocyclic group has lower alkenyl group as exemplified above as a substituent.

The processes for preparing the starting compound (II) are explained in details as follows.

1. The compound (XV) or a salt thereof can be prepared by reacting the compound (XIII) or a salt thereof with the compound (XIV) or its reactive derivative at the mercapto group.

Suitable salt of the compound (XIII) can be referred to the ones exemplified for the compound (Iₐ).

The suitable reactive derivative at the mercapto group of the compound (XIV) may include a metal salt such as alkali metal salts (e.g., sodium salt, potassium salt, etc.) or the like.

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other solvent which does not adversely affect the reaction, preferably in ones having strong polarities. Among the solvents, hydrophilic solvents may be used in a mixture with water. The reaction is preferably carried out in weekly basic or around neutral condition. When the compound (XIII) and/or the thiol compound (XIV) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming. The reaction product can be isolated from the reaction mixture by conventional methods.

2. The compound (II) or a salt thereof can be prepared by subjecting the compound (XV) or a salt thereof to elimination reaction of 5-amino-5-carboxyvaleryl group.

The present elimination reaction can be carried out by (i) reacting the compound (XV) or a salt thereof with a silylating agent, (ii) reacting the resulting compound with iminohalogenating agent, and then (iii) reacting the resulting compound with iminoetherifying agent.

Suitable salt of the compound (XV) can be referred to the ones exemplified for the compound ($I_a$).

Suitable silylating agent may include mono- or bis-trialkylsilylacetamide [e.g., trimethylsilylacetamide, bis(trimethylsilyl)acetamide, etc.], trimethylchlorosilane, dimethyldichlorosilane, hexamethyldisilazane, and the like. The reaction of the compound (XV) with a silylating agent may be carried out in the presence of a base under warming or heating.

Suitable iminohalogenating agent may include phosphorus trichloride, phosphorus pentachloride, phosphorus tribromide, phosphorus pentabromide, phosphorus oxychloride, thionyl chloride, phosgene and the like. The reaction temperature is not critical, and the reaction is usually carried out at ambient temperature or under cooling.

Suitable iminoetherifying agent reacted with thus obtained reaction product may include an alcohol, metal alkoxide and the like. Suitable alcohol may include alkanol (e.g., methanol, ethanol, propanol, isopropanol, butanol, t-butanol, etc.) which may be substituted with alkoxy (e.g., methoxy, ethoxy, propoxy, isopropoxy, butoxy, etc.). Suitable metal alkoxide may include alkali metal alkoxide (e.g., sodium alkoxide, potassium alkoxide, etc.), alkaline earth metal alkoxide (e.g., calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can be readily carried out by pouring the reaction mixture obtained above into water, but there may be previously added a hydrophilic solvent (e.g., methanol, ethanol, etc.), a base (e.g., alkali metal bicarbonate, trialkylamine, etc.) or an acid (e.g., diluted hydrochloric acid, acetic acid, etc.) to the water.

Among the starting compounds, the compound (III) is novel and can be prepared by the processes which are illustrated by the following scheme.

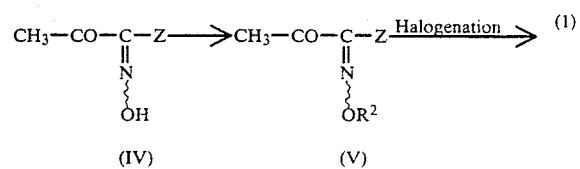

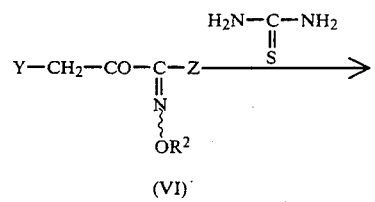

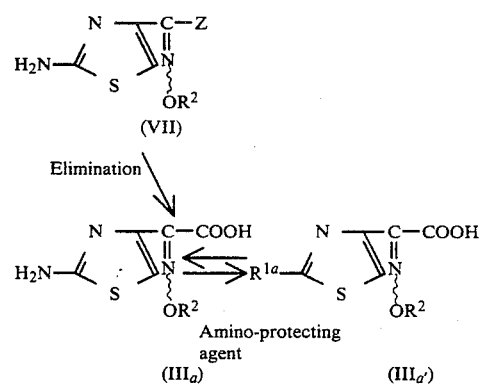

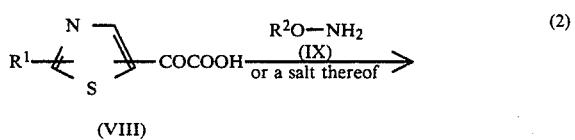

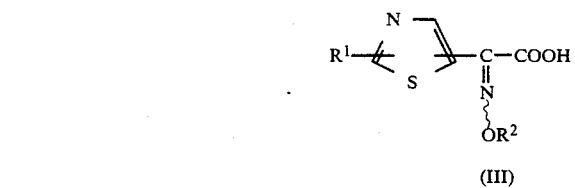

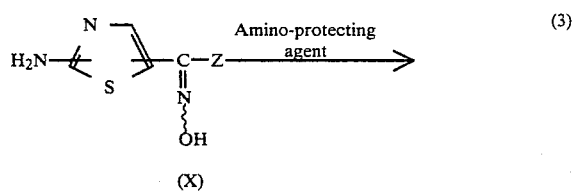

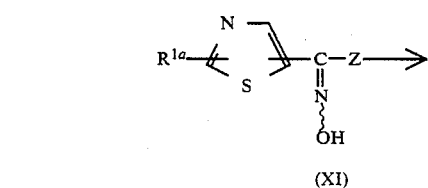

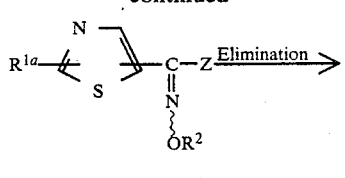

(XII)

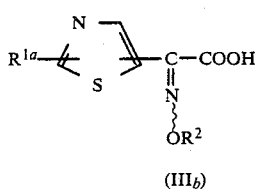

(IIIb)

wherein

R[1], R[1a] and R[2] are each as defined above,

Z is a protected carboxy and

Y is halogen.

Some of the other starting compound (II) is also novel and can be prepared by the processes as illustrated below.

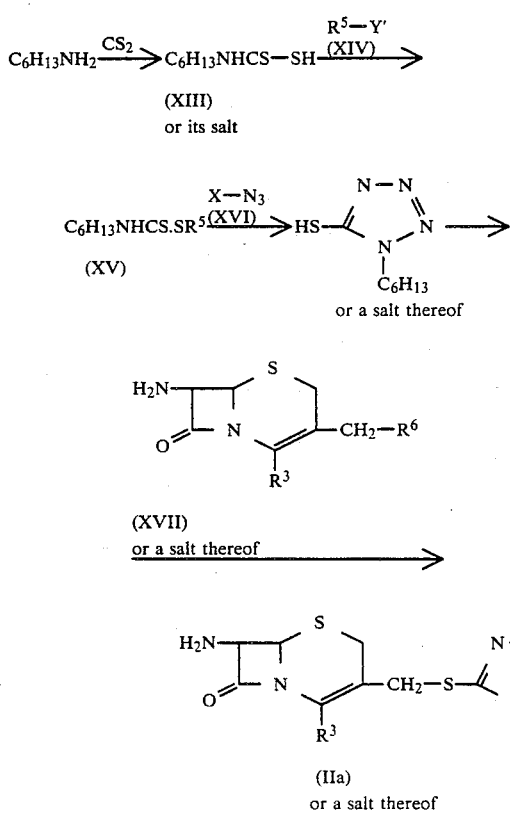

wherein

R[3] is as defined above,

Y' is an acid residue,

R[5] is lower alkyl,

R[6] is a group which is substituted by a group of the formula:

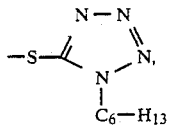

and

X is an alkali metal.

Suitable acid residue may include aforesaid halogen, lower alkanesulfonyloxy (e.g. mesyloxy, ethanesulfonyloxy, etc.), arenesulfonyloxy (e.g. benzenesulfonyloxy, p-toluenesulfonyloxy, etc.) and the like.

Suitable group which is substituted by a group of the formula:

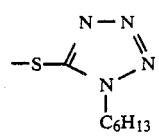

may include azido, aforesaid halogen, acyloxy and the like.

Suitable alkali metal may include sodium, potassium and the like.

The processes for preparing the starting compound (IIa) are explained in details as follows.

1. The compound (XIII) or its salt can be prepared by reacting hexylamine with carbon disulfide in the presence of a strong base.

Suitable strong base may include an inorganic base or an organic base, for example, alkali metal hydroxide (e.g. sodium hydroxide, potassium hydroxide, etc.), alkali metal alkoxide (e.g. sodium methoxide, sodium ethoxide, potassium methoxide, etc.), alkali metal hydride (e.g. sodium hydride, etc.) or the like.

The present reaction is usually carried out in a solvent such as water or any other solvent which does not adversely affect the reaction, and usually carried out under cooling or at ambient temperature.

2. The compound (XV) can be prepared by reacting the compound (XIII) or its salt with the compound (XIV).

The present reaction is usually carried out in a solvent such as water or any other solvent which does not adversely affect the reaction, and usually carried out under cooling or at ambient temperature.

3. 1-Hexyl-1H-tetrazole-5-thiol or a salt thereof can be prepared by reacting the compound (XV) with the compound (XVI).

The present reaction is usually carried out in a solvent such as an alcohol (e.g. methanol, ethanol, etc.), an aqueous alcohol or any other solvent which does not adversely affect the reaction, and preferably carried out under warming or heating.

4. The compound (IIa) or a salt thereof can be prepared by reacting 1-hexyl-1H-tetrazole-5-thiol or a salt thereof with the compound (XVII) or a salt thereof.

Suitable salt of the compound (XVII) can be referred to the ones exemplified for the compound (Ia).

The suitable salt of 1-hexyl-1H-tetrazole-5-thiol may include a metal salt such as alkali metal salts (e.g. sodium salt, potassium salt, etc.) or the like.

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, buffer solution or any other solvent which does not adversely affect the reaction, preferably in ones having strong polarities. Among the solvents, hydrophilic solvents may be used in a mixture with water. The reaction is preferably carried out in weekly basic or around neutral condition. When the compound (XVII) and/or 1-hexyl-1H-tetrazole-5-thiol is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming. The reaction product can be isolated from the reaction mixture by conventional methods.

Some of the other starting compound (II) is also novel and can be prepared by the processes as illustrated below.

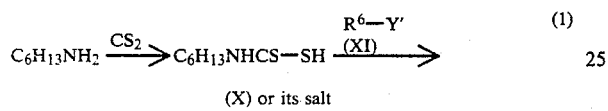

(X) or its salt

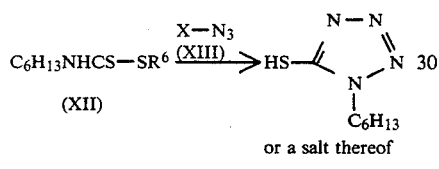

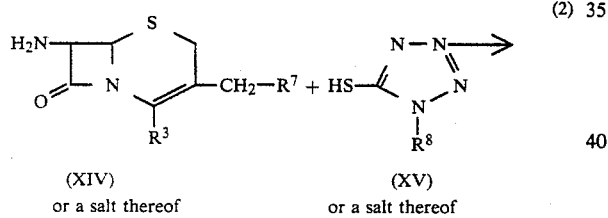

(II$_a$) or a salt thereof

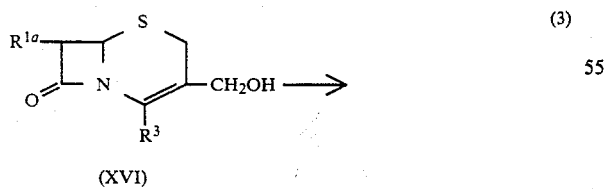

(XVI)

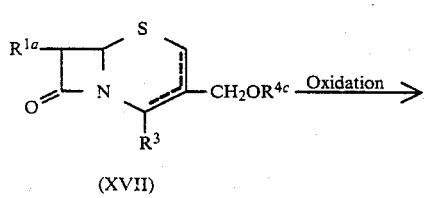

(XVII)

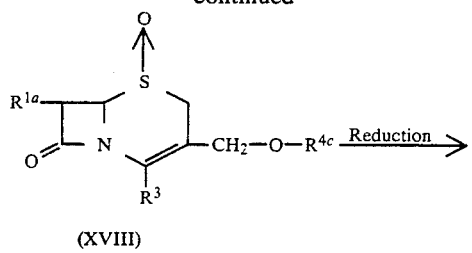

(XVIII)

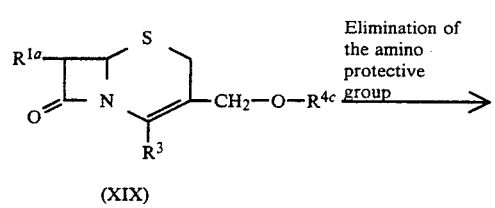

(XIX)

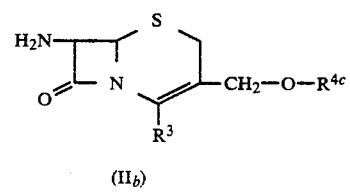

(II$_b$)

wherein
R$^{1a}$ and R$^3$ are each as defined above,
Y' is an acid residue,
R$^6$ is lower alkyl,
X is an alkali metal,
R$^7$ is a group which is substituted by a group of the formula:

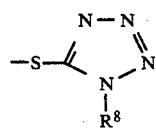

wherein
R$^8$ is alkyl having 3 to 6 carbon atoms,
R$^8$ is as defined above, and
R$^{4c}$ is carbamoyl having aryl which may have halogen, aryloxy(lower)alkanoyl which may have lower alkoxy, thenoyl, cyclo(lower)alkanecarbonyl, or aroyl having nitro.

Suitable group which is substituted by a group of the formula:

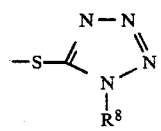

may include azido, aforesaid halogen, acyloxy and the like.

Suitable alkyl having 3 to 6 carbon atoms may include propyl, isopropyl, butyl, isobutyl, t-butyl, pentyl, hexyl and the like.

Suitable carbamoyl having aryl which may have halogen, aryloxy(lower)alkanoyl wich may have lower alkoxy,cyclo(lower)alkanecarbonyl and aroyl having nitro can be referred to the ones exemplified for acyl.

The processes for preparing the starting compound (II$_b$) are explained in details as follows.

1. The compound (XVII) can be prepared by reacting the compound (XVI) with acylating agent.

Suitable acylating agent may include a compound of the formula: R$^{4d}$—OH(XXI) wherein R$^{4d}$ is aryloxy(lower)alkanoyl which may have lower alkoxy, thenoyl, cyclo(lower)alkanecarbonyl or aroyl having nitro, or its reactive derivative, and a compound of the formula:

R$^9$—N=C=O     (XXII)

wherein R$^9$ is aryl which may have halogen.

Suitable reactive derivative of the compound (XXI) can be referred to the ones as exemplified for the compound (III).

Suitable aryl for R$^9$ may include phenyl, tolyl, xylyl, mesityl, cumenyl, naphthyl and the like, wherein said aryl group may have 1 to 3 halogen (e.g., chlorine, bromine, iodine or fluorine).

The present reaction is carried out according to a similar manner to that of Process 1.

In the formula of the compound (XVII), the structure of the following formula:

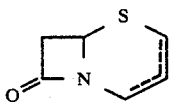

means a mixture of 3- and 2-cephem compounds.

2. The compound (XVIII) can be prepared by oxidizing the compound (XVII).

Suitable oxidizing agents may include conventional ones used for oxidation of sulfur atom at 1st position of cephalosporin compound, for example, per acid, (e.g., perbenzoic acid, 3-chloroperbenzoic acid), hydrogen peroxide/sodium tungstate, or the like.

The present reaction is usually carried out in a solvent such as ethyl acetate, tetrahydrofuran or any other solvent which does not adversely affect the reaction, and usually carried out under cooling or at ambient temperature.

3. The compound (XIX) can be prepared by reducing the compound (XVIII).

Suitable reducing agent may include conventional ones used for reduction of S-oxide, for example, phosphorus halide (e.g., phosphorus trichloride, phosphorus tribromide, etc.) or the like.

The reaction is preferably carried out in a solvent such as dimethylformamide or the like, and preferably carried out under cooling or at ambient temperature.

4. The compound (II$_b$) can be prepared by subjecting the compound (XIX) to elimination reaction of the amino protective group.

The present elimination reaction is carried out according to a similar manner to that of Process 2.

The following preparations and examples are given for the purpose of illustrating the present invention:

EXAMPLE 1

A mixture of dimethylformamide (2.81 g.) and phosphorus oxychloride (5.36 g.) was warmed at 40° C. for 1 hour. After cooling, methylene chloride (60 ml.) was added thereto and distilled off. To the residue was added dry ethyl acetate (50 ml.). Then, 2-methoxyimino-2-(3-hydroxyphenyl)acetic acid (syn isomer) (6.83 g.) was added thereto at 5° C. with stirring under ice-cooling. The resultant mixture was then stirred for 50 minutes at the same temperature. On the other hand, 7-amino-3-(1-methyl-1H-tetrazol-5-yl)thiomethyl-3-cephem-4-carboxylic acid (11.5 g.) and bis(trimethylsilyl)acetamide (28.4 g.) were dissolved in dry ethyl acetate (150 ml.) and stirred under cooling, to which was at a time added the above obtained solution at −40° C. After stirring for 2 hours at −30° to −20° C., a saturated sodium chloride aqueous solution (100 ml.) was added at −20° C. to the reaction mixture. The mixture was stirred for 5 minutes. The precipitates were filtered off and ethyl acetate layer in the filtrate was separated. The aqueous layer was extracted twice with ethyl acetate (50 ml.). Ethyl acetate layer separated from the filtrate and the extracts were combined. The combined ethyl acetate solution was washed with a saturated sodium chloride aqueous solution (50 ml.). To the ethyl acetate layer was added activated charcoal and the mixture was stirred for 5 minutes and filtered. Water (100 ml.) was added to the filtrate and the resulting mixture was adjusted to pH 7 with an aqueous solution of sodium bicarbonate. The aqueous layer was separated and washed with methylene chloride. After the aqueous layer was separated, methylene chloride was removed from the aqueous layer by bubbling of nitrogen gas under ice-cooling. After filtration, the aqueous layer was adjusted to pH 2 with 10% hydrochloric acid with stirring and ice-cooling. Precipitating crystals were collected by filtration, washed with water and dried to give 7-[2-methoxyimino-2-(3-hydroxyphenyl)acetamido]-3-(1-methyl-1H-tetrazol-5-yl)thiomethyl-3-cephem-4-carboxylic acid (syn isomer) (11.3 g.).

I.R. spectrum (Nujol): 3250, 1770, 1725, 1670 cm$^{-1}$.

N.M.R. spectrum (d$_6$-DMSO, δ) ppm: 9.76 (1H, d, J=8 Hz), 6.7–7.40 (4H, m), 5.86 (1H, dd, J=5,8 Hz), 5.18 (1H, d, J=5 Hz), 4.34 (2H, AB$_q$, J=13 Hz), 3.92 (6H, s), 3.72 (2H, AB$_q$, J=17 Hz).

EXAMPLE 2

A mixture of dimethylformamide (1.41 g.) and phosphorus oxychloride (2.95 g.) was warmed for 1 hour at 40° C. After cooling, methylene chloride (30 ml.) was added thereto and distilled off. To the residue was added dry ethyl acetate (20 ml.). 2-Methoxyimino-2-(3-hyroxyphenyl)acetic acid (syn isomer) (3.4 g.) was added thereto with stirring and ice-cooling and the mixture was stirred for 30 minutes under ice-cooling. On the other hand, 7-amino-3-carbamoyloxymethyl-3-cephem-4-carboxylic acid (4.8 g.) was dissolved in a solution of trimethylsilylacetamide (27.5 g.) in dry ethyl acetate (70 ml.). To the solution was at a time added the above obtained solution at −30° C. and the mixture was stirred for 1.5 hours at −30° to −10° C. A saturated sodium chloride aqueous solution was added to the reaction mixture at −20° C. The ethyl acetate layer was separated and the aqueous layer was extracted with ethyl acetate. Two ethyl acetate layers were combined, washed with a sodium chloride aqueous solution and treated with activated charcoal. After filtration, water (100 ml.) was added to the filtrate and the mixture was adjusted to pH 7 with a sodium bicarbonate aqueous solution. The aqueous layer was separated and ethyl acetate was added thereto. The mixture was adjusted to pH 5 with 10% hydrochloric acid and the aqueous layer was separated. Ethyl acetate was added thereto and the mixture was adjusted to pH 2 with 10% hydrochloric acid. The ethyl acetate layer was separated and the aqueous layer was further extracted with ethyl acetate. Two ethyl acetate layers were combined, washed with a sodium chloride aqueous solution and dried over magnesium sulfate. The solvent was distilled off and the residue was pulverized with diisopropyl ether. The powder was collected by filtration and dried to give 7-[2-methoxyimino-2-(3-hydroxyphenyl)acetamido]-3-carbamoyl-oxymethyl-3-cephem-4-carboxylic acid (syn isomer) (3.26 g.).

I.R. spectrum (Nujol): 3500–3200, 1765, 1720, 1655 cm$^{-1}$.

N.M.R. spectrum (d$_6$-DMSO, δ) ppm: 9.64 (1H, d, J=8 Hz), 6.70–7.20 (4H, m), 6.78 (2H, s), 5.92 (1H, dd, J=5,8 Hz), 5.16 (1H, d, J=5 Hz), 4.73 (2H, AB$_q$, J=13 Hz), 3.91 (3H, s), 3.72 (2H, AB$_q$, J=17 Hz). 7-[2-Methoxyimino-2-(3-hydroxyphenyl)acetamido]-3-carbamoyloxymethyl-3-cephem-4-carboxylic acid (syn isomer) (1.98 g.) was suspended in water (15 ml.) and dissolved by adding sodium bicarbonate (0.35 g.) with stirring at ambient temperature. The solution was lyophilized and dried to give sodium 7-[2-methoxyimino-2-(3-hydroxyphenyl)acetamido]-3-carbamoyloxymethyl-3-cephem-4-carboxylate (syn isomer) (1.9 g.).

I.R. spectrum (Nujol): 3300, 1765, 1715, 1665 cm$^{-1}$.

N.M.R. spectrum (D$_2$O, δ) ppm: 6.83–7.60 (4H, m), 5.85 (1H, d, J=5 Hz), 5.17 (1H, d, J=5 Hz), 4.77 (2H, AB$_q$, J=13 Hz), 4.03 (3H, s), 3.48 (2H, AB$_q$, J=18 Hz).

EXAMPLE 3

A mixture of dry dimethylformamide (0.18 g.) and phosphorus oxychloride (0.38 g.) was stirred for 30 minutes at 40° C. Dry methylene chloride (15 ml.) was added thereto and distilled off under reduced pressure. To the residue was added dry ethyl acetate (15 ml.) and 2-methoxyimino-2-(3-chloro-4-hydroxyphenyl)acetic acid (syn isomer) (0.53 g.) was added thereto with stirring at −20° C. The mixture was stirred for 1 hour below −10° C. On the other hand, a mixture of 7-amino-3-trichloroacetylcarbamoyloxymethyl-3-cephem-4-carboxylic acid (1 g.), trimethylsilylacetamide (5 g.) and dry ethyl acetate (25 ml.) was stirred for 1 hour at ambient temperature. To this solution was dropwise added the above obtained solution with stirring below −10° and the resulting mixture was stirred for 2 hours at the same temperature. Water (50 ml.) and ethyl acetate (50 ml.) were added to the reaction mixture at −20° C. and the mixture was shaken. The organic layer containing 7-[2-methoxyimino-2-(3-chloro-4-hydroxyphenyl)acetamido]-3-trichloroacetylcarbamoyloxymethyl-3-cephem-4-carboxylic acid (syn isomer) was adjusted to pH 7.0 by adding water (50 ml.) and sodium bicarbonate and the mixture was stirred for 2 hours at ambient temperature. Ethyl acetate (50 ml.) was added to the aqueous layer and the mixture was adjusted to pH 5.0 with 10% hydrochloric acid. The aqueous layer was separated, adjusted to pH 2.0 with 10% hydrochloric acid and extracted with ethyl acetate (50 ml.). The extract was washed with ice-water and dried over magnesium sulfate. The solvent was distilled off under reduced pressure. The residue was thoroughly washed with ether, collected by filtration and dried to give 7-[2-methoxyimino-2-(3-chloro-4-hydroxyphenyl)acetamido]-3-carbamoyloxymethyl-3-cephem-4-carboxylic acid (syn isomer) (0.3 g.).

I.R. spectrum (Nujol): 3450, 3300, 1770, 1730, 1715, 1660, 1650, 1600 cm$^{-1}$.

N.M.R. spectrum (d$_6$-DMSO, δ) ppm: 9.72 (1H, d, J=8 Hz), 7.48 (1H, d, J=2 Hz), 7.40 (1H, dd, J=2,8 Hz), 6.98 (1H, d, J=8 Hz), 6.60 (2H, s), 5.70 (1H, q, J=5 Hz), 5.20 (1H, d, J=5 Hz), 4.74 (2H, AB$_q$, J=13 Hz), 3.90 (3H, s), 3.50 (2H, AB$_q$, J=18 Hz).

EXAMPLE 4

2-Methoxyimino-2-(3-hydroxyphenyl)acetic acid (syn isomer) (1.1 g.) and 7-amino-3-trichloroacetylcarbamoyloxymethyl-3-cephem-4-carboxylic acid (2.35 g.) were reacted and post-treated according to a similar manner to that of Example 3 to give 7-[2-methoxyimino-2-(3-hydroxyphenyl)acetamido]-3-carbamoyloxymethyl-3-cephem-4-carboxylic acid (syn isomer) (0.5 g.). This compound is identified with the compound obtained in Example 2 by I.R. and N.M.R. spectra.

EXAMPLE 5

(a) 2-t-Butoxycarbonylmethoxyimino-2-(3-chloro-4-hydroxyphenyl)acetic acid (syn isomer) (1 g.) and 7-amino-3-(1-methyl-1H-tetrazol-5-yl)thiomethyl-3-cephem-4-carboxylic acid (1 g.) were reacted according to similar manners to those of Examples 1 and 2 to give powder of 7-[2-t-butoxycarbonylmethoxyimino-2-(3-chloro-4-hydroxyphenyl)acetamido]-3-(1-methyl-1H-tetrazol-5-yl)thiomethyl-3-cephem-4-carboxylic acid (syn isomer) (1.5 g.).

(b) The powder obtained in Example 5(a) (1.5 g.) was added to a mixture of anisole (1.5 ml.) and trifluoroacetic acid (6 ml.) and the resulting mixture was stirred for 30 minutes at ambient temperature. The reaction mixture was adjusted to pH 8 by adding a sodium bicarbonate aqueous solution (50 ml.), ethyl acetate (50 ml.) and sodium bicarbonate under ice-cooling. The aqueous layer was separated, adjusted to pH 5.0 with 10% hydrochloric acid and washed with ethyl acetate (50 ml.). The aqueous layer was further adjusted to pH 2.0 with 10% hydrochloric acid and extracted with ethyl acetate (100 ml.). The extract was washed with water and dried over magnesium sulfate. The solvent was distilled off under reduced pressure and the residue was dissolved in pH 5.0 acetate buffer and subjected to column chromatography on Woelm neutral alumina (trade mark: made by ICN Company) using pH 5.0 acetate buffer as developing solvent. The eluate was adjusted to pH 2.0 with 10% hydrochloric acid under ice-cooling. Precipitating materials were collected by filtration, washed with water and dried to give 7-[2-carboxymethoxyimino-2-(3-chloro-4-hydroxyphenyl)acetamido]-3-(1-methyl-1H-tetrazol-5-yl)thiomethyl-3-cephem-4-carboxylic acid (syn isomer) (0.5 g.), mp 145° to 148° C. (dec.).

I.R. spectrum (Nujol): 3400, 3200–3300, 2500–2600, 1780, 1720, 1670, 1600 cm$^{-1}$.

N.M.R. spectrum (d$_6$-DMSO, δ) ppm: 9.70 (1H, d, J=8 Hz), 7.50 (1H, d, J=2 Hz), 7.45 (1H, dd,J=2,8 Hz), 7.10 (1H, d, J=8 Hz), 5.90 (1H, q, J=5 Hz), 5.22 (1H, d, J=5 Hz), 4.70 (2H, s), 4.35 (2H, AB$_q$, J=13 Hz), 3.95 (3H, s), 3.75 (2H, AB$_q$, J=18 Hz).

EXAMPLE 6

(a) 2-(1-t-Butoxycarbonylethoxyimino)-2-(3-chloro-4-hydroxyphenyl)acetic acid (syn isomer) (2 g.) and 7-amino-3-(1-methyl-1H-tetrazol-5-yl)thiomethyl-3-cephem-4-carboxylic acid (2 g.) were reacted according to similar manners to those of Examples 1 and 2 to give powder of 7-[2-(1-t-butoxycarbonylethoxyimino)-2-(3-chloro-4-hydroxyphenyl)acetamido]-3-(1-methyl-1H- tetrazol-5-yl)thiomethyl-3-cephem-4-carboxylic acid (syn isomer) (3.6 g.).

(b) The powder obtained in Example 6(a) (3.6 g.), anisole (4 ml.) and trifluoroacetic acid (16 ml.) were reacted according to a similar manner to that of Example 5(b) to give yellow powder of 7-[2-(1-carboxyethoxyimino)-2-(3-chloro-4-hydroxyphenyl)acetamido]-3-(1-methyl-1H-tetrazol-5-yl)thiomethyl-3-cephem-4-carboxylic acid (syn isomer) (2.0 g.), mp 147° to 151° C. (dec.).

I.R. spectrum (Nujol): 3500, 3250, 2500–2600, 1780, 1730, 1660, 1630, 1600 cm$^{-1}$.

N.M.R. spectrum (d$_6$-DMSO, δ) ppm: 9.62 (1H, d, J=8 Hz), 7.46 (1H, d, J=2 Hz), 7.34 (1H, dd, J=2,8 Hz), 7.04 (1H, d, J=8 Hz), 5.90 (1H, q, J=5 Hz), 5.22 (1H, d, J=5 Hz), 4.73 (1H, q, J=6 Hz), 4.33 (2H, AB$_q$, J=13 Hz), 4.00 (3H, s), 3.73 (2H, AB$_q$, J=18 Hz), 1.37 (3H, d, J=6 Hz).

EXAMPLE 7

The following compounds were obtained according to similar manners to those of Examples 1 and 2

(1) 7-[2-Methoxyimino-2-(3-hydroxyphenyl)acetamido]-3-(4H-1,2,4-triazol-3-yl)thiomethyl-3-cephem-4-carboxylic acid (syn isomer).

I.R. spectrum (Nujol): 3250, 1775, 1710, 1665 cm$^{-1}$.

N.M.R. spectrum (d$_6$-DMSO, δ) ppm: 9.67 (1H, d, J=8 Hz), 8.40 (1H, s), 6.70–7.43 (4H, m), 5.82 (1H, dd, J=5,8 Hz), 5.13 (1H, d, J=5 Hz), 4.18 (2H, AB$_q$, J=13 Hz), 3.90 (3H, s), 3.67 (2H, broad s).

(2) 7-[2-Methoxyimino-2-(3-hydroxyphenyl)acetamido]-3-(1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.78 (1H, d, J=8 Hz), 9.55 (1H, s), 6.70–7.40 (4H, m), 5.89 (1H, dd, J=5,8 Hz), 5.22 (1H, d, J=5 Hz), 4.46 (2H, AB$_q$, J=13 Hz), 3.92 (3H, s), 3.76 (2H, AB$_q$, J=18 Hz).

(3) 7-[2-Methoxyimino-2-(3-hydroxyphenyl)acetamido]-3-(5-methyl-1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.72 (1H, d, J=8 Hz), 6.62–7.40 (4H, m), 5.94 (1H, dd, J=5,8 Hz), 5.18 (1H, d, J=5 Hz), 4.18 (2H, AB$_q$, J=13 Hz), 3.89 (3H, s), 3.70 (2H, AB$_q$, J=17 Hz), 2.65 (3H, s).

(4) 7-[2-Methoxyimino-2-(3-hydroxyphenyl)acetamido]cephalosporanic acid (syn isomer).

I.R. spectrum (Nujol): 3250, 1785, 1740, 1720 cm$^{-1}$.

N.M.R. spectrum (d$_6$-DMSO, δ) ppm: 9.78 (1H, d, J=8 Hz), 6.86–7.36 (4H, m), 5.86 (1H, dd, J=5,8 Hz), 5.18 (1H, d, J=5 Hz), 4.84 (2H, AB$_q$, J=13 Hz), 3.98 (3H, s), 3.54 (2H, AB$_q$, J=17 Hz), 2.00 (3H, s).

(5) 7-[2-Methoxyimino-2-(3-methoxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.78 (1H, d, J=8 Hz), 6.95–7.54 (4H, m), 5.94 (1H, dd, J=5,8 Hz), 5.18 (1H, d, J=5 Hz), 4.12 (2H, AB$_q$, J=13 Hz), 3.92 (6H, s), 3.76 (3H, s), 3.72 (2H, AB$_q$, J=18 Hz).

(6) 7-[2-Methoxyimino-2-(4-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.70 (1H, d, J=8 Hz), 7.44 (2H, d, J=8 Hz), 6.84 (2H, d, J=8 Hz), 5.86 (1H, dd, J=5,8 Hz), 5.18 (1H, J=5 Hz), 4.34 (2H, AB$_q$, J=13 Hz), 3.93 (3H, s), 3.87 (3H, s), 3.74 (2H, AB$_q$, J=18 Hz).

(7) 7-[2-Methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec.).

I.R. spectrum (Nujol): 3500, 3250, 2500–2600, 1780, 1720, 1655, 1625, 1600 cm$^{-1}$.

N.M.R. spectrum (d$_6$-DMSO, δ) ppm: 10.80 (1H, broad s), 9.68 (1H, d, J=2 Hz), 7.46 (1H, d, J=2 Hz), 7.32 (1H, q, J=2,8 Hz), 7.00 (1H, d, J=8 Hz), 5.80 (1H, q, J=5 Hz), 5.16 (1H, d, J=5 Hz), 4.28 (2H, AB$_q$, J=13 Hz), 3.92 (3H, s), 3.87 (3H, s), 3.72 (2H, AB$_q$, J=18 Hz).

(8) 7-[2-Methoxyimino-2-(3-chloro-4-methoxyphenyl)acetamido]-3-(1-methyl-1H-tetrazol-5-yl)thiomethyl-3-cephem-4-carboxylic acid (syn isomer), mp 143° to 145° C. (dec.).

I.R. spectrum (Nujol): 3300, 2500–2600, 1785, 1730, 1670, 1630, 1600 cm$^{-1}$.

N.M.R. spectrum (d$_6$-DMSO, δ) ppm: 9.76 (1H, d, J=8 Hz), 7.56 (1H, d, J=2 Hz), 7.48 (1H, dd, J=2,8 Hz), 7.22 (1H, d, J=8 Hz), 5.84 (1H, q, J=5 Hz), 5.18 (1H, d, J=5 Hz), 4.27 (2H, AB$_q$, J=13 Hz), 3.90 (6H, s), 3.88 (3H, s), 3.70 (2H, AB$_q$, J=18 Hz).

(9) 7-[2-Methoxyimino-2-(3-nitro-4-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3400–3450, 3200, 2500–2600, 1780, 1720, 1660, 1620, 1600, 1535, 1350 cm$^{-1}$.

N.M.R. specttrum (d$_6$-DMSO, δ) ppm: 9.72 (1H, d, J=8 Hz), 7.97 (1H, d, J=2 Hz), 7.72 (1H, dd, J=2 Hz), 7.21 (1H, d, J=8 Hz), 5.82 (1H, q, J=5 Hz), 5.16 (1H, d, J=5 Hz), 4.3 (2H, AB$_q$, J=13 Hz), 3.92 (3H, s), 3.87 (3H, s), 3.72 (2H, AB$_q$, J=18 Hz).

(10) 7-[2-Allyloxyimino-2-(3-chloro-4-hydroxyphenyl)acetamido]-3-(1-methyl-1H-tetrazol-5-yl)thiomethyl-3-cephem-4-carboxylic acid (syn isomer), mp 163° to 165° C. (dec.).

I.R. spectrum (Nujol): 3200–3300, 2500–2600, 1780, 1720, 1670, 1600 cm$^{-1}$.

N.M.R. spectrum (d$_6$-DMSO, δ) ppm: 9.70 (1H, d, J=8 Hz), 7.40 (1H, d, J=2 Hz), 7.30 (1H, dd, J=2,8 Hz), 6.95 (1H, d, J=8 Hz), 5.80 (2H, m), 5.30 (2H, d, J=8 Hz), 5.10 (1H, d, J=5 Hz), 4.60 (2H, d, J=5 Hz), 4.27 (2H, AB$_q$, J=13 Hz), 3.85 (3H, s), 3.65 (2H, AB$_q$, J=18 Hz).

(11) 7-[2-Allyloxyimino-2-(3-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3250–3350, 2550–2600, 1780, 1730, 1670, 1650, 1600 cm$^{-1}$.

N.M.R. spectrum (d$_6$-DMSO, δ) ppm: 9.70 (1H, d, J=8 Hz), 7.2–6.8 (4H, m), 6.1–5.8 (2H, m), 5.35 (2H, d, J=8 Hz), 5.17 (1H, d, J=5 Hz), 4.7 (2H, d, J=5 Hz), 4.17 (2H, AB$_q$, J=13 Hz), 3.93 (3H, s), 3.75 (2H, AB$_q$, J=18 Hz).

(12) Sodium 7-[2-methoxyimino-2-(3-hydroxyphenyl)acetamido]cephalosporanate (syn isomer).

I.R. spectrum (Nujol): 3250, 1765, 1730, 1665 cm$^{-1}$.

N.M.R. spectrum (D$_2$O, δ) ppm: 6.83–7.13 (4H, m), 5.83 (1H, d, J=5 Hz), 5.17 (1H, d, J=5 Hz), 4.82 (2H, AB$_q$, J=13 Hz), 4.03 (3H, s), 3.50 (2H, AB$_q$, J=17 Hz), 2.1 (3H, s).

(13) 7-[2-(3-Hydroxy-4-bromobenzyloxyimino)-2-(4-hydroxyphenyl)acetamido]-3-(1-methyl-1H-tetrazol-5- yl)thiomethyl-3-cephem-4-carboxylic acid (syn isomer), powder.

I.R. spectrum (Nujol): 3150, 1780, 1720, 1670 cm$^{-1}$.

N.M.R. spectrum (d$_6$-DMSO, δ) ppm: 9.60 (1H, d, J=8 Hz), 6.72-7.52 (7H, m), 5.80 (1H, dd, J=4,8 Hz), 5.15 (1H, d, J=4 Hz), 5.00 (2H, s), 4.28 (2H, AB$_q$, J=13 Hz), 3.90 (3H, s), 3.65 (2H, AB$_q$, J=18 Hz).

(14) 7-[2-(2-Thienylmethoxyimino)-2-(4-hydroxyphenyl)acetamido]-3-(1-methyl-1H-5-yl)thiomethyl-3-cephem-4-carboxylic acid (syn isomer), powder.

I.R. spectrum (Nujol): 3200-3300, 1780, 1720, 1660 cm$^{-1}$.

N.M.R. spectrum (d$_6$-DMSO, δ) ppm: 9.77 (1H, d, J=8 Hz), 6.7-7.7 (7H, m), 5.83 (1H, dd, J=5,8 Hz), 5.29 (2H, s), 5.15 (1H, d, J=5 Hz), 4.3 (2H, AB$_q$, J=13 Hz), 3.92 (3H, s), 3.72 (2H, AB$_q$, J=18 Hz).

(15) 7-[2-Ethoxyimino-2-(3-chloro-4-hydroxyphenyl)acetamido]-3-(1-methyl-1H-tetrazol-5-yl)thiomethyl-3-cephem-4-carboxylic acid (syn isomer), colorless powder, mp 153° to 156° C. (dec.).

I.R. spectrum (Nujol): 3450, 3250, 2550-2600, 1780, 1725, 1665, 1630, 1600 cm$^{-1}$.

N.M.R. spectrum (d$_6$-DMSO, δ) ppm: 9.71 (1H, d, J=8 Hz), 7.50 (1H, d, J=2 Hz), 7.36 (1H, dd, J=2,8 Hz), 7.03 (1H, d, J=8 Hz), 5.83 (1H, q, J=5 Hz), 5.17 (1H, d, J=5 Hz), 4.33 (2H, AB$_q$, J=13 Hz), 4.17 (2H, q, J=7 Hz), 3.97 (3H, s), 3.73 (2H, AB$_q$, J=18 Hz), 1.25 (3H, t, J=7 Hz).

(16) 7-[2-Allyloxyimino-2-(3-methoxyphenyl)acetamido]-3-(1-methyl-1H-tetrazol-5-yl)thiomethyl-3-cephem-4-carboxylic acid (syn isomer), powder, mp 135° to 138° C. (dec.).

I.R. spectrum (Nujol): 3300, 2600, 1785, 1730, 1670, 1645, 1600 cm$^{-1}$.

N.M.R. spectrum (d$_6$-DMSO, δ) ppm: 9.82 (1H, d, J=8 Hz), 7.0-7.45 (4H, m), 5.8-6.2 (2H, m), 5.36 (2H, t, J=10 Hz), 5.21 (1H, d, J=5 Hz), 4.72 (2H, d, J=5 Hz), 4.36 (2H, AB$_q$, J=13 Hz), 3.95 (3H, s), 3.91 (3H, s), 3.87 (2H, AB$_q$, J=18 Hz).

(17) 7-[2-Ethoxyimino-2-(3-hydroxyphenyl)acetamido]-3-(1-methyl-1H-tetrazol-5-yl)thiomethyl-3-cephem-4-carboxylic acid (syn isomer), yellow powder, mp 145° to 148° C. (dec.).

I.R. spectrum (Nujol): 3450, 3250, 2500-2600, 1775, 1720, 1665, 1620, 1600 cm$^{-1}$.

N.M.R. spectrum (d$_6$-DMSO, δ) ppm: 9.70 (1H, d, J=8 Hz), 6.8-7.4 (4H, s), 5.90 (1H, q, J=5 Hz), 5.20 (1H, d, J=5 Hz), 4.36 (2H, AB$_q$, J=13 Hz), 4.20 (2H, q, J=7 Hz), 4.00 (3H, s), 3.76 (2H, AB$_q$, J=18 Hz), 1.33 (3H, t, J=7 Hz).

(18) 7-[2-Ethoxyimino-2-(3-methoxyphenyl)acetamido]-3-(1-methyl-1H-tetrazol-5-yl)thiomethyl-3-cephem-4-carboxylic acid (syn isomer), pale yellow powder, mp 140° to 143° C. (dec.).

I.R. spectrum (Nujol): 3300, 2500-2600, 1785, 1730, 1670, 1630, 1600 cm$^{-1}$.

N.M.R. spectrum (d$_6$-DMSO, δ) ppm: 9.71 (1H, d, J=8 Hz), 6.9-7.5 (4H, m), 5.90 (1H, q, J=5 Hz), 5.17 (1H, d, J=5 Hz), 4.33 (2H, AB$_q$, J=13 Hz), 4.20 (2H, q, J=7 Hz), 3.95 (3H, s), 3.85 (3H, s), 3.75 (2H, AB$_q$, J=18 Hz), 1.30 (3H, t, J=7 Hz).

(19) 7-[2-Allyloxyimino-2-(3-chloro-4-methoxyphenyl)acetamido]-3-(1-methyl-1H-tetrazol-5-yl)thiomethyl-3-cephem-4-carboxylic acid (syn isomer), pale yellow powder, mp 153° to 156° C. (dec.).

I.R. spectrum (Nujol): 3250, 2600, 1780, 1720, 1670, 1645, 1630, 1600 cm$^{-1}$.

N.M.R. spectrum (d$_6$-DMSO, δ) ppm: 9.65 (1H, d, J=8 Hz), 7.27 (1H, d, J=2 Hz), 7.20 (1H, dd, J=2,8 Hz), 7.09 (1H, d, J=8 Hz), 5.85-6.15 (2H, m), 5.15 (2H, t, J=9 Hz), 5.05 (1H, d, J=5 Hz), 4.60 (2H, d, J=5 Hz), 4.15 (2H, AB$_q$, J=13 Hz), 3.95 (3H, s), 3.90 (3H, s), 3.47 (2H, AB$_q$, J=18 Hz).

(20) 7-[2-Methoxyimino-2-(3-acetoxyphenyl)acetamido]-3-carbamoyloxymethyl-3-cephem-4-carboxylic acid (syn isomer).

I.R. spectrum (Nujol): 3450, 3250, 1765, 1710, 1655, 1530 cm$^{-1}$.

N.M.R. spectrum (d$_6$-DMSO, δ) ppm: 9.77 (1H, d, J=8 Hz), 7.6-7.1 (4H, m), 6.56 (2H, s), 5.83 (1H, dd, J=4,8 Hz), 5.20 (1H, d, J=4 Hz), 4.76 (2H, AB$_q$, J=13 Hz), 3.94 (3H, s), 3.55 (2H, broad s), 2.28 (3H, s).

(21) 7-[2-Phenylthiomethoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3300, 1760, 1660, 1600, 1580, 1520 cm$^{-1}$.

N.M.R. spectrum (d$_6$-DMSO, δ) ppm: 9.7 (1H, d, J=8 Hz), 7.7-6.7 (9H, m), 5.8-5.4 (3H, broad s), 5.06 (1H, d, J=5 Hz), 4.33 (2H, broad s), 3.9 (3H, s), 3.56 (2H, broad s).

(22) 7-[2-Methoxyimino-2-(3-mesylaminophenyl)acetamido]-3-(1,3,4-thiadiazol-2-yl)thiomethyl-3-cephem-4-carboxylic acid (syn isomer), mp 155° C. (dec.).

I.R. spectrum (Nujol): 3300, 1780, 1730, 1670 cm$^{-1}$.

N.M.R. spectrum (d$_6$-DMSO, δ) ppm: 9.98 (1H, s), 9.81 (1H, d, J=9 Hz), 9.62 (1H, s), 5.90 (1H, dd, J=5, 9 Hz), 5.24 (1H, d, J=5 Hz), 4.49 (2H, ABq, J=14 Hz), 3.98 (3H, s), 3.77 (2H, broad s), 2.96 (3H, s).

(23) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670 1620, 1590, 1520 cm$^{-1}$.

N.M.R. spectrum (d$_6$-DMSO, δ) ppm: 9.77 (1H, d, J=7 Hz), 7.6-6.8 (6H, m), 5.83 (1H, dd, J=4, 7 Hz), 5.17 (1H, d, J=4 Hz), 4.31 (2H, ABq, J=14 Hz), 3.96 (6H, s), 3.72 (2H, broad s).

(24) 7-[2-Methoxyimino-2-(3-carbamoyloxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675 cm$^{-1}$.

N.M.R. spectrum (d$_6$-DMSO, δ) ppm: 9.81 (1H, d, J=8 Hz), 9.62 (1H, s), 6.7-7.58 (4H, m), 5.87 (1H, dd, J=5, 8 Hz), 5.2 (1H, d, J=5 Hz), 4.25, 4.63 (2H, ABq, J=14 Hz), 3.9 (3H, s), 3.7 (2H, broad s).

(25) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, δ) ppm: 9.86 (1H, d, J=8 Hz), 9.61 (1H, s), 7.00-7.65 (4H, m), 5.84 (1H, dd, J=5, 8 Hz), 5.2 (1H, d, J=5 Hz), 4.25, 4.63 (2H, ABq, J=14 Hz), 3.92 (3H, s), 3.53, 3.86 (2H, ABq, J=19 Hz), 2.3 (3H, s).

(26) 7-[2-(3-Phenylallyloxyimino)-2-(3-hydroxyphenyl)acetamido]-3-(1-methyl-1H-tetrazol-5-yl)thiomethyl-3-cephem-4-carboxylic acid (syn isomer), mp 138° to 142° C. (dec.)

I.R. spectrum (Nujol): 3300-2600, 1780, 1720, 1665, 1600 cm$^{-1}$.

N.M.R. spectrum (d$_6$-DMSO, δ) ppm: 9.80 (1H, d, J=8 Hz), 6.4-7.4 (11H, m), 5.85 (1H, dd, J=5, 8 Hz), 5.20 (1H, d, J=5 Hz), 4.83 (2H, d, J=5 Hz), 4.32 (2H, ABq, J=15 Hz), 3.95 (3H, s), 3.68 (2H, ABq, J=18 Hz).

(27) 7-[2-Methoxyimino-2-(4-dimethylaminophenyl)acetamido]-3-(1-methyl-1H-tetrazol-5-yl)thiomethyl-3-cephem-4-carboxylic acid (syn isomer), mp 88° C. (dec.).

I.R. spectrum (Nujol): 3250, 1780, 1730, 1680, 1610 cm$^{-1}$.

N.M.R. spectrum (d$_6$-DMSO, δ) ppm: 9.63 (1H, d, J=8 Hz), 7.40 (2H, d, J=8 Hz), 6.73 (2H, d, J=8 Hz), 5.83 (1H, dd, J=5, 8 Hz), 5.17 (1H, d, J=5 Hz), 4.33 (2H, ABq, J=13 Hz), 3.97 (3H, s), 3.87 (3H, s), 3.73 (2H, broad s), 3.00 (6H, s).

(28) 7-[2-Methoxyimino-2-(3-hydroxyphenyl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ) ppm: 9.67 (1H, d, J=9 Hz), 6.72-7.36 (4H, m), 5.78 (1H, dd, J=5, 9 Hz), 5.12 (1H, d, J=5 Hz), 4.55 (2H, broad s), 4.30 (2H, broad s), 3.90 (3H, s), 3.40-3.80 (2H, m), 3.14 (2H, broad s), 2.48 (6H, s).

(29) 7-[2-{2-(2-Hydroxyphenoxy)ethoxyimino}-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3270, 1780, 1725, 1670, 1560 cm$^{-1}$.

N.M.R. spectrum (d$_6$-DMSO, δ) ppm: 6.5-7.4 (8H, m), 5.86 (1H, dd, J=5, 8 Hz), 5.14 (1H, d, J=5 Hz), 4.0-4.6 (6H, m), 3.92 (3H, s), 3.52, 3.70 (2H, AB$_q$, J=7 Hz).

EXAMPLE 8

A mixture of dimethylformamide (0.73 g) and phosphorus oxychloride (1.6 g) was warmed for 30 minutes at 40° C. Benzene was added thereto and the mixture was concentrated. The residue was suspended in ethyl acetate (20 ml) and 2-methoxyimino-2-(3-hydroxyphenyl) acetic acid (syn isomer) (1.95 g) was added thereto at −15° to −5° C., after which the resulting mixture was stirred for 30 minutes at the same temperature. On the other hand, a solution of sodium hydroxide (0.9 g) in water (5 ml) was dropwise added at 0° to 5° C. over 25 minutes to a suspension of 7-aminocephalosporanic acid (2.7 g) in water (12.5 ml) and the mixture was stirred for 5 minutes, after which acetone (20 ml) was added thereto. To the resulting mixture containing sodium 7-amino-3-hydroxymethyl-3-cephem-4-carboxylate was dropwise added at 0° to 5° C. over 3 minutes the above obtained ethyl acetate solution keeping the pH value at 7.5 to 8.5 by adding triethylamine. After stirring for 30 minutes, the organic solvents were distilled off. The aqueous layer was washed with ethyl acetate (20 ml), adjusted to pH 2.0 with hydrochloric acid and extracted with ethyl acetate (60 ml) at 0° to 3° C. The aqueous layer was further extracted with ethyl acetate (30 ml). The combined ethyl acetate extracts were washed with a saturated aqueous solution of sodium chloride and dried. The solvent was distilled off and the residue was pulverized with diisopropyl ether to give a mixture of 7-[2-methoxyimino-2-(3-hydroxyphenyl)acetamido]-3-hydroxymethyl-3-cephem-4-carboxylic acid(syn isomer)(I) and 6-[2-methoxyimino-2-(3-hydroxyphenyl)acetamido]-5a,6-dihydro-3H,7H-azeto[2,1-b]-furo[3,4-d][1,3]thiazine-1,7(4H)-dione(syn isomer)(II) (2.64 g).

I.R. spectrum of (I) (Nujol): 3250, 1785, 1755, 1660, 1600, 1570, 1540 cm$^{-1}$.

N.M.R. spectrum of (I) (d$_6$-DMSO, δ) ppm: 9.83 (1H, d, J=8 Hz), 7.5-6.75 (4H, m), 5.8 (1H, dd, J=5,8 Hz), 5.21 (1H, d, J=5 Hz), 4.3 (2H, broad s), 3.95 (3H, s), 3.63 (2H, broad s).

I.R. spectrum of (II) (Nujol): 3250, 1785, 1755, 1660, 1600, 1570, 1540 cm$^{-1}$.

N.M.R. spectrum of (II) (d$_6$-DMSO, δ) ppm: 9.83 (1H, d, J=8 Hz), 7.5-6.75 (4H, m), 6.02 (1H, dd, J=5, 8 Hz), 5.21 (1H, d, J=5 Hz), 5.07 (2H, broad s), 3.95 (3H, s), 3.84 (2H, broad s).

EXAMPLE 9

7-[2-Methoxyimino-2-(3-hydroxyphenyl)acetamido]-3-carbamoyloxymethyl-3-cephem-4-carboxylic acid (syn isomer) (0.23 g) was dissolved in pyridine (1 ml) with stirring and ice-cooling, and acetyl chloride (0.082 g) was added thereto. The mixture was stirred for 40 minutes under ice-cooling. The reaction mixture was poured into ice-water, acidified with hydrochloric acid and extracted with ethyl acetate. The extract was washed with a saturated aqueous solution of sodium chloride and dried over magnesium sulfate. After treating with activated charcoal, it was filtered and the filtrate was concentrated. The residue was pulverized with diisopropyl ether to give a mixture of 7-[2-methoxyimino-2-(3-acetoxyphenyl)acetamido]-3-carbamoyloxymethyl-3-cephem-4-carboxylic acid (syn isomer) and 7-[2-methoxyimino-2-(3-acetoxyphenyl)acetamido]-3-carbamoyloxymethyl-2-cephem-4-carboxylic acid (syn isomer) (0.18 g).

N.M.R. spectrum (d$_6$-DMSO, δ) ppm: 9.82 (1H, d, J=8 Hz), 9.77 (1H, d, J=8 Hz), 7.6-7.1 (8H, m), 6.60 (1H, s), 6.56 (2H, s), 5.83 (1H, dd, J=4, 8 Hz), 5.60 (1H, dd, J=4,8 Hz), 5.24 (1H, d, J=4 Hz), 5.20 (1H, d, J=4 Hz), 4.84 (1H, s), 4.76 (2H, ABq, J=13 Hz), 4.56 (2H, broad s), 3.94 (6H, s), 3.55 (2H, broad s), 2.28 (6H, s).

EXAMPLE 10

The following compounds were obtained according to a similar manner to that of Example 9.

(1) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, δ) ppm: 9.86 (1H, d, J=8 Hz), 9.61 (1H, s), 7.00-7.65 (4H, m), 5.84 (1H, dd, J=5, 8 Hz), 5.2 (1H, d, J=5 Hz), 4.25, 4.63 (2H, ABq, J=14 Hz), 3.92 (3H, s), 3.53, 3.86 (2H, ABq, J=19 Hz), 2.3 (3H, s).

(2) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670, 1620, 1590, 1520 cm$^{-1}$.

N.M.R. spectrum (d$_6$-DMSO, δ) ppm: 9.77 (1H, d, J=7 Hz), 7.6-6.8 (6H, m), 5.83 (1H, dd, J=4, 7 Hz), 5.17 (1H, d, J=4 Hz), 4.31 (2H, ABq, J=14 Hz), 3.96 (6H, s), 3.72 (2H, broad s).

(3) 7-[2-Methoxyimino-2-(3-carbamoyl-oxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675 cm$^{-1}$.

N.M.R. spectrum (d$_6$-DMSO, δ) ppm: 9.81 (1H, d, J=8 Hz), 9.62 (1H, s), 6.7-7.58 (4H, m), 5.87 (1H, dd, J=5, 8 Hz), 5.2 (1H, d, J=5 Hz), 4.25, 4.63 (2H, ABq, J=14 Hz), 3.9 (3H, s), 3.7 (2H, broad s).

EXAMPLE 11

Phosphorus oxychloride (0.26 g.) was added under ice-cooling to dimethylformamide (0.15 g.) and the mixture was warmed at 40° C. for 1 hour. Ethyl acetate (1.5 ml.) was added thereto and to the mixture was at a time added 2-methoxyimino-2-(2-methyl-1,3-thiazol-4-yl)acetic acid (syn isomer) (0.3 g.) with stirring and ice-cooling, after which the resulting mixture was stirred for 20 minutes at 0° to 5° C. On the other hand, bis(trimethylsilyl)acetamide (1.2 g.) was added to a suspension of 7-amino-3-(1-methyl-1H-tetrazol-5-yl)thiomethyl-3-cephem-4-carboxylic acid (0.53 g.) in ethyl acetate (7 ml.) and the mixture was stirred at ambient temperature. To this solution was dropwise added the above obtained ethyl acetate solution at −20° C. and the mixture was stirred for 2 hours at −10° to −20° C. Water (20 ml.) was added to the reaction mixture below −25° C. and ethyl acetate (20 ml.) was added thereto, after which the mixture was stirred. An insoluble material was filtered off and the ethyl acetate layer was separated. Water (15 ml.) was added to the ethyl acetate layer and the mixture was adjusted to pH 7.5 with a saturated aqueous solution of sodium bicarbonate. The aqueous layer was separated, washed with methylene chloride and methylene chloride in the aqueous layer was removed by bubbling of nitrogen gas. The aqueous solution was adjusted to pH 2.2 with 10% hydrochloric acid and precipitates were collected by filtration and dried to give 7-[2-methoxyimino-2-(2-methyl-1,3-thiazol-4-yl)acetamido]-3-(1-methyl-1H-tetrazol-5-yl)thiomethyl-3-cephem-4-carboxylic acid (syn isomer) (0.28 g.).

I.R. spectrum (Nujol): 1780, 1710, 1675 cm$^{-1}$.

N.M.R. spectrum (d$_6$-DMSO, δ) ppm: 9.65 (1H, d, J=10 Hz), 7.66 (1H, s), 5.81 (1H, dd, J=5,10 Hz), 5.15 (1H, d, J=5 Hz), 4.31 (2H, AB$_q$, J=13 Hz), 3.93 (3H, s), 3.90 (3H, s), 3.70 (2H, AB$_q$, J=16 Hz), 2.65 (3H, s).

EXAMPLE 12

Phosphorus oxychloride (0.89 g.) and dry dimethylformamide (0.44 g.) were mixed under ice-cooling and then warmed for 30 minutes at 40° C. Dry methylene chloride (20 ml.) was added thereto and then distilled off. To the residue were added dry ethyl acetate (10 ml.) and then 2-methoxyimino-2-[2-(2,2,2-trifluoroacetamido)-1,3-thiazol-4-yl]acetic acid (syn isomer) (1.8 g.) with stirring and ice-cooling. The mixture was stirred for 40 minutes at the same temperature to give clear solution. On the other hand, trimethylsilylacetamide (6.36 g.) was added to a suspension of 7-aminocephalosporanic acid (1.65 g.) in dry ethyl acetate (25 ml.) with stirring at ambient temperature, after which the mixture was stirred for 1 hour to give a clear solution. To this solution was at a time added the above-obtained ethyl acetate solution with stirring at −20° to −25° C., and the resulting mixture was stirred for 2 hours at the same temperature. Water (30 ml.) was added to the reaction mixture at the same temperature, and then the mixture was stirred for 5 minutes at ambient temperature. The ethyl acetate layer was separated, and the aqueous layer was further extracted with ethyl acetate. The ethyl acetate layers were combined and water (50 ml.) was added thereto. The mixture was adjusted to pH 7.5 with sodium bicarbonate, and the aqueous layer was separated. Ethyl acetate (40 ml.) was added to the aqueous layer, and the mixture was adjusted to pH 2.5 with 10% hydrochloric acid with stirring and ice-cooling. The ethyl acetate layer was separated, and the aqueous layer was further extracted twice with ethyl acetate (30 ml.). The ethyl acetate layers were combined, washed with an aqueous solution of sodium chloride and treated with activated charcoal. The solvent was distilled off to give 7-[2-methoxyimino-2-{2-(2,2,2-trifluoroacetamido)-1,3-thiazol-4-yl}acetamido]cephalosporanic acid (syn isomer) (3.05 g.), mp 205° C. (dec.).

I.R. spectrum (Nujol): 3250, 1790, 1735, 1680, 1650 cm$^{-1}$.

N.M.R. spectrum (d$_6$-DMSO, δ) ppm: 9.8 (1H, d, J=8 Hz), 7.55 (1H, s), 5.88 (1H, dd, J=5,8 Hz), 5.25 (1H, d, J=5 Hz), 4.8 (2H, AB$_q$, J=13 Hz), 3.95 (3H, s), 3.59 (2H, broad s), 2.03 (3H, s).

EXAMPLE 13

Phosphorus oxychloride (2.0 g.) was at a time added at 5° to 10° C. to a suspension of 2-methoxyimino-2-(2-amino-1,3-thiazol-4-yl)acetic acid (syn isomer) (2 g.) in dry ethyl acetate (20 ml.). After stirring for 20 minutes at 7° to 10° C., bis(trimethylsilyl)acetamide (0.4 g.) was added thereto at the same temperature. After stirring for 10 minutes at 7° to 10° C., phosphorus oxychloride (2.0 g.) was dropwise added thereto at the same temperature. The resulting mixture was stirred for 10 minutes at 7° to 10° C., and dry dimethylformamide (0.8 g.) was dropwise added thereto at the same temperature. The mixture was stirred for 30 minutes at 7° to 10° C. to give a clear solution. On the other hand, trimethylsilylacetamide (7.35 g.) was added to a suspension of 7-aminocephalosporanic acid (2.45 g.) in dry ethyl acetate (8 ml.), after which the mixture was stirred at 40° C. to give a clear solution. To this solution was at a time added the above-obtained ethyl acetate solution at −15° C., and the resulting mixture was stirred for 1 hour at −10° to −15° C. The reaction mixture was cooled to −30° C., and water (80 ml.) was added thereto. The aqueous layer was separated, adjusted to pH 4.5 with sodium bicarbonate and subjected to column chromatography on Diaion HP-20 resin (Trademark: prepared by Mitsubishi Chemical Industries Ltd.) using 25% aqueous solution of isopropyl alcohol as an eluent. The eluate was lyophilized to give 7-[2-methoxyimino-2-(2-amino-1,3-thiazol-4-yl)acetamido]cephalosporanic acid (syn isomer) (1.8 g.), mp 227° C. (dec.).

I.R. spectrum (Nujol): 3300–3350, 1780, 1740, 1670 cm$^{-1}$.

N.M.R. spectrum (d$_6$-DMSO, δ) ppm: 9.6 (1H, d, J=8 Hz), 6.8 (1H, s), 5.8 (1H, dd, J=5,8 Hz), 5.2 (1H, d, J=5 Hz), 4.87 (2H, AB$_q$, J=13 Hz), 3.89 (3H, s), 3.6 (2H, broad s), 2.08 (3H, s).

EXAMPLE 14

Phosphorus oxychloride (3.8 g.) was dropwise added at 5° to 8° C. to a suspension of 2-methoxyimino-2-(2-amino-1,3-thiazol-4-yl)acetic acid (syn isomer) (4.0 g.) in dry ethyl acetate (40 ml.). After stirring for 30 minutes around 5° C., bis(trimethylsilyl)acetamide (0.86 g.) was added thereto at the same temperature. After stirring for 10 minutes at the same temperature, phosphorus oxychloride (3.8 g.) was dropwise added thereto at 5° to 8° C., after which the mixture was stirred for 30 minutes at the same temperature. Dry dimethylformamide (1.6 g.) was dropwise added thereto at 5° to 7° C., after which the resulting mixture was stirred for 30 minutes at the same temperature to give a clear solution. On the other hand, sodium acetate (3.3 g.) was added to a solution of 7-aminocephalosporanic acid (2.7 g.) in an aqueous solution (20 ml.) of sodium bicarbonate (1.7 g.), and then acetone (20 ml.) was added thereto. To this solution was dropwise added the above-obtained ethyl acetate solution with stirring at 0° to 5° C. keeping the pH of this solution at 7.0 to 7.5 by 20% aqueous solution of sodium carbonate. The mixture was stirred for 1 hour at the same temperature. An insoluble material was filtered off, and the aqueous layer in the filtrate was separated. The aqueous layer was concentrated under reduced pressure to remove the organic solvents, adjusted to pH 4.5 with sodium bicarbonate and subjected to column chromatography on Diaion HP-20 resin (Trademark: prepared by Mitsubishi Chemical Industries Ltd.) using 25% aqueous solution of isopropyl alcohol as an eluent. The eluate was lyophilized to give 7-[2-methoxyimino-2-(2-amino-1,3-thiazol-4-yl)acetamido]cephalosporanic acid (syn isomer) (2.8 g.). This compound was identified with the compound obtained in Example 13 by I.R. and N.M.R. spectra.

EXAMPLE 15

The following compounds were obtained according to similar manners to those of Examples 11 to 14.

(1) 7-[2-Methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3250, 1780, 1718, 1675 cm$^{-1}$.

N.M.R. spectrum (d$_6$-DMSO, δ) ppm: 9.80 (1H, d, J=8 Hz), 7.08 (1H, s), 5.80 (1H, dd, J=5,8 Hz), 5.18 (1H, d, J=5 Hz), 4.34 (2H, AB$_q$, J=13 Hz), 3.99 (3H, s), 3.96 (3H, s), 3.72 (2H, AB$_q$, J=17 Hz), 3.66 (3H, s), 2.98 (3H, s).

(2) 7-[2-Methoxyimino-2-(2-mesylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3300–3150, 1780, 1710, 1670 cm$^{-1}$.

N.M.R. spectrum (d$_6$-DMSO, δ) ppm: 9.84 (1H, d, J=8 Hz), 6.97 (1H, s), 5.76 (1H, dd, J=5,8 Hz), 5.12 (1H, d, J=5 Hz), 4.33 (2H, AB$_q$, J=13 Hz), 3.93 (6H, s), 3.74 (2H, AB$_q$, J=17 Hz), 2.96 (3H, s).

(3) 7-[2-Methoxyimino-2-(2-oxo-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1665 cm$^{-1}$.

N.M.R. spectrum (d$_6$-DMSO, δ) ppm: 11.67 (1H, s), 9.83 (1H, d, J=8 Hz), 6.61 (1H, s), 5.80 (1H, dd, J=5.5,8 Hz), 5.17 (1H, d, J=5.5 Hz), 4.37 (2H, broad s), 4.00 (3H, s), 3.96 (3H, s), 3.75 (2H, broad s).

(4) 7-[2-Methoxyimino-2-{2-(2,2,2-trifluoroacetamido)-1,3-thiazol-4-yl}acetamido]-3-(1-methyl-1H-tetrazol-5-yl)thiomethyl-3-cephem-4-carboxylic acid (syn isomer).

I.R. spectrum (Nujol): 1790, 1730, 1660 cm$^{-1}$.

N.M.R. spectrum (d$_6$-DMSO, δ) ppm: 9.73 (1H, d, J=8 Hz), 7.53 (1H, s), 5.83 (1H, dd, J=5,8 Hz), 5.15 (1H, d, J=5 Hz), 4.33 (2H, broad s), 3.93 (6H, s), 3.72 (2H, broad s).

(5) 7-[2-Methoxyimino-2-(2-t-pentyloxycarbonylamino-1,3-thiazol-4-yl)acetamido]-3-(5-methyl-1,3,4-thiadiazol-2-yl)thiomethyl-3-cephem-4-carboxylic acid (syn isomer).

I.R. spectrum (Nujol): 3200, 1780, 1720, 1680 cm$^{-1}$.

N.M.R. spectrum (d$_6$-DMSO, δ) ppm: 9.65 (1H, d, J=8 Hz), 7.28 (1H, s), 5.80 (1H, dd, J=5,8 Hz), 5.16 (1H, d, J=5 Hz), 4.38 (2H, AB$_q$, J=13 Hz), 3.86 (3H, s), 3.70 (2H, AB$_q$, J=17 Hz), 2.66 (3H, s), 1.78 (2H, q, J=8 Hz), 1.44 (6H, s), 0.88 (3H, t, J=8 Hz).

(6) 7-[2-Allyloxyimino-2-(2-mesylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100–3300, 1780, 1720, 1675 cm$^{-1}$.

N.M.R. spectrum (d$_6$-DMSO, δ) ppm: 9.90 (1H, d, J=8 Hz), 7.00 (1H, s), 6.07–5.63 (2H, m), 5.43 (2H, d, J=8 Hz), 5.18 (1H, d, J=5 Hz), 4.70 (2H, d, J=5 Hz), 4.37 (2H, broad s), 3.98 (3H, s), 3.75 (2H, broad s), 3.00 (3H, s).

(7) 7-[2-Allyloxyimino-2-(2-t-pentyloxycarbonylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3250, 1780, 1720, 1678, 1625 cm$^{-1}$.

N.M.R. spectrum (d$_6$-DMSO, δ) ppm: 9.74 (1H, d, J=8 Hz), 7.31 (1H, s), 6.28–5.76 (2H, m), 5.28 (2H, dd, J=8, 16 Hz), 5.18 (1H, d, J=5 Hz), 4.66 (2H, d, J=5 Hz), 4.36 (2H, ABq, J=13 Hz), 3.96 (3H, s), 3.74 (2H, ABq, J=17 Hz), 1.80 (2H, q, J=8 Hz), 1.45 (6H, s), 0.89 (3H, t, J=8 Hz).

(8) 7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200, 1765, 1600 cm$^{-1}$.

N.M.R. spectrum (d$_6$-DMSO, δ) ppm: 9.51 (1H, d, J=8.5 Hz), 7.22 (2H, broad s), 6.72 (1H, s), 5.59 (1H, dd, J=5, 8.5 Hz), 5.00 (1H, d, J=5 Hz), 4.35 (2H, Abq, J=12 Hz), 3.90 (3H, s), 3.81 (3H, s), 3.55 (2H, ABq, J=18 Hz).

(9) 7-[2-Methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer).

I.R. spectrum (Nujol): 3400–3150, 1770, 1670, 1625 cm$^{-1}$.

N.M.R. spectrum (d$_6$-DMSO, δ) ppm: 9.66 (1H, d, J=8 Hz), 7.34 (2H, broad s), 6.76 (1H, s), 5.78 (2H, dd, J=5,8 Hz), 5.16 (1H, d, J=5 Hz), 4.40 (2H, ABq, J=14 Hz), 3.85 (3H, s), 3.70 (2H, ABq, J=17 Hz), 2.68 (3H, s).

(10) 7-[2-Allyloxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100–3400, 1775, 1660, 1625 cm$^{-1}$.

N.M.R. spectrum (d$_6$-DMSO, δ) ppm: 9.70 (1H, d, J=8 Hz), 6.80 (1H, s), 6.30–5.60 (2H, m), 5.24 (2H, dd, J=8,16 Hz), 5.15 (1H, d, J=5 Hz), 4.63 (2H, d, J=5 Hz), 4.32 (2H, ABq, J=12 Hz), 3.94 (3H, s), 3.70 (2H, ABq, J=17 Hz).

(11) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer), mp 145° to 147° C. (dec.).

I.R. spectrum (Nujol): 3150–3400, 1780, 1725, 1680, 1640 cm$^{-1}$.

N.M.R. spectrum (d$_6$-DMSO, δ) ppm: 12.58 (1H, broad s), 9.70 (1H, d, J=8 Hz), 9.58 (1H, s), 8.50 (1H, s), 7.40 (1H, s), 5.82 (1H, dd, J=5,8 Hz), 5.17 (1H, d, J=5 Hz), 4.43 (2H, ABq, J=13 Hz), 3.88 (3H, s), 3.70 (2H, broad s).

(12) 7-[2-Methoxyimino-2-(2-acetamido-1,3-thiazol-4-yl)acetamido]-3-(1-methyl-1H-tetrazol-5-yl)thiomethyl-3-cephem-4-carboxylic acid (syn isomer), mp 171° to 173° C. (dec.).

I.R. spectrum (Nujol): 3500, 3250, 1780, 1720, 1670 cm$^{-1}$.

N.M.R. spectrum (d6-DMSO, δ) ppm: 9.65 (1H, d, J=8 Hz), 7.3 (1H, s), 5.8 (1H, dd, J=5, 8 Hz), 5.15 (1H, d, J=5 Hz), 4.35 (2H, broad s), 3.97 (3H, s), 3.9 (3H, s), 3.75 (2H, broad s), 2.15 (3H, s).

(13) 7-[2-Methoxyimino-2-{2-(2,2,2-trifluoroacetamido)-1,3-thiazol-4-yl}acetamido]-cephalosporanic acid (syn isomer), mp 205° C. (dec.).

I.R. spectrum (Nujol): 3250, 1790, 1735, 1680, 1650 cm$^{-1}$.

N.M.R. spectrum (d6-DMSO, δ) ppm: 9.8 (1H, d, J=8 Hz), 7.55 (1H, s), 5.88 (1H, dd, J=5, 8 Hz), 5.25 (1H, d, J=5 Hz), 4.8 (2H, ABq, J=13 Hz), 3.95 (3H, s), 3.59 (2H, broad s), 2.03 (3H, s).

(14) 7-[2-Methoxyimino-2-{2-(2,2,2-trifluoroacetamido)-1,3-thiazol-4-yl}acetamido]-3-carbamoyloxymethyl-3-cephem-4-carboxylic acid (syn isomer).

I.R. spectrum (Nujol): 3500, 3200, 1785, 1700, 1660 cm$^{-1}$.

N.M.R. spectrum (d6-DMSO, δ) ppm: 9.75 (1H, d, J=8 Hz), 8.4 (2H, m), 7.53 (1H, s), 6.6 (1H, m), 6.20 (1H, d, J=5 Hz), 5.83 (1H, m), 4.77 (2H, Abq, J=14 Hz), 3.91 (3H, s), 3.55 (2H, m).

(15) 7-[2-Methoxyimino-2-{2-(2,2,2-trifluoroacetamido)-1,3-thiazol-4-yl}acetamido]-3-(1,3,4-thiadiazol-2-yl)thiomethyl-3-cephem-4-carboxylic acid (syn isomer).

I.R. spectrum (Nujol): 3200, 1780, 1720, 1650 cm$^{-1}$.

N.M.R. spectrum (d6-DMSO, δ) ppm: 9.81 (1H, d, J=8 Hz), 9.6 (1H, m), 9.57 (1H, s), 7.56 (1H, s), 5.83 (1H, dd, J=5, 8 Hz), 5.20 (1H, d, J=5 Hz), 4.47 (2H, ABq, J=14 Hz), 3.96 (3H, s), 3.72 (2H, ABq, J=18 Hz).

(16) 7-[2-Methoxyimino-2-(2-amino-1,3-thiazol-4-yl)acetamido]-3-hydroxymethyl-3-cephem-4-carboxylic acid (syn isomer), mp 260° to 270° C. (dec.).

I.R. spectrum (Nujol): 3370, 3270, 1765, 1660, 1610, 1590, 1550 cm$^{-1}$.

N.M.R. spectrum (d6-DMSO, δ) ppm: 9.58 (1H, d, J=8 Hz), 6.76 (1H, s), 5.75 (1H, dd, J=5, 8 Hz), 5.12 (1H, d, J=5 Hz), 4.27 (2H, broad s), 3.85 (3H, s), 3.57 (2H, broad s).

(17) 7-[2-Methoxyimino-2-(2-amino-1,3-thiazol-4-yl)acetamido]cephalosporanic acid (syn isomer), mp 227° C. (dec.).

I.R. spectrum (Nujol): 3300-3350, 1780, 1740, 1670 cm$^{-1}$.

N.M.R. spectrum (d6-DMSO, δ) ppm: 9.6 (1H, d, J=8 Hz), 6.8 (1H, s), 5.8 (1H, dd, J=5, 8 Hz), 5.2 (1H, d, J=5 Hz), 4.87 (2H, ABq, J=13 Hz), 3.89 (3H, s), 3.6 (2H, broad s), 2.08 (3H, s).

(18) 7-[2-Methoxyimino-2-(2-amino-1,3-thiazol-4-yl)acetamido]-3-carbamoyloxymethyl-3-cepham-4-carboxylic acid (syn isomer), mp 210° to 220° C. (dec.).

I.R. spectrum (Nujol): 3250, 1765, 1650 cm$^{-1}$.

N.M.R. spectrum (d6-DMSO, δ) ppm: 9.64 (1H, d, J=8 Hz), 7.4 (2H, m), 6.79 (1H, s), 6.60 (2H, m), 5.77 (1H, dd, J=5, 8 Hz), 5.16 (1H, d, J=5 Hz), 4.75 (2H, ABq, J=12 Hz), 3.87 (3H, s), 3.53 (2H, ABq, J=18 Hz).

(19) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer), mp 172° to 175° C. (dec.).

I.R. spectrum (Nujol): 3300, 1770, 1665 cm$^{-1}$.

N.M.R. spectrum (d6-DMSO, δ) ppm: 9.80 (1H, d, J=8 Hz), 9.63 (1H, s), 6.95 (1H, s), 6.8 (2H, m), 5.82 (1H, dd, J=5, 8 Hz), 5.22 (1H, d, J=5 Hz), 4.48 (2H, ABq, J=15 Hz), 3.97 (3H, s), 3.76 (2H, ABq, J=18 Hz).

(20) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer), mp 185° C. (dec.).

I.R. spectrum (Nujol): 3150-3350, 1770, 1710, 1660, 1630 cm$^{-1}$.

N.M.R. spectrum (d6-DMSO, δ) ppm: 9.61 (1H, d, J=8 Hz), 8.69 (1H, s), 6.73 (1H, s), 5.72 (1H, dd, J=4, 8 Hz), 5.1 (1H, d, J=4 Hz), 4.1 (2H, ABq, J=13 Hz), 3.87 (3H, s), 3.65 (2H, broad s), 3.59 (3H, s).

(21) 7-[2-Methoxyimino-2-{2-(2,2,2-trifluoroacetamido)-1,3-thiazol-4-yl}acetamido]-3-hydroxymethyl-3-cephem-4-carboxylic acid (syn isomer), mp 155° to 160° C. (dec.).

I.R. spectrum (Nujol): 3250, 1780, 1730, 1660, 1585, 1520 cm$^{-1}$.

N.M.R. spectrum (d6-DMSO, δ) ppm: 9.76 (1H, d, J=8 Hz), 7.57 (1H, s), 5.80 (1H, dd, J=4, 8 Hz), 5.15 (1H, d, J=4 Hz), 4.29 (2H, s), 3.93 (3H, s), 3.60 (2H, s).

(22) 6-[2-Methoxyimino-2-(2-amino-1,3-thiazol-4-yl)acetamido]-5a,6-dihydro-3H,7H-azeto[2,1-b]furo[3,4-d][1,3]thiazine-1,7(4H)-dione (syn isomer), mp 210° to 215° C. (dec.).

I.R. spectrum (Nujol): 3270, 1780, 1740, 1655, 1610, 1525 cm$^{-1}$.

N.M.R. spectrum (d6-DMSO, δ) ppm: 9.70 (1H, d, J=8 Hz), 7.26 (2H, broad s), 6.77 (1H, s), 5.93 (1H, dd, J=5, 8 Hz), 5.16 (1H, d, J=5 Hz), 5.05 (2H, broad s), 3.85 (3H, s), 3.81 (2H, broad s).

(23) 7-[2-Methoxyimino-2-(2-amino-1,3-thiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d6-DMSO, δ) ppm: 9.56 (1H, d, J=8 Hz), 6.75 (1H, s), 5.75 (1H, m), 5.10 (1H, d, J=4 Hz), 4.58 (2H, broad s), 4.32 (2H, broad s), 3.82 (3H, s), 3.68 (2H, broad s), 3.20 (2H, broad s), 2.50 (6H, s).

(24) 7-[2-Methoxyimino-2-(2-formamido-1,3-thiazol-4-yl)acetamido]cephalosporanic acid (syn isomer).

I.R. spectrum (Nujol): 3280, 1785, 1740, 1700, 1650 cm$^{-1}$.

N.M.R. spectrum (d6-DMSO, δ) ppm: 12.68 (1H, broad s), 9.68 (1H, d, J=8 Hz), 8.54 (1H, s), 7.45 (1H, s), 5.86 (H, dd, J=5,8 Hz), 5.20 (1H, d, J=5 Hz), 4.90 (2H, AB$_q$, J=8 Hz), 3.61 (3H, broad s), 2.06 (3H, s).

(25) 7-[2-Methoxyimino-2-(2-ethoxycarbonylamino-1,3-thiazol-4-yl)acetamido]-3-(1,3,4-thiadiazol-2-yl)thiomethyl-3-cephem-4-carboxylic acid (syn isomer).

I.R. specetum (Nujol): 3200, 1775, 1720, 1680, 1660 cm$^{-1}$.

N.M.R. spectrum (d6-DMSO, δ) ppm: 11.9 (1H, m), 9.70 (1H, d, J=10 Hz), 9.55 (1H, s), 7.31 (1H, s), 5.80 (1H, dd, J=5,10 Hz), 5.18 (1H, d,J=5 Hz), 4.44 (2H, AB$_q$, J=16 Hz), 4.22 (2H, q, J=7 Hz), 3.89 (3H, s), 3.72 (2H, AB$_q$, J=16 Hz), 1.23 (3H, t, J=7 Hz).

(26) 7-[2-Methoxyimino-2-{2-(2,2,2-trifluoroacetamido)-1,3-thiazol-4-yl}acetamido]-3-formyl-3-cephem-4-carboxylic acid (syn isomer) [or this compound can be represented as 3-hydroxy-6-[2-methoxyimino-2-{2-(2,2,2-trifluoroacetamido)-1,3-thiazol-4-yl}acetamido]-5a,6-dihydro-3H,7H-azeto[2,1-b]furo[3,4-d][1,3]thiazine-1,7(4H)dione (syn isomer)].

I.R. spectrum (Nujol): 3150, 1790, 1720, 1655, 1560, 1500 cm$^{-1}$.

N.M.R. spectrum (d$_6$-DMSO, δ) ppm: 9.88 (1H, d, J=8 Hz), 7.60 (1H, s), 6.30 (1H, d, J=6 Hz), 6.05 (1H, dd, J=5, 8 Hz), 5.23 (1H, d, J=5 Hz), 3.96 (3H, s), 3.80 (2H, broad s).

(27) 7-[2-Methoxyimino-2-(2-formamido-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200–3300, 2600, 1780, 1720, 1690, 1675 cm$^{-1}$.

N.M.R. spectrum (d$_6$-DMSO, δ) ppm: 12.60 (1H, broad s), 9.70 (1H, d, J=8 Hz), 8.50 (1H, s), 7.44 (1H, s), 5.88 (1H, dd, J=5, 8 Hz), 5.19 (1H, d, J=5 Hz), 4.25 (2H, AB$_q$, J=13 Hz), 3.95 (3H, s), 3.85 (3H, s), 3.65 (2H, AB$_q$, J=18 Hz).

(28) 7-[2-Methoxyimino-2-(2-formamido-1,3-thiazol-4-yl)acetamido]-3-carbamoyloxymethyl-3-cephem-4-carboxylic acid (syn isomer).

I.R. spectrum (Nujol) 3300, 1780, 1705, 1680 cm$^{-1}$.

N.M.R. spectrum (d$_6$-DMSO, δ) ppm: 12.50 (1H, broad s), 9.67 (1H, d, J=8 Hz), 8.50 (1H, s), 7.43 (1H, s), 6.58 (2H, broad s), 5.80 (1H, dd, J=5, 8 Hz), 5.16 (1H, d, J=5 Hz), 4.78 (2H, AB$_q$, J=14 Hz), 3.95 (3H, s), 3.57 (2H, AB$_q$, J=18 Hz).

EXAMPLE 16

A solution of 7-[2-methoxyimino-2-{2-(2,2,2-trifluoroacetamido)-1,3-thiazol-4-yl}acetamido]-3-(1-methyl-1H-tetrazol-5-yl)thiomethyl-3-cephem-4-carboxylic acid (syn isomer) (0.3 g.) in a 0.1N aqueous solution of sodium hydroxide (10.5 ml.) was warmed at 45° C. for 6 hours. Water (15 ml.) and ethyl acetate (30 ml.) were added to the reaction mixture and the resulting mixture was adjusted to pH 3.5 with 10% hydrochloric acid. The aqueous layer was separated, washed with ethyl acetate and adjusted to pH 5.0 with an aqueous solution of sodium bicarbonate. The aqueous solution was subjected to column chromatography on Amberlite XAD-2 (20 ml.) (prepared by Rohm & Haas Co.) using 10% ethanol as developing solvent. The eluate containing object compound was collected and lyophilized to give 7-[2-methoxyimino-2-(2-amino-1,3-thiazol-4-yl)acetamido]-3-(1-methyl-1H-tetrazol-5-yl)thiomethyl-3-cephem-4-carboxylic acid (syn isomer) (0.12 g.).

I.R. spectrum (Nujol): 3200, 1765, 1600 cm$^{-1}$.

N.M.R. spectrum (d$_6$-DMSO, δ) ppm: 9.51 (1H, d, J=8.5 Hz), 7.22 (2H, broad s), 6.72 (1H, s), 5.59 (1H, dd, J=5,8.5 Hz), 5.00 (1H, d, J=5 Hz), 4.35 (2H, AB$_q$, J=12 Hz), 3.90 (3H, s), 3.81 (3H, s), 3.55 (2H, AB$_q$, J=18 Hz).

EXAMPLE 17

Trifluoroacetic acid (3 ml) was added under ice-cooling to 7-[2-methoxyimino-2-(2-t-pentyloxycarbonylamino-1,3-thiazol-4-yl)acetamido]-3-(5-methyl-1,3,4-thiadiazol-2-yl)thiomethyl-3-cephem-4-carboxylic acid (syn isomer) (0.5 g) and the mixture was stirred for 30 minutes at ambient temperature. To the mixture was added ether and precipitating powder was collected by filtration and dissolved in a mixture of water (20 ml) and an 1N aqueous solution of sodium hydroxide to adjust to pH 12 to 13. The solution was adjusted to pH 4.6 with 10% hydrochloric acid, washed with ethyl acetate and methylene chloride. Excess methylene chloride in the aqueous layer was thoroughly removed by bubbling of nitrogen gas. The aqueous layer was adjusted to pH 2 with stirring and ice-cooling to precipitate powder. The powder was collected by filtration and dried to give 7-[2-methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer) (0.128 g)

I.R. spectrum (Nujol): 3400–3150, 1770, 1670, 1625 cm$^{-1}$.

N.M.R. spectrum (d$_6$-DMSO, δ) ppm: 9.66 (1H, d, J=8 Hz), 7.34 (2H, broad s), 6.76 (1H, s), 5.78 (2H, dd, J=5, 8 Hz), 5.16 (1H, d, J=5 Hz), 4.40 (2H, ABq, J=14 Hz), 3.85 (3H, s), 3.70 (2H, ABq, J=17 Hz), 2.68 (3H, s).

EXAMPLE 18

Trifluoroacetic acid (4 ml.) and anisole (2 ml.) were added under ice-cooling to 7-[2-allyloxyimino-2-(2-t-pentyloxycarbonylamino-1,3-thiazol-4-yl)acetamido]-3-(1-methyl-1H-tetrazol-5-yl)thiomethyl-3-cephem-4-carboxylic acid (syn isomer) (0.9 g.) and the mixture was stirred for 40 minutes at ambient temperature. The reaction mixture was post-treated according to a similar manner to that of Example 17 to give 7-[2-allyloxyimino-2-(2-amino-1,3-thiazol-4-yl)acetamido]-3-(1-methyl-1H-tetrazol-5-yl)thiomethyl-3-cephem-4-carboxylic acid (syn isomer) (0.425 g.).

I.R. Spectrum (Nujol): 3100–3400, 1775, 1660, 1625 cm$^{-1}$.

N.M.R. spectrum (d$_6$-DMSO, δ) ppm: 9.70 (1H, d, J=8 Hz), 6.80 (1H, s), 6.30–5.60 (2H, m), 5.24 (2H, dd, J=8, 16 Hz), 5.15 (1H, d, J=5 Hz), 4.63 (2H, d, J=5 Hz), 4.32 (2H, ABq, J=12 Hz), 3.94 (3H, s), 3.70 (2H, ABq, J=17 Hz).

EXAMPLE 19

Disodium hydrogen phosphate (0.26 g) was added to a suspension of 7-[2-methoxyimino-2-{2-(2,2,2-trifluoroacetamido)-1,3-thiazol-4-yl}acetamido]cephalosphoranic acid (syn isomer) (1 g) in water (15 ml). A saturated aqueous solution of disodium hydrogen phosphate was further added thereto to adjust the pH value of the mixture at 6. The resulting mixture was stirred for 23 hours at ambient temperature. The reaction mixture was adjusted to pH 4 under ice-cooling with 10% hydrochloric acid, washed with ethyl acetate and adjusted to pH 2.5 with 10% hydrochloric acid. Precipitating crystals were collected by filtration, washed with cold water and dried to give 7-[2-methoxyimino-2-(2-amino-1,3-thiazol-4-yl)acetamido]cephalosporanic acid (syn isomer) (0.18 g), mp 227° C. (dec.).

I.R. spectrum (Nujol): 3300–3350, 1780, 1740, 1670 cm$^{-1}$.

N.M.R. spectrum (d$_6$-DMSO, δ) ppm: 9.6 (1H, d, J=8 Hz), 6.8 (1H, s), 5.8 (1H, dd, J=5, 8 Hz), 5.2 (1H, d, J=5 Hz), 4.87 (2H, ABq, J=13 Hz), 3.89 (3H, s), 3.6 (2H, broad s), 2.08 (3H, s).

EXAMPLE 20

7-[2-Methoxyimino-2-{2-(2,2,2-trifluoroacetamido)-1,3-thiazol-4-yl}acetamido]-3-(1,3,4-thiadiazol-2-yl)thiomethyl-3-cephem-4-carboxylic acid (syn isomer) (23 g) was suspended in a solution of sodium acetate trihydrate (74.8 g) in water (230 ml) and the suspension was stirred for 15 hours at ambient temperature. The reaction mixture was adjusted to pH 5.0 with conc. hydrochloric acid and insoluble material was filtered off. The filtrate was adjusted to pH 2.5 and precipitating crystals were collected by filtration and dried to give 7-[2-methoxyimino-2-(2-amino-1,3-thiazol-4-yl)acetamido]-3-(1,3,4-thiadiazol-2-yl)thiomethyl-3-cephem-4-carboxylic acid (syn isomer) (14 g), mp 172° to 175° C. (dec.).

I.R. spectrum (Nujol): 3300, 1770, 1665 cm$^{-1}$.

N.M.R. spectrum (d$_6$-DMSO, δ) ppm: 9.80 (1H, d, J=8 Hz), 9.63 (1H, s), 6.95 (1H, s), 6.8 (2H, m), 5.82 (1H, dd, J=5, 8 Hz), 5.22 (1H, d, J=5 Hz), 4.48 (2H, ABq, J=15 Hz), 3.97 (3H, s), 3.76 (2H, ABq, J=18 Hz).

EXAMPLE 21

7-[2-Methoxyimino-2-{2-(2,2,2-trifluoroacetamido)-1,3-thiazol-4-yl}acetamido]-3-carbamoyloxymethyl-3-cephem-4-carboxylic acid (syn isomer) (3.5 g.) was suspended in a solution of sodium acetate trihydrate (12.2 g.) in water (30 ml.). The mixture was stirred for 15 hours at ambient temperature. The reaction mixture was saturated with sodium chloride and adjusted to pH 5.0 with conc. hydrochloric acid with stirring and ice-cooling. Precipitating insoluble material was filtered off. The filtrate was adjusted to pH 3.0 with conc. hydrochloric acid and further adjusted to pH 1.5 with 10% hydrochloric acid. Precipitates were collected by filtration and dried to give 7-[2-methoxyimino-2-(2-amino-1,3-thiazol-4-yl)acetamido]-3-carbamoyloxymethyl-3-cephem-4-carboxylic acid (syn isomer) (2.1 g.), mp 210° to 220° C. (dec.).

I.R. spectrum (Nujol): 3250, 1765, 1650 cm$^{-1}$.

N.M.R. spectrum (d$_6$-DMSO, δ) ppm: 9.64 (1H, d, J=8 Hz), 7.4 (2H, m), 6.79 (1H, s), 6.60 (2H, m), 5.77 (1H, dd, J=5,8 Hz), 5.16 (1H, d, J=5 Hz), 4.75 (2H, AB$_q$, J=12 Hz), 3.87 (3H, s), 3.53 (2H, AB$_q$, J=18 Hz).

EXAMPLE 22

Conc. hydrochloric acid (10.4 ml.) was added with stirring at ambient temperature to a suspension of 7-[2-methoxyimino-2-(2-formamido-1,3-thiazol-4-yl)acetamido]cephalosporanic acid (syn isomer) (48.35 g.) in methanol (725 ml.). After stirring for 3 hours at ambient temperature, the reaction mixture was adjusted to pH 4.5 with aqueous solution of ammonia and methanol was distilled off. To the residue was added water (100 ml.). The mixture was adjusted to pH 6.5 with an aqueous solution of sodium bicarbonate, and insoluble material was collected by filtration to give 6-[2-methoxyimino-2-(2-amino-1,3-thiazol-4-yl)acetamido]-5a,6-dihydro-3H,7H-azeto[2,1-b]furo[3,4-d][1,3]thiazine-1,7(4H)dione (syn isomer) (6.5 g.). The filtrate was adjusted to pH 4.5 with acetic acid, adsorbed by Diaion HP-20 resin (Trademark: prepared by Mitsubishi Chemical Industries Ltd.) (600 ml.), washed with water (2 l.) and then eluted with 25% aqueous solution of isopropyl alcohol. Eluates containing the object compounds were collected and cooled after addition of isopropyl alcohol (⅓ volume of the eluates). Precipitates were collected by filtration, washed with isopropyl alcohol and dried to give 7-[2-methoxyimino-2-(2-amino-1,3-thiazol-4-yl)acetamido]cephalosporanic acid (syn isomer) (10.4 g.). The mother liquor was concentrated under reduced pressure until crystals began to precipitate. To the residue was added isopropyl alcohol (⅔ volume of the residue). The mixture was cooled and precipitates were collected by filtration to give the same object compound (5.8 g.). Total yield (16.2 g.). This compound was identified with the compound obtained in the foregoing Examples by I.R. and N.M.R. spectra.

EXAMPLE 23

7-[2-Methoxyimino-2-(2-formamido-1,3-thiazol-4-yl)acetamido]-3-(1,3,4-thiadiazol-2-yl)thiometyl-3-cephem-4-carboxylic acid (syn isomer) (10.8 g.) was added to methanol (200 ml.), and phosphorus oxychloride (7.2 g.) was dropwise added thereto with stirring and ice-cooling at 2° to 9° C. After stirring for 1.5 hours at the same temperature, the reaction mixture was concentrated under reduced pressure on a water bath of 25° to 28° C. to the volume of 100 ml. To the residue was added ether (300 ml.) with stirring and ice-cooling. Precipitates were collected by filtration and dried to give 7-[2-methoxyimino-2-(2-amino-1,3-thiazol-4-yl)acetamido]-3-(1,3,4-thiadiazol-2-yl)thiomethyl-3-cephem-4-carboxylic acid hydrochloride (syn isomer) (12.3 g.). This powder (12.3 g.) was suspended in water (100 ml.) and dissolved by adjusting pH of the suspension to 7.5 by addition of a saturated aqueous solution of sodium bicarbonate. To the solution was added ethyl acetate (100 ml.), and the mixture was adjusted to pH 2.5 with 10% hydrochloric acid. Precipitates were collected by filtration, washed with cold water and dried to give 7-[2-methoxyimino-2-(2-amino-1,3-thiazol-4-yl)acetamido]-3-(1,3,4-thiadiazol-2-yl)thiomethyl-3-cephem-4-carboxylic acid (syn isomer) (6.1 g.). The aqueous layer in the mother liquor was separated and stirred under cooling after addition of sodium chloride. Precipitates were collected by filtration to give the same object compound (3.8 g.). Total yield (9.9 g.). This compound was identified with the compound obtained in the foregoing Examples by I.R. and N.M.R. spectra.

EXAMPLE 24

The following compounds were obtained according to similar manners to those of Examples 16 to 23.

(1) 7-[2-Methoxyimino-2-(2-amino-1,3-thiazol-4-yl)acetamido]-3-hydroxymethyl-3-cephem-4-carboxylic acid (syn isomer), mp 260° to 270° C. (dec.).

I.R. spectrum (Nujol): 3370, 3270, 1765, 1660, 1610, 1590, 1550 cm$^{-1}$.

N.M.R. spectrum (d$_6$-DMSO, δ) ppm: 9.58 (1H, d, J=8 Hz), 6.76 (1H, s), 5.75 (1H, dd, J=5, 8 Hz), 5.12 (1H, d, J=5 Hz), 4.27 (2H, broad s), 3.85 (3H, s), 3.57 (2H, broad s).

(2) 7-[2-Methoxyimino-2-(2-amino-1,3-thiazol-4-yl)acetamido]-3-carbamoyloxymethyl-3-cephem-4-carboxylic acid (syn isomer), mp 210° to 220° C. (dec.).

I.R. spectrum (Nujol): 3250, 1765, 1650 cm$^{-1}$.

N.M.R. spectrum (d$_6$-DMSO, δ) ppm: 9.64 (1H, d, J=8 Hz), 7.4 (2H, m), 6.79 (1H, s), 6.60 (2H, m), 5.77 (1H, dd, J=5, 8 Hz), 5.16 (1H, d, J=5 Hz), 4.75 (2H, ABq, J=12 Hz), 3.87 (3H, s), 3.53 (2H, ABq, J=18 Hz).

(3) 7-[2-Methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer), mp 185° C. (dec.).

I.R. spectrum (Nujol): 3150–3350, 1770, 1710, 1660, 1630 cm$^{-1}$.

N.M.R. spectrum (d$_6$-DMSO, δ) ppm: 9.61 (1H, d, J=8 Hz), 8.69 (1H, s), 6.73 (1H, s), 5.72 (1H, dd, J=4, 8 Hz), 5.1 (1H, d, J=4 Hz), 4.1 (2H, ABq, J=13 Hz), 3.87 (3H, s), 3.65 (2H, broad s), 3.59 (3H, s).

(4) 6-[2-Methoxyimino-2-(2-amino-1,3-thiazol-4-yl)acetamido]-5a,6-dihydro-3H,7H-azeto[2,1-b]furo[3,4-d][1,3]thiazine-1,7(4H)-dione (syn isomer), mp 210° to 215° C. (dec.).

I.R. spectrum (Nujol): 3270, 1780, 1740, 1655, 1610, 1525 cm$^{-1}$.

N.M.R. spectrum (d$_6$-DMSO, δ) ppm: 9.70 (1H, d, J=8 Hz), 7.26 (2H, broad s), 6.77 (1H, s), 5.93 (1H, dd, J=5, 8 Hz), 5.16 (1H, d, J=5 Hz), 5.05 (2H, broad s), 3.85 (3H, s), 3.81 (2H, broad s).

(5) 7-[2-Methoxyimino-2-(2-amino-1,3-thiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ) ppm: 9.56 (1H, d, J=8 Hz), 6.75 (1H, s), 5.75 (1H, m), 5.10 (1H, d, J=4 Hz), 4.58 (2H, broad s), 4.32 (2H, broad s), 3.82 (3H, s), 3.68 (2H, broad s), 3.20 (2H, broad s), 2.50 (6H, s).

EXAMPLE 25

A suspension of 7-[2-methoxyimino-2-{2-(2,2,2-trifluoroacetamido)-1,3-thiazol-4-yl}acetamido]cephalosporanic acid (syn isomer) (2.76 g) and 4-methyl-4H-1,2,4-triazole-3-thiol (0.63 g) in pH 6.4 phosphate buffer solution (50 ml) was adjusted to pH 6.4 with sodium bicarbonate and stirred for 6 hours at 65° to 70° C. The reaction mixture was cooled and ethyl acetate was added thereto. The mixture was adjusted to pH 5 with 10% hydrochloric acid and washed with ethyl acetate. The aqueous layer was treated with activated charcoal and adjusted to pH 2.7 with 10% hydrochloric acid with stirring and ice-cooling. Precipitating crystals were collected by filtration, washed with cold water and dried to give 7-[2-methoxyimino-2-(2-amino-1,3-thiazol-4-yl)acetamido]-3-(4-methyl-4H-1,2,4-triazol-3-yl)thiomethyl-3-cephem-4-carboxylic acid (syn isomer) (0.7 g), mp 185° C. (dec.).

I.R. spectrum (Nujol): 3150–3350, 1770, 1710, 1660, 1630 cm$^{-1}$.

N.M.R. spectrum (d$_6$-DMSO, δ) ppm: 9.61 (1H, d, J=8 Hz), 8.69 (1H, s), 6.73 (1H, s), 5.72 (1H, dd, J=4, 8 Hz), 5.1 (1H, d, J=4 Hz), 4.1 (2H, ABq, J=13 Hz), 3.87 (3H, s), 3.59 (3H, s), 3.65 (2H, broad s).

EXAMPLE 26

The following compounds were obtained according to a similar manner to that of Example 25.

(1) 7-[2-Methoxyimino-2-(2-methyl-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1710, 1675 cm$^{-1}$.

N.M.R. spectrum (d$_6$-DMSO, δ) ppm: 9.65 (1H, d, J=10 Hz), 7.66 (1H, s), 5.81 (1H, dd, J=5, 10 Hz), 5.15 (1H, d, J=5 Hz), 4.31 (2H, ABq, J=13 Hz), 3.93 (3H, s), 3.90 (3H, s), 3.70 (2H, ABq, J=16 Hz), 2.65 (3H, s).

(2) 7-[2-Methoxyimino-2-(2-mesylimino-3-methyl-2,3-dihydro-1,3-thiazol-4-yl)acetamido]-3-(1-methyl-1H-tetrazol-5-yl)-thiomethyl-3-cephem-4-carboxylic acid (syn isomer).

I.R. spectrum (Nujol): 3250, 1780, 1718, 1675 cm$^{-1}$.

N.M.R. spectrum (d$_6$-DMSO, δ) ppm: 9.80 (1H, d, J=8 Hz), 7.08 (1H, s), 5.80 (1H, dd, J=5, 8 Hz), 5.18 (1H, d, J=5 Hz), 4.34 (2H, ABq, J=13 Hz), 3.99 (3H, s), 3.96 (3H, s), 3.72 (2H, ABq, J=17 Hz), 3.66 (3H, s), 2.98 (3H, s).

(3) 7-[2-Methoxyimino-2-(2-mesylamino-1,3-thiazol-4-yl)-acetamido]-3-(1-methyl-1H-tetrazol-5-yl)thiomethyl-3-cephem-4-carboxylic acid (syn isomer).

I.R. spectrum (Nujol): 3300–3150, 1780, 1710, 1670 cm$^{-1}$.

N.M.R. spectrum (d$_6$-DMSO, δ) ppm: 9.84 (1H, d, J=8 Hz), 6.97 (1H, s), 5.76 (1H, dd, J=5, 8 Hz), 5.12 (1H, d, J=5 Hz), 4.33 (2H, ABq, J=13 Hz), 3.93 (6H, s), 3.74 (2H, ABq, J=17 Hz), 2.96 (3H, s).

(4) 7-[2-Methoxyimino-2-(2-oxo-2,3-dihydro-1,3-thiazol-4-yl)acetamido]-3-(1-methyl-1H-tetrazol-5-yl)thiomethyl-3-cephem-4-carboxylic acid (syn isomer).

I.R. spectrum (Nujol): 1780, 1665 cm$^{-1}$.

N.M.R. spectrum (d$_6$-DMSO, δ) ppm: 11.67 (1H, s), 9.83 (1H, d, J=8 Hz), 6.61 (1H, s), 5.80 (1H, dd, J=5.5, 8 Hz), 5.17 (1H, d, J=5.5 Hz), 4.37 (2H, broad s), 4.00 (3H, s), 3.96 (3H, s), 3.75 (2H, broad s).

(5) 7-[2-Allyloxyimino-2-(2-mesylamino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100–3300, 1780, 1720, 1675 cm$^{-1}$.

N.M.R. spectrum (d$_6$-DMSO, δ) ppm: 9.90 (1H, d, J=8 Hz), 7.00 (1H, s), 6.07–5.63 (2H, m), 5.43 (2H, d, J=8 Hz), 5.18 (1H, d, J=5 Hz), 4.70 (2H, d, J=5 Hz), 4.37 (2H, broad s), 3.98 (3H, s), 3.75 (2H, broad s), 3.00 (3H, s).

(6) 7-[2-Methoxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200, 1765, 1600 cm$^{-1}$.

N.M.R. spectrum (d$_6$-DMSO, δ) ppm: 9.51 (1H, d, J=8.5 Hz), 7.22 (2H, broad s), 6.72 (1H, s), 5.59 (1H, dd, J=5, 8.5 Hz), 5.00 (1H, d, J=5 Hz), 4.35 (2H, ABq, J=12 Hz), 3.90 (3H, s), 3.81 (3H, s), 3.55 (2H, ABq, J=18 Hz).

(7) 7-[2-Methoxyimino-2-(2-amino-1,3-thiazol-4-yl)acetamido]-3-(5-methyl-1,3,4-thiadiazol-2-yl)thiomethyl-3-cephem-4-carboxylic acid (syn isomer).

I.R. spectrum (Nujol): 3400–3150, 1770, 1670, 1625 cm$^{-1}$.

N.M.R. spectrum (d$_6$-DMSO, δ) ppm: 9.66 (1H, d, J=8 Hz), 7.34 (2H, broad s), 6.76 (1H, s), 5.78 (1H, dd, J=5, 8 Hz), 5.16 (1H, d, J=5 Hz), 4.40 (2H, ABq, J=14 Hz), 3.85 (3H, s), 3.70 (2H, ABq, J=17 Hz), 2.68 (3H, s).

(8) 7-[2-Allyloxyimino-2-(2-amino-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3100–3400, 1775, 1660, 1625 cm$^{-1}$.

N.M.R. spectrum (d$_6$-DMSO, δ) ppm: 9.70 (1H, d, J=8 Hz), 6.80 (1H, s), 6.30–5.60 (2H, m), 5.24 (2H, dd, J=8, 16 Hz), 5.15 (1H, d, J=5 Hz), 4.63 (2H, d, J=5 Hz), 4.32 (2H, ABq, J=12 Hz), 3.94 (3H, s), 3.70 (2H, ABq, J=17 Hz).

(9) 7-[2-Methoxyimino-2-(2-formamido-1,3-thiazol-4-yl)acetamido]-3-(1,3,4-thiadiazol-2-yl)thiomethyl-3-cephem-4-carboxylic acid (syn isomer), mp 145° to 147° C. (dec.).

I.R. spectrum (Nujol): 3150–3400, 1780, 1725, 1680, 1640 cm$^{-1}$.

N.M.R. spectrum (d$_6$-DMSO, δ) ppm: 12.58 (1H, broad s), 9.70 (1H, d, J=8 Hz), 9.58 (1H, s), 8.50 (1H, s), 7.40 (1H, s), 5.82 (1H, dd, J=5, 8 Hz), 5.17 (1H, d, J=5 Hz), 4.43 (2H, ABq, J=13 Hz), 3.88 (3H, s), 3.70 (2H, broad s).

(10) 7-[2-Methoxyimino-2-(2-acetamido-1,3-thiazol-4-yl)-acetamido]-3-(1-methyl-1H-tetrazol-5-yl)thiomethyl-3-cephem-4-carboxylic acid (syn isomer), mp 171° to 173° C. (dec.).

I.R. spectrum (Nujol): 3500, 3250, 1780, 1720, 1670 cm$^{-1}$.

N.M.R. spectrum (d$_6$-DMSO, δ) ppm: 9.65 (1H, d, J=8 Hz), 7.3 (1H, s), 5.8 (1H, dd, J=5, 8 Hz), 5.15 (1H, d, J=5 Hz), 4.35 (2H, broad s), 3.97 (3H, s), 3.9 (3H, s), 3.75 (2H, broad s), 2.15 (3H, s).

(11) 7-[2-Methoxyimino-2-(2-amino-1,3-thiazol-4-yl)acetamido]-3-(1,3,4-thiadiazol-2-yl)thiomethyl-3-cephem-4-carboxylic acid (syn isomer), mp 172° to 175° C. (dec.).

I.R. spectrum (Nujol): 3300, 1770, 1665 cm$^{-1}$.

N.M.R. spectrum (d$_6$-DMSO, δ) ppm: 9.80 (1H, d, J=8 Hz), 9.63 (1H, s), 6.95 (1H, s), 6.8 (2H, m), 5.82 (1H, dd, J=5, 8 Hz), 5.22 (1H, d, J=5 Hz), 4.48 (2H, ABq, J=15 Hz), 3.97 (3H, s), 3.76 (2H, ABq, J=18 Hz).

(12) 7-[2-Methoxyimino-2-(2-amino-1,3-thiazol-4-yl)acetamido]-3-[1-(2-dimethylaminoethyl)-1H-tetrazol-5-yl]thiomethyl-3-cephem-4-carboxylic acid (syn isomer).

I.R. spectrum (Nujol): 1765 cm$^{-1}$.

N.M.R. spectrum (d$_6$-DMSO, δ) ppm: 9.56 (1H, d, J=8 Hz), 6.75 (1H, s), 5.75 (1H, m), 5.10 (1H, d, J=4 Hz), 4.58 (2H, broad s), 4.32 (2H, broad s), 3.82 (3H, s), 3.68 (2H, broad s), 3.20 (2H, broad s), 2.50 (6H, s).

(13) 7-[2-Methoxyimino-2-(2-ethoxycarbonylamino-1,3-thiazol-4-yl)acetamido]-3-(1,3,4-thiadiazol-2-yl)thiomethyl-3-cephem-4-carboxylic acid (syn isomer).

I.R. spectrum (Nujol): 3200, 1775, 1720, 1680, 1660 cm$^{-1}$.

N.M.R. spectrum (d$_6$-DMSO, δ) ppm: 11.9 (1H, m), 9.70 (1H, d, J=10 Hz), 9.55 (1H, s), 7.31 (1H, s), 5.80 (1H, dd, J=5,10 Hz), 4.44 (2H, ABq, J=16 Hz), 4.22 (2H, q, J=7 Hz), 3.89 (3H, s), 3.72 (2H, ABq, J=16 Hz), 1.23 (3H, t, J=7 Hz).

(14) 7-[2-Methoxyimino-2-(2-formamido-1,3-thiazol-4-yl)acetamido]-3-(1-methyl-1H-tetrazol-5-yl)thiomethyl-3-cephem-4-carboxylic acid (syn isomer).

I.R. spectrum (Nujol): 3200–3300, 2600, 1780, 1720, 1690, 1675 cm$^{-1}$.

N.M.R. spectrum (d$_6$-DMSO, δ) ppm: 12.60 (1H, broad s), 9.70 (1H, d, J=8 Hz), 8.50 (1H, s), 7.44 (1H, s), 5.88 (1H, dd, J=5,8 Hz), 5.19 (1H, d, J=5 Hz), 4.25 (2H, Ab$_q$, J=13 Hz), 3.95 (3H, s), 3.85 (3H, s), 3.65 (2H, AB$_q$, J=18 Hz).

(15) 7-[2-Methoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1770, 1725, 1670 cm$^{-1}$.

N.M.R. spectrum (d$_6$-DMSO, δ) ppm: 9.76 (1H, d, J=8 Hz), 6.7–7.40 (4H, m), 5.86 (1H, dd, J=5, 8 Hz), 5.18 (1H, d, J=5 Hz), 4.34 (2H, ABq, J=13 Hz), 3.92 (6H, s), 3.72 (2H, ABq, J=17 Hz).

(16) 7-[2-t-Butoxycarbonylmethoxyimino-2-(3-chloro-4-hydroxyphenyl)acetamido]-3-(1-methyl-1H-tetrazol-5-yl)thiomethyl-3-cephem-4-carboxylic acid (syn isomer), powder.

(17) 7-[2-Carboxy-methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec.).

I.R. spectrum (Nujol): 3400, 3200–3300, 2500–2600, 1780, 1720, 1670, 1600 cm$^{-1}$.

N.M.R. spectrum (d$_6$-DMSO, δ) ppm: 9.70 (1H, d, J=8 Hz), 7.50 (1H, d, J=2 Hz), 7.45 (1H, dd, J=2, 8 Hz), 7.10 (1H, d, J=8 Hz), 5.90 (1H, q, J=5 Hz), 5.22 (1H, d, J=5 Hz), 4.70 (2H, s), 4.35 (2H, ABq, J=13 Hz), 3.95 (3H, s), 3.75 (2H, ABq, J=18 Hz).

(18) 7-[2-(1-t-Butoxycarbonylethoxyimino)-2-(3-chloro-4-hydroxyphenyl)acetamido]-3-(1-methyl-1H-tetrazol-5-yl)thiomethyl-3-cephem-4-carboxylic acid (syn isomer), powder.

(19) 7-[2-(1-Carboxyethoxyimino)-2-(3-chloro-4-hydroxyphenyl)acetamido]-3-(1-methyl-1H-tetrazol-5-yl)thiomethyl-3-cephem-4-carboxylic acid (syn isomer), mp 147° to 151° C. (dec.).

I.R. spectrum (Nujol): 3500, 3250, 2500–2600, 1780, 1730, 1660, 1630, 1600 cm$^{-1}$.

N.M.R. spectrum (d$_6$-DMSO, δ) ppm: 9.62 (1H, d, J=8 Hz), 7.46 (1H, d, J=2 Hz), 7.34 (1H, dd, J=2, 8 Hz), 7.04 (1H, d, J=8 Hz), 5.90 (1H, q, J=5 Hz), 5.22 (1H, d, J=5 Hz), 4.73 (1H, q, J=6 Hz), 4.33 (2H, ABq, J=13 Hz), 4.00 (3H, s), 3.73 (2H, ABq, J=18 Hz), 1.37 (3H, d, J=6 Hz).

(20) 7-[2-Methoxyimino-2-(3-hydroxyphenyl)acetamido]-3-(4H-1,2,4-triazol-3-yl)thiomethyl-3-cephem-4-carboxylic acid (syn isomer).

I.R. spectrum (Nujol): 3250, 1775, 1710, 1665 cm$^{-1}$.

N.M.R. spectrum (d$_6$-DMSO, δ) ppm: 9.67 (1H, d, J=8 Hz), 8.40 (1H, s), 6.70–7.43 (4H, m), 5.82 (1H, dd, J=5, 8 Hz), 5.13 (1H, d, J=5 Hz), 4.18 (2H, ABq, J=13 Hz), 3.90 (3H, s), 3.67 (2H, broad s).

(21) 7-[2-Methoxyimino-2-(3-hydroxyphenyl)acetamido]-3-(1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.78 (1H, d, J=8 Hz), 9.55 (1H, s), 6.70–7.40 (4H, m), 5.89 (1H, dd, J=5, 8 Hz), 5.22 (1H, d, J=5 Hz), 4.46 (2H, ABq, J=13 Hz), 3.92 (3H, s), 3.76 (2H, ABq, J=18 Hz).

(22) 7-[2-Methoxyimino-2-(3-hydroxyphenyl)acetamido]-3-(5-methyl-1,3,4-thiadiazol-2-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.72 (1H, d, J=8 Hz), 6.62–7.40 (4H, m), 5.94 (1H, dd, J=5, 8 Hz), 5.18 (1H, d, J=5 Hz), 4.18 (2H, ABq, J=13 Hz), 3.89 (3H, s), 3.70 (2H, ABq, J=17 Hz), 2.65 (3H, s).

(23) 7-[2-Methoxyimino-2-(3-methoxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.78 (1H, d, J=8 Hz), 6.95–7.54 (4H, m), 5.94 (1H, dd, J=5, 8 Hz), 5.18 (1H, d, J=5 Hz), 4.12 (2H, ABq, J=13 Hz), 3.92 (6H, s), 3.76 (3H, s), 3.72 (2H, ABq, J=18 Hz).

(24) 7-[2-Methoxyimino-2-(4-hydroxyphenyl)acetamido]-3-(1-methyl-1H-tetrazol-5-yl)thiomethyl-3-cephem-4-carboxylic acid (syn isomer).

I.R. spectrum (Nujol): 3250, 1780, 1720, 1670 cm$^{-1}$.

N.M.R. spectrum (d$_6$-DMSO, δ) ppm: 9.70 (1H, d, J=8 Hz), 7.44 (2H, d, J=8 Hz), 6.84 (2H, d, J=8 Hz), 5.86 (1H, dd, J=5, 8 Hz), 5.18 (1H, d, J=5 Hz), 4.34 (2H, ABq, J=13 Hz), 3.93 (3H, s), 3.87 (3H, s), 3.74 (2H, ABq, J=18 Hz).

(25) 7-[2-Methoxyimino-2-(3-chloro-4-hydroxyphenyl)acetamido]-3-(1-methyl-1H-tetrazol-5-yl)thiomethyl-3-cephem-4-carboxylic acid (syn isomer), mp 145° to 148° C. (dec.).

I.R. spectrum (Nujol): 3500, 3250, 2500–2600, 1780, 1720, 1655, 1625, 1600 cm$^{-1}$.

N.M.R. spectrum (d$_6$-DMSO, δ) ppm: 10.80 (1H, broad s), 9.68 (1H, d, J=2 Hz), 7.46 (1H, d, J=2 Hz), 7.32 (1H, q, J=2, 8 Hz), 7.00 (1H, d, J=8 Hz), 5.80 (1H, q, J=5 Hz), 5.16 (1H, d, J=5 Hz), 4.28 (2H, ABq, J=13 Hz), 3.92 (3H, s), 3.87 (3H, s), 3.72 (2H, ABq, J=18 Hz).

(26) 7-[2-Methoxyimino-2-(3-chloro-4-methoxyphenyl)acetamido]-3-(1-methyl-1H-tetrazol-5-yl)thiomethyl-3-cephem-4-carboxylic acid (syn isomer), mp 143° to 145° C. (dec.).

I.R. spectrum (Nujol): 3300, 2500–2600, 1785, 1730, 1670, 1630, 1600 cm$^{-1}$.

N.M.R. spectrum (d$_6$-DMSO, δ) ppm: 9.76 (1H, d, J=8 Hz), 7.56 (1H, d, J=2 Hz), 7.48 (1H, dd, J=2, 8 Hz), 7.22 (1H, d, J=8 Hz), 5.84 (1H, q, J=5 Hz), 5.18 (1H, d, J=5 Hz), 4.27 (2H, ABq, J=13 Hz), 3.90 (6H, s), 3.88 (3H, s), 3.70 (2H, ABq, J=18 Hz).

(27) 7-[2-Methoxyimino-2-(3-nitro-4-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3400–3450, 3200, 2500–2600, 1780, 1720, 1660, 1620, 1600, 1535, 1350 cm$^{-1}$.

N.M.R. spectrum (d$_6$-DMSO, δ) ppm: 9.72 (1H, d, J=8 Hz), 7.97 (1H, d, J=2 Hz), 7.72 (1H, dd, J=2, 8 Hz), 7.21 (1H, d, J=8 Hz), 5.82 (1H, q, J=5 Hz), 5.16 (1H, d, J=5 Hz), 4.3 (2H, ABq, J=13 Hz), 3.92 (3H, s), 3.87 (3H, s), 3.72 (2H, ABq, J=18 Hz).

(28) 7-[2-Allyloxyimino-2-(3-chloro-4-hydroxyphenyl)acetamido]-3-(1-methyl-1H-tetrazol-5-yl)thiomethyl-3-cephem-4-carboxylic acid (syn isomer), mp 163° to 165° C. (dec.).

I.R. spectrum (Nujol): 3200–3300, 2500–2600, 1780, 1720, 1670, 1600 cm$^{-1}$.

N.M.R. spectrum (d$_6$-DMSO, δ) ppm: 9.70 (1H, d, J=8 Hz), 7.40 (1H, d, J=2 Hz), 7.30 (1H, dd, J=2, 8 Hz), 6.95 (1H, d, J=8 Hz), 5.80 (2H, m), 5.30 (2H, d, J=8 Hz), 5.10 (1H, d, J=5 Hz), 4.60 (2H, d, J=5 Hz), 4.27 (2H, ABq, J=13 Hz), 3.85 (3H, s), 3.65 (2H, ABq, J=18 Hz).

(29) 7-[2-Allyloxyimino-2-(3-hydroxyphenyl)acetamido]-3-(1-methyl-1H-tetrazol-5-yl)thiomethyl-3-cephem-4-carboxylic acid (syn isomer), mp 149° to 152° C. (dec.).

I.R. spectrum (Nujol): 3250–3350, 2550–2600, 1780, 1730, 1670, 1650, 1600 cm$^{-1}$.

N.M.R. spectrum (d$_6$-DMSO, δ) ppm: 9.70 (1H, d, J=8 Hz), 7.2–6.8 (4H, m), 6.1–5.8 (2H, m), 5.35 (2H, d, J=8 Hz), 5.17 (1H, d, J32 5 Hz), 4.7 (2H, d, J=5 Hz), 4.17 (2H, ABq, J=13 Hz), 3.93 (3H, s), 3.75 (2H, ABq, J=18 Hz).

(30) 7-[2-(3-Hydroxy-4-bromobenzyloxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3150, 1780, 1720, 1670 cm$^{-1}$.

N.M.R. spectrum (d$_6$-DMSO, δ) ppm: 9.60 (1H, d, J=8 Hz), 6.72–7.52(7H, m), 5.80 (1H, dd, J=4, 8 Hz), 5.15 (1H, d, J=4 Hz), 5.00 (2H, s), 4.28 (2H, ABq, J=13 Hz), 3.90 (3H, s), 3.65 (2H, ABq, J=18 Hz).

(31) 7-[2-(2-Thienylmethoxyimino)-2-(4-hydroxyphenyl)acetamido]-3-(1-methyl-1H-tetrazol-5-yl)thiomethyl-3-cephem-4-carboxylic acid (syn isomer), powder.

I.R. spectrum (Nujol): 3200–3300, 1780, 1720, 1660 cm$^{-1}$.

N.M.R. spectrum (d$_6$-DMSO, δ) ppm: 9.77 (1H, d, J=8 Hz), 6.7–7.7 (7H, m), 5.83 (1H, dd, J=5, 8 Hz), 5.29 (2H, s), 5.15 (1H, d, J=5 Hz), 4.3 (2H, ABq, J=13 Hz), 3.92 (3H, s), 3.72 (2H, ABq, J=18 Hz).

(32) 7-[2-Ethoxyimino-2-(3-chloro-4-hydroxyphenyl)acetamido]-3-(1-methyl-1H-tetrazol-5-yl)thiomethyl-3-cephem-4-carboxylic acid (syn isomer), colorless powder, mp 153° to 156° C. (dec.)

I.R. spectrum (Nujol) 3450, 3250, 2550–2600, 1780, 1725, 1665, 1630, 1600 cm$^{-1}$.

N.M.R. spectrum (d$_6$-DMSO,δ) ppm: 9.71 (1H, d, J=8 Hz), 7.50 (1H, d, J=2 Hz), 7.36 (1H, dd, J=2, 8 Hz), 7.03 (1H, d, J=8 Hz), 5.83 (1H, q, J=5 Hz), 5.17 (1H, d, J=5 Hz), 4.33 (2H, ABq, J=13 Hz), 4.17 (2H, q, J=7 Hz), 3.97 (3H, s), 3.73 (2H, ABq, J=18 Hz), 1.25 (3H, t, J=7 Hz).

(33) 7-[2-Allyloxyimino-2-(3-methoxyphenyl)acetamido]-3-(1-methyl-1H-tetrazol-5-yl)thiomethyl-3-cephem-4-carboxylic acid (syn isomer), powder, mp 135° to 138° C. (dec.).

I.R. spectrum (Nujol): 3300, 2600, 1785, 1730, 1670, 1645, 1600 cm$^{-1}$.

N.M.R. spectrum (d$_6$-DMSO, δ) ppm: 9.82 (1H, d, J=8 Hz), 7.0–7.45 (4H, m), 5.8–6.2 (2H, m), 5.36 (2H, t, J=10 Hz), 5.21 (1H, d, J=5 Hz), 4.72 (2H, d, J=5 Hz), 4.36 (2H, ABq, J=13 Hz), 3.95 (3H, s), 3.91 (3H, s), 3.87 (2H, ABq, J=18 Hz).

(34) 7-[2-Ethoxyimino-2-(3-hydroxyphenyl)acetamido]-3-(1-methyl-1H-tetrazol-5-yl)thiomethyl-3-cephem-4-carboxylic acid (syn isomer), yellow powder, mp 145° to 148° C. (dec.).

I.R. spectrum (Nujol): 3450, 3250, 2500–2600, 1775, 1720, 1665, 1620, 1600 cm$^{-1}$.

N.M.R. spectrum (d$_6$-DMSO, δ) ppm: 9.70 (1H, d, J=8 Hz), 6.8–7.4 (4H, m), 5.90 (1H, q, J=5 Hz), 5.20 (1H, d, J=5 Hz), 4.36 (2H, ABq, J=13 Hz), 4.20 (2H, q, J=7 Hz), 4.00 (3H, s), 3.76 (2H, ABq, J=18 Hz), 1.33 (3H, t, J=7 Hz).

(35) 7-[2-Ethoxyimino-2-(3-methoxyphenyl)acetamido]-3-(1-methyl-1H-tetrazol-5-yl)thiomethyl-3-cephem-4-carboxylic acid (syn isomer), pale yellow powder, mp 140° to 143° C. (dec.).

I.R. spectrum (Nujol): 3300, 2500–2600, 1785, 1730, 1670, 1630, 1600 cm$^{-1}$.

N.M.R. spectrum (d$_6$-DMSO, δ) ppm: 9.71 (1H, d, J=8 Hz), 6.9–7.5 (4H, m), 5.90 (1H, q, J=5 Hz), 5.17 (1H, d, J=5 Hz), 4.33 (2H, ABq, J=13 Hz), 4.20 (2H, q, J=7 Hz), 3.95 (3H, s), 3.85 (3H, s), 3.75 (2H, ABq, J=18 Hz), 1.30 (3H, t, J=7 Hz).

(36) 7-[2-Allyloxyimino-2-(3-chloro-4-methoxyphenyl)acetamido]-3-(1-methyl-1H-tetrazol-5-yl)thiomethyl-3-cephem-4-carboxylic acid (syn isomer), pale yellow powder, mp 153° to 156° C. (dec.).

I.R. spectrum (Nujol): 3250, 2600, 1780, 1720, 1670, 1645, 1630, 1600 cm$^{-1}$.

N.M.R. spectrum (d$_6$-DMSO, δ) ppm: 9.65 (1H, d, J=8 Hz), 7.27 (1H, d, J=2 Hz), 7.20 (1H, dd, J=2, 8 Hz), 7.09 (1H, d, J=8 Hz), 5.85–6.15(2H, m), 5.15 (2H, t, J=9 Hz), 5.05 (1H, d, J=5 Hz), 4.60 (2H, d, J=5 Hz), 4.15 (2H, ABq, J=13 Hz), 3.95 (3H, s), 3.90 (3H, s), 3.47 (2H, ABq, J=18 Hz).

(37) 7-[2-Phenylthiomethoxyimino-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3300, 1760, 1660, 1600, 1580, 1520 cm$^{-1}$.

N.M.R. spectrum (d$_6$-DMSO, δ) ppm: 9.7 (1H, d, J=8 Hz), 7.7–6.7 (9H, m), 5.8–5.4 (3H, broad s), 5.06 (1H, d, J=5 Hz), 4.33 (2H, broad s), 3.9 (3H, s), 3.56 (2H, broad s).

(38) 7-[2-Methoxyimino-2-(3-mesylaminophenyl)acetamido]-3-(1,3,4-thiadiazol-2-yl)thiomethyl-3-cephem-4-carboxylic acid (syn isomer), mp 155° C. (dec.).

I.R. spectrum (Nujol): 3300, 1780, 1730, 1670 cm$^{-1}$.

N.M.R. spectrum (d$_6$-DMSO, δ) ppm: 9.98 (1H, s), 9.81 (1H, d, J=9 Hz), 9.62 (1H, s), 5.90 (1H, dd, J=5,9 Hz), 5.24 (1H, d, J=5 Hz), 4.49 (2H, ABq, J=14 Hz), 3.98 (3H, s), 3.77 (2H, broad s), 2.96 (3H, s).

(39) 7-[2-Methoxyimino-2-(3-carbamoyloxyphenyl)acetamido]-3-(1-methyl-1H-tetrazol-5-yl)thiomethyl-3-cephem-4-carboxylic acid (syn isomer).

I.R. spectrum (Nujol): 3450, 3300, 3200, 1780, 1725, 1670, 1620, 1590, 1520 cm$^{-1}$.

N.M.R. spectrum (d$_6$-DMSO, δ) ppm: 9.77 (1H, d, J=7 Hz), 7.6–6.8 (6H, m), 5.83 (1H, dd, J=4, 7 Hz), 5.17 (1H, d, J=4 Hz), 4.31 (2H, ABq, J=14 Hz), 3.96 (6H, s), 3.72 (2H, broad s).

(40) 7-[2-Methoxyimino-2-(3-carbamoyloxyphenyl)acetamido]-3-(1,3,4-thiadiazol-2-yl)thiomethyl-3-cephem-4-carboxylic acid (syn isomer).

I.R. spectrum (Nujol): 3250, 1780, 1735, 1675, cm$^{-1}$.

N.M.R. spectrum (d$_6$-DMSO, δ) ppm: 9.81 (1H, d, J=8 Hz), 9.62 (1H, s), 6.7–7.58 (4H, m), 5.8 (1H, dd, J=5, 8 Hz), 5.2 (1H, d, J=5 Hz), 4.25, 4.63 (2H, ABq, J=14 Hz), 3.9 (3H, s), 3.7 (2H, broad s).

(41) 7-[2-Methoxyimino-2-(3-acetoxyphenyl)acetamido]-3-(1,3,4-thiadiazol-2-yl)thiomethyl-3-cephem-4-carboxylic acid (syn isomer).

I.R. spectrum (Nujol): 3250, 1780, 1740, 1720, 1680 cm$^{-1}$.

N.M.R. spectrum (d$_6$-DMSO, δ) ppm: 9.86 (1H, d, J=8 Hz), 9.61 (1H, s), 7.00–7.65 (4H, m), 5.84 (1H, dd, J=5, 8 Hz), 5.2 (1H, d, J=5 Hz), 4.25–4.63 (2H, ABq, J=14 Hz), 3.92 (3H, s), 3.53, 3.86 (2H, ABq, J=19 Hz), 2.3 (3H, s).

(42) 7-[2-(3-Phenylallyloxyimino)-2-(3-hydroxyphenyl)acetamido]-3-(1-methyl-1H-tetrazol-5-yl)thiomethyl-3-cephem-4-carboxylic acid (syn isomer), mp 138° to 142° C. (dec.).

I.R. spectrum (Nujol): 3300–3400, 2600, 1780, 1720, 1665, 1600 cm$^{-1}$.

N.M.R. spectrum (d$_6$-DMSO, δ) ppm: 9.80 (1H, d, J=8 Hz), 6.4–7.4 (11H, m), 5.85 (1H, dd, J=5, 8 Hz), 5.20 (1H, d, J=5 Hz), 4.83 (2H, d, J=5 Hz), 4.32 (2H, ABq, J=15 Hz), 3.95 (3H, s), 3.68 (2H, ABq, J=18 Hz).

(43) 7-[2-Methoxyimino-2-(4-dimethylaminophenyl)acetamido]-3-(1-methyl-1H-tetrazol-5-yl)thiomethyl-3-cephem-4-carboxylic acid (syn isomer), mp 88° C. (dec.).

I.R. spectrum (Nujol): 3250, 1780, 1730, 1680, 1610 cm$^{-1}$.

N.M.R. spectrum (d$_6$-DMSO, δ) ppm: 9.63 (1H, d, J=8 Hz), 7.40 (2H, d, J=8 Hz), 6.73 (2H, d, J=8 Hz), 5.83 (1H, dd, J=5, 8 Hz), 5.17 (1H, d, J=5 Hz), 4.33 (2H, ABq, J=13 Hz), 3.97 (3H, s), 3.87 (3H, s), 3.73 (2H, broad s), 3.00 (6H, s).

(44) 7-[2-Methoxyimino-2-(3-hydroxyphenyl)acetamido]-3-[1-(2-dimethylaminoethyl)-1H-tetrazol-5-yl]thiomethyl-3-cephem-4-carboxylic acid (syn isomer).

I.R. spectrum (Nujol) 1765 cm$^{-1}$.

N.M.R. spectrum (d$_6$-DMSO, δ) ppm: 9.67 (1H, d, J=9 Hz), 6.72–7.36 (4H, m), 5.78 (1H, dd, J=5, 9 Hz), 5.12 (1H, d, J=5 Hz), 4.55 (2H, broad s), 4.30 (2H, broad s), 3.90 (3H, s), 3.40–3.80 (2H, m), 3.14 (2H, broad s), 2.48 (6H, s).

(45) 7-[2-{2-(2-Hydroxyphenoxy)ethoxyimino}-2-(3-hydroxyphenyl)acetamido]-3-(1-methyl-1H-tetrazol-5-yl)thiomethyl-3-cephem-4-carboxylic acid (syn isomer).

I.R. spectrum (Nujol): 3270, 1780, 1725, 1670, 1560 cm$^{-1}$.

N.M.R. spectrum (d$_6$-DMSO, δ) ppm: 6.5–7.4 (8H, m), 5.86 (1H, dd, J=5, 8 Hz), 5.14 (1H, d, J=5 Hz), 4.0–4.6 (6H, m), 3.92 (3H, s), 3.52, 3.70 (2H, ABq, J=7 Hz).

EXAMPLE 27

A solution of 7-[2-methoxyimino-2-(2-amino-1,3-thiazol-4-yl)acetamido]-3-hydroxymethyl-3-cephem-4-carboxylic acid (syn isomer) (0.3 g) in a mixture of acetone (3 ml) and water (1.5 ml) was adjusted to pH 2 with 6N hydrochloric acid and stirred for 4 hours at ambient temperature. After the acetone was distilled off, to the residue was added water (1 ml). The mixture was adjusted to pH 7 with a saturated aqueous solution of sodium bicarbonate and ice-cooled for 1 hour. Precipitating crystals were collected by filtration, washed with water and dried to give 6-[2-methoxyimino-2-(2-amino-1,3-thiazol-4-yl)acetamido]-5a,6-dihydro-3H,7H-azeto[2,1-b]furo[3,4-d][1,3]thiazine-1,7(4H)-dione (syn isomer) (0.23 g), mp 210° to 215° C. (dec.).

I.R. spectrum (Nujol): 3270, 1780, 1740, 1655, 1610, 1525 cm$^{-1}$.

N.M.R. spectrum (d$_6$-DMSO, δ) ppm: 9.70 (1H, d, J=8 Hz), 7.26 (2H, broad s), 6.77 (1H, s), 5.93 (1H, dd, J=5, 8 Hz), 5.16 (1H, d, J=5 Hz), 5.05 (2H, broad s), 3.85 (3H, s), 3.81 (2H, broad s).

EXAMPLE 28

The following compound was obtained according to a similar manner to that of Example 27.

6-[2-methoxyimino-2-(3-hydroxyphenyl)acetamido]-5a,6-dihydro-3H,7H-azeto[2,1-b]furo[3,4-d][1,3]thiazine-1,7(4H)dione(syn isomer).

I.R. spectrum (Nujol): 3250, 1785, 1755, 1660, 1600, 1570, 1540 cm$^{-1}$.

N.M.R. spectrum (d$_6$-DMSO, δ) ppm: 9.83 (1H, d, J=8 Hz), 7.5–6.75 (4H, m), 6.02 (1H, dd, J=5, 8 Hz), 5.21 (1H, d, J=5 Hz), 5.07 (2H, broad s), 3.95 (3H, s), 3.84 (2H, broad s).

EXAMPLE 29

7-[2-Methoxyimino-2-{2-(2,2,2-trifluoroacetamido)-1,3-thiazol-4-yl}acetamido]-3-hydroxymethyl-3-cephem-4-carboxylic acid (syn isomer) (1.0 g.) was dissolved in a mixture of dimethylformamide (6 ml.) and acetone (30 ml.). Jones reagent (1.25 ml.), which was prepared from conc. sulfuric acid (0.28 ml.), chromium trioxide (0.33 g.) and water (0.9 ml.), was dropwise added thereto over 2 minutes with stirring and cooling at 0° to 2° C. After stirring for 20 minutes at the same temperature, the reaction mixture was poured into ice-water (50 ml.). After acetone was distilled off, the residue was twice extracted with ethyl acetate (50 ml.). The extracts were washed with a saturated aqueous solution of sodium chloride and dried over magnesium sulfate. The solvent was distilled off and the residue was pulverized with diisopropyl ether to give 7-[2-methoxyimino-2-{2-(2,2,2-trifluoroacetamido)-1,3-thiazol-4-yl}-acetamido]-3-formyl-3-cephem-4-carboxylic acid (syn isomer) [or this compound can be represented as 3-hydroxy-6-[2-methoxyimino-2-{2-(2,2,2-trifluoroacetamido)-1,3-thiazol-4-yl}acetamido]-5a,6-dihydro-3H,7H-azeto[2,1-b]furo[3,4-d][1,3]thiazine-1,7(4H)dione (syn isomer)] (0.56 g.).

I.R. spectrum (Nujol): 3150, 1790, 1720, 1655, 1560, 1500 cm$^{-1}$.

N.M.R. spectrum (d$_6$-DMSO, δ) ppm: 9.88 (1H, d, J=8 Hz), 7.60 (1H, s), 6.30 (1H, d, J=6 Hz), 6.05 (1H, dd, J=5,8 Hz), 5.23 (1H, d, J=5 Hz), 3.96 (3H, s), 3.80 (2H, broad s).

EXAMPLE 30

The following compounds were obtained by conducting elimination reaction of protective group of amino on carbamoyl group according to a similar manner to that of Example 3.

(1) 7-[2-Methoxyimino-2-(2-amino-1,3-thiazol-4-yl)acetamido]-3-carbamoyloxymethyl-3-cephem-4-carboxylic acid (syn isomer), mp 210° to 220° C. (dec.).

I.R. spectrum (Nujol):
3250, 1765, 1650 cm$^{-1}$.

N.M.R. spectrum (d$_6$-DMSO, δ) ppm: 9.64 (1H, d, J=8 Hz), 7.4 (2H, m), 6.79 (1H, s), 6.60 (2H, m), 5.77 (1H, dd, J=5,8 Hz), 5.16 (1H, d, J=5 Hz), 4.75 (2H, ABq, J=12 Hz), 3.87 (3H, s), 3.53 (2H, ABq, J=18 Hz).

(2) 7-[2-Methoxyimino-2-(2-formamido-1,3-thiazol-4-yl)acetamido]-3-carbamoyloxymethyl-3-cephem-4-carboxylic acid (syn isomer).

I.R. spectrum (Nujol): 3300, 1780, 1705, 1680 cm$^{-1}$.

N.M.R. spectrum (d$_6$-DMSO, δ) ppm: 12.50 (1H, broad s), 9.67 (1H, d, J=8 Hz), 8.50 (1H, s), 7.43 (1H, s), 6.58 (2H, broad s), 5.80 (1H, dd, J=5, 8 Hz), 5.16 (1H, d, J=5 Hz), 4.78 (2H, AB$_q$, J=14 Hz), 3.95 (3H, s), 3.57 (2H, AB$_q$, J=18 Hz).

Reference 1

Phosphorus pentachloride (3.3 g.) was added under ice-cooling to a suspension of 2-methoxyimino-2-(2-amino-1,3-thiazol-4-yl)acetic acid (syn isomer) (1.5 g.) in methylene chloride (30 ml.) and the mixture was stirred for 30 minutes at ambient temperature. Methylene chloride was distilled off under reduced pressure and acetone was added to the residue to give a suspension. On the other hand, a suspension of 7-amino-3-(1-methyl-1H-tetrazol-5-yl)thiomethyl-3-cephem-4-carboxylic acid (2.2 g.) in an aqueous solution of sodium bicarbonate (0.76 g. in 50 ml. of water) was stirred for 10 minutes and acetone (50 ml.) was added thereto to give a solution. To the solution was dropwise added the above obtained suspension containing acid chloride with stirring and ice-cooling and keeping the solution at pH 7.5 to 8.5 with a 20% aqueous solution of sodium carbonate. The mixture was stirred for 1 hour at 3° to 5° C. and pH 8.0. Acetone was distilled off under reduced pressure and the residue was adjusted to pH 7.4 with a saturated aqueous solution of sodium bicarbonate and further adjusted to pH 4.5 with 10% hydrochloric acid with stirring and ice-cooling. Precipitates were filtered off and the filtrate was saturated with sodium chloride, adjusted to pH 2.5 with 10% hydrochloric acid and stirred for 1 hour. Precipitates were collected by filtration, washed with water and dried to give 7-[2-methoxyimino-2-(2-amino-1,3-thiazol-4-yl)acetamido]-3-(1-methyl-1H-tetrazol-5-yl)thiomethyl-3-cephem-4-carboxylic acid (a mixture of syn and anti isomers) (0.95 g.).

I.R. spectrum (Nujol): 3400, 1775, 1710, 1670, 1630 cm$^{-1}$.

N.M.R. spectrum (d$_6$-DMSO, δ) ppm: 9.85 (1H, d, J=8 Hz), 9.50 (1H, d, J=8 Hz), 7.58 (1H, s), 6.87 (1H, s), 6.65 (4H, broad s), 5.77 (2H, m), 5.15 (2H, d, J=5 Hz), 4.35 (4H, broad s), 4.06 (6H, s), 3.97 (6H, s), 3.75 (4H, broad s).

Reference 2

A suspension of phosphorus pentachloride (1.7 g.) in methylene chloride (20 ml.) was changed to a solution by stirring for 2 hours at ambient temperature. 2-Methoxyimino-2-(2-amino-1,3-thiazol-4-yl)acetic acid (syn isomer) (0.8 g.) was added thereto at a time at ambient temperature and the mixture was stirred. Methylene chloride was distilled off under reduced pressure and the residue was dissolved in acetone (20 ml.). On the other hand, 7-amino-3-carbamoyloxymethyl-3-cephem-4-carboxylic acid (1.0 g.) was suspended in a solution of sodium bicarbonate (0.59 g.) in water (20 ml.) and dissolved by adding acetone (10 ml.). To this solution was dropwise added the above obtained solution containing acid chloride with stirring and ice-cooling and keeping the solution at pH 7.5 to 8.5 with a 20% aqueous solution of sodium carbonate. After stirring for 1 hour at pH 8 under ice-cooling, an insoluble material was filtered off. Acetone was distilled off under reduced pressure from the filtrate and an insoluble material was filtered off. The filtrate was adjusted to pH 2.5 with 10% hydrochloric acid. Precipitates were collected by filtration and dried to give 7-[2-methoxyimino-2-(2-amino-1,3-thiazol-4-yl)acetamido]-3-carbamoyloxymethyl-3-cephem-4-carboxylic acid (a mixture of syn and anti isomers) (0.4 g.). The filtrate was saturated with sodium chloride and stirred under ice-cooling to give precipitates. The precipitates were collected by filtration and dried to give the same object compound (0.3 g.). Total yield (0.7 g.).

I.R. spectrum (Nujol): 3400, 1775, 1705 cm$^{-1}$.

N.M.R. spectrum (d$_6$-DMSO, δ) ppm: 9.71 (1H, d, J=8 Hz), 9.42 (1H, d, J=8 Hz), 7.70 (1H, s), 7.40 (4H, broad s), 7.00 (1H, s), 6.61 (4H, s), 5.76 (2H, m), 5.16 (2H, d, J=4.5 Hz), 4.76 (4H, AB$_q$, J=12 Hz), 3.98 (3H, s), 3.89 (3H, s), 3.53 (4H, AB$_q$, J=18 Hz).

Reference 3

A mixture of dimethylformamide (0.22 g.) and phosphorus oxychloride (0.46 g.) was warmed for 1 hour at 40° C. The mixture was dissolved in dry methylene chloride (20 ml.) and 2-methoxyimino-2-(2-mesylimino-3-methyl-2,3-dihydro-1,3-thiazol-4-yl)acetic acid (anti isomer) (0.73 g.) was added thereto with stirring and ice-cooling, after which the resulting mixture was stirred for 1.5 hours under ice-cooling. On the other hand, 7-amino-3-(1-methyl-1H-tetrazol-5-yl)thiomethyl-3-cephem-4-carboxylic acid (0.82 g.) was dissolved in a solution of bis(trimethylsilyl)acetamide (1.5 g.) in dry methylene chloride (20 ml.). To this solution was added at −30° C. the above obtained methylene chloride solution, after which the mixture was stirred for 2 hours at −5° to −20° C. After distilling off methylene chloride at low temperature, water was added to the residue and the mixture was extracted with ethyl acetate. The extract was washed with a sodium chloride aqueous solution and water (50 ml.) was added thereto. The resulting mixture was adjusted to pH 7 with an aqueous solution of sodium bicarbonate and the aqueous layer was separated. The aqueous layer was adjusted to pH 1.5, saturated with sodium chloride and extracted with ethyl acetate. The extract was washed with a sodium chloride aqueous solution and dried over magnesium sulfate. The solvent was distilled off and the residue was pulverized by a mixture of diisopropyl ether and ether. The powder was collected by filtration and dried to give 7-[2-methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylic acid (anti isomer) (1.0 g.). This powder (1.0 g.) was suspended in water (30 ml.) and dissolved by adjusting to pH 6 by an aqueous solution of sodium bicarbonate. After removing the solvent by bubbling of nitrogen gas, the aqueous solution was lyophilized to give sodium 7-[2-methoxyimino-2-(2-mesylimino-3-methyl-2,3-dihydro-1,3-thiazol-4-yl)acetamido]-3-(1-methyl-1H-tetrazol-5-yl)thiomethyl-3-cephem-4-carboxylate (anti isomer) (0.98 g.).

I.R. spectrum (KBr): 1760, 1675 cm$^{-1}$.

N.M.R. spectrum (D$_2$O, δ) ppm: 8.05 (1H, s), 5.76 (1H, d, J=5 Hz), 5.16 (1H, d, J=5 Hz), 4.14 (2H, AB$_q$, J=13 Hz), 4.10 (3H, s), 4.02 (3H, s), 3.52 (2H, AB$_q$, J=17 Hz), 3.45 (3H, s), 3.24 (3H, s).

Reference 4

The following compounds were obtained according to a similar manner to that of Reference 3.

(1) 7-[2-Methoxyimino-2-(2-methyl-1,3-thiazol-4-yl)acetamido]-3-(1-methyl-1H-tetrazol-5-yl)thiomethyl-3-cephem-4-carboxylic acid (anti isomer).

I.R. spectrum (Nujol): 1790, 1720, 1680 cm$^{-1}$.

N.M.R. spectrum (d$_6$-DMSO, δ) ppm: 9.53 (1H, d, J=8 Hz), 8.27 (1H, s), 5.83 (1H, dd, J=5.5, 8 Hz), 5.15 (1H, d, J=5.5 Hz), 4.30 (2H, AB$_q$, J=14 Hz), 4.00 (3H, s), 3.93 (3H, s), 3.70 (2H, AB$_q$, J=16 Hz), 2.65 (3H, s).

(2) 7-[2-Methoxyimino-2-(2-amino-1,3-thiazol-4-yl)acetamido]-3-(1-methyl-1H-tetrazol-5-yl)thiomethyl-3-cephem-4-carboxylic acid (anti isomer).

I.R. spectrum (Nujol): 3400, 1775, 1670 cm$^{-1}$.

N.M.R. spectrum (d$_6$-DMSO, δ) ppm: 9.44 (1H, d, J=8 Hz), 7.71 (1H, s), 6.40 (2H, broad s), 5.77 (1H, dd, J=5, 8 Hz), 5.13 (1H, d, J=5 Hz), 4.31 (2H, broad s), 4.00 (3H, s), 3.95 (3H, s), 3.95 (3H, s), 3.70 (2H, broad s).

(3) 7-[2-Methoxyimino-2-(2-amino-1,3-thiazol-4-yl)acetamido]cephalosporanic acid (anti isomer).

I.R. spectrum (Nujol): 3400-3100, 1780, 1730, 1675 cm$^{-1}$.

N.M.R. spectrum (d$_6$-DMSO, δ) ppm: 9.43 (1H, d, J=8 Hz), 9.16 (2H, broad s), 7.73 (1H, s), 5.82 (1H, dd, J=5, 8 Hz), 5.18 (1H, d, J=5 Hz), 4.90 (2H, AB$_q$, J=13 Hz), 4.03 (3H, s), 3.60 (2H, broad s), 2.07 (3H, s).

(4) 7-[2-Methoxyimino-2-(2-formamido-1,3-thiazol-4-yl)acetamido]-3-(1,3,4-thiadiazol-2-yl)thiomethyl-3-cephem-4-carboxylic acid (anti isomer), mp 152° C. (dec.).

I.R. spectrum (Nujol): 3300-3100, 1775, 1720, 1670, 1630 cm$^{-1}$.

N.M.R. spectrum (d6-DMSO, δ) ppm: 12.63 (1H, broad s), 9.66 (1H, s), 9.57 (1H, d, J=8 Hz), 8.50 (1H, s), 8.07 (1H, s), 5.75 (1H, dd, J=5, 8 Hz), 5.15 (1H, d, J=5 Hz), 4.27 (2H, Ab$_q$, J=13 Hz), 4.00 (3H, s), 3.70 (2H, broad s).

(5) 7-[2-Methoxyimino-2-(3-hydroxyphenyl)acetamido]-3-(1-methyl-1H-tetrazol-5-yl)thiomethyl-3-cephem-4-carboxylic acid (anti isomer).

I.R. spectrum (Nujol): 3350, 1780, 1726, 1680 cm$^{-1}$.

N.M.R. spectrum (d$_6$-DMSO, δ) ppm: 9.24 (1H, d, J=8 Hz), $\left.\begin{array}{l} 7.36-7.10 \\ 7.00-6.74 \end{array}\right\}$ (4H, m)

5.70 (1H, dd, J=5, 8 Hz), 5.13 (1H, d, J=5 Hz), 4.34 (2H, AB$_q$, J=13 Hz), 3.95 (6H, s), 3.72 (2H, AB$_q$, J=17 Hz).

Preparation of the starting compounds to be used for the Examples and References

Preparation 1

A mixture of 3-chloro-4-hydroxyacetophenone (11.9 g.), benzyl chloride (9.35 g.), potassium carbonate (14.5 g.) and dimethylformamide (60 ml.) was stirred for 1 hour at 100° C. The reaction mixture was poured into water (150 ml.) and extracted with ethyl acetate. The extract was washed with a sodium chloride aqueous solution and dried over magnesium sulfate. After distilling off the solvent, the residue (18 g.) was recrystallized from ethanol (160 ml.) to give 3-chloro-4-benzyloxyacetophenone (13.2 g.), mp 110° to 112° C.

Preparation 2

(1) Selenium dioxide powder (12.6 g.) was added over 10 minutes to a solution of 3-chloro-4-benzyloxyacetophenone (19.7 g.) in dry pyridine (100 ml.) with stirring at 100° C., and the mixture was stirred for 3 hours at the same temperature. Precipitating selenium was filtered off and the filtrate was concentrated. The residue was dissolved in water (150 ml.) and the solution was washed with ether. The aqueous solution was acidified under cooling with conc. hydrochloric acid and extracted with ether. The extract was washed with a sodium chloride aqueous solution, dried over magnesium sulfate and concentrated to give 2-(3-chloro-4-benzyloxyphenyl)glyoxylic acid (15.9 g.), mp 134° to 135° C.

(2) The following compounds were obtained according to a similar manner to that of Preparation 2-1).

(1) 2-(3-Nitro-4-benzyloxyphenyl)glyoxylic acid, mp 161° to 164° C.

(2) 2-(3-Chloro-4-methoxyphenyl)glyoxylic acid, mp 81° to 82° C.

I.R. spectrum (Nujol): 2500-2600, 1715, 1670, 1600 cm$^{-1}$.

(3) 2-(3-Mesylaminophenyl)glyoxylic acid, mp 66° to 68° C.

I.R. spectrum (Nujol): 3560, 3250, 1720, 1670 cm$^{-1}$.

Preparation 3

(1) A mixture of 2-(3-nitro-4-benzyloxyphenyl)glyoxylic acid (30 g.), conc. hydrochloric acid (90 ml.) and acetic acid (120 ml.) was stirred for 3 hours at 100° C. To the reaction mixture was added under cooling ice-water (600 ml.) and the mixture was extracted with ethyl acetate. The extract was washed with ice-water, dried over magnesium sulfate and concentrated to dryness under reduced pressure. The residue was recrystallized from a mixture of benzene:ether:petroleum ether (2:1:4). The crystals were collected by filtration, washed with benzene and dried under reduced pressure to give 2-(3-nitro-4-hydroxyphenyl)glyoxylic acid (19.0 g.), mp 139° to 140.5° C.

(2) The following compound was obtained according to a similar manner to that of Preparation 3-1).

(1) 2-(3-Chloro-4-hydroxyphenyl)glyoxylic acid, mp 114° to 116° C.

Preparation 4

2-(3-Hydroxyphenyl)glyoxylic acid (3.32 g.) and 1N-methanol solution of hydroxylamine (45 ml.) were refluxed with stirring for 25 minutes. The reaction mixture was concentrated under reduced pressure. The residue was dissolved in 1N-aqueous solution of sodium hydroxide (70 ml.). An aqueous solution was washed with ether, acidified with dil. hydrochloric acid and then extracted with ethyl acetate. The extract was washed, dried and treated with an activated charcoal. The solvent was distilled off to give 2-hydroxyimino-2-(3-hydroxyphenyl)acetic acid (a mixture of syn and anti isomers) (2.9 g.).

I.R. spectrum (Nujol): 3200, 1700 cm$^{-1}$.

Preparation 5

(1)(a) Phenolphthalein indicator (3 drops) was added to a solution of O-methylhydroxylamine hydrocloride (5.5 g.) in dry methanol (60 ml.). To the solution was dropwise added with stirring at ambient temperature 1N methanol solution of sodium methoxide (65 ml.)

until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, 2-(3-hydroxyphenyl)-glyoxylic acid (9.85 g.) was added to the filtrate and the mixture was refluxed for 30 minutes. After methanol was distilled off at low temperature, a saturated sodium chloride aqueous solution was added to the residue. The mixture was adjusted to pH 1 with 10% hydrochloric acid and extracted with ether (300 ml.). The extract was dried over magnesium sulfate. Ether was distilled off at low temperature to give 2-methoxyimino-2-(3-hydroxyphenyl)acetic acid (a mixture of syn and anti isomers).

(b) This material was dissolved in ether (60 ml.) and a solution of diazomethane in ether was gradually added thereto under ice-cooling until the color of the mixture was changed to yellow. Acetic acid was immediately added thereto and the mixture was washed with a sodium bicarbonate aqueous solution and a saturated sodium chloride aqueous solution and dried over magnesium sulfate. Ether was distilled off to give oily residue (10.8 g.). The oily residue was subjected to column chromatography on silica gel (165 g.) using a mixture of benzene and ethyl acetate (9:1) as developing solvent. Firstly the eluate containing syn isomer was eluted and the eluate was collected and concentrated to give oily methyl 2-methoxyimino-2-(3-hydroxyphenyl)acetate (syn isomer) (7.9 g.). The oil was allowed to stand to give crystals, mp 39.5° to 40.5° C.

I.R. spectrum (Nujol): 3450, 1730 cm$^{-1}$.

N.M.R. spectrum (CDCl$_3$, δ) ppm: 6.7–7.42 (4H, m), 3.98 (3H, s), 3.92 (3H, s), After the eluate containing syn isomer was eluted, then the eluate containing anti isomer was eluted. The eluate was collected and concentrated to give methyl 2-methoxyimino-2-(3-hydroxyphenyl)acetate (anti isomer) (1.5 g.). This material was recrystallized from a mixture of benzene and petroleum ether to give crystals, mp 96° to 98° C.

I.R. spectrum (Nujol): 3350, 1715 cm$^{-1}$.

N.M.R. spectrum (CDCl$_3$, δ) ppm: 7.12–7.40 (1H, m), 6.96–7.02 (3H, m), 3.99 (3H, s), 3.84 (3H, s).

(c) A 2N aqueous solution of sodium hydroxide (40 ml.) was added with stirring at ambient temperature to a suspension of methyl 2-methoxyimino-2-(3-hydroxyphenyl)acetate (syn isomer) (7.55 g.) in water (70 ml.) and the mixture was stirred for 1 hour at ambient temperature. The reaction mixture was adjusted to pH 6.5 with 10% hydrochloric acid, subjected to salting-out and washed with ether (60 ml.). The aqueous layer was adjusted to pH 1 with conc. hydrochloric acid and extracted once with 100 ml. of and twice with 60 ml. of ether. The extract was washed twice with a saturated sodium chloride aqueous solution (60 ml.) and dried over magnesium sulfate. Ether was distilled off to give oil. Benzene was added thereto and removed (twice) to give crystals of 2-methoxyimino-2-(3-hydroxyphenyl)acetic acid (syn isomer) (6.44 g.), mp 98° to 101° C. (dec.).

I.R. spectrum (Nujol): 3370, 1720 cm$^{-1}$.

An aqueous solution of 2N sodium hydroxide (8 ml.) was added with stirring at ambient temperature to a solution of methyl 2-methoxyimino-2-(3-hydroxyphenyl)acetate (anti isomer) (1.56 g.) in methanol (30 ml). After stirring for 3 hours at the same temperature, methanol was distilled off. To the residue was added water and the mixture was washed with ether. The aqueous layer was adjusted to pH 1 with 10% hydrochloric acid, subjected to salting-out and extracted with ether. The extract was washed with a sodium chloride aqueous solution and dried over magnesium sulfate. Ether was distilled off to give crystals of 2-methoxyimino-2-(3-hydroxyphenyl)acetic acid (anti isomer) (1.07 g.). The crystals were recrystallized from a mixture of petroleum ether and ether to give crystals (0.7 g.), mp 99° to 101° C. (dec.).

I.R. spectrum (Nujol): 3350, 1690 cm$^{-1}$.

(2)(a) Phenolphthalein indicator (3 drops) were added to a solution of O-methylhydroxylamine hydrochloride (3.7 g.) in dry methanol (45 ml.). To the solution was dropwise added with stirring at ambient temperature 1N methanol solution of sodium methoxide (39 ml.) until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, 2-(4-hydroxyphenyl)glyoxylic acid (6.56 g.) was added to the filtrate and the mixture was stirred for 1 hour at ambient temperature. After methanol was distilled off at low temperature, a saturated sodium chloride aqueous solution was added to the residue. The mixture was adjusted to pH 1 with 10% hydrochloric acid, subjected to salting-out and extracted with ether. The extract was dried over magnesium sulfate. Ether was distilled off at low temperature to give 2-methoxyimino-2-(4-hydroxyphenyl)acetic acid (syn isomer).

(b) This material was dissolved in ether (50 ml.) and a solution of diazomethane in ether was gradually added thereto under ice-cooling until the color of the mixture was changed to yellow. Acetic acid was immediately added thereto and the mixture was washed with a sodium bicarbonate aqueous solution and a saturated sodium chloride aqueous solution and dried over magnesium sulfate. Ether was distilled off to give oily residue (8 g.). The oily residue was subjected to column chromatography on silica gel using a mixture of benzene and ethyl acetate (9:1) as developing solvent to give methyl 2-methoxyimino-2-(4-hydroxyphenyl)acetate (syn isomer) (6.39 g.).

I.R. spectrum (Nujol): 3350, 1720 cm$^{-1}$.

N.M.R. spectrum (CDCl$_3$, δ) ppm: 7.40 (2H, d, J=8 Hz), 6.80 (2H, d, J=8 Hz), 3.96 (3H, s), 3.92 (3H, s).

(c) A 2N aqueous solution of sodium hydroxide (11 ml.) was added with stirring at ambient temperature to a solution of methyl 2-methoxyimino-2-(4-hydroxyphenyl)acetate (syn isomer) (2.1 g.) in methanol (30 ml.) and the mixture was stirred for 18 hours at ambient temperature. The reaction mixture was adjusted to pH 7 with 10% hydrochloric acid and methanol was removed. To the residue was added water and the mixture was washed with ether. The aqueous layer was adjusted to pH 1 with 10% hydrochloric acid, subjected to salting out and extracted with ethyl acetate. The extract was washed with a saturated sodium chloride aqueous solution and dried over magnesium sulfate. Ethyl acetate was distilled off to give crystals of 2-methoxyimino-2-(4-hydroxyphenyl)acetic acid (syn isomer) (1.5 g.).

I.R. spectrum (Nujol): 3150, 1700 cm$^{-1}$.

(3)(a) Phenolphthalein indicator (2 drops) was added to a solution of O-methylhydroxylamine hydrochloride (2.74 g.) in dry methanol (30 ml.). To the solution was dropwise added with stirring at ambient temperature 1N methanol solution of sodium methoxide until the color of the solution was changed to purplish red. O-Methylhydroxylamine hydrochloride was added thereto by small portions until the solution was changed to colorless solution. The mixture was stirred for 1 hour at ambient temperature. After precipitating sodium chloride was filtered off, 2-(3-nitro-4-hydroxyphenyl)-glyoxylic acid (6.75 g.) was added to the filtrate and the mixture was stirred for 1 hour at ambient temperature. After methanol was distilled off at 35° C., a saturated sodium chloride aqueous solution was added to the residue. The mixture was adjusted to pH 1 with 10% hydrochloric acid and extracted with ether. The extract was dried over magnesium sulfate. Ether was distilled off at 35° C. under reduced pressure to give yellow crystals of 2-methoxyimino-2-(3-nitro-4-hydroxyphenyl)acetic acid (a mixture of syn and anti isomers) (7 g.).

(b) This material was dissolved in a mixture of tetrahydrofuran (15 ml.) and ether (100 ml.) and a solution of diazomethane in ether was gradually added thereto at ambient temperature until the color of the mixture was changed to yellow. Acetic acid was immediately added thereto and the mixture was concentrated to dryness at 35° C. under reduced pressure. The residue was disolved in a mixed solvent of ethyl acetate and benzene (1:9) and subjected to column chromatography on silica gel using the same mixed solvent as developing solvent. The eluate containing syn isomer was collected and concentrated to give methyl 2-methoxyimino-2-(3-nitro-4-hydroxyphenyl)acetate (syn isomer) (3.7 g.), mp 93° to 95° C.

I.R. spectrum (Nujol): 3300, 1745, 1630, 1535, 1350 cm$^{-1}$.

N.M.R. spectrum (CDCl$_3$, δ) ppm: 10.87 (1H, s), 8.22 (1H, d, J=2 Hz), 7.86 (1H, dd, J=2,8 Hz), 7.20 (1H, d, J=8 Hz), 4.03 (3H, s), 3.95 (3H, s).

(c) A 2N aqueous solution of sodium hydroxide (14 ml.) was added with stirring at ambient temperature to a solution of methyl 2-methoxyimino-2-(3-nitro-4-hydroxyphenyl)acetate (syn isomer) (3.5 g.) in methanol (70 ml.) and the mixture was stirred for 60 hours at ambient temperature. The reaction mixture was concentrated to dryness at 40° C. under reduced pressure and the residue was dissolved in water. The solution was washed with ethyl acetate, adjusted to pH 1 with 10% hydrochloric acid under ice-cooling and extracted with ethyl acetate. The extract was back-extracted with a saturated sodium bicarbonate aqueous solution. The aqueous extract was adjusted to pH 1 with conc. hydrochloric acid under ice-cooling and extracted with ethyl acetate. The extract was washed with ice-water and dried over magnesium sulfate. The solvent was concentrated to dryness at 40° C. under reduced pressure to give yellow crystals of 2-methoxyimino-2-(3-nitro-4-hydroxyphenyl)acetic acid (syn isomer) (3.2 g.), mp 142° to 143° C. (dec.).

I.R. spectrum (Nujol): 3300, 2500-2600, 1710, 1630, 1600, 1535, 1375 cm$^{-1}$.

N.M.R. spectrum (CDCl$_3$, δ) ppm: 10.67 (2H, s), 8.33 (1H, d, J=2 Hz), 7.95 (1H, dd, J=2, 8 Hz), 7.22 (1H, d, J=8 Hz), 4.13 (3H, s).

(4)(a) 2-(3-Chloro-4-hydroxyphenyl)glyoxylic acid (6.45 g.) and O-methylhydroxylamine hydrochloride (2.74 g.) were reacted according to a similar manner to that of Preparation 5-(3)(a) to give oil of 2-methoxyimino-2-(3-chloro-4-hydroxyphenyl)acetic acid (a mixture of syn and anti isomers) (7 g.).

(b) 2-Methoxyimino-2-(3-chloro-4-hydroxyphenyl)acetic acid (a mixture of syn and anti isomers) (7 g.) and diazomethane (1.5 g.) were reacted and the product was purified by column chromatography according to a similar manner to that of Preparation 5-(3)(b) to give crystals of methyl 2-methoxyimino-2-(3-chloro-4-hydroxyphenyl)acetate (syn isomer) (3.0 g.).

I.R. spectrum (Film): 3450, 1735, 1605, 1600 cm$^{-1}$.

N.M.R. spectrum (CDCl$_3$, δ) ppm: 7.55 (1H, d, J=2 Hz), 7.37 (1H, dd, J=2,8 Hz), 6.95 (1H, d, J=8 Hz), 6.12 (1H, s), 3.97 (3H, s), 3.91 (3H, s).

(c) Methyl 2-methoxyimino-2-(3-chloro-4-hydroxyphenyl)acetate (syn isomer) (2.6 g.) and a 2N aqueous solution of sodium hydroxide (10.6 ml.) were treated according to a similar manner to that of Preparation 5-(3)(c) to give 2-methoxyimino-2-(3-chloro-4-hydroxyphenyl)acetic acid (syn isomer) (2.4 g.), mp 147° to 150° C. (dec.).

I.R. spectrum (Nujol): 3500, 2500-2600, 1745, 1610, 1600 cm$^{-1}$.

N.M.R. spectrum (CDCl$_3$, δ) ppm: 8.40 (2H, broad s), 7.65 (1H, d, J=2 Hz), 7.40 (1H, dd, J=2,8 Hz), 7.00 (1H, d, J=8 Hz), 4.07 (3H, s).

(5) 2-(3-Hydroxyphenyl)glyoxylic acid (2.0 g.) and O-allylhydroxylamine hydrochloride (1.7 g.) were reacted according to a similar manner to that of Preparation 5-(2)(a) to give oil of 2-allyloxyimino-2-(3-hydroxyphenyl)acetic acid (syn isomer) (2.7 g.).

I.R. spectrum (Film): 3350, 2550-2600, 1720, 1645, 1600 cm$^{-1}$.

(6) 2-(3-Chloro-4-hydroxyphenyl)glyoxylic acid (2 g.) and O-allylhydroxylamine hydrochloride (1.1 g.) were reacted according to a similar manner to that of Preparation 5-(2)(a) to give oil of 2-allyloxyimino-2-(3-chloro-4-hydroxyphenyl)acetic acid (syn isomer) (2.5 g.).

I.R. spectrum (Film): 3450, 2600, 1730, 1700, 1650, 1610, 1600 cm$^{-1}$.

N.M.R. spectrum (d$_6$-DMSO, δ) ppm: 9.5-10.5 (2H, broad s), 7.52 (1H, d, J=2 Hz), 7.42 (1H, dd, J=2,8 Hz), 7.12 (1H, d, J=8 Hz), 6.0 (1H, m), 5.40 (2H, t, J=8 Hz), 4.70 (2H, d, J=5 Hz).

(7) A mixture of 2-(3-chloro-4-hydroxyphenyl)-glyoxylic acid (2.0 g.), O-t-butoxycarbonylmethylhydroxylamine (1.62 g.) and methanol (20 ml.) was adjusted to pH 5 to 6 by adding an 1N methanol solution of sodium methoxide and stirred for 3 hours at ambient temperature. The reaction mixture was concentrated to dryness under reduced pressure and the residue was dissolved in an 1N aqueous solution of sodium hydroxide to adjust to pH 7.0. The aqueous solution was washed with ether, adjusted to pH 2.0 with 10% hydrochloric acid under ice-cooling and extracted with ether. The extract was washed with water and dried over magnesium sulfate. The solution was concentrated to dryness under reduced pressure to give crystals of 2-t-butoxycarbonylmethoxyimino-2-(3-chloro-4-hydroxyphenyl)acetic acid (syn isomer) (2.6 g.), mp 116° to 118° C. (dec.).

I.R. spectrum (Nujol): 3250, 2600, 1735, 1690, 1670, 1610, 1590 cm$^{-1}$.

N.M.R. spectrum (d$_6$-DMSO, δ) ppm: 11.00 (2H, broad s), 7.50 (1H, d, J=2 Hz), 7.40 (1H, dd, J=2,8 Hz), 7.08 (1H, d, J=8 Hz), 4.68 (2H, s), 1.45 (9H, s).

(8)(a) Potassium carbonate (49.7 g.) and dimethyl sulfate (45.4 g.) were added to a solution of 2-hydroxyimino-2-(3-hydroxyphenyl)acetic acid (a mixture of syn and anti isomers) (18.1 g.) in dry acetone (250 ml.)

and the mixture was refluxed with stirring for 8.5 hours. After acetone was distilled off, the residue was dissolved in water and extracted with ethyl acetate. The extract was washed with a sodium chloride aqueous solution and dried over magnesium sulfate. The solvent was distilled off to give oil (24 g.). The oil was subjected to column chromatography on silica gel using benzene as developing solvent. Firstly the eluate containing syn isomer was eluted and the eluate was collected and concentrated to give oil of methyl 2-methoxyimino-2-(3-methoxyphenyl)acetate (syn isomer) (9.2 g.).

I.R. spectrum (Film): 1738 cm$^{-1}$.

N.M.R. spectrum (CDCl$_3$, δ) ppm: 7.47–6.77 (4H, m), 4.00 (3H, s), 3.92 (3H, s), 3.82 (3H, s).

After the eluate containing syn isomer was eluted, then the eluate containing anti isomer was eluted. The eluate was collected and concentrated to give methyl 2-methoxyimino-2-(3-methoxyphenyl)acetate (anti isomer) (3.9 g.), mp 66° to 68° C. This substance was recrystallized from petroleum ether to give prisms, mp 65° to 65.5° C.

I.R. spectrum (Nujol): 1720 cm$^{-1}$.

N.M.R. spectrum (CDCl$_3$, δ) ppm: 7.14–7.44 (1H, m), 6.80–7.04 (3H, m), 4.02 (3H, s), 3.84 (3H, s), 3.76 (3H, s).

(b) Methyl 2-methoxyimino-2-(3-methoxyphenyl)acetate (syn isomer) (1.6 g.) and a 2N aqueous solution of sodium hydroxide (4 ml.) were treated according to a similar manner to that of Preparation 5-(3)(c) to give oil of 2-methoxyimino-2-(3-methoxyphenyl)acetic acid (syn isomer) (1.23 g.).

I.R. spectrum (Film): 1735 cm$^{-1}$.

Methyl 2-methoxyimino-2-(3-methoxyphenyl)acetate (anti isomer) (1.6 g.) and a 2N aqueous solution of sodium hydroxide (4 ml.) were treated according to a similar manner to that of Preparation 5-(3)(c) to give colorless prisms of 2-methoxyimino-2-(3-methoxyphenyl)acetic acid (anti isomer) (1.3 g.), mp 97° to 98° C.

I.R. spectrum (Nujol): 1695 cm$^{-1}$.

(9)(a) A solution of diazomethane in ether was added at ambient temperature to a solution of 2-methoxyimino-2-(3-chloro-4-hydroxyphenyl)acetic acid (syn isomer) (7 g.) in dry ether (50 ml.) until the color of the mixture was changed to yellow. Acetic acid was immediately added thereto and the reaction mixture was concentrated to dryness at 35° C. under reduced pressure. The residue was subjected to column chromatography on silica gel (120 g.) using a mixture of benzene and ethyl acetate (9:1) as a developing solvent. The first eluate was collected and concentrated at 40° C. under reduced pressure to give oil of methyl 2-methoxyimino-2-(3-chloro-4-methoxyphenyl)acetate (syn isomer) (3.1 g.).

I.R. spectrum (Film): 2850, 1735, 1610, 1600, 1250 cm$^{-1}$.

N.M.R. spectrum (CDCl$_3$, δ) ppm: 7.57 (1H, d, J=2 Hz), 7.37 (1H, dd, J=2,8 Hz), 6.87 (1H, d, J=8 Hz), 3.97 (3H, s), 3.91 (3H, s), 3.88 (3H, s).

(b) Methyl 2-methoxyimino-2-(3-chloro-4-methoxyphenyl)acetate (syn isomer) (2.7 g.) and a 2N aqueous solution of sodium hydroxide (10.6 ml.) were treated according to a similar manner to that of Preparation 5-(3)(c) to give crystals of 2-methoxyimino-2-(3-chloro-4-methoxyphenyl)acetic acid (syn isomer) (2.6 g.), mp 133° to 135° C. (dec.).

I.R. spectrum (Nujol): 2500–2600, 1745, 1610, 1600 cm$^{-1}$.

N.M.R. spectrum (CDCl$_3$, δ) ppm: 9.95 (1H, broad s), 7.72 (1H, d, J=2 Hz), 7.50 (1H, dd, J=2,8 Hz), 6.92 (1H, d, J=8 Hz), 4.08 (3H, s), 3.95 (3H, s).

(10)(a) A solution of 2-bromopropionyl bromide (25 g.) in dry chloroform (50 ml.) was dropwise added with stirring and ice-cooling to a solution of N,N-dimethylaniline (24 g.) in t-butanol (11 g.) and the mixture was refluxed for 2 hours. After cooling, the reaction mixture was poured into 6N sulfuric acid (150 ml.) and extracted with ether. The extract was in turn washed with 6N sulfuric acid, water, a 10% potassium carbonate aqueous solution and water and dried over magnesium sulfate. The solvent was distilled off to give oil of t-butyl 2-bromopropionate (21 g.).

(b) This oil (21 g.) was added with stirring at ambient temperature to a mixture of N-hydroxyphthalimide (16.3 g.), triethylamine (24 g.), dimethylformamide (20 ml.) and dimethylsulfoxide (20 ml.) and the resulting mixture was stirred for 4 hours at ambient temperature. The reaction mixture was poured into water (800 ml.) and precipitating materials were collected by filtration, washed with water and dried to give t-butyl 2-phthalimidoxypropionate (22.7 g.).

(c) This compound (22.7 g.) was dissolved in methylene chloride (200 ml.). A solution of 10% hydrazine hydrate (9 ml.) in methanol (20 ml.) was added thereto and the mixture was stirred for 2 hours at ambient temperature. Precipitating materials were dissolved by adding 5N aqueous solution of ammonia and the aqueous layer was extracted with methylene chloride. Two methylene chloride layers were combined and dried over magnesium sulfate. The solvent was distilled off under reduced pressure to give oil of O-(1-t-butoxycarbonylethyl)hydroxylamine (13.5 g.).

I.R. spectrum (Film): 3350, 3250, 1745 cm$^{-1}$.

(d) 2-(3-Chloro-4-hydroxyphenyl)glyoxylic acid (2.0 g.) and O-(1-t-butoxycarbonylethyl)hydroxylamine (3.2 g.) were reacted according to a similar manner to that of Preparation 5-(7) to give 2-(1-t-butoxycarbonylethoxyimino)-2-(3-chloro-4-hydroxyphenyl)acetic acid (syn isomer) (3.3 g.), mp 148° to 151° C.

I.R. spectrum (Nujol): 3450, 2500–2600, 1725, 1690, 1620, 1600 cm$^{-1}$.

N.M.R. spectrum (d$_6$-DMSO, δ) ppm: 7.46 (1H, d, J=2 Hz), 7.33 (1H, dd, J=2,8 Hz), 7.07 (1H, d, J=8 Hz), 4.67 (1H, q, J=6 Hz), 1.50 (12H, s).

(11) Phenolphthalein indicator (3 drops) was added to a solution of O-methylhydroxylamine hydrochloride (8.8 g.) in dry methanol (60 ml.). To the solution was dropwise added with stirring at ambient temperature 1N methanol solution of sodium methoxide (105 ml.) until the color of the solution was changed to pale pink. O-Methylhydroxylamine hydrochloride was added thereto by small portions until the solution was changed to colorless solution. The pH value of the solution was 8.0 to 8.5. The mixture was stirred for 30 minutes at ambient temperature. After precipitating sodium chloride was filtered off, 2-(3-hydroxyphenyl)glyoxylic acid (16.6 g.) was added to the filtrate and the mixture was stirred for 1 hour at ambient temperature. After methanol was distilled off at low temperature, water was added to the residue. The mixture was adjusted to pH 7 with an aqueous solution of sodium bicarbonate, washed with ether, adjusted to pH 1 with 10% hydrochloric acid, subjected to salting-out and extracted with ether. The extract was washed with a saturated sodium chloride aqueous solution and dried over magnesium sulfate. Ether was distilled off and the operation that benzene was added to the residue and distilled off was repeated twice to give crystals of 2-methoxyimino-2-(3-hydroxyphenyl)acetic acid (syn isomer) (14.8 g.). This compound was identified with the compound obtained in Preparation 5-(1)(c) by I.R. spectrum.

(12) A solution of 2-(3-methoxyphenyl)glyoxylic acid (1.8 g.) in an aqueous solution of sodium bicarbonate was adjusted to pH 7.0. On the other hand, a solution of O-ethylhydroxylamine hydrochloride (1.4 g.) in water (20 ml.) was adjusted to pH 7.0 with sodium bicarbonate. Two solutions were combined together, adjusted to pH 5.5 with 10% hydrochloric acid and stirred overnight at ambient temperature. The reaction mixture was adjusted to pH 7.5 with sodium bicarbonate and washed with ethyl acetate. The aqueous layer was adjusted to pH 1.0 with conc. hydrochloric acid under ice-cooling and extracted with ethyl acetate. The extract was washed with ice-water and dried over magnesium sulfate. The solvent was distilled off under reduced pressure to give oil of 2-ethoxyimino-2-(3-methoxyphenyl)acetic acid (syn isomer) (2.2 g.).

I.R. spectrum (Film): 2600, 1735, 1700, 1610, 1600 cm$^{-1}$.

(13) The following compounds were obtained according to similar manners to those of Preparation 5-(5) to 5-(7) and 5-(10) to 5-(12).

(1) 2-Ethoxyimino-2-(3-chloro-4-hydroxyphenyl)acetic acid (syn isomer), oil.

I.R. spectrum (Film): 3450, 2250–2600, 1700–1720, 1610, 1600 cm$^{-1}$.

(2) 2-Ethoxyimino-2-(3-hydroxyphenyl)acetic acid (syn isomer) oil.

I.R. spectrum (Film): 3400, 2600, 1700–1730, 1605, 1600 cm$^{-1}$.

(3) 2-(3-Hydroxy-4-bromobenzyloxyimino)-2-(4-hydroxyphenyl)acetic acid (syn isomer), colorless powder.

I.R. spectrum (Nujol): 3500, 3200, 1700 cm$^{-1}$.

N.M.R. spectrum (d$_6$-acetone, δ) ppm: 6.68–8.05 (7H, m), 5.15 (2H, s).

(4) 2-(2-Thienylmethoxyimino)-2-(4-hydroxyphenyl)acetic acid (syn isomer), powder.

I.R. spectrum (Nujol): 1705 cm$^{-1}$.

N.M.R. spectrum (d$_6$-DMSO, δ) ppm: 6.7–7.7 (7H, m), 5.28 (2H, s).

(5) 2-Allyloxyimino-2-(3-methoxyphenyl)acetic acid (syn isomer), oil.

I.R. spectrum (Film): 3050–3100, 2600, 1730, 1645, 1610, 1600 cm$^{-1}$.

N.M.R. spectrum (d$_6$-DMSO, δ) ppm: 7.00–7.50 (4H, m), 5.80–6.30 (1H, m), 5.33 (2H, t, J=9 Hz), 4.70 (2H, d, J=5 Hz), 3.82 (3H, s).

(6) 2-Allyloxyimino-2-(3-chloro-4-methoxyphenyl)acetic acid (syn isomer), pale yellow oil.

I.R. spectrum (Film): 3100, 2600, 1710–1730, 1645, 1610, 1600 cm$^{-1}$.

N.M.R. spectrum (d$_6$-DMSO, δ) ppm: 7.63 (1H, d, J=2 Hz), 7.50 (1H, dd, J=2,8 Hz), 7.23 (1H, d, J=8 Hz), 5.9–6.3 (1H, m), 5.33 (2H, t, J=9 Hz), 4.73 (2H, d, J=5 Hz), 3.91 (3H, s).

(7) 2-Phenylthiomethoxyimino-2-(3-hydroxyphenyl)acetic acid (syn isomer), oil.

I.R. spectrum (Film): 3300, 1730 cm$^{-1}$.

N.M.R. spectrum (CDCl$_3$, δ) ppm: 6.8–7.7 (9H, m), 5.54 (2H, s).

(8) 2-Methoxyimino-2-(3-mesylaminophenyl) acetic acid (syn isomer), mp 128° C. (dec.).

I.R. spectrum (Nujol): 3300, 1740 cm$^{-1}$.

(9) 2-(3-Phenylallyloxyimino)-2-(3-hydroxyphenyl)acetic acid (syn isomer), mp 115° to 116° C.

I.R. spectrum (Nujol): 3400, 1725 cm$^{-1}$.

(10) 2-Methoxyimino-2-(4-dimethylamino-phenyl)acetic acid (syn isomer), mp 88° to 89° C. (dec.).

I.R. spectrum (Nujol): 2700–2100, 1720, 1660, 1612, 1590 cm$^{-1}$.

(14) Acetyl chloride (4.1 g.) was added with stirring and ice-cooling to a solution of 2-methoxyimino-2-(3-hydroxyphenyl)acetic acid (syn isomer) (5 g.) in pyridine (20 ml.) and the mixture was stirred for 50 minutes at ambient temperature. The reaction mixture was poured into ice-water, adjusted to pH 2.1 and extracted three times with ether. The extract was washed with a saturated sodium chloride aqueous solution and dried over magnesium sulfate. The solvent was thoroughly removed under reduced pressure to give 2-methoxyimino-2-(3-acetoxyphenyl)acetic acid (syn isomer) (6.1 g.).

I.R. spectrum (Film): 3500, 2950, 1760, 1735, 1605, 1575, 1485, 1440, 1425, 1370 cm$^{-1}$.

N.M.R. spectrum (CDCl$_3$, δ) ppm: 7.94 (1H, s), 7.6–7.0 (4H, m), 4.05 (3H, s), 2.30 (3H, s).

(15) Trichloroacetyl isocyanate (70 ml) was dropwise added over 6 minutes at ambient temperature to a solution of 2-methoxyimino-2-(3-hydroxyphenyl)acetic acid (syn isomer) (40 g) in dry dioxane (200 ml), and the resulting mixture was stirred for 5 hours at ambient temperature. Dioxane was distilled off and to the residue were added ethyl acetate (200 ml) and by small portions water (200 ml) under ice-cooling. The mixture containing trichloroacetylcarbamoyl 2-methoxyimino-2-(3-trichloroacetylcarbamoyloxyphenyl)acetate was stirred for 5 hours at ambient temperature keeping the pH value of the mixture at 6.0 to 6.4 by adding an aqueous solution of sodium bicarbonate. The resulting mixture was wahsed twice with ethyl acetate. The aqueous layer was adjusted to pH2 with a 10% hydrochloric acid and extracted three times with ethyl acetate. The combined ethyl acetate extracts were washed twice with an aqueous solution of sodium chloride and dried over magnesium sulfate. The solvent was distilled off and precipitating crystals were collected by filtration to give colorless crystals of 2-methoxyimino-2-(3-carbamoyloxyphenyl)acetic acid (syn isomer) (15 g), mp 163° C. (dec.). The same compound (5.4 g) was obtained from the mother liquor.

I.R. spectrum (Nujol): 3480, 3360, 1730, 1660 cm$^{-1}$.
N.M.R. spectrum (d$_6$-DMSO, δ) ppm: 3.97 (3H, s), 7.16(2H, broad s), 7.1–7.7 (4H, m), 9.7 (1H, broad s).

Preparation 6

(1) A solution of sodium nitrite (12.4 g.) in water (150 ml.) was dropwise added with stirring at 5° to 7° C. to a solution of ethyl 4-bromoacetoacetate (30 g.) in acetic acid (200 ml.) and the mixture was stirred for 2 hours at 10° C. Water (200 ml.) was added to the reaction mixture and the resultant mixture was extracted with ether (500 ml.). The extract was washed twice with water (200 ml.) and with a sodium chloride aqueous solution (200 ml.) and dried over magnesium sulfate. The solvent was distilled off under reduced pressure to give yellowish brown crystals of ethyl 2-hydroxyimino-4-bromoacetoacetate (a mixture of syn and anti isomers) (32.6 g.).

I.R. spectrum (Film): 3350, 1740, 1710, 1620 cm$^{-1}$.
N.M.R. spectrum (CDCl$_3$, δ) ppm: 8.75 (2H, broad s), 4.35 (8H, m), 1.35 (6H, m).

(2) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp 55° to 64° C./0.5 mm Hg.

I.R. spectrum (Film): 1745, 1695, 1600 cm$^{-1}$.

N.M.R. spectrum (CDCl$_3$, δ) ppm: 4.33 (4H, q, J=8 Hz), 4.08 (3H, s), 3.95 (3H, s), 2.40 (3H, s), 1.63 (3H, s), 1.33 (6H, t, J=8 Hz).

(3) Bromine (100 g.) was dropwise added over 40 minutes under reflux to a solution of ethyl 2-methoxyiminoacetoacetate (a mixture of syn and anti isomers) (100 g.) in a mixture of carbon tetrachloride (300 ml.) and acetic acid (300 ml.). The mixture was stirred at 70° to 80° C. until the evolution of hydrogen bromide ceased. The reaction mixture was washed twice with water (300 ml.), a sodium bicarbonate aqueous solution and a saturated sodium chloride aqueous solution and dried over magnesium sulfate. The solution was treated with activated charcoal (2 g.) and concentrated under reduced pressure to give ethyl 2-methoxyimino-4-bromoacetoacetate (a mixture of syn and anti isomers) (120.8 g.).

I.R. spectrum (Film): 1740, 1705, 1600 cm$^{-1}$.

N.M.R. spectrum (CDCl$_3$, δ) ppm: 4.17–4.54 (8H, m), 4.15 (3H, s), 4.13 (3H, s), 1.33 (6H, t, J=8 Hz).

(4) A mixture of selenium dioxide (11.1 g.), dioxane (250 ml.) and water (5 ml.) was stirred for 15 minutes at 110° to 115° C. to give yellow solution. Ethyl 2-(2-mesylamino-1,3-thiazol-4-yl)acetate (26.4 g) was added thereto with stirring at the same temperature. After stirring for 1 hour, the reaction mixture was decanted with heating and cooled to precipitate yellow crystals. The crystals were collected by filtration, washed with dioxane and ether and dried to give ethyl 2-(2-mesylamino-1,3-thiazol-4-yl)glyoxylate (23.5 g.).

I.R. spectrum (Nujol): 3300, 1718, 1682 cm$^{-1}$.

(5) Ethyl 2-(2-mesylamino-1,3-thiazol-4-yl)glyoxylate (13.9 g.) was added with stirring at ambient temperature to a solution of sodium hydroxide (5.0 g.) in water (150 ml.). The mixture was stirred for 1 hour at ambient temperature, adjusted to pH 7 with conc. hydrochloric acid and washed with ethyl acetate. The aqueous layer was adjusted to pH 0.5 with conc. hydrochloric acid to precipitate yellow crystals. The crystals were collected by filtration, washed with water and dried to give 2-(2-mesylamino-1,3-thiazol-4-yl)glyoxylic acid (10.16 g.).

I.R. spectrum (Nujol): 3350, 1725, 1650 cm$^{-1}$.

(6) To a solution of ethyl 2-(2-amino-1,3-thiazol-4-yl)acetate (14 g.) in a mixture of pyridine (40 g.) and methylene chloride (300 ml.) was gradually added diethyl ether solution of t-pentyl chloroformate (70 ml.) containing 0.35 mole of t-pentyl chloroformate over 10 minutes at −20° C. with stirring, and the mixture was stirred for 2 hours at the same temperature and further stirred for 0.5 hour at 0° C. After the reaction, the reaction mixture was poured into water (200 ml.), and then the organic layer was separated. The organic layer was washed with 2N hydrochloric acid, water, 5% sodium bicarbonate aqueous solution and water in turn and then dried over magnesium sulfate. The solvent was distilled off from the organic layer to give dark brown oil of ethyl 2-(2-t-pentyloxycarbonylamino-1,3-thiazol-4-yl)acetate (12 g.).

I.R. spectrum (liquid): 1667, 1660 (CO) cm$^{-1}$.

N.M.R. spectrum (CDCl$_3$, δ) ppm: 3.75 (2H, s), 6.75 (1H, s).

(7) Ethyl 2-(2-t-pentyloxycarbonylamino-1,3-thiazol-4-yl)acetate (0.3 g.) and selenium dioxide (0.11 g.) were treated according to a similar manner to that of Preparation 6-4) to give brown oil of ethyl 2-(2-t-pentyloxycarbonylamino-1,3-thiazol-4-yl)glyoxylate (0.22 g.).

I.R. spectrum (liquid):
1720, 1690 (CO) cm$^{-1}$.

N.M.R. spectrum (CDCl$_3$, δ) ppm: 8.3 (1H, s).

(8) Ethyl 2-(2-t-pentyloxycarbonylamino-1,3-thiazol-4-yl)glyoxylate (2.8 g.) and a solution of sodium hydroxide (0.54 g.) in water (20 ml.) were treated according to a similar manner to that of Preparation 6-5) to give brown powder of 2-(2-t-pentyloxycarbonylamino-1,3-thiazol-4yl)glyoxylic acid (1.75 g.).

I.R. spectrum (Nujol): 1730, 1680 (CO) cm$^{-1}$.

N.M.R. spectrum (d$_6$-dimethylsulfoxide, δ) ppm: 8.4 (1H, s).

(9) A mixture of ethyl 2-hydroxyimino-2-(2-amino-1,3-thiazol-4-yl)acetate (a mixture of syn and anti isomers) (0.37 g), ethanol (5 ml), water (5 ml) and sodium bisulfite (0.72 g) was stirred for 12 hours at 65° to 70° C. The reaction mixture was concentrated and water (10 ml) was added to the residue. The resulting mixture was subjected to salting-out and extracted with ethyl acetate. The extract was dried over magnesium sulfate and concentrated to give yellow crystals of ethyl 2-(2-amino-1,3-thiazol-4-yl)glyoxylate (0.18 g), mp 115° to 120° C.

I.R. spectrum (Nujol): 3420, 3250, 3120, 1730, 1665, 1612 cm$^{-1}$.

(10) Sulfuryl chloride (235 ml.) was dropwise added over 20 minutes with stirring and ice-cooling to a solution of ethyl 2-methoxyiminoacetoacetate (syn isomer) (500 g.) in acetic acid (500 ml.), and the mixture was stirred overnight under cooling with water. Nitrogen gas was introduced to the reaction mixture for 2 hours, and the resulting mixture was poured into water (2.5 l). After extracting with methylene chloride (500 ml.) and twice with methylene chloride (200 ml.), the extracts were combined. The combined extracts were washed with a saturated aqueous solution of sodium chloride, and adjusted to pH 6.5 by adding water (800 ml.) and sodium bicarbonate. Methylene chloride layer was separated, washed with an aqueous solution of sodium chloride and dried over magnesium sulfate. The solvent was distilled off to give ethyl 2-methoxyimino-4-chloroacetoacetate (syn isomer) (559 g.).

I.R. spectrum (Film): 1735, 1705 cm$^{-1}$.

(11) To a suspension of ethyl 2-hydroxyimino-3-oxobutyrate (syn isomer) (40 g.) and potassium carbonate (52 g.) in dimethylformamide (200 ml.) was added pentyl bromide (37.9 g.) with stirring, and the mixture was stirred for 1.5 hours at ambient temperature. The insoluble material was collected by filtration and washed with dimethylformamide. The filtrate and the washings were combined together and evaporated to dryness under reduced pressure. To the residue was added water and the mixture was extracted with chloroform. The extract was washed with a saturated aqueous solution of sodium chloride, dried over magnesium sulfate and concentrated under reduced pressure to give an oil of ethyl 2-pentyloxyimino-3-oxobutyrate (syn isomer) (57.5 g.).

I.R. (Film): 1745, 1680, 1470 cm$^{-1}$.

N.M.R. (CCl$_4$,δ): 4.1–4.6 (4H, m), 2.36 (3H, s), 0.7–2.2 (12H, m).

(12) Ethyl 2-pentyloxyimino-3-oxobutyrate (syn isomer) (57.5 g.) and sulfuryl chloride (20.9 ml.) were reacted in acetic acid (58.5 ml.) according to a similar manner to that of Preparation 6-10) to give an oil of ethyl 2-pentyloxyimino-3-oxo-4-chlorobutyrate (syn isomer). (51.1 g.).

I.R. (Film): 1750, 1715, 1470 cm$^{-1}$.

N.M.R. (CCl$_4$,δ): 4.48 (2H, s), 4.1–4.6 (4H, m), 0.7–2.1 (11H, m).

Preparation 7

(1) A mixture of ethyl 2-hydroxyimino-4-bromoacetoacetate (a mixture of syn and anti isomers) (22.0 g.), thioacetamide (7.5 g.) and benzene (100 ml.) was refluxed for 3 hours. After cooling triethylamine (10 g.) was added thereto and the mixture was stirred for 1 hour. An insoluble material was filtered off and the filtrate was concentrated under reduced pressure to give ethyl 2-hydroxyimino-2-(2-methyl-1,3-thiazol-4-yl)acetate (a mixture of syn and anti isomers) (8.6 g.). This substance was subjected to column chromatography on silica gel (80 g.) using benzene as developing solvent. Firstly the eluate containing anti isomer was eluted, collected and concentrated to give ethyl 2-hydroxyimino-2-(2-methyl-1,3-thiazol-4-yl)acetate (anti isomer) (2.5 g), mp 90° to 92° C.

I.R. spectrum (Nujol): 1720 cm$^{-1}$.

N.M.R. spectrum (d$_6$DMSO, δ) ppm: 12.55 (1H, s), 8.25 (1H, s), 4.27 (2H, q, J=7 Hz), 2.63 (3H, s), 1.25 (3H, t, J=7 Hz).

After the eluate containing anti isomer was eluted, the eluate containing syn isomer was eluted, collected and concentrated to give ethyl 2-hydroxyimino-2-(2-methyl-1,3-thiazol-4-yl)acetate (syn isomer) (0.5 g.), mp 134° to 136° C.

I.R. spectrum (Nujol): 1720 cm$^{-1}$.

N.M.R. spectrum (d$_6$-DMSO, δ) ppm: 11.81 (1H, s), 7.81 (1H, s), 4.35 (2H, q, J=7 Hz), 2.70 (3H, s), 1.30 (3H, t, J=7 Hz).

(2) Phenolphthalein indicator (3 drops) was added to a solution of hydroxylamine hydrochloride (4.2 g.) in dry methanol (60 ml.). To the solution was dropwise added with stirring at ambient temperature 1N methanol solution of sodium methoxide (60 ml.) until the color of the solution was changed to purplish red. Hydroxylamine hydrochloride was added thereto by small portions until the solution was changed to colorless solution. The mixture was stirred for 30 minutes at ambient temperature. After precipitating sodium chloride was filtered off, 2-(2-mesylamino-1,3-thiazol-4-yl)glyoxylic acid (12.5 g.) was added to the filtrate and the mixture was refluxed with stirring for 1.5 hours. The reaction mixture was cooled to precipitate crystals. The crystals were collected by filtration and dried to give crude 2-hydroxyimino-2-(2-mesylamino-1,3-thiazol-4-yl)acetic acid (a mixture of syn and anti isomers) (5.5 g.). The filtrate was concentrated to the volume of ¼ and ether was added thereto. Precipitating crystals were collected by filtration, washed with ether and dried to give the same compound (8.78 g.). Total yield (14.3 g.).

(3) A mixture of ethyl 2-hydroxyimino-4-bromoacetoacetate (a mixture of syn and anti isomers) (2.4 g) and thiourea (0.76 g) in ethanol (15 ml) was stirred for 1 hour at 60° C. Ethanol was distilled off under reduced pressure and water was added to the residue. The resultant mixture was adjusted to pH 1.0 and washed with ethyl acetate. The aqueous layer was adjusted to pH 4.5 with triethylamine and extracted with ethyl acetate. The extract was washed with water and a saturated sodium chloride aqueous solution and dried over magnesium sulfate. The solvent was distilled off under reduced pressure and the residue was subjected to column chromatography on silica gel using a mixture of ethyl acetate and benzene (1:3) as developing solvent. The eluates containing syn isomer were collected and concentrated to give ethyl 2-hydroxyimino-2-(2-amino-1,3-thiazol-4-yl)acetate (syn isomer) (0.3 g).

I.R. spectrum (Nujol): 3450, 3300, 3200, 1725, 1620 cm$^{-1}$.

N.M.R. spectrum (CDCl$_3$, δ) ppm: 7.65 (1H, s), 5.33 (2H, broad s), 4.40 (2H, q, J=7.5 Hz), 1.38 (3H, t, J=7.5 Hz).

After the eluates containing syn isomers were collected, the eluates containing a mixture of syn and anti isomers were collected and concentrated to give ethyl 2-hydroxyimino-2-(2-amino-1,3-thiazol-4-yl)acetate (a mixture of syn and anti isomers) (0.3 g.).

I.R. spectrum (Nujol): 3400, 3300, 3200, 1715, 1620 cm$^{-1}$.

N.M.R. spectrum (d$_6$-DMSO, δ) ppm: 12.42 (1H, broad s), 11.55 (1H, s), 7.52 (1H, s), 7.12 (4H, broad s), 6.83 (1H, s), 4.23 (4H, m), 1.26 (6H, m).

(4) A solution of ethyl 2-hydroxyimino-2-(2-amino-1,3-thiazol-4-yl)acetate (a mixture of syn and anti isomers) (1.1 g) in an 1N aqueous solution of sodium hydroxide (15 ml) was allowed to stand for 2 hours at ambient temperature. The reaction mixture was adjusted to pH 3.5 with 10% hydrochloric acid and precipitating crystals were collected by filtration, washed with acetone and dried to give 2-hydroxyimino-2-(2-amino-1,3-thiazol-4-yl)acetic acid (a mixture of syn and anti isomers) (0.52 g), mp 184° to 186° C. (dec.).

I.R. spectrum (Nujol): 3200, 1670, 1530 cm$^{-1}$.

Preparation 8

(1) Thioacetamide (3.8 g.) was added to a solution of ethyl 2-methoxyimino-4-bromoacetoacetate (a mixture of syn and anti isomers) (12.6 g.) in ethanol (50 ml.) and the mixture was stirred for 5 hours at 50° C. Ethanol was distilled off under reduced pressure and water was added to the residue. The resulting mixture was extracted with ethyl acetate. The extract was in turn washed with water, a sodium bicarbonate aqueous solution and a saturated sodium chloride aqueous solution and dried over magnesium sulfate. The solvent was distilled off under reduced pressure to give ethyl 2-methoxyimino-2-(2-methyl-1,3-thiazol-4-yl)acetate (a mixture of syn and anti isomers) (9.0 g.).

(2) A mixture of ethyl 2-methoxyimino-4-bromoacetoacetate (a mixture of syn and anti isomers) (7.6 g.), O-ethyl thiocarbamate (3.0 g.) and dimethylacetamide (5 ml.) was stirred for 3 hours at 50° C. Ethyl acetate (50 ml.) was added to the reaction mixture and the resulting mixture was washed with water and with a saturated sodium chloride aqueous solution and dried over magnesium sulfate. Ethyl acetate was distilled off to give crystalline residue. The residue was washed with diisopropyl ether to give ethyl 2-methoxyimino-2-(2-oxo-2,3-dihydro-1,3-thiazol-4-yl)acetate (syn isomer) (2.35 g.).

I.R. spectrum (Nujol): 3200, 1735, 1680, 1650 cm$^{-1}$.

N.M.R. spectrum (CDCl$_3$, δ) ppm: 9.13 (1H, broad s), 6.37 (1H, s), 4.40 (2H, q, J=6 Hz), 4.01 (3H, s), 1.38 (3H, t, J=6 Hz).

The mother liquor of diisopropyl ether was concentrated and the residue was subjected to column chromatography on silica gel (70 g.) using a mixture of benzene and ethyl acetate (9:1) as developing solvent. The eluate containing syn isomer was collected and concentrated to further give the above obtained syn isomer (0.65 g.). Total yield (3.0 g.). Thereafter a mixture of benzene and ethyl acetate (5:1) was used as developing solvent. The eluate containing anti isomer was collected and concentrated to give ethyl 2-methoxyimino-2-(2-oxo-2,3-dihydro-1,3-thiazol-4-yl)acetate (anti isomer) (0.26 g.).

I.R. spectrum (Nujol): 3250, 3200, 1720, 1690 cm$^{-1}$.

N.M.R. spectrum (CDCl$_3$, δ) ppm: 9.90 (1H, broad s), 7.30 (1H, s), 4.40 (2H, q, J=6 Hz), 4.03 (3H, s), 1.38 (3H, t, J=6 Hz).

(3) A solution of ethyl 2-methoxyimino-4-bromoacetoacetate (a mixture of syn and anti isomers) (17.4 g.) and thiourea (5.4 g.) in ethanol (100 ml.) was refluxed for 4 hours. The reaction mixture was allowed to stand and cooled in refrigerator to precipitate crystals. The crystals were collected by filtration, washed with ethanol and dried to give ethyl 2-methoxyimino-2-(2-amino-1,3-thiazol-4-yl)acetate hydrobromide (anti isomer) (9.5 g.). The filtrate and the washings were put together and concentrated under reduced pressure. Water (100 ml.) was added to the residue and the mixture was washed with ether. The aqueous layer was alkalized with a 28% aqueous solution of ammonia and extracted with ethyl acetate. The extract was washed with water and a saturated sodium chloride aqueous solution and dried over magnesium sulfate. The solvent was distilled off under reduced pressure to give crystalline substance of ethyl 2-methoxyimino-2-(2-amino-1,3-thiazol-4-yl)acetate (syn isomer) (5.2 g.).

I.R. spectrum (Nujol): 3400, 3300, 3150, 1725, 1630, 1559 cm$^{-1}$.

N.M.R. spectrum (CDCl$_3$, δ) ppm: 6.72 (1H, s), 5.91 (2H, broad s), 4.38 (2H, q, J=7 Hz), 4.03 (3H, s), 1.38 (3H, t, J=7 Hz).

The above obtained ethyl 2-methoxyimino-2-(2-amino-1,3-thiazol-4-yl)acetate hydrobromide (anti isomer) (9.5 g.) was suspended in ethyl acetate (200 ml.) and triethylamine (4.0 g.) was added thereto. After stirring for 1 hour at ambient temperature, an insoluble material was filtered off and the filtrate was concentrated under reduced pressure to give crystalline substance of ethyl 2-methoxyimino-2-(2-amino-1,3-thiazol-4-yl)acetate (anti isomer) (6.15 g.).

I.R. spectrum (Nujol): 3450, 3250, 3150, 1730, 1620 cm$^{-1}$.

N.M.R. spectrum (CDCl$_3$, δ) ppm: 7.50 (1H, s), 5.60 (2H, broad s), 4.35 (2H, q, J=7 Hz), 4.08 (3H, s), 1.33 (3H, t, J=7 Hz).

(4) Phenolphthalein indicator (3 drops) was added to a solution of O-methyl-hydroxylamine hydrochloride (1.25 g.) in dry methanol (15 ml.). To the solution was dropwise added with stirring at ambient temperature 1N methanol solution of sodium methoxide (13 ml.) until the color of the solution was changed to purplish red. O-Methylhydroxylamine hydrochloride was added thereto by small portions until the solution was changed to colorless solution. The mixture was stirred for 30 minutes at ambient temperature. After precipitating sodium chloride was filtered off, ethyl 2-(2-mesylamino-1,3-thiazol-4-yl)glyoxylate (3.8 g.) was added to the filtrate and the mixture was refluxed with stirring for 2 hours. After methanol was distilled off, the residue was dissolved in ethyl acetate. An insoluble material was filtered off and the filtrate was concentrated. The residue was subjected to column chromatography on silica gel using a mixture of benzene and ethyl acetate (9:1) as developing solvent. The eluate containing syn isomer was collected and concentrated to give ethyl 2-methoxyimino-2-(2-mesylamino-1,3-thiazol-4-yl)acetate (syn isomer) (2.8 g.).

I.R. spectrum (Nujol): 1725 cm$^{-1}$.

N.M.R. spectrum (CDCl$_3$, δ) ppm: 6.76 (1H, s), 4.44 (2H, q, J=7 Hz), 4.04 (3H, s), 3.04 (3H, s), 1.37 (3H, t, J=7 Hz).

(5) Pulverized potassium carbonate (0.33 g.) was suspended in a solution of ethyl 2-hydroxyimino-2-(2-methyl-1,3-thiazol-4-yl)acetate (syn isomer) (0.5 g.) in acetone (20 ml.). A solution of dimethyl sulfate (0.3 g.) in acetone (5 ml.) was dropwise added thereto with stirring at 40° to 45° C. After stirring for 2 hours at the same temperature, an insoluble material was filtered off. The filtrate was concentrated and water was added to the residue. The resulting mixture was extracted with ethyl acetate. The extract was in turn washed with water, a sodium bicarbonate aqueous solution and a saturated sodium chloride aqueous solution and dried over magnesium sulfate. The solvent was distilled off under reduced pressure to give pale yellow oil of ethyl 2-methoxyimino-2-(2-methyl-1,3-thiazol-4-yl)acetate (syn isomer) (0.5 g.).

I.R. spectrum (Film): 1740, 1710, 1595 cm$^{-1}$.

N.M.R. spectrum (CDCl$_3$, δ) ppm: 7.40 (1H, s), 4.25 (2H, q, J=7 Hz), 4.03 (3H, s), 2.73 (3H, s), 1.38 (3H, t, J=7 Hz).

(6) 2-Hydroxyimino-2-(2-mesylamino-1,3-thiazol-4-yl)acetic acid (a mixture of syn and anti isomers) (14.3 g.) obtained in Preparation 7-2) was suspended in dry acetone (300 ml.). To the suspension were added potassium carbonate (22.8 g.) and dimethyl sulfate (20.8 g.). The mixture was refluxed with stirring for 9 hours. Acetone was distilled off from the reaction mixture and water was added to the residue. The resulting mixture was extracted with ethyl acetate. The extract was washed with a sodium chloride aqueous solution and dried over magnesium sulfate. The solvent was distilled off to give oil (13 g.). The oil was subjected to column chromatography on silica gel using a mixture of benzene and ethyl acetate (9:1) as developing solvent. Firstly the eluate containing anti isomer was eluted, collected and concentrated. The residual oil (2.4 g.) was triturated under cooling to crystallize. The crystals were collected by filtration by adding petroleum ether to give methyl 2-methoxyimino-2-(2-mesylimino-3-methyl-2,3-dihydro-1,3-thiazol-4-yl)acetate (anti isomer) (2.1 g.).

I.R. spectrum (Nujol): 1740 cm$^{-1}$.

N.M.R. spectrum (CDCl$_3$, δ) ppm: 7.90 (1H, s), 4.10 (3H, s), 3.90 (3H, s), 3.47 (3H, s), 3.07 (3H, s).

After the eluate containing anti isomer was eluted, the eluate containing syn isomer was eluted, collected and concentrated to give crystals of methyl 2-methoxyimino-2-(2-mesylimino-3-methyl-2,3-dihydro-1,3-thiazol-4-yl)acetate (syn isomer) (5.5 g.).

I.R. spectrum (Nujol): 1740 cm$^{-1}$.

N.M.R. spectrum (CDCl$_3$, δ) ppm: 6.72 (1H, s), 4.05 (3H, s), 3.92 (3H, s), 3.72 (3H, s), 3.01 (3H, s).

(7) The following compound was obtained according to a similar manner to that of Preparation 8-4). Ethyl 2-methoxyimino-2-(2-amino-1,3-thiazol-4-yl)acetate (syn isomer).

I.R. spectrum (Nujol): 3400, 3300, 3150, 1725, 1630, 1559 cm$^{-1}$.

N.M.R. spectrum (CDCl$_3$, δ) ppm: 6.72 (1H, s), 5.91 (2H, broad s), 4.38 (2H, q, J=7 Hz), 4.03 (3H, s), 1.38 (3H, t, J=7 Hz).

(8) A mixture of acetic anhydride (6.1 g) and formic acid (2.8 g) was stirred for 2 hours at 50° C. The resulting mixture was cooled and ethyl 2-methoxyimino-2-(2-amino-1,3-thiazol-4-yl)acetate (syn isomer) (4.6 g) was added thereto at 15° C. After the mixture was stirred for 3.5 hours at ambient temperature, cooled water (100 ml) was added thereto. The resulting mixture was extracted with ethyl acetate (200 ml). The extract was washed with water and then with a saturated aqueous solution of sodium bicarbonate until the washing was changed to weakly alkaline solution. The extract was further washed with a saturated aqueous solution of sodium chloride and dried over magnesium sulfate. The solvent was distilled off and the residue was washed with diisopropyl ether, collected by filtration and dried to give ethyl 2-methoxyimino-2-(2-formamido-1,3-thiazol-4-yl)acetate (syn isomer) (4.22 g), mp 122° to 124° C. (dec.).

I.R. spectrum (Nujol): 3150, 1728, 1700 cm$^{-1}$.

N.M.R. spectrum (CDCl$_3$, δ) ppm: 12.58 (1H, broad s), 8.95 (1H, s), 7.17 (1H, s), 4.42 (2H, q, J=8 Hz), 4.00 (3H, s), 1.37 (3H, t, J=8 Hz).

(9) Pyridine (3 g.) was added to a solution of ethyl 2-methoxyimino-2-(2-amino-1,3-thiazol-4-yl)acetate (syn isomer) (6.5 g.) in a mixture of ethyl acetate (60 ml.) and dimethylformamide (20 ml.). To the solution was dropwise added with stirring at 4° C. ethyl chloroformate (8 g.). After adding water (50 ml.) to the reaction mixture, the organic layer was separated, washed with water and then with a saturated aqueous solution of sodium chloride and dried over magnesium sulfate. The solvent was distilled off under reduced pressure. The residue was subjected to column chromatography on silica gel (120 g.) using a mixture of ether and petroleum ether (5:2) as an eluent to give ethyl 2-methoxyimino-2-(2-ethoxycarbonylamino-1,3-thiazol-4-yl)acetate (syn isomer) (5.4 g.).

N.M.R. spectrum (CDCl$_3$, δ) ppm: 9.36 (1H, broad s), 7.10 (1H, s), 4.00-4.66 (4H, m), 4.00 (3H, s), 1.20-1.60 (6H, m).

(10) Ethyl 2-methoxyimino-4-chloroacetoacetate (syn isomer) (50 g.) was added over 3 minutes with stirring at ambient temperature to a solution of thiourea (18.4 g.) and sodium acetate (19.8 g.) in a mixture of methanol (250 ml.) and water (250 ml.). After stirring for 35 minutes at 40° to 45° C., the reaction mixture was cooled with ice and adjusted to pH 6.3 with a saturated aqueous solution of sodium bicarbonate. After stirring for 30 minutes at the same temperature, precipitates were collected by filtration, washed with water (200 ml.) and then with diisopropyl ether (100 ml.), and dried to give colorless crystals of ethyl 2-methoxyimino-2-(2-amino-1,3-thiazol-4-yl)acetate (syn isomer) (37.8 g.), mp 161° to 162° C.

I.R. spectrum (Nujol): 3400, 3300, 3150, 1725, 1630, 1559 cm$^{-1}$.

N.M.R. spectrum (CDCl$_3$, δ) ppm: 6.72 (1H, s), 5.91 (2H, broad s), 4.38 (2H, q, J=7 Hz), 4.03 (3H, s), 1.38 (3H, t, J=7 Hz).

(11) Ethyl 2-hydroxyimino-2-(2-methyl-1,3-thiazol-4-yl)acetate (anti isomer) (0.3 g.) and dimethyl sulfate (0.18 g.) were reacted according to a similar manner to that of Preparation 8-5) to give pale yellow oil of ethyl 2-methoxyimino-2-(2-methyl-1,3-thiazol-4-yl)acetate (anti isomer) (0.27 g.).

I.R. spectrum (Film): 1750, 1605 cm$^{-1}$.

N.M.R. spectrum (CDCl$_3$, δ) ppm: 8.07 (1H, s), 4.41 (2H, q, J=7 Hz), 4.13 (3H, s), 2.75 (3H, s), 1.40 (3H, t, J=7 Hz).

(12) The following compound was obtained according to a similar manner to that of Prepration 8-8). ethyl 2-methoxyimino-2-(2-formamido-1,3-thiazol-4-yl)acetate (anti isomer), mp 96° to 99° C. (dec.).

I.R. spectrum (Nujol): 3150, 1740, 1650, 1600 cm$^{-1}$.

N.M.R. spectrum (CDCl$_3$, δ) ppm: 11.20 (1H, broad s), 8.60 (1H, s), 7.90 (1H, s), 4.32 (2H, q, J=8 Hz), 4.13 (3H, s), 1.32 (3H, t, J=8 Hz).

(13) Ethyl 2-pentyloxyimino-3-oxo-4-chlorobutyrate (syn isomer) (51.1 g.) and thiourea (14.7 g.) were reacted in the presence of sodium acetate trihydrate (26.4 g.) in a mixture of water (125 ml.) and ethanol (175 ml.) according to a similar manner to that of Preparation 8-10) to give crystals of ethyl 2-pentyloxyimino-2-(2-amino-1,3-thiazol-4-yl)acetate (syn isomer) (28.7 g.), mp 86° to 88° C.

I.R. (Nujol): 3450, 3250, 3130, 1715, 1535 cm$^{-1}$.

N.M.R. (d$_6$-DMSO, δ): 7.25 (2H, s), 6.90 (1H, s), 4.32 (2H, q, J=7 Hz), 4.11 (2H, t, J=6 Hz), 0.6-2.0 (12H, m).

Preparation 9

(1) Ethanol (10 ml.) was added to a suspension of ethyl 2-methoxyimino-2-(2-amino-1,3-thiazol-4-yl)acetate (syn isomer) (2.2 g.) in a 1N aqueous solution of sodium hydroxide (12 ml.) and the mixture was stirred for 15 hours at ambient temperature. The reaction mixture was adjusted to pH 7.0 with 10% hydrochloric acid and ethanol was distilled off under reduced pressure. The residual aqueous solution was washed with ethyl acetate, adjusted to pH 2.8 with 10% hydrochloric acid and stirred under ice-cooling to precipitate crystals. The crystals were collected by filtration, washed with acetone and recrystallized from ethanol to give colorless needles of 2-methoxyimino-2-(2-amino-1,3-thiazol-4-yl)acetic acid (syn isomer) (1.1 g.).

I.R. spectrum (Nujol): 3150, 1670, 1610, 1585 cm$^{-1}$.

N.M.R. spectrum (d$_6$-DMSO, δ) ppm: 7.20 (2H, broad s), 6.85 (1H, s), 3.83 (3H, s), (2) 1N-Aqueous solution of sodium hydroxide (1.5 ml.) was added to a solution of ethyl 2-methoxyimino-2-(2-methyl-1,3-thiazol-4-yl)acetate (syn isomer) (0.3 g.) in ethanol (5 ml.) and the resulting mixture was stirred for 2 hours at 40° C. The reaction mixture was adjusted to pH 7.0 with 10% hydrochloric acid, concentrated under reduced pressure, adjusted to pH 1.5 with 10% hydrochloric acid and extracted with ethyl acetate. The extract was washed with water and a saturated sodium chloride aqueous solution and dried over magnesium sulfate. The solvent was distilled off to give crystalline substance of 2-methoxyimino-2-(2-methyl-1,3-thiazol-4-yl)acetic acid (syn isomer) (0.14 g.).

I.R. spectrum (Nujol): 1730 cm$^{-1}$.

N.M.R. spectrum (d$_6$-DMSO, δ) ppm: 7.80 (1H, s), 3.85 (3H, s), 2.62 (3H, s).

(3) The following compounds were obtained according to similar manners to those of Preparation 9-1) to 9-2).

(1) 2-Methoxyimino-2-(2-oxo-2,3-dihydro-1,3-thiazol-4-yl)acetic acid (syn isomer).

I.R. spectrum (Nujol): 3250, 1710, 1650 cm$^{-1}$.

N.M.R. spectrum (d$_6$-DMSO, δ) ppm: 10.61 (1H, broad s), 6.73 (1H, s), 3.95 (3H, s).

(2) 2-Methoxyimino-2-(2-mesylamino-1,3-thiazol-4-yl)acetic acid (syn isomer).

I.R. spectrum (Nujol): 3150, 1720 cm$^{-1}$.

N.M.R. spectrum (d$_6$-DMSO, δ) ppm: 7.17 (1H, s), 3.93 (3H, s), 3.02 (3H, s).

(3) 2-Methoxyimino-2-(2-mesylimino-3-methyl-2,3-dihydro-1,3-thiazol-4-yl)acetic acid (syn isomer).

I.R. Spectrum (Nujol): 1730 cm$^{-1}$.

(4) 2-Methoxyimino-2-(2-formamido-1,3-thiazol-4-yl)acetic acid (syn isomer), mp 152° C. (dec.).

I.R. spectrum (Nujol): 3200, 2800-2100, 1950, 1600 cm$^{-1}$.

N.M.R. spectrum (d$_6$-DMSO, δ) ppm: 8.60 (1H, s), 7.62 (1H, s), 3.98 (1H, s).

(5) 2-Methoxyimino-2-(2-ethoxycarbonylamino-1,3-thiazol-4-yl)acetic acid (syn isomer).

I.R. spectrum (Nujol): 3200, 1730, 1710, 1690, 1570 cm$^{-1}$.

N.M.R. spectrum (d$_6$-DMSO, δ) ppm: 12.16 (1H, broad s), 7.50 (1H, s), 7.20 (1H, broad s), 4.25 (2H, q, J=7 Hz), 3.93 (3H, s), 1.25 (3H, t, J=7 Hz).

(4) Pyridine (5 ml.) was added to a suspension of 2-methoxyimino-2-(2-amino-1,3-thiazol-4-yl)acetic acid (syn isomer) (2.0 g.) in ethyl acetate (20 ml.). A solution of bis(2,2,2-trifluoroacetic)anhydride (2.5 g.) in ethyl acetate (3 ml.) was dropwise added thereto with stirring at 5° to 7° C. and the mixture was stirred for 30 minutes at 3° to 5° C. Water (30 ml.) was added to the reaction mixture and the ethyl acetate layer was separated. The aqueous layer was further extracted with ethyl acetate and two ethyl acetate layers were combined together, washed with water and a saturated sodium chloride aqueous solution and dried over magnesium sulfate. The solvent was distilled off under reduced pressure to give 2-methoxyimino-2-[2-(2,2,2-trifluoroacetamido)-1,3-thiazol-4-yl]acetic acid (syn isomer) (0.72 g.).

I.R. spectrum (Nujol): 1725, 1590 cm$^{-1}$.

N.M.R. spectrum (d$_6$-DMSO, δ) ppm: 7.68 (1H, s), 3.91 (3H, s).

(5) The following compound was obtained according to a similar manner to that of Preparation 9-4). 2-Methoxyimino-2-(2-acetamido-1,3-thiazol-4-yl)acetic acid (syn isomer), mp 184° to 185° C. (dec.).

I.R. spectrum (Nujol): 3200, 3050, 1695, 1600 cm$^{-1}$.

(6) Phenolphthalein indicator (3 drops) was added to a solution of O-allyl-hydroxylamine hydrochloride (0.84 g.) in dry methanol (10 ml.). To the solution was dropwise added with stirring at ambient temperature 1N methanol solution of sodium methoxide (6 ml.) until the color of the solution was changed to pale pink. O-Allylhydroxylamine hydrochloride was added thereto by small portions until the solution was changed to colorless solution. The mixture was stirred for 30 minutes at ambient temperature. After precipitating sodium chloride was filtered off, 2-(2-t-pentyloxycarbonylamino-1,3-thiazol-4-yl)glyoxylic acid (2.0 g.) was added to the filtrate and the mixture was stirred for 1 hour at ambient temperature. After methanol was distilled off at low temperature, the residue was dissolved in an 1N aqueous solution of sodium hydroxide. The solution was washed with ether and ethyl acetate was added thereto. The mixture was adjusted to pH 1.5 with phosphoric acid and extracted with ethyl acetate. The extract was washed with a sodium chloride aqueous solution and dried over magnesium sulfate. Ethyl acetate was distilled off and the residue was washed with diisopropyl ether, collected by filtration and dried to give 2-allyloxyimino-2-(2-t-pentyloxycarbonylamino-1,3-thiazol-4-yl)acetic acid (syn isomer) (1.62 g.).

I.R. spectrum (Nujol): 3200, 1712 cm$^{-1}$.

N.M.R. spectrum (d$_6$-DMSO, δ) ppm: 7.40 (1H, s), 6.24-5.76 (1H, m), 5.26 (2H,dd, J=9, 10 Hz), 4.65 (2H, d, J=5 Hz), 1.78 (2H, q, J=8 Hz), 1.44 (6H, s), 0.88 (3H, t, J=8 Hz).

(7) The following compounds were obtained according to a similar manner to that of Preparation 9-6).

(1) 2-Methoxyimino-2-(2-t-pentyloxycarbonylamino-1,3-thiazol-4-yl)acetic acid (syn isomer).

I.R. spectrum (Nujol): 3200, 1712 cm$^{-1}$.

N.M.R. spectrum (d$_6$-DMSO, δ) ppm: 7.40 (1H, s), 3.88 (3H, s), 1.77 (2H, q, J=8 Hz), 1.44 (6H, s), 0.88 (3H, t, J=8 Hz).

(2) 2-Allyloxyimino-2-(2-mesylamino-1,3-thiazol-4-yl)acetic acid (syn isomer).

I.R. spectrum (Nujol): 3150, 1710, 1605 cm$^{-1}$.

(3) 2-Methoxyimino-2-(2-amino-1,3-thiazol-4-yl)acetic acid (syn isomer).

I.R. spectrum (Nujol): 3150, 1670, 1610, 1585 cm$^{-1}$.

N.M.R. spectrum (d$_6$-DMSO, δ) ppm: 7.20 (2H, broad s), 6.85 (1H, s), 3.83 (3H, s).

(8) Ethyl 2-methoxyimino-2-(2-amino-1,3-thiazol-4-yl)acetate hydrobromide (anti isomer) (15.5 g.) was dissolved in a solution of sodium hydroxide (4.4 g.) in water (150 ml.) and the resulting solution was stirred for 1 hour at ambient temperature. An insoluble material was filtered off and the filtrate was adjusted to pH 5.0 to precipitate crystals. The crystals were collected by filtration and dried to give 2-methoxyimino-2-(2-amino-1,3-thiazol-4-yl)acetic acid (anti isomer) (8.0 g.).

I.R. spectrum (Nujol): 3150, 1655, 1595, 1550 cm$^{-1}$.

N.M.R. spectrum (d$_6$-DMSO, δ) ppm: 7.53 (1H, s), 7.23 (2H, broad s), 3.99 (3H, s).

(9) The following compounds were obtained according to similar manner to that of Preparation 9-8).

(1) 2-Methoxyimino-2-(2-methyl-1,3-thiazol-4-yl)acetic acid (anti isomer).

I.R. spectrum (Nujol): 1730, 1590 cm$^{-1}$.

N.M.R. spectrum (d$_6$-DMSO, δ) ppm: 8.10 (1H, s), 4.00 (3H, s), 2.65 (3H, s).

(2) 2-Methoxyimino-2-(2-mesylimino-3-methyl-2,3-dihydro-1,3-thiazol-4-yl)acetic acid (anti isomer).

I.R. spectrum (Nujol): 1730 cm$^{-1}$.

(3) 2-Methoxyimino-2-(2-formamido-1,3-thiazol-4-yl)acetic acid (anti isomer), mp 156° to 158° C. (dec.).

I.R. spectrum (Nujol): 3200, 2700-2100, 1690, 1590, 1560 cm$^{-1}$.

N.M.R. spectrum (d$_6$-DMSO,δ) ppm: 8.05 (1H, s), 4.02 (3H, s).

(10) Ethyl 2-pentyloxyimino-2-(2-amino-1,3-thiazol-4-yl)acetate (syn isomer) (28.6 g.) and 2N sodium hydroxide aqueous solution (100.2 ml.) were reacted in a mixture of methanol (100 ml.) and tetrahydrofuran (100 ml.) according to similar manners to those of Preparation (9-1) and (9-2) to give 2-pentyloxyimino-2-(2- amino-1,3-thiazol-4-yl)acetic acid (syn isomer) (22.4 g.), mp 176° C. (dec.)

I.R. (Nujol): 3160, 1655, 1620, 1460 cm$^{-1}$.

N.M.R. (d$_6$-DMSO, δ): 7.20 (2H, s), 6.82 (1H, s), 4.07 (2H, t, J=6 Hz), 0.6–2.2 (9H, m).

Preparation 10

(1) 1-Allyl-1H-tetrazole-5-thiol (21.3 g) was added at 76° to 78° C. to a solution of sodium bicarbonate (10.6 g) in water (220 ml). Sodium 7-(5-amino-5-carboxyvaleramido)cephalosporanate (54.9 g) was added thereto over 15 minutes and the mixture was stirred for 10 minutes at 76° to 78° C. The reaction mixture was adjusted to pH 3.0 with 6N hydrochloric acid under ice-cooling and filtered. The filtrate was subjected to column chromatography on non-ionic adsorption resin "Diaion HP-20" (Trademark: prepared by Mitsubishi Chemical Industries Ltd.) and eluted with 30% aqueous solution of isopropyl alcohol. The eluate was adjusted to pH 6.5 with 28% aqueous solution of ammonia, concentrated and lyophilized to give ammonium 7-(5-amino-5-carboxyvaleramido)-3-(1-allyl-1H-tetrazol-5-yl)thiomethyl-3-cephem-4-carboxylate (21.7 g).

I.R. (Nujol): 3175, 1760, 1590 cm$^{-1}$.

N.M.R. (d$_6$-DMSO,δ): 1.23–2.42 (6H, m), 3.12–3.97 (3H, m), 4.37 (2H, broad s), 4.80–5.15 (3H, m), 5.15–5.51 (2H, m), 5.51–6.25 (2H, m), 8.77 (1H, d, J=8 Hz).

(2) N,N-Dimethylaniline (18.2 ml) was added to a mixture of ammonium 7-(5-amino-5-carboxyvaleramido)-3-(1-allyl-1H-tetrazol-5-yl)thiomethyl-3-cephem-4-carboxylate (10.0 g), trimethylsilyl chloride (20.9 ml) and methylene chloride (75 ml), and the mixture was stirred under reflux for 2.5 hours. Phosphorus pentachloride (5.83 g) was added thereto at −30° to −35° C. and the mixture was stirred for 2 hours at the same temperature. 2-Ethoxyethanol (38 ml) was added dropwise thereto at the same temperature and the mixture was stirred for 1 hour at the same temperature. Water (80 ml) was added thereto at −5° to −10° C. over 10 minutes and the resulting mixture was stirred for 5 minutes at the same temperature. The aqueous layer was separated and adjusted to pH 4.2 with 28% aqueous solution of ammonia. Precipitates were collected by filtration, washed with 70% aqueous acetone (40 ml) and methanol (40 ml), and dried to give 7-amino-3-(1-allyl-1H-tetrazol-5-yl)thiomethyl-3-cephem-4-carboxylic acid (4.1 g).

I.R. (Nujol): 3150, 1800, 1610, 1530 cm$^{-1}$.

N.M.R. (d$_6$-DMSO,δ): 3.65 (2H, ABq, J=18 Hz), 4.33 (2H, ABq, J=13 Hz), 6.38–4.70 (7H, m).

Preparation 11

(1) Ethyl 2-(2-propynyloxyimino)-3-oxobutyrate (syn isomer) (71.2 g) was obtained by reacting ethyl 2-hydroxyimino-3-oxobutyrate (syn isomer) (56.7 g) with 2-propynyl bromide (43 g) in the presence of potassium carbonate (72.3 g) and N,N-dimethylformamide (280 ml).

I.R. (Film): 3280, 3220, 2120, 1735, 1670 cm$^{-1}$.

(2) Ethyl 2-(2-propynyloxyimino)-3-oxo-4-chlorobutyrate (syn isomer) (61.6 g) was obtained by reacting ethyl 2-(2-propynyloxyimino)-3-oxobutyrate (syn isomer) (71.2 g) with sulfuryl chloride (50.2 g) in acetic acid (81 ml).

I.R. (Film): 3300, 2130, 1745, 1720, 1675 cm$^{-1}$.

(3) Ethyl 2-(2-propynyloxyimino)-2-(2-aminothiazol-4-yl)acetate (syn isomer) (35.6 g) was obtained by reacting ethyl 2-(2-propynyloxyimino)-3-oxo-4-chlorobutyrate (syn isomer) (61 g) with thiourea (20 g) in the presence of sodium acetate trihydrate (35.8 g), water (150 ml) and ethanol (180 ml).

I.R. (Nujol): 3290, 2220, 1729 cm$^{-1}$.

(4) 2-(2-propynyloxyimino)-2-(2-aminethiazol-4-yl)acetic acid (syn isomer)(1.924 g) was obtained by hydrolyzing ethyl 2-(2-propynyloxyimino)-2-(2-aminothiazol-4-yl)acetate (syn isomer)(2.8 g) in the presence of 1N aqueous solution of sodium hydroxide (22.17 ml), mathanol (23 ml) and tetrahydrofuran (20 ml).

I.R. (Nujol): 2190, 1740 cm$^{-1}$.

Preparation 12

Formic acid (107 g) was added to acetic anhydride (239 g) under ice-cooling, and the mixture was stirred for 1 hour at 50° C. and then cooled to 20° C. To the mixture was added 2-(2-propynyloxyimino)-2-(2-aminothiazol-4-yl)acetic acid (syn isomer)(135 g), and the mixture was stirred for 3 hours at ambient temperature. To the mixture was added diisopropyl ether (400 ml) and then the precipitated crystals were collected by filtration, washed with diisopropyl ether and then dried to give 2-(2-propynyloxyimino)-2-(2-formamidothiazol-4-yl)acetic acid (syn isomer)(118.4 g).

I.R. (Nujol): 3250, 2130, 1685, 1600, 1560 cm$^{-1}$.

N.M.R. (d$_6$-DMSO,δ): 3.53 (1H, m), 4.87 (2H, d, J=2 Hz), 7.63 (1H, s), 8.61 (1H, s), 12.7 (1H, broad s).

Preparation 13

To a solution of 2-(2-formamidothiazol-4-yl)glyoxylic acid (30 g) and sodium bicarbonate (12.6 g) in water (1300 ml) was added allyloxyamine hydrochloride (19.8 g), and the mixture was stirred for 7 hours at ambient temperature at pH 6. To the reaction mixture was added ethyl acetate (500 ml). After the mixture was adjusted to pH 1.9 with 10% hydrochloric acid, the ethyl acetate layer was separated. The ethyl acetate layer was washed with an aqueous solution of sodium chloride, dried over magnesium sulfate and then the solvent was distilled off. The residue was pulverized in diisopropyl ether, collected by filtration and then dried to give 2-allyloxyimino-2-(2-formamidothiazol-4-yl)acetic acid (syn isomer)(25.3 g).

I.R. (Nujol): 3110, 1730, 1660, 1540 cm$^{-1}$.

N.M.R. (d$_6$-DMSO,δ): 4.70 (2H, m), 5.13–5.60 (2H, m), 5.73–6.27 (1H, m), 7.57 (1H, s), 8.35 (1H, s).

Preparation 14

(1) Sulfuryl chloride (35.2 g) was added all at once to the stirred solution of ethyl 2-ethoxyimino-3-oxobutyrate (syn isomer)(48.9 g) in acetic acid (49 ml) at room temperature, and stirred at the same temperature for an hour. After adding the resultant solution into water (200 ml), the solution was extracted with methylene chloride. The extract was washed with a saturated aqueous solution of sodium chloride, neutralized with an aqueous solution of sodium bicarbonate and washed with water. The solution was dried over magnesium sulfate and concentrated under reduced pressure to give ethyl 2-ethoxyimino-3-oxo-4-chlorobutyrate (syn isomer)(53.8 g), pale yellow oil.

(2) A mixture of ethyl 2-ethoxyimino-3-oxo-4-chlorobutyrate (syn isomer)(38.7 g), thiourea (13.2 g), sodium acetate (14.3 g), methanol (95 ml) and water (95 ml) was stirred at 48° C. for 40 minutes. After the resultant solution was adjusted to pH 6.5 with an aqueous solution of sodium bicarbonate, the appeared precipitates were collected by filtration and washed with diisopropyl ether to give ethyl 2-ethoxyimino-2-(2-aminothiazol-4-yl)acetate (syn isomer)(14.7 g), mp 130° to 131° C.

I.R. (Nujol): 3450, 3275, 3125, 1715, 1620 cm$^{-1}$.

(3) Ethyl 2-ethoxyimino-2-(2-aminothiazol-4-yl)acetate (syn isomer)(5 g) was added to a mixture of 1N sodium hydroxide (45.9 ml) and ethanol (30 ml) and stirred at room temperature for 5 hours. After removing ethanol from the resultant solution under reduced pressure, the residue was dissolved in water (60 ml) and adjusted to pH 2.0 with 10% hydrochloric acid. The solution was subjected to salting-out, and the precipitates were collected by filtration and dried to give 2-ethoxyimino-2-(2-aminothiazol-4-yl)acetic acid (syn isomer)(2.9 g).

I.R. (Nujol): 3625, 3225 (shoulder), 3100, 1650, 1615 cm$^{-1}$.

N.M.R. (d$_6$-DMSO,δ): 1.20 (3H, t, J=7 Hz), 4.09 (2H, q, J=7 Hz), 6.82 (1H, s), 7.24 (2H, broad s).

(4) 2-Ethoxyimino-2-(2-aminothiazol-4-yl)acetic acid (syn isomer)(100 g), formic acid (85.5 g) and acetic anhydride (190.1 g) were treated in a similar manner to that of Preparation 12 to give 2-ethoxyimino-2-(2-formamidothiazol-4-yl)acetic acid (syn isomer) (99.1 g).

I.R. (Nujol): 3200, 3140, 3050, 1700 cm$^{-1}$.

N.M.R. (d$_6$-DMSO,δ): 1.18 (3H, t, J=6 Hz), 4.22 (2H, q, J=6 Hz), 7.56 (1H, s), 8.56 (1H, s), 12.62 (1H, broad s).

Preparation 15

(1) Ethyl 2-hydroxyimino-2-(2-aminothiazol-4-yl)acetate (syn isomer)(126.4 g), formic acid (81.3 g) and acetic anhydride (180 g) were treated in a similar manner to that of Preparation 12 to give ethyl 2-hydroxyimino-2-(2-formamidothiazol-4-yl)acetate (syn isomer)(109.6 g).

I.R. (Nujol): 3320, 3140, 3050, 1710, 1555 cm$^{-1}$.

N.M.R. (d$_6$-DMSO,δ): 1.30 (3H, t, J=7 Hz), 4.33 (2H,q, J=7 Hz), 7.54 (1H, s), 8.54 (1H, s), 11.98 (1H, s), 12.58 (1H, s).

(2) A mixture of chloromethylthiomethane (7.97 g), powdered potassium iodide (15.1 g) and acetone (79 ml) was stirred at ambient temperature for an hour, the resulting mixture was filtered and washed with a small amount of acetone. The washings and the filtrate were combined and added to a stirred suspension of ethyl 2-hydroxyimino-2-(2-formamidothiazol-4-yl)acetate (syn isomer)(17.5 g) and powdered potassium carbonate (15.5 g) in acetone (300 ml). The mixture was stirred at ambient temperature for 3 hours, filtered and washed with acetone. The washings and the filtrate were combined and concentrated in vacuo. The residue was dissolved in ethyl acetate washed with a saturated aqueous solution of sodium chloride twice, dried over magnesium sulfate and concentrated in vacuo. The oily residue was subjected to column chromatography on silica gel and eluted with chloroform to give ethyl 2-methylthiomethoxyimino-2-(2-formamidothiazol-4-yl)acetate (syn isomer)(2.4 g), mp. 130° to 131° C.

I.R. (Nujol): 3160, 3125, 3050, 1740, 1695 cm$^{-1}$.

N.M.R. (d$_6$-DMSO, δ): 1.32 (3H, t, J=7 Hz), 2.22 (3H, s), 4.38 (2H, q, J=7 Hz), 5.33 (2H, s), 7.67 (1H, s), 8.56 (1H, s).

(3) A mixture of ethyl 2-methylthiomethoxyimino-2-(2-formamidothiazol-4-yl)acetate (syn isomer)(2.4 g), 1N aqueous sodium hydroxide (23.8 ml) and methanol (19.8 ml) was stirred at 30° C. for 2.5 hours. The resultant solution was adjusted to pH 7 with 10% hydrochloric acid and methanol was distilled off in vacuo. The aqueous solution was adjusted to pH 1 with 10% hydrochloric acid under ice cooling, and extracted with ethyl acetate three times. The extracts were washed with a saturated aqueous solution of sodium chloride, dried over magnesium sulfate and concentrated in vacuo to give 2-methylthiomethoxyimino-2-(2-formamidothiazol-4-yl)acetic acid (syn isomer)(1.13 g), mp. 157° C. (dec.).

I.R. (Nujol): 3210, 3160, 3075, 1700, 1555 cm$^{-1}$.

N.M.R. (d$_6$-DMSO, δ): 2.24 (3H, s), 5.31 (2H, s), 7.61 (1H, s), 8.57 (1H, s), 12.73 (1H, s).

Preparation 16

The following compounds were obtained according to similar manners to those of Preparations 11 to 15

(1) 2-Isopropoxyimino-2-(2-formamidothiazol-4-yl)acetic acid (syn isomer), mp 168° to 169° C. (dec.).

I.R. (Nujol): 3200, 3130, 1710, 1600, 1560 cm$^{-1}$.

(2) 2-Butoxyimino-2-(2-formamidothiazol-4-yl)acetic acid (syn isomer).

I.R. (Nujol): 3350, 3160, 3050, 1700, 1680, 1570 cm$^{-1}$.

(3) 2-Hexyloxyimino-2-(2-formamidothiazol-4-yl)acetic acid (syn isomer), mp. 115° to 116° C. (dec.).

I.R. (Nujol): 3170, 3070, 1720, 1700, 1660 cm$^{-1}$.

N.M.R. (d$_6$-DMSO, δ): 0.6–2.1 (11H, m), 4.15 (2H, t, J=6 Hz), 7.53 (1H, s), 8.56 (1H, s), 12.69 (1H, s).

(4) 2-(2-Formyloxyethoxy)imino-2-(2-formamidothiazol-4-yl)acetic acid (syn isomer).

I.R. (Nujol): 3200, 1710, 1690 cm$^{-1}$.

(5) 2-Benzyloxyimino-2-(2-aminothiazol-4-yl)acetic acid (syn isomer).

I.R. (Nujol): 3330, 3200, 3100, 1660, 1590 cm$^{-1}$.

(6) 2-Ethoxycarbonylmethoxyimino-2-(2-formamidothiazol-4-yl)acetic acid (syn isomer), mp. 112° C. (dec.).

I.R. (Nujol): 3150, 1740, 1670, 1550 cm$^{-1}$.

(7) 2-t-Butoxycarbonylmethoxyimino-2-(2-formamidothiazol-4-yl)acetic acid (syn isomer), mp. 117° C. (dec.).

I.R. (Nujol): 3180, 3140, 1750, 1690, 1630 cm$^{-1}$.

(8) 2-(3-Isoxazolyl)methoxyimino-2-(2-formamidothiazol-4-yl)acetic acid (syn isomer), mp. 110° C. (dec.).

I.R. (Nujol): 3270, 3130, 1680, 1540 cm$^{-1}$.

EXAMPLE 31

2-Allyloxyimino-2-(2-formamidothiazol-4-yl)acetic acid (syn isomer)(0.80 g) and dry ethyl acetate (10 ml) were added at 0° to 5° C. with stirring to a suspension of Vilsmeier reagent prepared from dry dimethylformamide (0.25 g) and phosphorus oxychloride (0.528 g) in dry ethyl acetate (0.75 ml) by conventional method, and the resulting mixture was stirred for 30 minutes at the same temperature to give an yellow solution. The solution was added at −10° C. with stirring to a solution of 7-amino-3-(1-allyl-1H-tetrazol-5-yl)thiomethyl-3-cephem-4-carboxylic acid (1.11 g) and trimethylsilylacetamide (2.96 g) in dry ethyl acetate (15 ml), and the mixture was stirred for 1.5 hours at the same temperature. After addition of water (15 ml) to the reaction mixture, the ethyl acetate layer was separated and extracted with an aqueous solution of sodium bicarbonate (30 ml). The aqueous extract was acifified to pH 2.0 with 10% hydrochloric acid and extracted with ethyl acetate (150 ml). The extract was washed with water, dried and evaporated. The residue was pulverized with diisopropyl ether to give colorless powder of 7-[2-allyloxyimino-2-(2-formamidothiazol-4-yl)acetamido]-3-(1-allyl-1H-tetrazol-5-yl)thiomethyl-3-cephem-4-carboxylic acid (syn isomer)(1.48 g).

I.R. (Nujol): 3180, 1775, 1665 cm$^{-1}$.

N.M.R. (d$_6$-DMSO,δ): 9.68 (1H, d, J=8 Hz), 8.51 (1H, s), 7.40 (1H, s), 5.60–6.33 (3H, m), 4.85–5.57 (7H, m), 4.27–4.77 (4H, m), 3.70 (2H, ABq, J=18 Hz).

EXAMPLE 32

The Vilsmeier reagent was prepared from dry dimethylformamide (0.526 g), phosphorus oxychloride (1.10 g) and dry ethyl acetate (1.5 ml) by the conventional method. Ethyl acetate (10 ml) was added thereto and then 2-methoxyimino-2-(2-formamidothiazl-4-yl)acetic acid (syn isomer)(1.50 g) was added thereto at 0° C. The mixture was stirred for 30 minutes at the same temperature. The resulting mixture was added under −10° C. to a stirred solution of 7-amino-3-(1-allyl-1H-tetrazol-5-yl)thiomethyl-3-cephem-4-carboxylic acid (2.32 g) and trimethylsilylacetamide (6.18 g) in dry ethyl acetate (30 ml), and the mixture was stirred for 1 hour at the same temperature. The reaction mixture was extracted by adding ethyl acetate (20 ml) and water (30 ml). The ethyl acetate layer was separated and extracted with a saturated aqueous solution of sodium bicarbonate (20 ml). The aqueous layer was adjusted to pH 20 with 10% hydrochloric acid. Precipitates were collected by filtration, washed with water and dried to give 7-[2-methoxyimino-2-(2-formamidothiazol-4-yl)acetamido]-3-(1-allyl-1H-tetrazol-5-yl)thiomethyl-3-cephem-4-carboxylic acid (syn isomer) (2.60 g).

I.R. (Nujol): 3200, 1770, 1710, 1665 cm$^{-1}$.

N.M.R. (d$_6$-DMSO, δ): 3.72 (2H, broad s), 3.93 (3H, s), 4.40 (2H, ABq, J=14 Hz), 4.87–5.50 (5H, m), 5.73–6.37 (2H, m), 7.45 (1H, s), 8.55 (1H, s), 9.70 (1H, d, J=8 Hz).

EXAMPLE 33

The Vilsmeier reagent was prepared from dry dimethylformamide (0.4 g), phosphorus oxychloride (0.9 g) and dry ethyl acetate (1.6 ml) by the conventional method. Dry ethyl acetate (18 ml) was added thereto and then 2-ethoxyimino-2-(2-formamidothiazol-4-yl)acetic acid (syn isomer)(1.3 g) was added thereto at 0° C. The mixture was stirred for 30 minutes at the same temperature. The resulting mixture was added under −10° C. to a stirred solution of 7-amino-3-(1-allyl-1H-tetrazol-5-yl)thiomethyl-3-cephem-4-carboxylic acid (1.8 g) and trimethylsilylacetamide (4.6 g) in dry ethyl acetate (36 ml), and the mixture was stirred for 1 hour at the same temperature. To the reaction mixture was added water (30 ml). The ethyl acetate layer was separated and extracted with a saturated aqueous solution of sodium bicarbonate (pH 7.5). The aqueous layer was washed three times with ethyl acetate and adjusted to pH 2.0 with conc. hydrochloric acid after addition of ethyl acetate (100 ml). The ethyl acetate layer was separated, washed with a saturated aqueous solution of sodium chloride, dried over magnesium sulfate, treated with an activated charcoal and concentrated to dryness to give 7-[2-ethoxyimino-2-(2-formamidothiazol-4-yl)acetamido]-3-(1-allyl-1H-tetrazol-5-yl)thiomethyl-3-cephem-4-carboxylic acid (syn isomer) (2.56 g).

I.R. (Nujol): 3200, 1765, 1665 cm$^{-1}$.

N.M.R. (d$_6$-DMSO, δ): 1.26 (3H, t, J=7.0 Hz), 3.68 (2H, m), 4.18 (2H, q, J=7.0 Hz), 4.36 (2H, ABq, J=14.0 Hz), 4.75–5.57 (5H, m), 5.68–6.40 (2H, m), 7.37 (1H, s), 8.48 (1H, s), 9.60 (1H, d, J=8.0 Hz).

EXAMPLE 34

The Vilsmeier reagent was prepared from dry dimethylformamide (0.5 g), phosphorus oxychloride (1.3 g) and dry ethyl acetate (2.0 ml) by the conventional method. Dry tetrahydrofuran (20 ml) was added thereto and then 2-(2-propynyl)oxyimino-2-(2-formamidothiazol-4-yl)acetic acid (syn isomer)(1.6 g) was added thereto at 0° C. The mixture was stirred for 30 minutes at the same temperature. The resulting mixture was added at −10° C. to a stirred solution of 7-amino-3-(1-allyl-1H-tetrazol-5-yl)thiomethyl-3-cephem-4-carboxylic acid (2.0 g) and trimethylsilylacetamide (5.1 g) in dry ethyl acetate (40 ml), and the mixture was stirred for 1 hour at −10° to −20° C. To the reaction mixture was added water (30 ml). The organic layer was separated and extracted with a saturated aqueous solution of sodium bicarbonate (30 ml). The aqueous layer was adjusted to pH 2.2 with conc. hydrochloric acid. Precipitates were collected by filtration, washed with water and dried to give colorless powder of 7-[2-(2-propynyl)oxyimino-2-(2-formamidothiazol-4-yl)acetamido]-3-(1-allyl-1H-tetrazol-5-yl)thiomethyl-3-cephem-4-carboxylic acid (syn isomer)(2.40 g).

I.R. (Nujol): 3310, 2170, 1780, 1680 cm$^{-1}$.

N.M.R. (d$_6$-DMSO, δ): 3.49 (1H, m), 3.72 (2H, m), 4.38 (2H, ABq, J=14 Hz), 4.57–5.52 (7H, m), 5.69–6.40 (2H, m), 7.46 (1H, s), 8.55 (1H, s), 9.75 (1H, d, J=8 Hz).

EXAMPLE 35

The Vilsmeier reagent was prepared from dry dimethylformamide (0.209 g), phosphorus oxychloride (0.434 g) and dry ethyl acetate (0.75 ml) by the conventional method. Dry tetrahydrofuran (6.5 ml) was added thereto and then 2-methylthiomethoxyimino-2-(2-formamidothiazol-4-yl)acetic acid (syn isomer)(0.65 g) was added thereto at 0° C. The mixture was stirred for 30 minutes at the same temperature. The resulting mixture was dropwise added at −5° to 0° C. to a stirred solution of 7-amino-3-(1-allyl-1H-tetrazol-5-yl)thiomethyl-3-cephem-4-carboxylic acid (1.25 g) in a mixture of water (10 ml) and acetone (10 ml) keeping the pH at 7.5 by triethylamine, and the mixture was stirred for 30 minutes at the same temperature at pH 7.5. To the reaction mixture was added ethyl acetate (60 ml) and the mixture was adjusted to pH 2.5 with 10% hydrochloric acid. Insoluble material was filtered off and the filtrate was extracted twice with ethyl acetate. The combined extracts were washed twice with a saturated sodium chloride aqueous solution and dried over magnesium sulfate. The solvent was distilled off and the residue was pulverized with diethyl ether to give yellowish powder of 7-[2-methylthiomethoxyimino-2-(2-formamidothiazol-4-yl)acetamido]-3-(1-allyl-1H-tetrazol-5-yl)thiomethyl-3-cephem-4-carboxylic acid (syn isomer)(1.03 g).

I.R. (Nujol): 3250, 3200, 1780, 1670, 1540 cm$^{-1}$.

N.M.R. (d$_6$-DMSO, δ): 2.23 (3H, s), 3.72 (2H, s), 4.38 (2H, ABq, J=14 Hz), 4.8–5.6 (7H, m), 5.7–6.4 (2H, m), 7.48 (1H, s), 8.55 (1H, s), 9.75 (1H, d, J=8 Hz), 12.69 (1H, broad s).

EXAMPLE 36

The Vilsmeier reagent was prepared from dry dimethylformamide (0.74 g), phosphorus oxychloride (1.56 g) and dry ethyl acetate (2.0 ml) by the conventional method. Dry tetrahydrofuran (15 ml) was added thereto and then 2-(3-isoxazolyl)methoxyimino-2-(2-formamidothiazol-4-yl)acetic acid (syn isomer) (1.50 g)

was added thereto at 0° C. The mixture was stirred for 30 minutes at the same temperature. The resulting mixture was added dropwise at −5° to 0° C. to a stirred solution of 7-amino-3-(1-allyl-1H-tetrazol-5-yl)thiomethyl-3-cephem-4-carboxylic acid (2.34 g) in a mixture of water (11.5 ml) and acetone (11.5 ml) keeping the pH at 7.5 by triethylamine, and the mixture was stirred for 30 minutes at the same temperature at pH 7.5. To the reaction mixture was added ethyl acetate (60 ml) and the mixture was adjusted to pH 2.5 with 10% hydrochloric acid. Insoluble material was filtered off and the filtrate was extracted twice with ethyl acetate. The combined extracts were washed twice with a saturated sodium chloride aqueous solution and dried over magnesium sulfate. The solvent was distilled off and the residue was pulverized with diethyl ether to give yellowish powder of 7-[2-(3-isoxazolyl)methoxyimino-2-(2-formamidothiazol-4-yl)acetamido]-3-(1-allyl-1H-tetrazol-5-yl)thiomethyl-3-cephem-4-carboxylic acid (syn isomer)(2.15 g).

I.R. (Nujol): 3250, 1780, 1670, 1550 cm$^{-1}$.

N.M.R. (d$_6$-DMSO, δ): 3.72 (2H, s), 4.40 (2H, ABq, J=14 Hz), 4.8–5.6 (7H, m), 5.6–6.5 (2H, m), 6.67 (1H, d, J=2 Hz), 7.50 (1H, s), 8.56 (1H, s), 8.92 (1H, d, J=2 Hz), 9.80 (1H, d, J=8 Hz), 12.72 (1H, broad s).

EXAMPLE 37

Phosphorus oxychloride (1.0 g) was added at a time to a suspension of 2-benzyloxyimino-2-(2-aminothiazol-4-yl)acetic acid (syn isomer)(1.4 g) in dry tetrahydrofuran (14 ml) at 2° C. and the mixture was stirred for 15 minutes at 2° to 4° C. Trimethylsilylacetamide (1.0 g) was added dropwise thereto and the resulting mixture was stirred for 20 minutes at 2° to 6° C. Phosphorus oxychloride (1.0 g) was added thereto and the mixture was stirred for 20 minutes. Dry dimethylformamide (0.5 g) was added thereto at a time at 4° to 6° C. and the mixture was stirred for 1 hour to give a clear solution. On the other hand, trimethylsilylacetamide (5.3 g) was added to a stirred suspension of 7-amino-3-(1-allyl-1H-tetrazol-5-yl)thiomethyl-3-cephem-4-carboxylic acid (1.8 g) in dry ethyl acetate (27 ml) and the solution was stirred for 30 minutes at 40° C. To this solution was added the above-obtained tetrahydrofuran solution at a time at −30° C., and the resulting mixture was stirred for 1 hour at −5° to −20° C. To the reaction mixture was added water (30 ml) and ethyl acetate (20 ml). An organic layer was separated and extracted with an aqueous solution of sodium bicarbonate. The extract was adjusted to pH 3.0 with 10% hydrochloric acid. Precipitates were collected by filtration, washed with water to give 7-[2-benzyloxyimino-2-(2-aminothiazol-4-yl)acetamido]-3-(1-allyl-1H-tetrazol-5-yl)thiomethyl-3--cephem-4-carboxylic acid (syn isomer)(0.85 g).

I.R. (Nujol): 3350, 3230, 1780, 1675, 1635 cm$^{-1}$.

N.M.R. (d$_6$-DMSO, δ): 3.67 (2H, m), 4.40 (2H, ABq, J=15.0 Hz), 4.85–5.56 (6H, m), 5.62–6.45 (2H, m), 6.77 (1H, s), 7.01–7.65 (7H, m), 9.71 (1H, d, J=8 Hz).

EXAMPLE 38

The Vilsmeier reagent was prepared from dry dimethylformamide (0.44 g), phosphorus oxychloride (0.9 g) and dry ethyl acetate (1.0 ml) by the conventional method. Dry ethyl acetate (20 ml) was added thereto and then 2-methoxyimino-2-(2-formamidothiazol-4-yl)acetic acid (syn isomer)(1.1 g) was added thereto at −5° to −10° C. The mixture was stirred for 10 minutes at the same temperature. The resulting mixture was dropwise added at 0° to 5° C. and pH 6.5 to 7.5 with stirring to a solution of 7-amino-3-(4-allyl-4H-1,2,4-triazol-3-yl)thiomethyl-3-cephem-4-carboxylic acid (2.12 g) and sodium bicarbonate (2 g) in a mixture of water (20 ml) and acetone (20 ml), and the mixture was stirred for 20 minutes at the same temperature. The aqueous layer was separated and acetone was evaporated. The aqueous layer was adjusted under ice-cooling and stirring to pH 3.0 with 10% hydrochloric acid. Precipitates were collected by filtration, washed with water and dried to give 7-[2-methoxyimino-2-(2-formamidothiazol-4-yl)acetamido]-3-(4-allyl-4H-1,2,4-triazol-3-yl)thiomethyl-3-cephem-4-carboxylic acid (syn isomer)(0.94 g).

I.R. (Nujol): 3200, 1780, 1680, 1550 cm$^{-1}$.

N.M.R. (d$_6$-DMSO, δ): 3.72 (2H, broad s), 3.93 (3H, s), 4.20 (2H, broad s), 4.65 (2H, m), 4.72–5.43 (3H, m), 5.55–6.45 (2H, m), 7.43 (1H, s), 8.55 (1H, s), 8.65 (1H, s), 9.68 (1H, d, J=8 Hz), 12.82 (1H, m).

EXAMPLE 39

The following compounds were obtained according to similar manners to those of Examples 31 to 38.

(1) 7-[2-Isopropoxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3220, 1780, 1670cm$^{-1}$.

N.M.R. (d$_6$-DMSO, δ): 1.20 (3H, s), 1.32 (3H, s), 3.70 (2H, broad s), 4.07–4.87 (3H, m), 4.93–5.50 (4H, m), 5.67–6.23 (2H, m), 7.40 (1H, s), 8.50 (1H, s), 9.58 (1H, d, J=8 Hz).

(2) 7-[2-Butoxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3200, 1780, 1695, 1675, 1655 cm$^{-1}$.

N.M.R. (d$_6$-DMSO, δ): 0.88 (3H, m), 1.10–2.01 (4H, m), 3.71 (2H, m), 4.14 (2H, t, J=7.0 Hz), 4.38 (2H, ABq, J=14.0 Hz), 4.83–5.51 (5H, m), 5.63–6.40 (2H, m), d, J=9.0 Hz).

(3) 7-[2-Hexyloxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3175, 1780, 1757, 1684, 1640 cm$^{-1}$.

N.M.R. (d$_6$-DMSO, δ): 0.84 (3H, m), 1.06–2.03 (8H, m), 3.73 (2H, m), 4.14 (2H, t, J=6.0 Hz), 4.40 (2H, ABq, J=14.0 Hz), 4.85–5.52 (5H, m), 5.75–6.45 (2H, m), 6.97 (1H, broad s), 7.41 (1H, s), 8.54 (1H, s), 9.63 (1H, d, J=8.0 Hz).

(4) 7-[2-(2-Formyloxyethoxy)imino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3265, 1780, 1720, 1680 cm$^{-1}$.

N.M.R. (d$_6$-DMSO, δ): 3.74 (2H, m), 4.13–4.70 (6H, m), 4.85–5.53 (5H, m), 5.70–6.42 (2H, m), 7.48 (1H, s), 8.26 (1H, s), 8.56 (1H, s), 9.69 (1H, d, J=9.0 Hz).

(5) 7-[2-Ethoxycarbonylmethoxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3500, 3280, 1780, 1735, 1690 cm$^{-1}$.

N.M.R (d$_6$-DMSO, δ): 1.24 (3H, t, J=7 Hz), 3.74 (2H, s), 4.20 (2H, q, J=7 Hz), 4.42 (2H, s), 4.77 (2H, s), 4.5–5.6 (5H, m), 5.7–6.4 (3H, m), 7.50 (1H, s), 8.57 (1H, s), 9.68 (1H, d, J=8 Hz), 12.69 (1H, broad s).

(6) 7-[2-t-Butoxycarbonylmethoxyimino-2-(2-formamidothiazol-4-yl)acetamido]-3-(1-allyl-1H-tetrazol-5-yl)thiomethyl-3-cephem-4-carboxylic acid (syn isomer).

I.R. (Nujol): 3250, 1780, 1720, 1680, 1540 cm$^{-1}$.

N.M.R. (d$_6$-DMSO, δ): 1.44 (9H, s), 3.71 (2H, ABq, J=18 Hz), 4.37 (2H, ABq, J=14 Hz), 4.62 (2H, s), 4.8–5.4 (5H, m), 5.5–6.4 (2H, m), 7.46 (1H, s), 8.52 (1H, s), 9.58 (1H, d, J=8 Hz), 12.60 (1H, broad s).

(7) 7-[2-Methoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3225, 1770, 1670, 1630 cm$^{-1}$.

(8) 7-[2-Ethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 1780, 1675, 1635 cm$^{-1}$.

(9) 7-[2-Isopropoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 3250, 1780, 1675, 1630 cm$^{-1}$.

(10) 7-[2-Butoxyimino-2-(2-aminothiazol-4-yl)acetamido]-B 3-(1-allyl-1H-tetrazol-5-yl)thiomethyl-3-cephem-4-carboxylic acid (syn isomer).

I.R. (Nujol): 3360, 1780, 1672 cm$^{-1}$.

(11) 7-[2-Hexyloxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 3240, 1780, 1675, 1630 cm$^{-1}$.

(12) 7-[2-Allyloxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 3210, 1778, 1675 cm$^{-1}$.

(13) 7-[2-(2-Propynyl)oxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3330, 2170, 1780, 1683, 1630 cm$^{-1}$.

(14) 7-[2-Ethoxycarbonylmethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3360, 3230, 1780, 1680, 1630 cm$^{-1}$.

(15) 7-[2-t-Butoxycarbonylmethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3330, 1780, 1730, 1680, 1630 cm$^{-1}$.

(16) 7-[2-Methylthiomethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3270, 1760, 1650, 1520 cm$^{-1}$.

(17) 7-[2-(3-Isoxazolyl)methoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3300, 1770, 1660, 1530 cm$^{-1}$.

(18) 7-[2-Carboxymethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3360, 1780, 1680, 1630 cm$^{-1}$.

(19) 7-[2-Methoxyimino-2-(2-aminothiazol-4-yl)acetamido]-3-(4-allyl-4H-1,2,4-triazol-3-yl)thiomethyl-3-cephem-4-carboxylic acid (syn isomer).

I.R. (Nujol): 3350, 1775, 1670, 1530 cm$^{-1}$.

EXAMPLE 40

Conc. hydrochloric acid (0.33 g) was added to a solution of 7-[2-allyloxyimino-2-(2-formamidothiazol-4-yl)acetamido]-3-(1-allyl-1H-tetrazol-5-yl)thiomethyl-3-cephem-4-carboxylic acid (syn isomer)(1.30 g) in methanol (13 ml) and the mixture was stirred for 4.5 hours at ambient temperature. The solvent was distilled off under reduced pressure and the residue was dissolved in a saturated aqueous solution of sodium bicarbonate (25 ml). The aqueous solution was washed with ethyl acetate (25 ml) and adjusted to pH 2.0 with 10% hydrochloric acid. Precipitates were collected by filtration, washed with water and dried to give colorless powder of 7-[2-allyloxyimino-2-(2-aminothiazol-4-yl)acetamido]-3-(1-allyl-1H-tetrazol-5-yl)thiomethyl-3-cephem-4-carboxylic acid (syn isomer)(0.95 g).

I.R. (Nujol): 3350, 3210, 1778, 1675 cm$^{-1}$.

N.M.R. (d$_6$-DMSO, δ): 3.68 (2H, ABq, J=18 Hz), 4.40–4.71 (4H, m), 4.80–5.45 (7H, m), 5.64–6.24 (3H, m), 6.74 (1H, s), 7.35 (2H, broad s), 9.62 (1H, d, J=8 Hz).

EXAMPLE 41

A mixture of 7-[2-methoxyimino-2-(2-formamidothiazol-4-yl)acetamido]-3-(1-allyl-1H-tetrazol-5-yl)thiomethyl-3-cephem-4-carboxylic acid (syn isomer) (2.60 g), conc.hydrochloric acid (0.70 g) and methanol (36 ml) was stirred for 2 hours at ambient temperature. The solvent was distilled off under reduced pressure and the residue was dissolved in a saturated aqueous solution of sodium bicarbonate. The volume of the solution was increased to 50 ml. by adding water. The aqueous solution was washed with ethyl acetate (25 ml) and adjusted to pH 1.5 with 10% hydrochloric acid. Precipitates were collected by filtration, washed with water and dried to give 7-[2-methoxyimino-2-(2-aminothiazol-4-yl)acetamido]-3-(1-allyl-1H-tetrazol-5-yl)thiomethyl-3-cephem-4-carboxylic acid (syn isomer) (1.90 g).

I.R. (Nujol): 3225, 1770, 1670, 1630 cm$^{-1}$.

N.M.R. (d$_6$-DMSO, δ): 3.70 (2H, broad s), 3.87 (3H, s), 4.36 (2H, ABq, J=14 Hz), 4.87–5.47 (5H, m), 5.63–6.33 (2H, m), 6.76 (1H, s), 9.60 (1H, d, J=8 Hz).

EXAMPLE 42

Conc. hydrochloric acid (0.9 g) was added at ambient temperature to a solution of 7-[2-ethoxyimino-2-(2-formamidothiazol-4-yl)acetamido]-3-(1-allyl-1H-tetrazol-5-yl)thiomethyl-3-cephem-4-carboxylic acid (syn isomer)(2.4 g) in a mixture of methanol (16.8 ml) and tetrahydrofuran (4.8 ml) and the mixture was stirred for 3 hours at 30° C. The solvent was distilled off under reduced pressure and the residue was dissolved in a saturated aqueous solution of sodium bicarbonate. The aqueous solution was washed with ethyl acetate and adjusted to pH 2.8 with conc.hydrochloric acid. Precipitates were collected by filtration, washed with water and dried to give 7-[2-ethoxyimino-2-(2-aminothiazol-4-yl)acetamido]-3-(1-allyl-1H-tetrazol-5-yl)thiomethyl-3-cephem-4-carboxylic acid (syn isomer) (1.72 g).

I.R. (Nujol): 3350, 1780, 1675, 1635 cm$^{-1}$.

N.M.R. (d$_6$-DMSO, δ): 1.24 (3H, t, J=7.3 Hz), 3.71 (2H, m), 4.13 (2H, q, J=7.3 Hz), 4.37 (2H, ABq, J=13.5 Hz), 4.80–5.53 (5H, m), 5.64–6.45 (2H, m), 6.77 (1H, s), 7.25 (2H, broad s), 9.62 (1H, d, J=8.0 Hz).

EXAMPLE 43

To a solution of 7-[2-(2-propynyl)oxyimino-2-(2-formamidothiazol-4-yl)acetamido]-3-(1-allyl-1H-tetrazol-5-yl)thiomethyl-3-cephem-4-carboxylic acid (syn isomer)(2.0 g) in methanol (14 ml) was added conc.hydrochloric acid (0.3 g) and the mixture was stirred for 3.5 hours at ambient temperature. The solvent was distilled off under reduced pressure and the residue was dissolved in a saturated aqueous solution of sodium bicarbonate. The aqueous solution was washed with ethyl acetate and adjusted to pH 2.8 with conc.hydrochloric acid. Precipitates were collected by filtration, washed with water and dried to give 7-[2-(2-propynyl)oxyimino-2-(2-aminothiazol-4-yl)acetamido]-3-(1-allyl-1H-tetrazol-5-yl)thiomethyl-3-cephem-4-carboxylic acid (syn isomer)(1.43 g).

I.R. (Nujol): 3330, 2170, 1780, 1680, 1630 cm$^{-1}$.

N.M.R. (d$_6$-DMSO, δ): 3.46 (1H, m), 3.70 (2H, m), 4.37 (2H, ABq, J=13.5 Hz), 4.57-5.47 (7H, m). 5.60-6.49 (2H, m), 6.77 (1H, s), 7.25 (2H, broad s), 9.64 (1H, d, J=8.0 Hz).

EXAMPLE 44

A mixture of 7-[2-methylthiomethoxyimino-2-(2-formamidothiazol-4-yl)acetamido]-3-(1-allyl-1H-tetrazol-5-yl)thiomethyl-3-cephem-4-carboxylic acid (syn isomer)(0.95 g), conc.hydrochloric acid (0.324 g), methanol (9.5 ml) and tetrahydrofuran (2 ml) was stirred for 2 hours at ambient temperature. The solvent was distilled off under reduced pressure and the residue was dissolved in a saturated aqueous solution of sodium bicarbonate. The aqueous solution was washed with ethyl acetate (25 ml) and adjusted to pH 1.5 with 10% hydrochloric acid. Precipitates were collected by filtration, washed with water and dried to give 7-[2-methylthiomethoxyimino-2-(2-aminothiazol-4-yl)acetamido]-3-(1-allyl-1H-tetrazol-5-yl)thiomethyl-3-cephem-4-carboxylic acid (syn isomer)(0.78 g).

I.R. (Nujol): 3270, 1760, 1650, 1520 cm$^{-1}$.

N.M.R. (d$_6$-DMSO, δ): 2.21 (3H, s), 3.72 (2H, s), 4.38 (2H, ABq, J=14 Hz), 4.8-5.6 (7H, m), 5.7-6.4 (2H, m), 6.80 (1H, s), 7.26 (2H, broad s), 9.66 (1H, d, J=8 Hz).

EXAMPLE 45

A mixture of 7-[2-(3-isoxazolyl)methoxyimino-2-(2-formamidothiazol-4-yl)acetamido]-3-(1-allyl-1H-tetrazol-5-yl)thiomethyl-3-cephem-4-carboxylic acid (syn isomer) (1.5 g), conc.hydrochloric acid (0.497 g), methanol (15 ml) and tetrahydrofuran (3 ml) was stirred for 2 hours at ambient temperature. The solvent was distilled off under reduced pressure and the residue was dissolved in a saturated aqueous solution of sodium bicarbonate. The aqueous solution was washed with ethyl acetate (25 ml) and adjusted to pH 1.5 with 10% hydrochloric acid. Precipitates were collected by filtration, washed with water and dried to give 7-[2-(3-isoxazolyl)methoxyimino-2-(2-aminothiazol-4-yl)acetamido]-3-(1-allyl-1H-tetrazol-5-yl)thiomethyl-3-cephem-4-carboxylic acid (syn isomer)(0.65 g).

I.R. (Nujol): 3300, 1770, 1660, 1530 cm$^{-1}$.

N.M.R. (d$_6$-DMSO, δ): 3.71 (2H, s), 4.40 (2H, d, J=14 Hz), 4.8-5.6 (7H, m), 5.6-6.5 (2H, m), 6.62 (1H, d, J=2 Hz), 6.83 (1H, s), 7.29 (2H, broad s), 8.92 (1H, d, J=2 Hz), 9.73 (1H, d, J=8 Hz).

EXAMPLE 46

A mixture of 7-[2-methoxyimino-2-(2-formamidothiazol-4-yl)acetamido]-3-(4-allyl-4H-1,2,4-triazol-3-yl)thiomethyl-3-cephem-4-carboxylic acid (syn isomer)(0.9 g), conc.hydrochloric acid (0.3 ml), methanol (7 ml) and tetrahydrofuran (7 ml) was stirred for 4.5 hours at ambient temperature. The solvent was distilled off under reduced pressure and the residue was dissolved in a saturated aqueous solution of sodium bicarbonate. The aqueous solution was washed with ethyl acetate (25 ml) and adjusted to pH 2.0 with 10% hydrochloric acid. Precipitates were collected by filtration, washed with water and dried to give 7-[2-methoxyimino-2-(2-aminothiazol-4-yl)acetamido]-3-(4-allyl-4H-1,2,4-triazol-3-yl)thiomethyl-3-cephem-4-carboxylic acid (syn isomer)(0.5 g).

I.R. (Nujol): 3350, 1775, 1670, 1530 cm$^{-1}$.

N.M.R. (d$_6$-DMSO, δ): 3.65 (2H, broad s), 3.83 (3H, s), 4.15 (2H, broad s), 4.58 (2H, m), 4.77-5.5 (3H, m), 5.58-6.33 (2H, m), 6.73 (1H, s), 8.60 (1H, s), 9.58 (1H, d, J=8 Hz).

EXAMPLE 47

The following compounds were obtained according to similar manners to those of Examples 40 to 46.

(1) 7-[2-Benzyloxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 3230, 1780, 1675, 1635 cm$^{-1}$.

(2) 7-[2-Isopropoxyimino-2-(2-aminothiazol-4-yl)acetamido]-3-(1-allyl-1H-tetrazol-5-yl)thiomethyl-3-cephem-4-carboxylate acid (syn isomer).

I.R. (Nujol): 3350, 3250, 1780, 1675, 1630 cm$^{-1}$.

N.M.R. (d$_6$-DMSO, δ): 1.20 (3H, s), 1.30 (3H, s), 3.70 (2H, broad s), 4.30 (3H, m), 4.97-5.40 (4H, m), 5.63-6.27 (2H, m), 6.70 (1H, s), 9.55 (1H, d, J=8 Hz).

(3) 7-[2-Butoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3360, 1780, 1672 cm$^{-1}$.

N.M.R. (d$_6$-DMSO, δ): 0.91 (3H, t, J=6.0 Hz), 1.18-1.96 (4H, m), 3.73 (2H, m), 3.87-4.73 (4H, m), 4.83-5.57 (5H, m), 5.63-6.40 (2H, m), 6.74 (1H, s), 7.20 (2H, broad s), 9.55 (1H, d, J=8.0 Hz).

(4) 7-[2-Hexyloxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3350, 3240, 1780, 1675, 1630 cm$^{-1}$.

N.M.R. (d$_6$-DMSO, δ): 0.85 (3H, m), 1.00-2.00 (8H, m), 3.68 (2H, m), 4.05 (2H, m), 4.37 (2H, m), 4.80-5.47 (5H, m), 5.60-6.47 (2H, m), 6.69 (1H, s), 7.20 (2H, broad s), 9.50 (1H, d, J=8.0 Hz).

(5) 7-[2-Ethoxycarbonylmethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3360, 3230, 1780, 1680, 1630 cm$^{-1}$.

N.M.R. (d$_6$-DMSO, δ): 1.21 (3H, t, J=7 Hz), 3.68 (2H, s), 4.14 (2H, q, J=7 Hz), 4.38 (2H, s), 4.66 (2H, s), 4.8-5.5 (5H, m), 5.6-6.4 (3H, m), 6.80 (1H, s), 7.20 (2H, broad s), 9.48 (1H, d, J=8 Hz).

(6) 7-[2-t-Butoxycarbonylmethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3330, 1780, 1730, 1680, 1630 cm$^{-1}$.

N.M.R. (d$_6$-DMSO, δ): 1.43 (9H, s), 3.67 (2H, s), 4.37 (2H, ABq, J=14 Hz), 4.56 (2H, s), 4.8-5.5 (5H, m), 5.6-6.4 (2H, m), 6.78 (1H, s), 7.20 (2H, broad s), 9.43 (1H, d,J=8 Hz).

(7) 7-[2-Carboxymethoxyimino-2-(2-aminothiazol-4-yl)acetamido]-3-(1-allyl-1H-tetrazol-5-yl)thiomethyl-3-cephem-4-carboxylic acid (syn isomer).

I.R. (Nujol): 3360, 1780, 1680, 1630 cm$^{-1}$.

EXAMPLE 48

Trifluoroacetic acid (20 ml) was added under ice-cooling to a stirred suspension of 7-[2-t-butoxycarbonylmethoxyimino-2-(2-aminothiazol-4-yl)acetamido]-3-(1- allyl-1H-tetrazol-5-yl)thiomethyl-3-cephem-4-carboxylic acid (syn isomer)(2.05 g) in anisole (2 ml), and the resultant mixture was stirred for 2 hours at ambient temperature. The reaction mixture was concentrated under reduced pressure and diethyl ether was added thereto. Precipitates were collected by filtration, washed with diethyl ether, dried and dissolved in an aqueous solution of sodium bicarbonate. An insoluble material was filtered off and the filtrate was adjusted to pH 3.2 with conc.hydrochloric acid. Precipitates were collected by filtration, washed with water and dried to give 7-[2-carboxymethoxyimino-2-(2-aminothiazol-4-yl)acetamido]-3-(1-allyl-1H-tetrazol-5-yl)thiomethyl-3-cephem-4-carboxylic acid (syn isomer)(0.8 g).

I.R. (Nujol): 3360, 1780, 1680, 1630 cm$^{-1}$.

N.M.R. (d$_6$-DMSO, δ): 3.68 (2H, ABq, J=19 Hz), 4.36 (2H, ABq, J=14 Hz), 4.60 (2H, s), 4.60–6.2 (7H, m), 6.80 (1H, s), 7.24 (2H, broad s), 9.51 (1H, d, J=9 Hz).

Preparation 17

(1) Water (500 ml.) was added to hexylamine (490.0 g.) and a solution of sodium hydroxide (193.6 g.) in water (700 ml.) was added thereto under ice-cooling and stirring. Carbon disulfide (367.8 g.) was added dropwise thereto over 2 hours at 2° to 10° C. and then methyl iodide (687.3 g.) was added dropwise thereto over 1 hour at 0° to 5° C. The resulting mixture was stirred for 30 minutes at the same temperature and for 2 hours at ambient temperature. The reaction mixture was extracted with diethyl ether (1.5 l.). The extract was washed with a saturated aqueous solution of sodium chloride (300 ml.), dried over magnesium sulfate and concentrated to give an oil of methyl N-hexyldithiocarbamate (825.5 g.).

I.R. (Film): 3225, 2960, 2935, 2860 cm$^{-1}$.

N.M.R. (CDCl$_3$, δ): 0.86 (3H, t, J=5.0 Hz), 1.10~1.90 (8H, m), 2.58 (3H, s), 3.72 (2H, m).

(2) Sodium azide (155.9 g.) and water (0.8 l.) were added under stirring to a solution of methyl N-hexyldithiocarbamate (430 g.) in ethanol (1.7 l.) and the resulting mixture was refluxed for 3.5 hours at 90° C. Ethanol was distilled off from the reaction mixture and the residue was washed with diethyl ether (1 l.), adjusted to pH 2.0 with conc. hydrochloric acid and extracted with diethyl ether (1 l.). The extract was washed with water, dried over magnesium sulfate and concentrated to give an oil of 1-hexyl-1H-tetrazole-5-thiol (431.3 g.).

I.R. (Film): 3110, 2960, 2930, 2860 cm$^{-1}$.

N.M.R. (CDCl$_3$, δ): 0.91 (3H, t, J=5.0 Hz), 1.10–1.65 (6H, m), 1.97 (2H, m), 4.33 (2H, t, J=7.0 Hz).

(3) To 7-aminocephalosporanic acid (150.0 g.) was added 0.2M phosphate buffer solution (3 l.), which was prepared by dissolving sodium biphosphate dihydrate (62.1 g.) and disodium hydrogen phosphate (25.5 g.) in water (3 l.), and the resulting mixture was adjusted to pH 6.5 with 2N aqueous solution of sodium carbonate. To the mixture was added 1-hexyl-1H-tetrazole-5-thiol (154.6 g.) and the resulting mixture was stirred for 2 hours at 60° to 65° C. and at pH 6.0 to 6.5 with bubbling of nitrogen gas. The reaction mixture was adjusted to pH 3.5 with conc. hydrochloric acid under ice-cooling. Precipitates were collected by filtration and washed with water, and methanol (4 l.) and conc. hydrochloric acid (400 ml.) were added thereto. The mixture was stirred for 2 hours and an insoluble material was filtered off. The filtrate was treated with an activated charcoal and adjusted to pH 3.5 with 28% aqueous solution of ammonia. Precipitates were collected by filtration, in turn washed with water, acetone and diethyl ether and dried to give powder of 7-amino-3-(1-hexyl-1H-tetrazol-5-yl)thiomethyl-3-cephem-4-carboxylic acid (116.38 g.).

I.R. (Nujol): 1803, 1620, 1350 cm$^{-1}$.

N.M.R. (d$_6$-DMSO, δ): 0.95 (3H, t, J=6.5 Hz), 1.26 (6H, m), 1.80 (2H, m), 3.65 (2H, AB$_q$, J=18 Hz), 4.00~4.50 (4H, m), 4.79 (1H, d, J=6.0 Hz), 4.95 (1H, d, J=6.0 Hz).

Preparation 18

(1) Sodium bicarbonate (0.84 g.) was added to a suspension of 2-(2-formamidothiazol-4-yl)glyoxylic acid (2 g.) in water (120 ml.) to prepare a solution. Ethyl 2-aminooxyacetate hydrochloride (4.56 g.) was added to the solution and stirred at ambient temperature for 3 hours while adjusting a pH 6 with sodium bicarbonate. The resultant solution was adjusted to pH 1.5 with hydrochloric acid, salted out and extracted with ethyl acetate three times. The extract was dried over magnesium sulfate and concentrated in vacuo. The residue was pulverized with diethyl ether, and the precipitates were collected by filtration and dried to give 2-ethoxycarbonylmethoxyimino-2-(2-formamidothiazol-4-yl)acetic acid (syn isomer) (1.44 g.), mp. 112° C. (dec.).

I.R. (Nujol): 3150, 1740, 1670, 1550 cm$^{-1}$.

N.M.R. (DMSO-d$_6$, δ): 1.23 (3H, t, J=7 Hz), 4.16 (2H, q, J=7 Hz), 4.77 (2H, s), 7.56 (1H, s), 8.54 (1H, s).

(2) A mixture of 2-ethoxycarbonylmethoxyimino-2-(2-formamidothiazol-4-yl)acetic acid (syn isomer) (7.2 g.), conc. hydrochloric acid (10 ml.), ethanol (70 ml.) and tetrahydrofuran (20 ml.) was stirred for 2 hours at ambient temperature. After removing the solvent from the reaction mixture in vacuo, water was added thereto and the mixture was adjusted to pH 3.3 with an aqueous solution of sodium bicarbonate under ice-cooling. Precipitates were collected by filtration and dried to give 2-ethoxycarbonylmethoxyimino-2-(2-aminothiazol-4-yl)acetic acid (syn isomer) (4.6 g.).

I.R. (Nujol): 3170, 1720, 1660, 1620 cm$^{-1}$.

N.M.R. (d$_6$-DMSO, δ): 1.27 (3H, t, J=7 Hz), 4.25 (2H, q, J=7 Hz), 4.77 (2H, s), 6.96 (1H, s).

Preparation 19

Sodium bicarbonate (4.2 g.) was added to a suspension of 2-(2-formamidothiazol-4-yl)glyoxylic acid (10 g.) in water (500 ml.) to prepare a solution. t-Butyl 2-aminooxyacetate hydrochloride (8.1 g.) was added to the solution and stirred at ambient temperature for 3 hours while adjusting to pH 6 with sodium bicarbonate. The resultant solution was adjusted to pH 1.5 with hydrochloric acid, salted out and extracted with ethyl acetate three times. The extract was dried over magnesium sulfate and concentrated in vacuo. The residue was pulverized with diethyl ether, and the precipitates were collected by filtration and dried to give 2-t-butoxycarbonylmethoxyimino-2-(2-formamidothiazol-4-yl)acetic acid (syn isomer) (11.3 g.), mp. 117° C. (dec.).

I.R. (Nujol): 3180, 3140, 1750, 1690, 1630 cm$^{-1}$.

N.M.R. (DMSO-d$_6$, δ): 1.46 (9H, s), 4.66 (2H, s), 7.56 (1H, s), 8.56 (1H, s), 12.67 (1H, broad s).

Preparation 20

(1) 2-Bromoethyl benzoate (27.5 g.) was added dropwise to a stirred mixture of ethyl 2-hydroxyimino-3-oxobutyrate (syn isomer) (15.7 g.), potassium carbonate (20.7 g.) and N,N-dimethylformamide (25 ml.) under ice cooling over 10 minutes, and stirred at ambient temperature for 4 hours. The resultant mixture was filtered and washed with acetone. The filtrate and washings were combined and concentrated in vacuo. After adding water (100 ml.) to the residue, the solution was extracted with methylene chloride three times. The extracts were washed with a saturated aqueous solution of sodium chloride, dried over magnesium sulfate and concentrated in vacuo to give ethyl 2-(2-benzoyloxyethoxyimino)-3-oxobutyrate (syn isomer) (28 g.).

(2) A mixture of ethyl 2-(2-benzoyloxyethoxyimino)-3-oxobutyrate (syn isomer) (28 g.), sulfuryl chloride (13.5 g.) and acetic acid (30 ml.) was stirred at 40° C. for 10 minutes and at room temperature for 5.5 hours. After adding water (200 ml.) to the resultant solution, the mixture was extracted with methylene chloride. The extract was washed with water, a saturated aqueous solution of sodium bicarbonate and a saturated aqueous solution of sodium chloride in turn, dried over magnesium sulfate, and then concentrated in vacuo to give ethyl 2-(2-benzoyloxyethoxyimino)-4-chloro-3-oxobutyrate (syn isomer) (29 g.).

(3) A mixture of ethyl 2-(2-benzoyloxyethoxyimino)-4-chloro-3-oxobutyrate (syn isomer) (29 g.), thiourea (7.76 g.), sodium acetate (8.37 g.), water (75 ml.) and ethanol (75 ml.) was stirred at 40° C. for an hour. The resultant solution was concentrated in vacuo and the residue was extracted twice with ethyl acetate. The extracts were washed with a saturated aqueous solution of sodium chloride, dried over magnesium sulfate and concentrated in vacuo. After adding diethyl ether (200 ml.) to the oily residue, the soluble substance was separated by decantation and the solution was concentrated in vacuo. The residue was crystallized with diisopropyl ether and the precipitates were collected by filtration to give ethyl 2-(2-benzoyloxyethoxyimino)-2-(2-aminothiazol-4-yl)acetate(syn isomer)(9 g.).

N.M.R. (DMSO-d$_6$, δ): 1.28 (3H, t, J=7 Hz), 4.34 (2H, q, J=7 Hz), 4.56 (4H, m), 6.44 (2H, broad s), 6.68 (1H, s), 7.68-7.34 (3H, m), 8.06 (2H, d,d, J=8 Hz, 2 Hz).

(4) A mixture of ethyl 2-(2-benzoyloxyethoxyimino)-2-(2-aminothiazol-4-yl)acetate (syn isomer) (8.5 g.), 1N aqueous sodium hydroxide (35 ml.), methanol (40 ml.) and tetrahydrofuran (40 ml.) was stirred at 35° to 40° C. for 9 hours and at ambient temperature for 12 hours. After adjusting the resultant solution to pH 6.5 with conc. hydrochloric acid, the solution was concentrated to about ⅔ volume of the initial. The concentrate was adjusted to pH 3.5 with conc. hydrochloric acid under ice-cooling, and the precipitates were collected by filtration, washed with water and acetone in turn and then dried over phosphorus pentoxide under reduced pressure to give 2-(2-hydroxyethoxyimino)-2-(2-aminothiazol-4-yl)acetic acid (syn isomer) (3.3 g.).

I.R. (Nujol): 3350, 3075, 1680, 1620 cm$^{-1}$.

N.M.R. (DMSO-d$_6$, δ): 3.64 (2H, t, J=5 Hz), 4.10 (2H, t, J=5 Hz), 6.84 (1H, s), 7.16 (2H, m).

(5) A solution of formic acid (1.6 g.) and acetic anhydride (3.6 g.) was stirred at 50° C. for an hour. After cooling, 2-(2-hydroxyethoxyimino)-2-(2-amino thiazol-4-yl)acetic acid (syn isomer) (1 g.) was added to the solution and stirred at ambient temperature for 3 hours. Diisopropyl ether was added to the resultant solution, and the precipitates were filtered off. The filtrate was concentrated in vacuo, and the residue was pulverized with diisopropyl ether. The precipitates were collected by filtration to give 2-(2-formyloxyethoxyimino)-2-(2-formamidothiazol-4-yl)acetic acid (syn isomer) (0.7 g.).

I.R. (Nujol): 3200, 1710, 1690 cm$^{-1}$.

N.M.R. (DMSO-d$_6$, δ): 4.38 (4H, s), 7.58 (1H, s), 8.26 (1H, s), 8.54 (1H, s).

Preparation 21

(1) Ethyl 2-hydroxyimino-2-(2-aminothiazol-4-yl)acetate (syn isomer) (126.4 g.), formic acid (81.3 g.) and acetic anhydride (180 g.) were treated in a similar manner to that of Preparation 20 (5) to give ethyl 2-hydroxyimino-2-(2-formamidothiazol-4-yl)acetate (syn isomer) (109.6 g.).

I.R. (Nujol): 3320, 3140, 3050, 1710, 1555 cm$^{-1}$.

N.M.R. (d$_6$-DMSO, δ): 1.30 (3H, t, J=7 Hz), 4.33 (2H, q, J=7 Hz), 7.54 (1H, s), 8.54 (1H, s), 11.98 (1H, s), 12.58 (1H, s).

(2) A mixture of chloromethylthiomethane (7.97 g.), powdered potassium iodide (15.1 g.) and acetone (79 ml.) was stirred at ambient temperature for an hour, the resulting mixture was filtered and washed with a small amount of acetone. The washings and the filtrate were combined and added to a stirred suspension of ethyl 2-hydroxyimino-2-(2-formamidothiazol-4-yl)acetate (syn isomer) (17.5 g.) and powdered potassium carbonate (15.5 g.) in acetone (300 ml.). The mixture was stirred at ambient temperature for 3 hours, filtered and washed with acetone. The washings and the filtrate were combined and concentrated in vacuo. The residue was dissolved in ethyl acetate, washed with a saturated aqueous solution of sodium chloride twice, dried over magnesium sulfate and concentrated in vacuo. The oily residue was subjected to column chromatography on silica gel and eluted with chloroform to give ethyl 2-methylthiomethoxyimino-2-(2-formamidothiazol-4-yl)acetate (syn isomer) (2.4 g.), mp. 130° to 131° C.

I.R. (Nujol): 3160, 3125, 3050, 1740, 1695 cm$^{-1}$.

N.M.R. (d$_6$-DMSO, δ): 1.32 (3H, t, J=7 Hz), 2.22 (3H, s), 4.38 (2H, q, J=7 Hz), 5.33 (2H, s), 7.67 (1H, s), 8.56 (1H, s).

(3) A mixture of ethyl 2-methylthiomethoxyimino-2-(2-formamidothiazol-4-yl)acetate (syn isomer) (2.4 g.), 1N aqueous sodium hydroxide (23.8 ml.) and methanol (19.8 ml.) was stirred at 30° C. for 2.5 hours. The resultant solution was adjusted to pH 7 with 10% hydrochloric acid and methanol was distilled off in vacuo. The aqueous solution was adjusted to pH 1 with 10% hydrochloric acid under ice-cooling, and extracted with ethyl acetate three times. The extracts were washed with a saturated aqueous solution of sodium chloride, dried over magnesium sulfate and concentrated in vacuo to give 2-methylthiomethoxyimino-2-(2-formamidothiazol-4-yl)acetic acid (syn isomer) (1.13 g.), mp. 157° C. (dec.).

I.R. (Nujol): 3210, 3160, 3075, 1700, 1555 cm$^{-1}$.

N.M.R. (d$_6$-DMSO, δ): 2.24 (3H, s), 5.31 (2H, s), 7.61 (1H, s), 8.57 (1H, s), 12.73 (1H, s).

Preparation 22

The following compounds were obtained according to similar manners to those of Preparations 18 to 21.

(1) 2-Benzyloxyimino-2-(2-aminothiazol-4-yl)acetic acid (syn isomer).

I.R. (Nujol): 3330, 3200, 3100, 1660, 1590 cm$^{-1}$.

(2) 2-(3-Isoxazolyl)methoxyimino-2-(2-formamidothiazol-4-yl)acetic acid (syn isomer), mp. 110° C. (dec.).

I.R. (Nujol): 3270, 3130, 1680, 1540 cm$^{-1}$.

(3) 2-(2-Ethoxyethoxy)imino-2-(2-formamidothiazol-4-yl)acetic acid (syn isomer).

I.R. (Nujol): 3350, 3140, 1740, 1700 cm$^{-1}$.

EXAMPLE 49

The Vilsmeier reagent was prepared from dry dimethylformamide (0.139 g.), phosphorus oxychloride (0.290 g.) and dry tetrahydrofuran (1.0 ml.) by the conventional method. Dry tetrahydrofuran (3.0 ml.) was added thereto and then 2-methylthiomethoxyimino-2-(2-formamidothiazol-4-yl)acetic acid (syn isomer) (0.4 g.) was added thereto at −5° to 0° C. The mixture was stirred for 30 minutes at the same temperature. The resulting mixture was dropwise added at −5° to 0° C. to a stirred solution of 7-amino-3-(1,3,4-thiadiazol-2-yl)thiomethyl-3-cephem-4-carboxylic acid (0.725 g.) in a mixture of water (7 ml.) and acetone (7 ml.) keeping the pH at 7.5 to 8.5 by triethylamine and the mixture was stirred for 30 minutes at the same temperature at pH 7.5 to 8.5. Acetone was removed from the reaction mixture. To the residue were added ethyl acetate and water and the mixture was adjusted to pH 2.0 with 10% hydrochloric acid. Insoluble material was filtered off and the filtrate was extracted twice with ethyl acetate. The combined extracts were washed twice with a saturated sodium chloride aqueous solution and dried over magnesium sulfate. The solvent was distilled off and the residue was pulverized with diethyl ether to give 7-[2-methylthiomethoxyimino-2-(2-formamidothiazol-4-yl)acetamido]-3-(1,3,4-thiadiazol-2-yl)thiomethyl-3-cephem-4-carboxylic acid (syn isomer) (0.64 g.).

I.R. (Nujol): 3230, 1780, 1680, 1550 cm$^{-1}$.

N.M.R. (d$_6$-DMSO, δ): 2.22 (3H, s), 3.72 (2H, AB$_q$, J=18 Hz), 4.44 (2H, AB$_q$, J=14 Hz), 5.18 (1H, d, J=5 Hz), 5.23 (2H, s), 5.84 (1H, d,d, J=5 and 9 Hz), 7.46 (1H, s), 8.52 (1H, s), 9.54 (1H, s), 9.74 (1H, d, J=9 Hz), 12.64 (1H, broad s).

EXAMPLE 50

Phosphorus oxychloride (2.3 g.) was added at a time to a suspension of 2-benzyloxyimino-2-(2-aminothiazol-4-yl)acetic acid (syn isomer) (3.4 g.) in dry tetrahydrofuran (30 ml.) at −3° C. and the mixture was stirred for 20 minutes at the same temperature. Trimethylsilylacetamide (2.4 g.) and tetrahydrofuran (5 ml.) were added dropwise thereto and the resulting mixture was stirred for 20 minutes at the same temperature. Phosphorus oxychloride (2.3 g.) was added thereto and the mixture was stirred for 30 minutes at 0° to 3° C. Dry dimethylformamide (1.1 g.) was added thereto at a time at 0° to 3° C. and the mixture was stirred for 1 hour at the same temperature to give a clear solution. On the other hand, trimethylsilylacetamide (12.7 g.) was added to a stirred suspension of 7-amino-3-(1,3,4-thiadiazol-2-yl)thiomethyl-3-cephem-4-carboxylic acid (4.0 g.) in dry ethyl acetate (60 ml.) and the solution was stirred for 1 hour at ambient temperature. To this stirred solution was added the above-obtained tetrahydrofuran solution at a time at −20° C., and the resulting mixture was stirred for 2 hours at −5° to −15° C. To the reaction mixture were added a saturated aqueous solution of sodium chloride (50 ml.). An organic layer was separated and extracted with a saturated aqueous solution of sodium bicarbonate (pH 7.0). The extract was washed with ethyl acetate, treated with an activated charcoal and adjusted to pH 4.5 with 10% hydrochloric acid. Precipitates were collected by filtration, washed with water and dried to give powder of 7-[2-benzyloxyimino-2-(2-aminothiazol-4-yl)acetamido]-3-(1,3,4-thiadiazol-2-yl)thiomethyl-3-cephem-4-carboxylic acid (syn isomer) (1.03 g.).

I.R. (Nujol): 3320, 3200, 1770, 1670, 1610 cm$^{-1}$.

N.M.R. (d$_6$-DMSO, δ): 3.59 (2H, AB$_q$, J=18.0 Hz), 4.47 (2H, AB$_q$, J=12.0 Hz), 5.09 (1H, d, J=4.0 Hz), 5.15 (2H, s), 5.73 (1H, d,d, J=4.0 and 8.0 Hz), 6.74 (1H, s), 7.36 (5H, m), 9.56 (1H, s), 9.69 (1H, d, J=8.0 Hz).

EXAMPLE 51

The Vilsmeier reagent was prepared from dry dimethylformamide (0.667 g.), phosphorus oxychloride (1.40 g.) and dry ethyl acetate (4 ml.) by the conventional method. Dry ethyl acetate (16 ml.) was added thereto and then 2-t-butoxycarbonylmethoxyimino-2-(2-formamidothiazol-4-yl)acetic acid (syn isomer) (2 g.) was added thereto at 0° C. The mixture was stirred for 30 minutes at the same temperature. The resulting mixture was added dropwise at −15° C. to a stirred solution of 7-amino-3-(1,3,4-thiadiazol-2-yl)thiomethyl-3-cephem-4-carboxylic acid (3.01 g.) and trimethylsilylacetamide (9.6 g.) in dry ethyl acetate (30 ml.), and the mixture was stirred for 50 minutes at −15° to −5° C. To the reaction mixture was added water (50 ml.). An insoluble material was filtered off and the filtrate was extracted twice with ethyl acetate. The extracts were washed twice with a saturated aqueous solution of sodium chloride, dried over magnesium sulfate and evaporated in vacuo. The residue was pulverized with diethyl ether and the powder was collected by filtration and dried to give 7-[2-t-butoxycarbonylmethoxyimino-2-(2-formamidothiazol-4-yl)acetamido]-3-(1,3,4-thiadiazol-2-yl)thiomethyl-3-cephem-4-carboxylic acid (syn isomer) (2.67 g.).

I.R. (Nujol): 3225, 1780, 1725, 1685, 1550 cm$^{-1}$.

N.M.R. (d$_6$-DMSO, δ): 1.38 (9H, s), 3.64 (2H, AB$_q$, J=17 Hz), 4.38 (2H, AB$_q$, J=14 Hz), 4.56 (2H, s), 5.12 (1H, d, J=5 Hz), 5.77 (1H, d,d, J=5 and 9 Hz), 7.38 (1H, s), 8.47 (1H, s), 9.49 (1H, s), 9.54 (1H, d, J=9 Hz), 12.57 (1H, broad s).

EXAMPLE 52

The following compounds were obtained according to similar manners to those of Examples 49 to 51.

(1) 7-[2-Methylthiomethoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3250, 1780, 1675, 1550 cm$^{-1}$.

N.M.R. (d$_6$-DMSO, δ): 2.22 (3H, s), 3.72 (2H, AB$_q$, J=19 Hz), 3.96 (3H, s), 4.33 (2H, AB$_q$, J=14 Hz), 5.17 (1H, d, J=5 Hz), 5.26 (2H, s), 5.85 (1H, d,d, J=5 and 8 Hz), 7.48 (1H, s), 8.54 (1H, s), 9.78 (1H, d, J=8 Hz), 12.64 (1H, s).

(2) 7-[2-(2-Ethoxyethoxy)imino-2-(2-formamidothiazol-4-yl)acetamido]-3-(1,3,4-thiadiazol-2-yl)thiomethyl-3-cephem-4-carboxylic acid (syn isomer).

I.R. (Nujol): 3500, 3200, 1780, 1720, 1680 cm$^{-1}$.

N.M.R. (d$_6$-DMSO, δ): 1.13 (3H, t, J=7 Hz), 3.2~4.0 (6H, m), 4.30 (2H, t, J=4 Hz), 4.50 (2H, AB$_q$, J=13 Hz), 5.23 (1H, d, J=5 Hz), 5.87 (1H, d,d, J=5 and 8 Hz), 7.48 (1H, s), 8.58 (1H, s), 9.60 (1H, s), 9.70 (1H, d, J=8 Hz).

(3) 7-[2-(2-Formyloxyethoxy)imino-2-(2-formamidothiazol-4-yl)acetamido]-3-carbamoyloxymethyl-3-cephem-4-carboxylic acid (syn isomer).

I.R. (Nujol): 1770, 1710, 1670 cm$^{-1}$.

N.M.R. (d$_6$-DMSO, δ): 3.50 (2H, m), 4.10~4.60 (4H, m) 4.79 (2H, m), 5.16 (1H, d, J=5.0 Hz), 5.81 (1H, d,d,

J=5.0 and 8.0 Hz), 6.58 (2H, broad s), 7.47 (1H, s), 8.28 (1H, s), 8.55 (1H, s).

(4) 7-[2-(2-Formyloxyethoxy)imino-2-(2-formamidothiazol-4-yl)acetamido]-3-methyl-3-cephem-4-carboxylic acid (syn isomer).

I.R. (Nujol): 3150, 1765, 1675 cm$^{-1}$.

N.M.R. (d$_6$-DMSO, δ): 2.03 (3H, s), 3.45 (2H, AB$_q$, J=18 Hz), 4.36 (4H, m), 5.11 (1H, d, J=5 Hz), 5.75 (1H, d,d, J=5 and 8 Hz), 7.46 (1H, s), 8.24 (1H, s), 8.53 (1H, s), 9.63 (1H, d, J=8 Hz).

(5) 7-[2-(2-Formyloxyethoxy)imino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3160, 1775, 1710, 1670 cm$^{-1}$.

N.M.R. (d$_6$-DMSO, δ): 3.71 (2H, AB$_q$, J=18.0 Hz), 3.96 (3H, s), 4.00~4.54 (6H, m), 5.16 (1H, d, J=4.5 Hz), 5.84 (1H, d,d, J=4.5 and 9.0 Hz), 7.45 (1H, s), 8.24 (1H, s), 8.53 (1H, s), 9.70 (1H, d, J=9.0 Hz).

(6) 7-[2-(2-Formyloxyethoxy)imino-2-(2-formamidothiazol-4-yl)acetamido]-3-(1,3,4-thiadiazol-2-yl)thiomethyl-3-cephem-4-carboxylic acid (syn isomer).

I.R. (Nujol): 3180, 1775, 1673 cm$^{-1}$.

N.M.R. (d$_6$-DMSO, δ): 3.75 (2H, m), 4.25~4.65 (6H, m), 5.22 (1H, d, J=5.0 Hz), 5.88 (1H, d,d, J=5.0 and 9.0 Hz), 7.49 (1H, s), 8.26 (1H, s), 8.57 (1H, s), 9.59 (1H, s), 9.71 (1H, d, J=9.0 Hz).

(7) 7-[2-Ethoxycarbonylmethoxyimino-2-(2-aminothiazol-4-yl)acetamido]cephalosporanic acid (syn isomer).

I.R. (Nujol): 3350, 1780, 1740, 1680, 1640, 1540 cm$^{-1}$.

N.M.R. (d$_6$-DMSO, δ): 1.23 (3H, t, J=7 Hz), 2.07 (3H, s), 3.58 (2H, broad s), 4.18 (2H, q, J=7 Hz), 4.70 (2H, s), 4.78 (2H, AB$_q$, J=13 Hz), 5.20 (1H, d, J=5 Hz), 5.83 (1H, d,d, J=5 and 8 Hz), 6.82 (1H, s), 7.27 (2H, broad s), 9.52 (1H, d, J=8 Hz).

(8) 7-[2-Ethoxycarbonylmethoxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3250, 1775, 1720, 1680, 1540 cm$^{-1}$.

N.M.R. (d$_6$-DMSO, δ): 1.22 (3H, t, J=7 Hz), 3.74 (2H, s), 4.20 (2H, q, J=7 Hz), 4.77 (2H, s), 5.22 (1H, d, J=5 Hz), 5.88 (1H, d,d, J=5 and 8 Hz), 7.51 (1H, s), 8.58 (1H, s), 9.63 (1H, s), 9.70 (1H, d, J=8 Hz), 12.68 (1H, broad s).

(9) 7-[2-Ethoxycarbonylmethoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3250, 1780, 1725, 1680, 1540 cm$^{-1}$.

N.M.R. (d$_6$-DMSO, δ): 1.22 (3H, t, J=7 Hz), 3.73 (2H, s), 3.97 (3H, s), 4.18 (2H, q, J=7 Hz), 4.35 (2H, AB$_q$, J=14 Hz), 4.76 (2H, s), 5.18 (1H, d, J=5 Hz), 5.86 (1H, d,d, J=5 and 9 Hz), 7.48 (1H, s), 8.56 (1H, s), 9.67 (1H, d, J=9 Hz), 12.69 (1H, broad s).

(10) 7-[2-t-Butoxycarbonylmethoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3180, 1785, 1725, 1690, 1550 cm$^{-1}$.

N.M.R. (d$_6$-DMSO, δ): 1.45 (9H, s), 3.72 (2H, AB$_q$, J=17 Hz), 3.96 (3H, s), 4.33 (2H, AB$_q$, J=14 Hz), 4.64 (2H, s), 5.17 (1H, d, J=5 Hz), 5.84 (1H, d,d, J=5 and 9 Hz), 7.46 (1H, s), 8.52 (1H, s), 9.62 (1H, d, J=9 Hz), 12.61 (1H, broad s).

(11) 7-[2-Benzyloxyimino-2-(2-aminothiazol-4-yl)acetamido]cephalosporanic acid (syn isomer).

I.R. (Nujol): 3300, 1780, 1710, 1660, 1630, 1540 cm$^{-1}$.

N.M.R. (d$_6$-DMSO, δ): 2.05 (3H, s), 3.55 (2H, broad s), 4.87 (2H, AB$_q$, J=13 Hz), 5.17 (2H, s), 5.18 (1H, d, J=5 Hz), 5.83 (1H, d,d, J=5 and 8 Hz), 6.75 (1H, s), 7.35 (5H, s), 9.70 (1H, d, J=8 Hz).

(12) 7-[2-Benzyloxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3300, 1780, 1720, 1670 cm$^{-1}$.

N.M.R. (d$_6$-DMSO, δ): 3.68 (2H, broad s), 3.97 (3H, s), 4.33 (2H, broad s), 5.15 (1H, d, J=5 Hz), 5.17 (2H, s), 5.80 (1H, d,d, J=5 and 8 Hz), 6.83 (1H, s), 7.38 (5H, s), 9.77 (1H, d, J=8 Hz).

(13) 7-[2-Benzyloxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3350, 3250, 1780, 1680, 1633 cm$^{-1}$.

N.M.R. (d$_6$-DMSO, δ): 0.86 (3H, m), 0.97~1.53 (6H, m), 1.53~2.10 (2H, m), 3.70 (2H, m), 4.10~4.77 (4H, m), 5.00~5.50 (3H, m), 5.85 (1H, d,d, J=5.0 and 8.0 Hz), 6.80 (1H, s), 6.98~7.63 (7H, m), 9.71 (1H, d, J=8.0 Hz).

(14) 7-[2-(3-Isoxazolyl)methoxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3200, 1775, 1675, 1540 cm$^{-1}$.

N.M.R. (d$_6$-DMSO, δ): 3.72 (2H, s), 4.45 (2H, AB$_q$, J=13 Hz), 5.18 (1H, d, J=5 Hz), 5.30 (2H, s), 5.96 (1H, d,d, J=5 and 8 Hz), 6.67 (1H, d, J=2 Hz), 7.50 (1H, s), 8.55 (1H, s), 8.90 (1H, d, J=2 Hz), 9.58 (1H, s) 9.79 (1H, d, J=8 Hz), 12.69 (1H, s).

(15) 7-[2-Methylthiomethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3340, 3200, 1775, 1670 cm$^{-1}$.

(16) 7-[2-Methylthiomethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3300, 1770, 1670, 1530 cm$^{-1}$.

(17) 7-[2-(2-Ethoxyethoxy)imino-2-(2-aminothiazol-4-yl)acetamido]-3-(1,3,4-thiadiazol-2-yl)thiomethyl-3-cephem-4-carboxylic acid (syn isomer).

I.R. (Nujol): 3160, 3100, 1780, 1670, 1630 cm$^{-1}$.

(18) 7-[2-Ethoxycarbonylmethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3350, 3220, 1780, 1680, 1630 cm$^{-1}$.

(19) 7-[2-Ethoxycarbonylmethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3230, 3100, 1780, 1680, 1630 cm$^{-1}$.

(20) 7-[2-t-Butoxycarbonylmethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3300, 1775, 1730, 1675, 1630 cm$^{-1}$.

(21) 7-[2-Carboxymethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3340, 3200, 1775, 1675, 1630 cm$^{-1}$.

(22) 7-[2-(3-Isoxazolyl)methoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3230, 3110, 1775, 1675 cm$^{-1}$.

(23) 7-[2-Carboxymethoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3200, 1780, 1720, 1680, 1545 cm$^{-1}$.

(24) 7-[2-Carboxymethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3360, 3240, 3100, 1780, 1680, 1635 cm$^{-1}$.

EXAMPLE 53

A mixture of 7-[2-methoxythiomethoxyimino-2-(2-formamidothiazol-4-yl)acetamido]-3-(1,3,4-thiadiazol-2-yl)thiomethyl-3-cephem-4-carboxylic acid (syn isomer) (0.58 g.), conc. hydrochloric acid (0.405 g.), methanol (8.7 ml.) and tetrahydrofuran (5 ml.) was stirred for 2 hours and 10 minutes at ambient temperature. The solvent was distilled off under reduced pressure and the residue was dissolved in a 10% aqueous solution of sodium hydroxide (pH 7~8.5). An insoluble material was filtered off and the filtrate was adjusted to pH 3.4 with 10% hydrochloric acid under ice-cooling and stirred for 30 minutes. Precipitates were collected by filtration, washed with water and dried to give 7-[2-methylthiomethoxyimino-2-(2-aminothiazol-4-yl)acetamido]-3-(1,3,4-thiadiazol-2-yl)thiomethyl-3-cephem-4-carboxylic acid (syn isomer) (0.4 g.).

I.R. (Nujol): 3340, 3200, 1775, 1670 cm$^{-1}$.

N.M.R. (d$_6$-DMSO, δ): 2.23 (3H, s), 3.74 (2H, s), 4.48 (2H, AB$_q$, J=13 Hz), 5.20 (1H, d, J=5 Hz), 5.24 (2H, s), 5.83 (1H, d,d, J=5 and 9 Hz), 6.83 (1H, s), 7.28 (2H, broad s), 9.62 (1H, s), 9.68 (1H, d, J=9 Hz).

EXAMPLE 54

A mixture of 7-[2-t-butoxycarbonylmethoxyimino-2-(2-formamidothiazol-4-yl)acetamido]-3-(1,3,4-thiadiazol-2-yl)thiomethyl-3-cephem-4-carboxylic acid (syn isomer) (2.3 g.), conc. hydrochloric acid (3.74 g.) and methanol (35 ml.) was stirred for 2 hours and 40 minutes at ambient temperature. The solvent was distilled off under reduced pressure and the residue was dissolved in a 10% aqueous solution of sodium hydroxide (pH 7~8). The aqueous solution was adjusted to pH 3.0 with 10% hydrochloric acid under ice-cooling and stirring and stirred for 30 minutes. Precipitates were collected by filtration, washed with water and dried to give 7-[2-t-butoxycarbonylmethoxyimino-2-(2-aminothiazol-4-yl)acetamido]-3-(1,3,4-thiadiazol-2-yl)thiomethyl-3-cephem-4-carboxylic acid (syn isomer) (1.1 g.).

I.R. (Nujol): 3300, 1775, 1730, 1675, 1630 cm$^{-1}$.

N.M.R. (d$_6$-DMSO, δ): 1.46 (9H, s), 3.67 (2H, s), 4.42 (2H, AB$_q$, J=14 Hz), 4.55 (2H, s), 5.16 (1H, d, J=5 Hz), 5.78 (1H, d,d, J=5 and 9 Hz), 6.77 (1H, s), 7.21 (2H, s), 9.43 (1H, d, J=9 Hz), 9.52 (1H, s).

EXAMPLE 55

The following compounds were obtained according to similar manners to those of Examples 53 and 54.

(1) 7-[2-Ethoxycarbonylmethoxyimino-2-(2-aminothiazol-4-yl)acetamido]cephalosporanic acid (syn isomer).

I.R. (Nujol): 3350, 1780, 1740, 1680, 1640, 1540 cm$^{-1}$.

(2) 7-[2-Benzyloxyimino-2-(2-aminothiazol-4-yl)acetamido]cephalosporanic acid (syn isomer).

I.R. (Nujol): 3300, 1780, 1710, 1660, 1630, 1540 cm$^{-1}$.

(3) 7-[2-Benzyloxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3320, 3200, 1770, 1670, 1610 cm$^{-1}$.

(4) 7-[2-Benzyloxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3300, 1780, 1720, 1670 cm$^{-1}$.

(5) 7-[2-Benzyloxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3350, 3250, 1780, 1680, 1633 cm$^{-1}$.

(6) 7-[2-Methylthiomethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3300, 1770, 1670, 1530 cm$^{-1}$.

N.M.R. (d$_6$-DMSO, δ): 2.20 (3H, s), 3.72 (2H, s), 3.97 (3H, s), 4.36 (2H, s), 5.17 (1H, d, J=5 Hz), 5.22 (2H, s), 5.82 (1H, d,d, J=5 and 8 Hz), 6.82 (1H, s), 7.28 (2H, broad s), 9.60 (1H, d, J=8 Hz).

(7) 7-[2-(2-Ethoxyethoxy)imino-2-(2-aminothiazol-4-yl)acetamido]-3-(1,3,4-thiadiazol-2-yl)thiomethyl-3-cephem-4-carboxylic acid (syn isomer).

I.R. (Nujol): 3160, 3100, 1780, 1670, 1630 cm$^{-1}$.

N.M.R. (d$_6$-DMSO, δ): 1.08 (3H, t, J=7 Hz), 3.45 (2H, q, J=7 Hz), 3.5~3.90 (4H, m), 4.20 (2H, t, J=4 Hz), 4.47 (2H, AB$_q$, J=13 Hz), 5.17 (1H, d, J=5 Hz), 5.80 (1H, d,d, J=5 and 8 Hz), 6.77 (1H, s), 9.55 (1H, s), 9.55 (1H, d, J=8 Hz).

(8) 7-[2-Ethoxycarbonylmethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3350, 3220, 1780, 1680, 1630 cm$^{-1}$.

N.M.R. (d$_6$-DMSO, δ): 1.23 (3H, t, J=7 Hz), 3.70 (2H, s), 3.97 (3H, s), 4.16 (2H, q, J=7 Hz), 4.35 (2H, s), 4.69 (2H, s), 5.15 (1H, d, J=5 Hz), 5.80 (1H, d,d, J=5 and 9 Hz), 6.81 (1H, s), 7.24 (2H, broad s), 9.54 (1H, d, J=9 Hz).

(9) 7-[2-Ethoxycarbonylmethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3230, 3100, 1780, 1680, 1630 cm$^{-1}$.

N.M.R. (d$_6$-DMSO, δ): 1.21 (3H, t, J=7 Hz), 3.72 (2H, AB$_q$, J=18 Hz), 4.18 (2H, q, J=7 Hz), 4.70 (2H, s), 5.20 (1H, d, J=5 Hz), 5.84 (1H, d,d, J=5 and 8 Hz), 6.84 (1H, s), 7.26 (2H, broad s), 9.56 (1H, d, J=8 Hz), 9.60 (1H, s).

(10) 7-[2-Carboxymethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3340, 3200, 1775, 1675, 1630 cm$^{-1}$.

N.M.R. (d$_6$-DMSO, δ): 3.68 (2H, s), 3.94 (3H, s), 4.32 (2H, AB$_q$, J=14 Hz), 4.70 (2H, s), 5.14 (1H, d, J=5 Hz), 5.78 (1H, d,d, J=5 and 9 Hz), 6.81 (1H, s), 7.1 (2H, broad s), 9.59 (1H, d, J=9 Hz).

(11) 7-[2-(3-Isoxazolyl)methoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3230, 3110, 1775, 1675 cm$^{-1}$.

N.M.R. (d$_6$-DMSO, δ): 3.71 (2H, AB$_q$, J=18 Hz), 4.46 (2H, AB$_q$, J=14 Hz), 5.17 (1H, d, J=5 Hz), 5.27 (2H, s), 5.82 (1H, d,d, J=5 and 8 Hz), 6.66 (1H, s), 6.83 (1H, s), 7.30 (2H, broad s), 8.87 (1H, s), 9.57 (1H, s), 9.75 (1H, d, J=8 Hz).

(12) 7-[2-Carboxymethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3360, 3240, 3100, 1780, 1680, 1635 cm$^{-1}$.

EXAMPLE 56

Trifluoroacetic acid (4 ml.) was added under ice-cooling to a stirred suspension of 7-[2-t-butoxycarbonyl-methoxyimino-2-(2-aminothiazol-4-yl)acetamido]-3-(1,3,4-thiadiazol-2-yl)thiomethyl-3-cephem-4-carboxylic acid (syn isomer) (1.0 g.) in anisole (1 ml.), and the resultant mixture was stirred for 70 minutes at ambient temperature. The reaction mixture was concentrated under reduced pressure and diethyl ether was added thereto. Precipitates were collected by filtration, washed with diethyl ether, dried, suspended in water (10 ml.) and then dissolved in a 10% aqueous solution of sodium hydroxide (pH 7-7.5). The solution was adjusted to pH 3.0 with 10% hydrochloric acid under ice-cooling and stirring and stirred for 30 minutes under ice-cooling. Precipitates were collected by filtration, washed with water and dried to give 7-[2-carboxymethoxyimino-2-(2-aminothiazol-4-yl)acetamido]-3-(1,3,4-thiadiaziol-2-yl)thiomethyl-3-cephem-4-carboxylic acid (syn isomer) (0.75 g.).

I.R. (Nujol): 3360, 3240, 3100, 1780, 1680, 1635 cm$^{-1}$.

N.M.R. (d$_6$-DMSO, δ): 3.68 (2H, s), 4.46 (2H, AB$_q$, J=15 Hz), 4.61 (2H, s), 5.17 (1H, d, J=5 Hz), 5.82 (1H, d,d, J=5 and 9 Hz), 6.83 (1H, s), 7.23 (2H, broad s), 9.50 (1H, d, J=9 Hz), 9.53 (1H, s).

EXAMPLE 57

The following compounds were obtained according to a similar manner to that of Example 56.

(1) 7-[2-Carboxymethoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3200, 1780, 1720, 1680, 1545 cm$^{-1}$.

N.M.R. (d$_6$-DMSO, δ): 3.72 (2H, AB$_q$, J=16 Hz), 3.96 (3H, s), 4.33 (2H, AB$_q$, J=14 Hz), 4.67 (2H, s), 5.17 (1H, d, J=5 Hz), 5.86 (1H, d,d, J=5 and 9 Hz), 7.47 (1H, s), 8.52 (1H, s), 9.64 (1H, d, J=9 Hz), 12.64 (1H, broad s).

(2) 7-[2-Carboxymethoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3340, 3200, 1775, 1675, 1630 cm$^{-1}$.

Preparation 23

(1) Ethyl 2-(2-propynyloxyimino)-3-oxobutyrate (syn isomer) (71.2 g.) was obtained by reacting ethyl 2-hydroxyimino-3-oxobutyrate (syn isomer) (56.7 g.) with 2-propynyl bromide (43 g.) in the presence of potassium carbonate (72.3 g.) and N,N-dimethylformamide (280 ml.).

I.R. (Film): 3280, 3220, 2120, 1735, 1670 cm$^{-1}$.

(2) Ethyl 2-(2-propynyloxyimino)-3-oxo-4-chlorobutyrate (syn isomer) (61.6 g.) was obtained by reacting ethyl 2-(2-propynyloxyimino)-3-oxobutyrate (syn isomer) (71.2 g.) with sulfuryl chloride (50.2 g.) in acetic acid (81 ml.).

I.R. (Film): 3300, 2130, 1745, 1720, 1675 cm$^{-1}$.

(3) Ethyl 2-(2-propynyloxyimino)-2-(2-aminothiazol-4-yl)acetate (syn isomer) (35.6 g.) was obtained by reacting ethyl 2-(2-propynyloxyimino)-3-oxo-4-chlorobutyrate (syn isomer) (61 g.) with thiourea (20 g.) in the presence of sodium acetate trihydrate (35.8 g.), water (150 ml.) and ethanol (180 ml.).

I.R. (Nujol): 3290, 2220, 1729 cm$^{-1}$.

(4) 2-(2-Propynyloxyimino)-2-(2-aminothiazol-4-yl)acetic acid (syn isomer) (1.924 g.) was obtained by hydrolyzing ethyl 2-(2-propynyloxyimino)-2-(2-aminothiazol-4-yl)acetate (syn isomer) (2.8 g.) in the presence of 1N aqueous solution of sodium hydroxide (22.17 ml.), methanol (23 ml.) and tetrahydrofuran (20 ml.).

I.R. (Nujol): 2190, 1740 cm$^{-1}$.

Preparation 24

Formic acid (107 g.) was added to acetic anhydride (239 g.) under ice-cooling, and the mixture was stirred for 1 hour at 50° C. and then cooled to 20° C. To the mixture was added 2-(2-propynyloxyimino)-2-(2-aminothiazol-4-yl)acetic acid (syn isomer) (135 g.), and the mixture was stirred for 3 hours at ambient temperature. To the mixture was added diisopropyl ether (400 ml.) and then the precipitated crystals were collected by filtration, washed with diisopropyl ether and then dried to give 2-(2-propynyloxyimino)-2-(2-formamidothiazol-4-yl)acetic acid (syn isomer) (118.4 g.).

I.R. (Nujol): 3250, 2130, 1685, 1600, 1560 cm$^{-1}$.

N.M.R. (d$_6$-DMSO, δ): 3.53 (1H, m), 4.87 (2H, d, J=2 Hz), 7.63 (1H, s), 8.61 (1H, s), 12.7 (1H, broad s).

Preparation 25

To a solution of 2-(2-formamidothiazol-4-yl)glyoxylic acid (30 g.) and sodium bicarbonate (12.6 g.) in water (1300 ml.) was added allyloxyamine hydrochloride (19.8 g.), and the mixture was stirred for 7 hours at ambient temperature at pH 6. To the reaction mixture was added ethyl acetate (500 ml.). After the mixture was adjusted to pH 1.9 with 10% hydrochloric acid, the ethyl acetate layer was separated. The ethyl acetate layer was washed with an aqueous solution of sodium chloride, dried over magnesium sulfate and then the solvent was distilled off. The residue was pulverized in diisopropyl ether, collected by filtration and then dried to give 2-allyloxyimino-2-(2-formamidothiazol-4-yl)acetic acid (syn isomer) (25.3 g.).

I.R. (Nujol): 3110, 1730, 1660, 1540 cm$^{-1}$.

N.M.R. (d$_6$-DMSO, δ): 4.70 (2H, m), 5.13-5.60 (2H, m), 5.73-6.27 (1H, m), 7.57 (1H, s), 8.35 (1H, s).

Preparation 26

(1) Sulfuryl chloride (35.2 g.) was added all at once to the stirred solution of ethyl 2-ethoxyimino-3-oxobutyrate (syn isomer) (48.9 g.) in acetic acid (49 ml.) at room temperature, and stirred at the same temperature for an hour. After adding the resultant solution into water (200 ml.), the solution was extracted with methylene chloride. The extract was washed with a saturated aqueous solution of sodium chloride, neutralized with an aqueous solution of sodium bicarbonate and washed with water. The solution was dried over magnesium sulfate and concentrated under reduced pressure to give ethyl 2-ethoxyimino-3-oxo-4-chlorobutyrate (syn isomer) (53.8 g.), pale yellow oil.

(2) A mixture of ethyl 2-ethoxyimino-3-oxo-4-chlorobutyrate (syn isomer) (38.7 g.), thiourea (13.2 g.), sodium acetate (14.3 g.), methanol (95 ml.) and water (95 ml.) was stirred at 48° C. for 40 minutes. After the resultant solution was adjusted to pH 6.5 with an aqueous solution of sodium bicarbonate, the appeared precipitates were collected by filtration and washed with diisopropyl ether to give ethyl 2-ethoxyimino-2-(2-aminothiazol-4- yl)acetate (syn isomer) (14.7 g.), mp. 130° to 131° C.

I.R. (Nujol): 3450, 3275, 3125, 1715, 1620 cm$^{-1}$.

(3) Ethyl 2-ethoxyimino-2-(2-aminothiazol-4-yl)acetate (syn isomer) (5 g.) was added to a mixture of 1N sodium hydroxide (45.9 ml.) and ethanol (30 ml.) and stirred at ambient temperature for 5 hours. After removing ethanol from the resultant solution under reduced pressure, the residue was dissolved in water (60 ml.) and adjusted to pH 2.0 with 10% hydrochloric acid. The solution was subjected to salting-out, and the precipitates were collected by filtration and dried to give 2-ethoxyimino-2-(2-aminothiazol-4-yl)acetic acid (syn isomer) (2.9 g.).

I.R. (Nujol): 3625, 3225 (shoulder), 3100, 1650, 1615 cm$^{-1}$.

N.M.R. ($d_6$-DMSO, δ): 1.20 (3H, t, J=7 Hz), 4.09 (2H, q, J=7 Hz), 6.82 (1H, s), 7.24 (2H, broad s).

(4) 2-Ethoxyimino-2-(2-aminothiazol-4-yl)acetic acid (syn isomer) (100 g.), formic acid (85.5 g.) and acetic anhydride (190.1 g.) were treated in a similar manner to that of Preparation 24 to give 2-ethoxyimino-2-(2-formamidothiazol-4-yl)acetic acid (syn isomer) (99.1 g.).

I.R. (Nujol): 3200, 3140, 3050, 1700 cm$^{-1}$.

N.M.R. ($d_6$-DMSO, δ): 1.18 (3H, t, J=6 Hz), 4.22 (2H, q, J=6 Hz), 7.56 (1H, s), 8.56 (1H, s), 12.62 (1H, broad s).

Preparation 27

The following compounds were obtained according to similar manners to those of Preparations 23 to 26.

(1) 2-Propoxyimino-2-(2-formamidothiazol-4-yl)acetic acid (syn isomer), mp. 164° C. (dec.).

I.R. (Nujol): 3200, 3120, 3050, 1700, 1550 cm$^{-1}$.

(2) 2-Isopropoxyimino-2-(2-formamidothiazol-4-yl)acetic acid (syn isomer), mp. 168° to 169° C. (dec.).

I.R. (Nujol): 3200, 3130, 1710, 1600, 1560 cm$^{-1}$.

(3) 2-Butoxyimino-2-(2-formamidothiazol-4-yl)acetic acid (syn isomer).

I.R. (Nujol): 3350, 3160, 3050, 1700, 1680, 1570 cm$^{-1}$.

(4) 2-Hexyloxyimino-2-(2-formamidothiazol-4-yl)acetic acid (syn isomer), mp. 115° to 116° C. (dec.).

I.R. (Nujol): 3170, 3070, 1720, 1700, 1660 cm$^{-1}$.

N.M.R. ($d_6$-DMSO, δ): 0.6–2.1 (11H, m), 4.15 (2H, t, J=6 Hz), 7.53 (1H, s), 8.56 (1H, s), 12.69 (1H, s).

(5) 2-Methoxyimino-(2-isobutoxycarbonylaminothiazol-4-yl)acetic acid (syn isomer).

I.R. (Nujol): 3200, 3130, 1735, 1600, 1570 cm$^{-1}$.

N.M.R. ($d_6$-DMSO, δ): 0.94 (6H, d, J=7 Hz), 1.95 (1H, m), 3.92 (3H, s), 3.96 (2H, d, J=7 Hz), 7.44 (1H, s), 12.08 (1H, broad s).

(6) 2-Pentyloxyimino-2-(2-formamidothiazol-4-yl)acetic acid (syn isomer), mp 125° C. (dec.).

I.R. (Nujol): 3200, 3140, 1700, 1565 cm$^{-1}$.

Preparation 28

(1) Water (500 ml.) was added to hexylamine (490.0 g.) and a solution of sodium hydroxide (193.6 g.) in water (700 ml.) was added thereto under ice-cooling and stirring. Carbon disulfide (367.8 g.) was added dropwise thereto over 2 hours at 2° to 10° C. and then methyl iodide (687.3 g.) was added dropwise thereto over 1 hour at 0° to 5° C. The resulting mixture was stirred for 30 minutes at the same temperature and for 2 hours at ambient temperature. The reaction mixture was extracted with diethyl ether (1.5 l.). The extract was washed with a saturated aqueous solution of sodium chloride (300 ml.), dried over magnesium sulfate and concentrated to give an oil of methyl N-hexyldithiocarbamate (825.5 g.).

I.R. (Film): 3225, 2960, 2935, 2860 cm$^{-1}$.

N.M.R. (CDCl$_3$, δ): 0.86 (3H, t, J=5.0 Hz), 1.10~1.90 (8H, m), 2.58 (3H, s), 3.72 (2H, m).

(2) Sodium azide (155.9 g.) and water (0.8 l.) were added under stirring to a solution of methyl N-hexyldithiocarbamate (430 g.) in ethanol (1.7 l.) and the resulting mixture was refluxed for 3.5 hours at 90° C. Ethanol was distilled off from the reaction mixture and the residue was washed with diethyl ether (1 l.), adjusted to pH 2.0 with conc. hydrochloric acid and extracted with diethyl ether (1 l.). The extract was washed with water, dried over magnesium sulfate and concentrated to give an oil of 1-hexyl-1H-tetrazole-5-thiol (431.3 g.).

I.R. (Film): 3110, 2960, 2930, 2860 cm$^{-1}$.

N.M.R. (CDCl$_3$, δ): 0.91 (3H, t, J=5.0 Hz), 1.10~1.65 (6H, m), 1.97 (2H, m), 4.33 (2H, t, J=7.0 Hz).

(3) To 7-aminocephalosporanic acid (150.0 g.) was added 0.2M phosphate buffer solution (3 l.) which was prepared by dissolving sodium biphosphate dihydrate (62.1 g.) and disodium hydrogen phosphate (25.5 g.) in water (3 l.), and the resulting mixture was adjusted to pH 6.5 with 2N aqueous solution of sodium carbonate. To the mixture was added 1-hexyl-1H-tetrazole-5-thiol (154.6 g.) and the resulting mixture was stirred for 2 hours at 60° to 65° C. and at pH 6.0 to 6.5 with bubbling of nitrogen gas. The reaction mixture was adjusted to pH 3.5 with conc. hydrochloric acid under ice-cooling. Precipitates were collected by filtration and washed with water, and methanol (4 l.) and conc. hydrochloric acid (400 ml.) were added thereto. The mixture was stirred for 2 hours and an insoluble material was filtered off. The filtrate was treated with an activated charcoal and adjusted to pH 3.5 with 28% aqueous solution of ammonia. Precipitates were collected by filtration, in turn washed with water, acetone and diethyl ether and dried to give powder of 7-amino-3-(1-hexyl-1H-tetrazol-5-yl)thiomethyl-3-cephem-4-carboxylic acid (116.38 g.).

I.R. (Nujol): 1803, 1620, 1350 cm$^{-1}$.

N.M.R. ($d_6$-DMSO, δ): 0.95 (3H, t, J=6.5 Hz), 1.26 (6H, m), 1.80 (2H, m), 3.65 (2H, AB$_q$, J=18 Hz), 4.00~4.50 (4H, m), 4.79 (1H, d, J=6.0 Hz), 4.95 (1H, d, J=6.0 Hz).

Preparation 29

7-Aminocephalosporanic acid (283.0 g.) and 1-propyl-1H-tetrazole-5-thiol (225.0 g.) were treated in 0.2M phosphate buffer solution (5.5 l.) in a similar manner to that of Preparation 28-(3) to give 7-amino-3-(1-propyl-1H-tetrazol-5-yl)thiomethyl-3-cephem-4-carboxylic acid (125.0 g.).

I.R. (Nujol): 3300, 1795, 1610 cm$^{-1}$.

N.M.R. ($d_6$-DMSO, δ): 0.91 (3H, t, J=7.5 Hz), 1.60~2.28 (2H, m), 3.63 (2H, AB$_q$, J=18.0 Hz), 3.98~4.58 (4H, m), 5.08 (1H, d, J=5.0 Hz), 5.49 (1H, d, J=5.0 Hz).

Preparation 30

(1) 3-Chlorophenylisocyanate (3.7 g.) was added at ambient temperature to a solution of benzhydryl 7-(2-phenylacetamido)-3-hydroxymethyl-3-cephem-4-carboxylate (10.3 g.) in a mixture of tetrahydrofuran (200 ml.) and triethylamine (2.4 g.), and the mixture was stirred for 1 hour. The reaction mixture was concentrated under reduced pressure. The residue was dissolved in ethyl acetate (200 ml.), and the solution was in turn washed with 10% hydrochloric acid, a saturated aqueous solution of sodium bicarbonate and a saturated aqueous solution of sodium chloride to give a solution containing a mixture of benzhydryl 7-(2-phenylacetamido)-3-[N-(3-chlorophenyl)carbamoyloxymethyl]-3-cephem-4-carboxylate and benzhydryl 7-(2-phenylacetamido)-3-[N-(3-chlorophenyl)carbamoyloxymethyl]-2-cephem-4-carboxylate.

(2) To the above-obtained ethyl acetate solution was added dropwise at 7° to 10° C. a solution of 3-chloroperbenzoic acid (5.2 g.) in ethyl acetate, and the mixture was stirred for 1 hour at the same temperature. Precipitates were collected by filtration, washed with diethyl ether and dried to give benzhydryl 7-(2-phenylaetamido)-3-[N-(3-chlorophenyl)carbamoyloxymethyl]-3-cephem-4-carboxylate-1-oxide (7.7 g.).

I.R. (Nujol): 3280, 1790, 1700, 1650, 1600, 1530 cm$^{-1}$.

(3) Phosphorus trichloride (3.2 g.) was added at −40° C. to a stirred solution of benzhydryl 7-(2-phenylacetamido)-3-[N-(3-chlorophenyl)carbamoyloxymethyl]-3-cephem-4-carboxylate-1-oxide (7.6 g.) in dimethylformamide (50 ml.), and the mixture was stirred for 1 hour at −20° to −40° C. The reaction mixture was poured into cooled water. Precipitates were collected by filtration, washed with water and dried to give benzhydryl 7-(2-phenylacetamido)-3-[N-(3-chlorophenyl)carbamoyloxymethyl]-3-cephem-4-carboxylate (5.0 g.).

I.R. (Nujol): 3280, 3190, 1780, 1730, 1710, 1660, 1620, 1600, 1540 cm$^{-1}$.

N.M.R. (d$_6$-DMSO, δ): 3.56 (2H, s), 3.64 (2H, s), 4.86 (2H, AB$_q$, J=12 Hz), 5.14 (1H, d, J=5 Hz), 5.76 (1H, d,d, J=5 and 8 Hz), 6.95 (1H, s), 7.00~7.70 (19H, m), 9.10 (1H, d, J=8 Hz), 10.00 (1H, s).

(4) Pyridine (1.9 g.) was added to a solution of phosphorus pentachloride (4.93 g.) in methylene chloride (50 ml.) at 5° C. and the suspension was stirred for 30 minutes at ambient temperature. To the reaction mixture was added benzhydryl 7-(2-phenylacetamido)-3-[N-(3-chlorophenyl)carbamoyloxymethyl]-3-cephem-4-carboxylate (5.0 g.) at 5° C. and stirred for 1.5 hours at 5° to 7° C. to give a homogeneous solution. To the above solution cooled to −30° C. was added methanol (8 ml.). After the solution was stirred for 1 hour at −10° to −20° C., water (5 ml.) was added and continued to stir for 30 minutes at 0° to 5° C. After removing the solvent under reduced pressure, water (80 ml.) and diethyl ether (100 ml.) were added to the residue, and the aqueous layer containing oil was separated. The aqueous solution containing oil was adjusted to pH 8.0 with 20% aqueous solution of sodium carbonate and extracted with ethyl acetate. The extracts were washed with a saturated aqueous solution of sodium chloride, dried over magnesium sulfate and concentrated under reduced pressure. The residue was pulverized with diisopropyl ether to give benzhydryl 7-amino-3-[N-(3-chlorophenyl)carbamoyloxymethyl]-3-cephem-4-carboxylate (2.2 g.).

I.R. (Nujol): 3410, 3360, 1760, 1700, 1650, 1595, 1520 cm$^{-1}$.

N.M.R. (d$_6$-DMSO, δ): 3.60 (2H, broad s), 4.80 (1H, d, J=5 Hz), 4.83 (2H, AB$_q$, J=13 Hz), 5.05 (1H, d, J=5 Hz), 6.93 (1H, s), 6.90~7.70 (14H, m), 9.97 (1H, s).

Preparation 31

(1) Benzhydryl 7-(2-phenylacetamido)-3-hydroxymethyl-3-cephem-4-carboxylate (10.3 g.) and 2-(4-methoxyphenoxy)acetyl chloride (7.4 g.) were reacted according to a similar manner to that of Preparation 30-(1) to give a solution containing a mixture of benzhydryl 7-(2-phenylacetamido)-3-[2-(4-methoxyphenoxy)acetoxymethyl]-3-cephem-4-carboxylate and benzhydryl 7-(2-phenylacetamido)-3-[2-(4-methoxyphenoxy)acetoxymethyl]-2-cephem-4-carboxylate.

(2) The above-obtained solution was reacted with 3-chloroperbenzoic acid (4.7 g.) according to a similar manner to that of Preparation 30-(2) to give benzhydryl 7-(2-phenylacetamido)-3-[2-(4-methoxyphenoxy)acetoxymethyl]-3-cephem-4-carboxylate-1-oxide (7.1 g.).

I.R. (Nujol): 3270, 1780, 1760, 1720, 1650, 1520, 1500 cm$^{-1}$.

N.M.R. (d$_6$-DMSO, δ): 3.63 (2H, s), 3.67 (3H, s), 3.75 (2H, AB$_q$, J=19 Hz), 4.65 (2H, s), 4.90 (1H, d, J=5 Hz), 4.97 (2H, AB$_q$, J=13 Hz), 5.93 (1H, d,d, J=5 and 8 Hz), 6.85 (4H, s), 6.96 (1H, s), 7.00~7.70 (15H, m), 8.41 (1H, d, J=8 Hz).

(3) Benzhydryl 7-(2-phenylacetamido)-3-[2-(4-methoxyphenoxy)acetoxymethyl]-3-cephem-4-carboxylate-1-oxide (6.9 g.) and phosphorus trichloride (2.7 g.) were reacted according to a similar manner to that of Preparation 30 (3) to give benzhydryl 7-(2-phenylacetamido)-3-[2-(4-methoxyphenoxy)acetoxymethyl]-3-cephem-4-carboxylate (6.1 g.).

I.R. (Nujol): 3300, 1775, 1740, 1730, 1650 cm$^{-1}$.

N.M.R. (d$_6$-DMSO, δ): 3.50 (4H, broad s), 3.63 (3H, s), 4.62 (2H, s), 4.83 (2H, AB$_q$, J=15 Hz), 5.07 (1H, d, J=5 Hz), 5.72 (1H, d,d, J=5 and 8 Hz), 6.77 (4H, s), 6.85 (1H, s), 6.70~7.60 (15H, m), 9.00 (1H, d, J=8 Hz).

(4) Benzhydryl 7-(2-phenylacetamido)-3-[2-(4-methoxyphenoxy)acetoxymethyl]-3-cephem-4-carboxylate (6.0 g.), phosphorus pentachloride (5.65 g.), pyridine (2.2 g.) and methanol (7.3 ml.) were reacted according to a similar manner to that of Preparation 30 (4) to give benzhydryl 7-amino-3-[2-(4-methoxyphenoxy)acetoxymethyl]-3-cephem-4-carboxylate (4.6 g.).

N.M.R. (d$_6$-DMSO, δ): 3.52 (2H, broad s), 3.68 (3H, s), 4.69 (2H, s), 4.60~5.10 (4H, m), 6.89 (4H, s), 6.96 (1H, s), 7.00~7.70 (10H, m).

Preparation 32

The following compounds were obtained according to a similar manner to that of Preparation 30.

(1) Benzhydryl 7-amino-3-(2-thenoyl)oxymethyl-3-cephem-4-carboxylate.

I.R. (Nujol): 3400~3300, 1770, 1710, 1610, 1520 cm$^{-1}$.

N.M.R. (d$_6$-DMSO, δ): 3.68 (2H, broad s), 4.90 (1H, d, J=5 Hz), 5.03 (2H, AB$_q$, J=13 Hz), 5.12 (1H, d, J=5 Hz), 6.97 (1H, s), 7.17~7.67 (11H, m), 7.73~8.1 (2H, m).

(2) Benzhydryl 7-amino-3-cyclohexanecarbonyloxymethyl-3-cephem-4-carboxylate.

I.R. (Nujol): 3200, 1800, 1730, 1620 cm$^{-1}$.

N.M.R. (d$_6$-DMSO, δ): 0.83~2.0 (10H, m), 3.07~3.40 (1H, m), 3.58 (2H, broad s), 4.66~5.33 (4H, m), 6.93 (1H, s), 7.0~7.58 (10H, m).

(3) Benzhydryl 7-amino-3-(N-phenylcarbamoyloxymethyl)-3-cephem-4-carboxylate.

I.R. (Nujol): 3420, 3380, 1770, 1725, 1660, 1600, 1530 cm$^{-1}$.

N.M.R. (d$_6$-DMSO, δ): 3.65(2H, broad s), 4.83 (2H, AB$_q$, J=13 Hz), 4.90 (1H, d, J=5 Hz), 5.10 (1H, d, J=5 Hz), 7.00 (1H, s), 6.83~7.73 (15H, m), 9.78 (1H, s).

(4) Benzhydryl 7-amino-3-(4-nitrobenzoyloxymethyl)-3-cephem-4-carboxylate hydrochloride.

I.R. (Nujol): 3400, 3350, 1770, 1720, 1630, 1600, 1540 cm$^{-1}$.

N.M.R. (d$_6$-DMSO, δ): 3.74 (2H, broad s), 4.72~5.32 (4H, m), 6.92 (1H, s), 7.0~7.64 (10H, m), 8.12 (2H, d, J=9 Hz), 8.32 (2H, d, J=9 Hz).

EXAMPLE 58

2-Ethoxyimino-2-(2-formamidothiazol-4-yl)acetic acid (syn isomer) (3.0 g.) and dry ethyl acetate (40 ml.) were added at 0° to 5° C. with stirring to a suspension of Vilsmeier reagent prepared from dry dimethylformamide (1.0 g.) and phosphorus oxychloride (2.1 g.) in dry ethyl acetate (4.0 ml.) by conventional method, and the resulting mixture was stirred for 30 minutes at the same temperature. The solution was added at −10° C. with stirring to a solution of 7-amino-3-(1,3,4-thiadiazol-2-yl)thiomethyl-3-cephem-4-carboxylic acid (3.7 g.), trimethylsilylacetamide (10.3 g.) and bis(trimethylsilyl)acetamide (6.8 g.) in dry ethyl acetate (80 ml.), and the mixture was stirred for 1.5 hours at the same temperature. After addition of water (50 ml.) to the reaction mixture, an insoluble material was filtered off, the ethyl acetate layer in the filtrate was separated and extracted with an aqueous solution of sodium bicarbonate (50 ml.). The aqueous extract was washed with ethyl acetate and acidified to pH 2.0 with conc. hydrochloric acid. Precipitates were collected by filtration, washed with water and dried to give powder of 7-[2-ethoxyimino-2-(2-formamidothiazol-4-yl)acetamido]-3-(1,3,4-thiadiazol-2-yl)thiomethyl-3-cephem-4-carboxylic acid (syn isomer) (2.3 g.).

I.R. (Nujol): 3250, 1780, 1680 cm$^{-1}$.

N.M.R. (d$_6$-DMSO, δ): 1.31 (3H, t, J=7.0 Hz), 3.77 (2H, m), 4.28 (2H, q, J=7.0 Hz), 4.43 (2H, AB$_q$, J=13.0 Hz), 5.18 (1H, d, J=5.4 Hz), 5.84 (1H, d,d, J=5.4 and 9.8 Hz), 7.42 (1H, s), 8.53 (1H, s), 9.57 (1H, s), 9.66 (1H, d, J=9.8 Hz).

EXAMPLE 59

Phosphorus oxychloride (0.96 g.) was added at a time to a suspension of 2-(2-propynyloxyimino)-2-(2-aminothiazol-4-yl)acetic acid (syn isomer) (1.13 g.) in dry tetrahydrofuran (10 ml.) at 2° C. and the mixture was stirred for 15 minutes at 2° to 4° C. Trimethylsilylacetamide (1.0 g.) was added dropwise thereto and the resulting mixture was stirred for 20 minutes at 2° to 6° C. Phosphorus oxychloride (0.96 g.) was added thereto and the mixture was stirred for 20 minutes. Dry dimethylformamide (0.45 g.) was added thereto at a time at 4° to 6° C. and the mixture was stirred for 1 hour to give a clear solution. On the other hand, trimethylsilylacetamide (4.6 g.) was added to a stirred suspension of 7-amino-3-(1,3,4-thiadiazol-2-yl)thiomethyl-3-cephem-4-carboxylic acid (1.65 g.) in dry ethyl acetate (20 ml.) and the solution was stirred for 30 minutes at 40° C. To this solution was added the above-obtained tetrahydrofuran solution at a time at −30° C., and the resulting mixture was stirred for 1 hour at −5° to −20° C. To the reaction mixture were added water (30 ml.) and ethyl acetate (20 ml.). An organic layer was separated and extracted with an aqueous solution of sodium bicarbonate. The extract was adjusted to pH 3.0 with 10% hydrochloric acid. Precipitates were collected by filtration, washed with water to give 7-[2-(2-propynyl)oxyimino-2-(2-aminothiazol-4-yl)acetamido]-3-(1,3,4-thiadiazol-2-yl)thiomethyl-3-cephem-4-carboxylic acid (syn isomer) (1.4 g.).

I.R. (Nujol): 3300, 1780, 1680 cm$^{-1}$.

N.M.R. (d$_6$-DMSO, δ): 3.43 (1H, m), 3.67 (2H, broad s), 4.42 (2H, AB$_q$, J=13 Hz), 4.68 (2H, broad s), 5.13 (1H, d, J=5 Hz), 5.77 (1H, d,d, J=5 and 8 Hz), 6.77 (1H, s), 7.18 (2H, broad s), 9.50 (1H, s), 9.60 (1H, d, J=8 Hz).

EXAMPLE 60

The Vilsmeier reagent was prepared from dry dimethylformamide (0.44 g.), phosphorus oxychloride (0.9 g.) and dry ethyl acetate (1 ml.) by the conventional method. Dry ethyl acetate (15 ml.) was added thereto and then 2-methoxyimino-2-(2-formamidothiazol-4-yl)acetic acid (syn isomer) (1.1 g.) was added thereto at 0° C. The mixture was stirred for 30 minutes at the same temperature. The resulting mixture was added at −15° C. to a stirred solution of 7-amino-3-(3-methyl-1,2,4-thiadiazol-5-yl)thiomethyl-3-cephem-4-carboxylic acid (1.7 g.) and trimethylsilylacetamide (5.3 g.) in dry ethyl acetate (20 ml.) and the mixture was stirred for 1 hour at the same temperature. The reaction mixture was extracted by adding ethyl acetate (20 ml.) and water (30 ml.). The ethyl acetate layer was separated and extracted with a saturated aqueous solution of sodium bicarbonate (20 ml.). The aqueous layer was adjusted to pH 2.0 with 10% hydrochloric acid. Precipitates were collected by filtration, washed with water and dried to give 7-[2-methoxyimino-2-(2-formamidothiazol-4-yl)acetamido]-3-(3-methyl-1,2,4-thiadiazol-5-yl)thiomethyl-3-cephem-4-carboxylic acid (syn isomer) (2.3 g.).

I.R. (Nujol): 3300, 1780, 1680, 1660, 1550 cm$^{-1}$.

N.M.R. (d$_6$-DMSO, δ): 2.57 (3H, s), 3.70 (2H, AB$_q$, J=18 Hz), 3.95 (3H, s), 4.50 (2H, AB$_q$, J=13 Hz), 5.20 (1H, d, J=5 Hz), 5.83 (1H, d,d, J=5 and 8 Hz), 7.45 (1H, s), 8.57 (1H, s), 9.70 (1H, d, J=8 Hz), 12.65 (1H, broad s).

EXAMPLE 61

The Vilsmeier reagent was prepared from dry dimethylformamide (1.0 g.), dry ethyl acetate (4 ml.) and phosphorus oxychloride (2.1 g.) by the conventional method. Dry ethyl acetate (45 ml.) and 2-methoxyimino-2-(2-formamidothiazol-4-yl)acetic acid (syn isomer) (2.85 g.) were added thereto. This solution was added at −10° C. to a stirred solution, which was prepared by stirring for 1 hour at 40° C. a mixture of 7-amino-3-(1-hexyl-1H-tetrazol-5-yl)thiomethyl-3-cephem-4-carboxylic acid (4.5 g.), trimethylsilylacetamide (10.4 g.) and dry ethyl acetate (90 ml.), and the resulting mixture was stirred for 1.5 hours at −5° to −10° C. Water (50 ml.) was added to the reaction mixture and the ethyl acetate layer was separated. Water (40 ml.) was added thereto and the mixture was adjusted to pH 7.0 with a saturated aqueous solution of sodium bicarbonate. The aqueous layer was separated, washed with ethyl acetate and adjusted to pH 2.5 with 10% hydrochloric acid. Precipitates were collected by filtration, washed with water and dried under reduced pressure to give powder of 7-[2-methoxyimino-2-(2-formamidothiazol-4-yl)acetamido]-3-(1-hexyl-1H-tetrazol-5-yl)thiomethyl-3-cephem-4-carboxylic acid (syn isomer) (6.18 g.).

I.R. (Nujol): 3250, 1777, 1680 cm$^{-1}$.

N.M.R. (d$_6$-DMSO, δ): 0.85 (3H, t, J=5 Hz), 1.65 (6H, m), 2.78 (2H, m), 3.72 (2H, m), 3.93 (3H, s), 4.07~4.59 (4H, m), 5.17 (1H, d, J=5.0 Hz), 5.83 (1H, d,d, J=5.0, 8.2 Hz), 7.46 (1H, s), 9.56 (1H, s), 9.70 (1H, d, J=8.2 Hz).

EXAMPLE 62

The following compounds were obtained according to similar manners to those of Example 58 to 61.

(1)  7-[2-Propoxyimino-2-(2-formamidothiazol-4-yl)acetamido]-3-methyl-3-cephem-4-carboxylic acid (syn isomer).

I.R. (Nujol): 3450, 3300, 1775, 1725, 1680, 1655, 1620, 1590, 1555 cm$^{-1}$.

N.M.R. (d$_6$-DMSO, δ): 0.88 (3H, t, J=7 Hz), 1.67 (2H, m), 2.00 (3H, s), 3.43 (2H, AB$_q$, J=14 Hz), 4.03 (2H, t, J=7 Hz), 5.10 (1H, d, J=5 Hz), 5.75 (1H, d,d, J=5 and 8 Hz), 7.40 (1H, s), 8.53 (1H, s), 9.60 (1H, d, J=8 Hz), 12.7 (1H, broad s).

(2)  7-[2-Hexyloxyimino-2-(2-formamidothiazol-4-yl)acetamido]-3-methyl-3-cephem-4-carboxylic acid (syn isomer).

I.R. (Nujol): 3310, 3230, 3080, 1780, 1690, 1660 cm$^{-1}$.

N.M.R. (d$_6$-DMSO, δ): 0.6~2.2 (11H, m), 2.05 (3H, s), 3.64 (2H, AB$_q$, J=19 Hz), 4.12 (2H, t, J=6 Hz), 5.13 (1H, d, J=5 Hz), 5.74 (1H, d,d, J=5 and 8 Hz), 7.41 (1H, s), 8.52 (1H, s), 9.57 (1H, d, J=8 Hz), 12.69 (1H, broad s).

(3)  7-[2-Methoxyimino-2-(2-t-pentyloxycarbonylaminothiazol-4-yl)acetamido]-3-(1,3,4-thiadiazol-2-yl)thiomethyl-3-cephem-4-carboxylic acid (syn isomer).

I.R. (Nujol): 3250, 1785, 1730, 1680, 1630, 1560 cm$^{-1}$.

N.M.R. (d$_6$-DMSO, δ): 0.88 (3H, t, J=7 Hz), 1.45 (6H, s), 1.76 (2H, q, J=7 Hz), 3.73 (2H, broad s), 3.90 (3H, s), 4.48 (2H, AB$_q$, J=13 Hz), 5.20 (1H, d, J=5 Hz), 5.82 (1H, d,d, J=5 and 8 Hz), 7.30 (1H, s), 9.60 (1H, s), 9.70 (1H, d, J=8 Hz).

(4)  7-[2-Methoxyimino-2-(2-isobutoxycarbonylaminothiazol-4-yl)acetamido]-3-(1,3,4-thiadiazol-2-yl)thiomethyl-3-cephem-4-carboxylic acid (syn isomer).

I.R. (Nujol): 3300, 1782, 1730, 1670, 1570 cm$^{-1}$.

N.M.R. (d$_6$-DMSO, δ): 0.9 (6H, d, J=7 Hz), 1.92 (1H, m), 3.70 (2H, AB$_q$, J=16 Hz), 3.88 (3H, s), 3.94 (2H, d, J=4 Hz), 4.44 (2H, AB$_q$, J=13 Hz), 5.16 (1H, d, J=5 Hz), 5.80 (1H, d,d, J=5 and 8 Hz), 7.32 (1H, s), 9.56 (1H, s).

(5)  7-[2-Isopropoxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3300, 3050, 1777, 1727, 1672 cm$^{-1}$.

N.M.R. (d$_6$-DMSO, δ): 1.28 (6H, d, J=6 Hz), 3.75 (2H, broad s), 4.43 (3H, m), 4.8~5.6 (1H), 5.90 (1H, d,d, J=5 and 8 Hz), 7.45 (1H, s), 8.58 (1H, broad s), 9.60 (1H, s), 9.77 (1H, d, J=8 Hz), 12.80 (1H, broad s).

(6)  7-[2-Pentyloxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3300, 3250, 1785, 1680 cm$^{-1}$.

N.M.R. (d$_6$-DMSO, δ): 0.6~1.9 (9H, m), 3.72 (2H, broad s), 4.11 (2H, t, J=6 Hz), 4.47 (2H, AB$_q$, J=13 Hz), 5.18 (1H, d, J=5 Hz), 5.82 (1H, d,d, J=5 and 8 Hz), 7.41 (1H, s), 8.53 (1H, s), 9.57 (1H, s), 9.64 (1H, d, J=8 Hz), 12.65 (1H, s).

(7)  7-[2-Butoxyimino-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3300, 2550~2600, 1775, 1710, 1690, 1670, 1645 cm$^{-1}$.

N.M.R. (d$_6$-DMSO, δ): 0.90 (3H, m), 1.2~1.8 (4H, m), 3.70 (2H, AB$_q$, J=18 Hz), 3.94 (3H, s), 4.12 (2H, m), 4.32 (2H, AB$_q$, J=13 Hz), 5.16 (1H, d, J=5 Hz), 5.80 (1H, d,d, J=5 and 8 Hz), 7.37 (1H, s), 8.50 (1H, s), 9.62 (1H, d, J=8 Hz), 12.6 (1H, s).

(8)  7-[2-(2-Propynyloxyimino)-2-(2-formamidothiazol-4-yl)acetamido]-3-(1-methyl-1H-tetrazol-5-yl)thiomethyl-3-cephem-4-carboxylic acid (syn isomer).

I.R. (Nujol): 3240, 2110, 1770, 1665 cm$^{-1}$.

N.M.R. (d$_6$-DMSO, δ): 3.49 (1H, m), 3.70 (2H, m), 3.96 (3H, s), 4.33 (2H, AB$_q$, J=15.0 Hz), 4.76 (2H, m), 5.14 (1H, d, J=5.0 Hz), 5.80 (1H, d,d, J=5.0 and 8.0 Hz), 7.44 (1H, s), 8.53 (1H, s), 9.74 (1H, d, J=8.0 Hz).

(9)  7-[2-Methoxyimino-2-(2-formamidothiazol-4-yl)acetamido]-3-(1-propyl-1H-tetrazol-5-yl)thiomethyl-3-cephem-4-carboxylic acid (syn isomer).

I.R. (Nujol): 3180, 1775, 1665 cm$^{-1}$.

N.M.R. (d$_6$-DMSO, δ): 0.85 (3H, t, J=8.0 Hz), 1.82 (2H, m), 3.69 (2H, m), 3.88 (3H, s), 4.06~4.66 (4H, m), 5.13 (1H, d, J=5.0 Hz), 5.81 (1H, d,d, J=5.0 and 8.0 Hz), 7.42 (1H, s), 8.52 (1H, s), 9.65 (1H, d, J=8.0 Hz).

(10)  7-[2-Allyloxyimino-2-(2-formamidothiazol-4-yl)acetamido]-3-(1-propyl-1H-tetrazol-5-yl)thiomethyl-3-cephem-4-carboxylic acid (syn isomer).

I.R. (Nujol): 3180, 1775, 1670 cm$^{-1}$.

N.M.R. (d$_6$-DMSO, δ): 0.87 (3H, t, J=8.0 Hz), 1.65 (2H, m), 3.73 (2H, AB$_q$, J=16.0 Hz), 4.00~4.53 (4H, m), 4.69 (2H, d, J=5.0 Hz), 5.00~5.68 (3H, m), 5.68~6.36 (2H, m), 7.45 (1H, s), 8.56 (1H, s), 9.72 (1H, d, J=8.0 Hz).

(11)  7-[2-(2-Propynyloxyimino)-2-(2-formamidothiazol-4-yl)acetamido]-3-(1-propyl-1H-tetrazol-5-yl)thiomethyl-3-cephem-4-carboxylic acid (syn isomer).

I.R. (Nujol): 3270, 2125, 1780, 1680 cm$^{-1}$.

N.M.R. (d$_6$-DMSO, δ): 0.87 (3H, t, J=8.0 Hz), 1.84 (2H, m), 3.50 (1H, m), 3.73 (2H, broad s), 4.03~4.59 (4H, m), 4.78 (2H, m), 5.17 (1H, d, J=5.0 Hz), 5.84 (1H, d,d, J=5.0 and 8.0 Hz), 7.47 (1H, s), 8.56 (1H, s), 9.76 (1H, d, J=8.0 Hz).

(12)  7-[2-Isopropoxyimino-2-(2-formamidothiazol-4-yl)acetamido]-3-(1-hexyl-1H-tetrazol-5-yl)thiomethyl-3-cephem-4-carboxylic acid (syn isomer).

I.R. (Nujol): 3175, 1780, 1670 cm$^{-1}$.

N.M.R. (d$_6$-DMSO, δ): 0.66 (3H, t, J=5.0 Hz), 1.05~1.57 (6H, m), 1.92 (2H, m), 3.77 (2H, m), 4.10~4.72 (5H, m), 5.24 (1H, d, J=5.0 Hz), 5.90 (1H, d,d J=5.0 and 8.4 Hz), 7.43 (1H, s), 8.56 (1H, s), 9.64 (1H, d, J=8.4 Hz).

(13)  7-[2-Hexyloxyimino-2-(2-formamidothiazol-4-yl)acetamido]-3-(1-hexyl-1H-tetrazol-5-yl)thiomethyl-3-cephem-4-carboxylic acid (syn isomer).

I.R. (Nujol): 3175, 1785, 1642 cm$^{-1}$.

N.M.R. (d₆-DMSO, δ): 0.86 (6H, m), 1.00~1.57 (12H, m), 1.57~2.07 (4H, m), 3.75 (2H, m), 3.97~4.60 (8H, m), 5.18 (1H, d, J=5.2 Hz), 5.85 (1H, d,d J=5.2 and 8.4 Hz), 7.41 (1H, s), 8.56 (1H, s), 9.65 (1H, d, J=8.4 Hz).

(14) 7-[2-Allyloxyimino-2-(2-formamidothiazol-4-yl)acetamido]-3-(1-hexyl-1H-tetrazol-5-yl)thiomethyl-3-cephem-4-carboxylic acid (syn isomer).

I.R. (Nujol): 3180, 1780, 1680 cm⁻¹.

N.M.R. (d₆-DMSO, δ): 0.64~1.97 (11H, m), 3.68 (2H, AB$_q$, J=18 Hz), 4.30 (4H, m), 4.64 (2H, m), 5.00~5.46 (3H, m), 5.56~6.24 (2H, m), 7.37 (1H, s), 8.48 (1H, s), 9.67 (1H, d, J=8 Hz).

(15) Benzhydryl 7-[2-methoxyimino-2-(2-aminothiazol-4-yl)acetamido]-3-cyclohexanecarbonyloxymethyl-3-cephem-4-carboxylate (syn isomer).

I.R. (KBr): 3300, 1780, 1730, 1690, 1630 cm⁻¹.

N.M.R. (d₆-DMSO, δ): 1.0~2.10 (10H, m), 3.13 (1H, m), 3.60 (2H, broad s), 3.93 (3H, s), 4.93 (2H, AB$_q$, J=13 Hz), 5.22 (1H, d, J=5 Hz), 5.83 (1H, d,d, J=5 and 8 Hz), 6.87 (1H, s), 6.96 (1H, s), 7.17~7.67 (10H, m), 9.70 (1H, d, J=8 Hz).

(16) Benzhydryl 7-[2-methoxyimino-2-(2-aminothiazol-4-yl)acetamido]-3-[2-(4-methoxyphenoxy)acetoxymethyl]-3-cephem-4-carboxylate (syn isomer).

I.R. (Nujol): 3300, 1780, 1725, 1680, 1620, 1530, 1510 cm⁻¹.

N.M.R. (d₆-DMSO, δ): 3.58 (2H, broad s), 3.70 (3H, s), 3.87 (3H, s), 4.70 (2H, s), 4.91 (2H, AB$_q$, J=14 Hz), 5.22 (1H, d, J=5 Hz), 5.92 (1H, d,d, J=5 and 8 Hz), 6.78 (1H, s), 6.88 (4H, s), 6.95 (1H, s), 7.04~7.64 (10H, m), 9.64 (1H, d, J=8 Hz).

(17) Benzhydryl 7-[2-methoxyimino-2-(2-aminothiazol-4-yl)acetamido]-3-pivaloyloxymethyl-3-cephem-4-carboxylate (syn isomer).

I.R. (Nujol): 3300, 1780, 1725, 1680, 1620, 1530 cm⁻¹.

N.M.R. (d₆-DMSO, δ): 1.13 (9H, s), 3.62 (2H, broad s), 3.88 (3H, s), 4.86 (2H, AB$_q$, J=14 Hz), 5.26 (1H, d, J=5 Hz), 5.96 (1H, d,d, J=5 and 8 Hz), 6.80 (1H, s), 6.98 (1H, s), 7.12~7.68 (10H, m), 9.73 (1H, d, J=8 Hz).

(18) Benzhydryl 7-[2-methoxyimino-2-(2-aminothiazol-4-yl)acetamido]-3-(2-thenoyl)oxymethyl-3-cephem-4-carboxylate (syn isomer).

I.R. (Nujol): 3300, 1780, 1710, 1670, 1610 cm⁻¹.

N.M.R. (d₆-DMSO, δ): 3.73 (2H, broad s), 3.87 (3H, s), 5.03 (2H, AB$_q$, J=13 Hz), 5.27 (1H, d, J=5 Hz), 5.93 (1H, d,d, J=5 and 8 Hz), 6.77 (1H, s), 6.97 (1H, s), 7.1~7.67 (11H, m), 7.77~8.1 (2H, m), 9.67 (1H, d, J=8 Hz).

(19) Benzhydryl 7-[2-methoxyimino-2-(2-aminothiazol-4-yl)acetamido]-3-[N-(3-chlorophenyl)carbamoyloxymethyl]-3-cephem-4-carboxylate (syn isomer).

I.R. (Nujol): 3300, 1770, 1720, 1670, 1600, 1530 cm⁻¹.

N.M.R. (d₆-DMSO δ): 3.70 (2H, broad s), 3.90 (3H, s), 4.90 (2H, AB$_q$, J=13 Hz), 5.27 (1H, d, J=5 Hz), 5.93 (1H, d,d, J=5 and 8 Hz), 6.80 (1H, s), 6.97 (1H, s), 6.87~7.77 (14H, m), 9.60 (1H, d, J=8 Hz), 10.00 (1H, s).

(20) Benzhydryl 7-[2-methoxyimino-2-(2-aminothiazol-4-yl)acetamido]-3-(N-phenylcarbamoyloxymethyl)-3-cephem-4-carboxylate (syn isomer).

I.R. (Nujol): 3300, 1780, 1720, 1675, 1600, 1530, 1500 cm⁻¹.

N.M.R. (d₆-DMSO, δ): 3.63 (2H, broad s), 3.80 (3H, s), 4.80 (2H, AB$_q$, J=13 Hz), 5.20 (1H, d, J=5 Hz), 5.86 (1H, d,d, J=5 and 8 Hz), 6.73 (1H, s), 6.93 (1H, s), 6.83~7.67 (15H, m), 9.57 (1H, d, J=8 Hz), 9.73 (1H, s).

(21) 7-[2-(2-Propynyloxyimino)-2-(2-formamidothiazol-4-yl)acetamido]-3-(1,3,4-thiadiazol-2-yl)thiomethyl-3-cephem-4-carboxylic acid (syn isomer).

I.R. (Nujol): 3250, 1780, 1690, 1660, 1620, 1550, 1530 cm⁻¹.

N.M.R. (d₆-DMSO, δ): 3.44 (1H, m), 3.68 (2H, AB$_q$, J=18 Hz), 4.44 (2H, AB$_q$, J=13 Hz), 4.74 (2H, m), 5.16 (1H, d, J=5 Hz), 5.80 (1H, d,d, J=5 and 8 Hz), 7.44 (1H, s), 8.50 (1H, s), 9.76 (1H, d, J=8 Hz), 12.66 (1H, broad s).

(22) 7-[2-Ethoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3300, 1775, 1660 cm⁻¹.

(23) 7-[2-Methoxyimino-2-(2-aminothiazol-4-yl)acetamido]-3-(3-methyl-1,2,4-thiadiazol-5-yl)thiomethyl-3-cephem-4-carboxylic acid (syn isomer).

I.R. (Nujol): 3350, 3250, 1780, 1680, 1630, 1530 cm⁻¹.

(24) 7-[2-Propoxyimino-2-(2-aminothiazol-4-yl)acetamido]-3-methyl-3-cephem-4-carboxylic acid (syn isomer).

I.R. (Nujol): 3300, 1775, 1655, 1635, 1545 cm⁻¹.

(25) 7-[2-Hexyloxyimino-2-(2-aminothiazol-4-yl)acetamido]-3-methyl-3-cephem-4-carboxylic acid (syn isomer).

I.R. (Nujol): 3420, 3170, 3070, 1765, 1720, 1670, 1630 cm⁻¹.

(26) 7-[2-Isopropoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3325, 1774, 1656 cm⁻¹.

(27) 7-[2-Pentyloxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3200, 1775, 1675 cm⁻¹.

(28) 7-[2-Butoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3350, 3250, 2550~2600, 1780, 1700, 1670, 1630 cm⁻¹.

(29) 7-[2-(2-Propynyloxyimino)-2-(2-aminothiazol-4-yl)acetamido]-3-(1-methyl-1H-tetrazol-5-yl)thiomethyl-3-cephem-4-carboxylic acid (syn isomer).

I.R. (Nujol): 3280, 2130, 1765, 1690, 1630 cm⁻¹.

(30) 7-[2-Methoxyimino-2-(2-aminothiazol-4-yl)acetamido]-3-(1-propyl-1H-tetrazol-5-yl)thiomethyl-3-cephem-4-carboxylic acid (syn isomer).

I.R. (Nujol): 3350, 1780, 1670, 1630 cm⁻¹.

(31) 7-[2-Allyloxyimino-2-(2-aminothiazol-4-yl)acetamido]3-(1-propyl-1H-tetrazol-5-yl)thiomethyl-3-cephem-4-carboxylic acid (syn isomer).

I.R. (Nujol): 3340, 3230, 1780, 1680, 1630 cm⁻¹.

(32) 7-[2-(2-Propynyloxyimino)-2-(2-aminothiazol-4-yl)acetamido]-3-(1-propyl-1H-tetrazol-5-yl)thiomethyl-3-cephem-4-carboxylic acid (syn isomer).

I.R. (Nujol): 3330, 2150, 1770, 1677, 1635 cm⁻¹.

(33) 7-[2-Methoxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3350, 3230, 1777, 1675, 1627 cm⁻¹.

(34) 7-[2-Isopropoxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3320, 1780, 1675, 1630 cm⁻¹.

(35) 7-[2-Hexyloxyimino-2-(2-aminothiazol-4-yl)acetamido]-3-(1-hexyl-1H-tetrazol-5-yl)thiomethyl-3-cephem-4-carboxylic acid (syn isomer).
I.R. (Nujol): 3350, 3230, 1765, 1670, 1615 cm$^{-1}$.

(36) 7-[2-Allyloxyimino-2-(2-aminothiazol-4-yl)acetamido]-3-(1-hexyl-1H-tetrazol-5-yl)thiomethyl-3-cephem-4-carboxylic acid hydrochloride (syn isomer).
I.R. (Nujol): 3240, 1780, 1720, 1675 cm$^{-1}$.

(37) Hexanoyloxymethyl 7-[2-methoxyimino-2-(2-aminothiazol-4-yl)acetamido]-3-(1,3,4-thiadiazol-2-yl)thiomethyl-3-cephem-4-carboxylate (syn isomer).
I.R. (Nujol): 3500, 3300, 3130, 1785, 1755, 1745, 1680, 1660 cm$^{-1}$.

(38) Hexanoyloxymethyl 7-[2-methoxyimino-2-(2-aminothiazol-4-yl)acetamido]cephalosporanate (syn isomer).
I.R. (Nujol): 3300, 1780, 1740, 1670, 1620, 1530 cm$^{-1}$.

(39) 7-[2-Methoxyimino-2-(2-aminothiazol-4-yl)acetamido]-3-[N-(3-chlorophenyl)carbamoyloxymethyl]-3-cephem-4-carboxylic acid (syn isomer).
I.R. (Nujol): 3320, 1780, 1710, 1680, 1600, 1540 cm$^{-1}$.

(40) 7-[2-Methoxyimino-2-(2-aminothiazol-4-yl)acetamido]-3-cyclohexanecarbonyloxymethyl-3-cephem-4-carboxylic acid (syn isomer).
I.R. (Nujol): 3300, 1780, 1730, 1670 cm$^{-1}$.

(41) 7-[2-(Methoxyimino-2-(2-aminothiazol-4-yl)acetamido]-3-[2-(4-methoxyphenoxy)acetoxymethyl]-3-cephem-4-carboxylic acid (syn isomer).
I.R. (Nujol): 3300, 1780, 1730, 1680, 1635 cm$^{-1}$.

(42) 7-[2-Methoxyimino-2-(2-aminothiazol-4-yl)acetamido]-3-pivaloyloxymethyl-3-cephem-4-carboxylic acid (syn isomer).
I.R. (Nujol): 3300, 1780, 1720, 1670, 1540 cm$^{-1}$.

(43) 7-[2-Methoxyimino-2-(2-aminothiazol-4-yl)acetamido]-3-(2-thenoyl)oxymethyl-3-cephem-4-carboxylic acid (syn isomer).
I.R. (Nujol): 3250, 1780, 1710, 1680, 1635, 1530 cm$^{-1}$.

(44) Benzhydryl 7-[2-methoxyimino-2-(2-aminothiazol-4-yl)acetamido]-3-(4-nitrobenzoyloxymethyl)-3-cephem-4-carboxylate (syn isomer).
I.R. (Nujol): 3300, 1780, 1720, 1670, 1600 1520 cm$^{-1}$.
N.M.R. (d$_6$-DMSO, δ): 3.43 (2H, broad s), 3.92 (3H, s), 5.08 (2H, AB$_q$, J=13 Hz), 5.2 (1H, d, J=5 Hz), 6.00 (1H, d,d, J=5 and 8 Hz), 6.83 (1H, s), 7.00 (1H, s), 7.10~7.80 (10H, m), 8.15 (2H, d, J=9 Hz), 8.38 (2H, d, J=9 Hz), 9.73 (1H, d, J=8 Hz).

(45) Benzhydryl 7-[2-methoxyimino-2-(2-aminothiazol-4-yl)acetamido]-3-(4-aminobenzoyloxymethyl)-3-cephem-4-carboxylate (syn isomer).
I.R. (Nujol): 3280, 1780, 1710, 1670, 1605, 1520 cm$^{-1}$.

(46) 7-[2-Methoxyimino-2-(2-aminothiazol-4-yl)acetamido]-3-(4-aminobenzoyloxymethyl)-3-cephem-4-carboxylic acid (syn isomer).
I.R. (Nujol): 3350, 1780, 1680, 1605, 1540 cm$^{-1}$.

(47) 7-[2-Methoxyimino-2-(2-aminothiazol-4-yl)acetamido]-3-(N-phenylcarbamoyloxymethyl)-3-cephem-4-carboxylic acid (syn isomer).
I.R. (Nujol): 3300, 1780, 1710, 1670, 1600 cm$^{-1}$.

EXAMPLE 63

Conc. hydrochloric acid (0.85 g.) was added under ice-cooling to a stirred solution of 7-[2-ethoxyimino-2-(2-formamidothiazol-4-yl)acetamido]-3-(1,3,4-thiadiazol-2-yl)thiomethyl-3-cephem-4-carboxylic acid (syn isomer) (2.3 g) in a mixture of methanol (23 ml.) and tetrahydrofuran (23 ml.), and the mixture was stirred for 2.5 hours at ambient temperature. The solvent was distilled off under reduced pressure and the residue was dissolved in a saturated aqueous solution of sodium bicarbonate (pH 7.0). The aqueous solution was washed with ethyl acetate and adjusted to pH 3.5 with conc. hydrochloric acid. Precipitates were collected by filtration, washed with water and dried to give powder of 7-[2-ethoxyimino-2-(2-aminothiazol-4-yl)acetamido]-3-(1,3,4-thiadiazol-2-yl)thiomethyl-3-cephem-4-carboxylic acid (syn isomer) (1.865 g.).
I.R. (Nujol): 3300, 1775, 1660 cm$^{-1}$.
N.M.R. (d$_6$-DMSO, δ): 1.67 (3H, t, J=7.6 Hz), 3.75 (2H, m), 4.16 (2H, q, J=7.6 Hz), 4.48 (2H, AB$_q$, J=13.6 Hz), 5.18 (1H, d, J=5.2 Hz), 5.83 (1H, d,d, J=5.2 and 8.0 Hz), 6.79 (1H, s), 7.38 (2H, broad s), 9.63 (1H, s), 9.63 (1H, d, J=8.0 Hz).

EXAMPLE 64

A mixture of 7-[2-methoxyimino-2-(2-formamidothiazol-4-yl)acetamido]-3-(3-methyl-1,2,4-thiadiazol-5-yl)thiomethyl-3-cephem-4-carboxylic acid (syn isomer) (2.2 g.), conc. hydrochloric acid (0.8 ml.) and methanol (16 ml.) was stirred for 3 hours at ambient temperature. The solvent was distilled off under reduced pressure and the residue was dissolved in a saturated aqueous solution of sodium bicarbonate (pH 7.5). The aqueous solution was adjusted to pH 3.5 with 10% hydrochloric acid and stirred for 1 hour. Precipitates were collected by filtration, washed with water and dried to give 7-[2-methoxyimino-2-(2-aminothiazol-4-yl)acetamido]-3-(3-methyl-1,2,4-thiadiazol-5-yl)thiomethyl-3-cephem-4-carboxylic acid (syn isomer) (1.35 g.).
I.R. (Nujol): 3350, 3250, 1780, 1680, 1630, 1530 cm$^{-1}$.
N.M.R. (d$_6$-DMSO, δ): 2.52 (3H, s), 3.67 (2H, AB$_q$, J=18 Hz), 3.83 (3H, s), 4.43 (2H, AB$_q$, J=14 Hz), 5.15 (1H, d, J=5 Hz), 5.77 (1H, d,d, J=5 and 8 Hz), 6.73 (1H, s), 9.67 (1H, d, J=8 Hz).

EXAMPLE 65

Conc. hydrochloric acid (2.1 g.) was added under ice-cooling and stirring to a solution of 7-[2-methoxyimino-2-(2-formamidothiazol-4-yl)acetamido]-3-(1-hexyl-1H-tetrazol-5-yl)thiomethyl-3-cephem-4-carboxylic acid (syn isomer) (6.0 g.) in methanol (60 ml.), and the mixture was stirred for 4 hours at ambient temperature. The solvent was removed from the reaction mixture and ethyl acetate (50 g.) was added thereto. The mixture was adjusted to pH 7.0 under stirring with a saturated aqueous solution of sodium bicarbonate. The aqueous layer was separated, washed with ethyl acetate and adjusted to pH 3.5 with conc. hydrochloric acid. Precipitates were collected by filtration, washed with water and dried under reduced pressure to give powder of 7-[2-methoxyimino-2-(2-aminothiazol-4-yl)acetamido]-3-(1-hexyl-1H-tetrazol-5-yl)thiomethyl-3-cephem-4-carboxylic acid (syn isomer) (4.62 g.).
I.R. (Nujol): 3350, 3230, 1777, 1675, 1627 cm$^{-1}$.
N.M.R. (d$_6$-DMSO, δ): 0.82 (3H, t, J=5.0 Hz), 1.23 (6H, m), 1.80 (2H, m), 3.69 (2H, m), 3.85 (3H, s), 4.05~4.63 (4H, m), 5.12 (1H, d, J=5.0 Hz), 5.75 (1H, d,d, J=5.0, 8.6 Hz), 6.76 (1H, s), 7.23 (2H, broad s), 9.59 (1H, d, J=8.6 Hz).

EXAMPLE 66

The following compounds were obtained according to similar manners to those of Examples 63 to 65.

(1) 7-[2-Propoxyimino-2-(2-aminothiazol-4-yl)acetamido]-3-methyl-3-cephem-4-carboxylic acid (syn isomer).

I.R. (Nujol): 3300, 1775, 1655, 1635, 1545 cm$^{-1}$.

N.M.R. (d$_6$-DMSO, δ): 0.9 (3H, t, J=8 Hz), 1.67 (2H, m), 2.03 (3H, s), 3.43 (2H, AB$_q$, J=18 Hz), 4.0 (2H, m), 5.1 (1H, d, J=5 Hz), 5.7 (1H, d,d, J=5 and 8 Hz), 6.7 (1H, s), 9.5 (1H, d, J=8 Hz).

(2) 7-[2-Hexyloxyimino-2-(2-aminothiazol-4-yl)acetamido]-3-methyl-3-cephem-4-carboxylic acid (syn isomer).

I.R. (Nujol): 3420, 3170, 3070, 1765, 1720, 1670, 1630 cm$^{-1}$.

N.M.R. (d$_6$-DMSO, δ): 0.87 (3H, t, J=6 Hz), 0.9~2.0 (8H, m), 2.05 (3H, s), 3.48 (2H, AB$_q$, J=18 Hz), 4.08 (2H, t, J=6 Hz), 5.13 (1H, d, J=5 Hz), 5.73 (1H, d,d, J=5 and 8 Hz), 6.76 (1H, s), 7.30 (2H, broad s), 9.53 (1H, d, J=8 Hz)).

(3) 7-[2-Isopropoxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3325, 1774, 1656 cm$^{-1}$.

N.M.R. (d$_6$-DMSO, δ): 1.22 (6H, d, J=6 Hz), 3.70 (2H, broad s), 4.37 (3H, m), 5.15 (1H, d, J=5 Hz), 5.77 (1H, d,d, J=5 and 8 Hz), 6.70 (1H, s), 7.20 (2H, m), 9.50 (1H, d, J=8 Hz), 9.55 (1H, s).

(4) 7-[2-Pentyloxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350, 3200, 1775, 1675 cm$^{-1}$.

N.M.R. (d$_6$-DMSO, δ): 0.62~2.0 (9H, m), 3.72 (2H, broad s), 4.06 (2H, t, J=6 Hz), 4.45 (2H, AB$_q$, J=13 Hz), 5.17 (1H, d, J=5 Hz), 5.78 (1H, d,d, J=5 and 8 Hz), 6.73 (1H, s), 7.2 (2H, s), 9.5 (1H, d, J=8 Hz), 9.55 (1H, s).

(5) 7-[2-Butoxyimino-2-(2-aminothiazol-4-yl)acetamido]-3-(1-methyl-1H-tetrazol-5-yl)thiomethyl-3-cephem-4-carboxylic acid (syn isomer).

I.R. (Nujol): 3350, 3250, 2550~2600, 1780, 1700, 1670, 1630 cm$^{-1}$.

N.M.R. (d$_6$-DMSO, δ): 1.0 (3H, m), 1.2~1.7 (4H, m), 3.77 (2H, AB$_q$, J=19 Hz), 3.95 (3H, s), 4.15 (2H, m), 4.33 (2H, AB$_q$, J=13 Hz), 5.20 (1H, d, J=5 Hz), 5.82 (1H, d,d, J=5, 8 Hz), 6.73 (1H, s), 9.56 (1H, d, J=8 Hz).

(6) 7-[2-(2-Propynyloxyimino)-2-(2-aminothiazol-4-yl)acetamido]-3-(1-methyl-1H-tetrazol-5-yl)thiomethyl-3-cephem-4-carboxylic acid (syn isomer).

I.R. (Nujol): 3280, 2130, 1765, 1690, 1630 cm$^{-1}$.

N.M.R. (d$_6$-DMSO, δ): 3.45 (1H, m), 3.70 (2H, m), 3.96 (3H, s), 4.33 (2H, AB$_q$, J=16 Hz), 4.71 (2H, m), 5.14 (1H, d, J=5.0 Hz), 5.79 (1H, d,d, J=5.0 and 8.0 Hz), 6.79 (1H, s), 7.65 (2H, broad s), 9.33 (1H, d, J=8.0 Hz).

(7) 7-[2-Methoxyimino-2-(2-aminothiazol-4-yl)acetamido]-3-(1-propyl-1H-tetrazol-5-yl)thiomethyl-3-cephem-4-carboxylic acid (syn isomer).

I.R. (Nujol): 3350, 1780, 1670, 1630 cm$^{-1}$.

N.M.R. (d$_6$-DMSO, δ): 0.87 (3H, t, J=7.0 Hz), 1.84 (2H, m), 3.73 (2H, broad s), 3.89 (3H, s), 4.06~4.72 (4H, m), 5.14 (1H, d, J=5.0 Hz), 5.80 (1H, d,d, J=5.0 and 8.0 Hz), 6.78 (1H, s), 7.23 (2H, broad s), 9.59 (1H, d, J=8.0 Hz).

(8) 7-[2-Allyloxyimino-2-(2-aminothiazol-4-yl)acetamido]-3-(1-propyl-1H-tetrazol-5-yl)thiomethyl-3-cephem-4-carboxylic acid (syn isomer).

I.R. (Nujol): 3340, 3230, 1780, 1680, 1630 cm$^{-1}$.

N.M.R. (d$_6$-DMSO, δ): 0.86 (3H, t, J=7.0 Hz), 1.83 (2H, m), 3.71 (2H, broad s), 4.05~4.80 (6H, m), 5.01~5.53 (3H, m), 5.63~6.42 (2H, m), 6.75 (1H, s), 7.20 (2H, broad s), 9.59 (1H, d, J=8.2 Hz).

(9) 7-[2-(2-Propynyloxyimino)-2-(2-aminothiazol-4-yl)acetamido]-3-(1-propyl-1H-tetrazol-5-yl)thiomethyl-3-cephem-4-carboxylic acid (syn isomer).

I.R. (Nujol): 3330, 2150, 1770, 1677, 1635 cm$^{-1}$.

N.M.R. (d$_6$-DMSO, δ): 0.86 (3H, t, J=7.0 Hz), 1.84 (2H, m), 3.49 (1H, m), 3.73 (2H, m), 3.91~4.60 (4H, m), 4.75 (2H, m), 5.17 (1H, d, J=5.0 Hz), 5.80 (1H, d,d, J=5.0 and 8.0 Hz), 6.86 (1H, s), 9.72 (1H, d, J=8.0 Hz).

(10) 7-[2-Isopropoxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3320, 1780, 1675, 1630 cm$^{-1}$.

N.M.R. (d$_6$-DMSO, δ): 0.84 (3H, t, J=6.0 Hz), 1.00~1.50 (12H, m), 1.80 (2H, m), 3.72 (2H, AB$_q$, J=17.0 Hz), 4.10~4.60 (5H, m), 5.15 (1H, d, J=5.0 Hz), 5.81 (1H, d,d, J=5.0, 8.0 Hz), 6.77 (1H, s), 9.59 (1H, d, J=8.0 Hz).

(11) 7-[2-Hexyloxyimino-2-(2-aminothiazol-4-yl)acetamido]-3-(1-hexyl-1H-tetrazol-5-yl)thiomethyl-3-cephem-4-carboxylic acid (syn isomer).

I.R. (Nujol): 3350, 3230, 1765, 1670, 1615 cm$^{-1}$.

N.M.R. (d$_6$-DMSO, δ): 0.84 (6H, m), 1.26 (12H, m), 1.70 (4H, m), 3.20~4.60 (8H, m), 5.40 (1H, d, J=5.0 Hz), 5.68 (1H, d,d, J=5.0, 8.0 Hz), 6.72 (1H, s), 7.23 (2H, broad s), 9.49 (1H, d, J=8.0 Hz).

(12) 7-[2-Allyloxyimino-2-(2-aminothiazol-4-yl)acetamido]-3-(1-hexyl-1H-tetrazol-5-yl)thiomethyl-3-cephem-4-carboxylic acid hydrochloride (syn isomer).

I.R. (Nujol): 3240, 1780, 1720, 1675 cm$^{-1}$.

N.M.R. (d$_6$-DMSO, δ): 0.63~2.13 (11H, m), 3.73 (2H, AB$_q$, J=18 Hz), 4.08~4.90 (6H, m), 5.10~6.30 (5H, m), 6.94 (1H, s), 7.93 (2H, broad s), 9.80 (1H, d, J=8 Hz).

EXAMPLE 67

A solution of iodomethyl hexanoate (1.58 g.) in dimethylformamide (3 ml.) was added at a time under ice-cooling to a stirred solution of sodium 7-[2-methoxyimino-2-(2-aminothiazol-4-yl)acetamido]-3-(1,3,4-thiadiazol-2-yl)thiomethyl-3-cephem-4-carboxylate (syn isomer) (3.0 g.) in dimethylformamide (15 ml.). The mixture was stirred for 10 minutes at the same temperature and poured into a mixture of water (50 ml.) and ethyl acetate (100 ml.). The aqueous layer was separated and extracted twice with ethyl acetate (50 ml.). The combined ethyl acetate layer was filtered and the filtrate was washed three times with an aqueous solution of sodium bicarbonate and a saturated aqueous solution of sodium chloride and dried over magnesium sulfate. The solution was concentrated in vacuo to a volume of 20 ml. to give precipitates, which were collected by filtration, washed with ethyl acetate (10 ml.) and dried to give hexanoyloxymethyl 7-[2-methoxyimino-2-(2-aminothiazol-4-yl)acetamido]-3-(1,3,4-thiadiazol-2-yl)thiomethyl-3-cephem-4-carboxylate (syn isomer) (2.1 g.).

I.R. (Nujol): 3500, 3300, 3130, 1785, 1755, 1745, 1680, 1660 cm$^{-1}$.

N.M.R. (d$_6$-DMSO, δ): 0.87 (3H, t, J=6 Hz), 1.0~2.0 (6H, m), 2.39 (2H, t, J=6 Hz), 3.80 (2H, s), 3.88 (3H, s), 4.46 (2H, AB$_q$, J=14 Hz), 5.20 (1H, d, J=5 Hz), 5.6~6.2 (3H, m), 6.76 (1H, s), 7.23 (2H, broad s), 9.56 (1H, s), 9.60 (1H, d, J=8 Hz).

EXAMPLE 68

The following compound was obtained according to a similar manner to that of Example 67. Hexanoyloxymethyl 7-[2-methoxyimino-2-(2-aminothiazol-4-yl)acetamido]cephalosporanate (syn isomer).

I.R. (Nujol): 3300, 1780, 1740, 1670, 1620, 1530 cm$^{-1}$.

N.M.R. (d$_6$-DMSO, δ): 0.67~1.87 (9H, m), 2.03 (3H, s), 2.38 (2H, t, J=7.5 Hz), 3.65 (2H, broad s), 3.87 (3H, s), 4.85 (2H, AB$_q$, J=13 Hz), 5.22 (1H, d, J=5 Hz), 5.70~6.17 (3H, m), 6.76 (1H, s), 9.67 (1H, d, J=8 Hz).

EXAMPLE 69

Trifluoroacetic acid (10.1 g.) was added under ice-cooling to a stirred solution of benzhydryl 7-[2-methoxyimino-2-(2-aminothiazol-4-yl)acetamido]-3-(N-phenylcarbamoyloxymethyl)-3-cephem-4-carboxylate (syn isomer) (3.1 g.) and anisole (3.8 g.) in methylene chloride (30 ml.), and the mixture was stirred for 30 minutes at ambient temperature. After removing methylene chloride from the reaction mixture, diethyl ether was added thereto. Precipitates were collected by filtration. Water and ethyl acetate were added to the precipitates, and the mixture was adjusted to pH 7.5 with an aqueous solution of sodium bicarbonate. The separated aqueous solution was adjusted to pH 6.0 with 10% hydrochloric acid, washed with ethyl acetate and evaporated to remove organic solvent. The aqueous solution was adjusted to pH 3.0 with 10% hydrochloric acid under ice-cooling, and precipitates were collected by filtration and dried to give 7-[2-methoxyimino-2-(2-aminothiazol-4-yl)acetamido]-3-(N-phenylcarbamoyloxymethyl)-3-cephem-4-carboxylic acid (syn isomer) (1.35 g.).

I.R. (Nujol): 3300, 1780, 1710, 1670, 1600 cm$^{-1}$.

N.M.R. (d$_6$-DMSO, δ): 3.67 (2H, broad s), 3.91 (3H, s), 4.98 (2H, AB$_q$, J=13 Hz), 5.23 (1H, d, J=5 Hz), 5.83 (1H, d,d, J=5 and 8 Hz), 6.83 (1H, s), 6.97~7.67 (5H, m), 9.67 (1H, d, J=8 Hz), 9.8 (1H, s).

EXAMPLE 70

The following compounds were obtained according to a similar manner to that of Example 69.

(1) 7-[2-Methoxyimino-2-(2-aminothiazol-4-yl)acetamido]-3-[N-(3-chlorophenyl)carbamoyloxymethyl]-3-cephem-4-carboxylic acid (syn isomer).

I.R. (Nujol): 3320, 1780, 1710, 1680, 1600, 1540 cm$^{-1}$.

N.M.R. (d$_6$-DMSO, δ): 3.67 (2H, broad s), 3.90 (3H, s), 4.95 (2H, AB$_q$, J=13 Hz), 5.20 (1H, d, J=5 Hz), 5.81 (1H, d,d, J=5 and 8 Hz), 6.78 (1H, s), 6.83~7.76 (4H, m), 9.63 (1H, d, J=8 Hz), 10.1 (1H, s).

(2) 7-[2-Methoxyimino-2-(2-aminothiazol-4-yl)acetamido]-3-cyclohexanecarbonyloxymethyl-3-cephem-4-carboxylic acid (syn isomer).

I.R. (Nujol): 3300, 1780, 1730, 1670 cm$^{-1}$.

N.M.R. (d$_6$-DMSO, δ): 1.0~2.03 (10H, m), 3.53 (2H, broad s), 3.83 (1H, m), 3.87 (3H, s), 4.88 (2H, AB$_q$, J=13 Hz), 5.18 (1H, d, J=5 Hz), 5.82 (1H, d,d, J=5 and 8 Hz), 6.77 (1H, s), 7.28 (2H, broad s), 9.62 (1H, d, J=8 Hz).

(3) 7-[2-Methoxyimino-2-(2-aminothiazol-4-yl)acetamido]-3-[2-(4-methoxyphenoxy)acetoxymethyl]-3-cephem-4-carboxylic acid (syn isomer).

I.R. (Nujol): 3300, 1780, 1730, 1680, 1635 cm$^{-1}$.

N.M.R. (d$_6$-DMSO, δ): 3.52 (2H, AB$_q$, J=17 Hz), 3.68 (3H, s), 3.93 (3H, s), 4.74 (2H, s), 4.96 (2H, AB$_q$, J=13 Hz), 5.14 (1H, d, J=5 Hz), 5.78 (1H, d,d, J=5 and 8 Hz), 6.90 (1H, s), 6.86 (4H, s), 9.80 (1H, d, J=8 Hz).

(4) 7-[2-Methoxyimino-2-(2-aminothiazol-4-yl)acetamido]-3-pivaloyloxymethyl-3-cephem-4-carboxylic acid (syn isomer).

I.R. (Nujol): 3300, 1780, 1720, 1670, 1540 cm$^{-1}$.

N.M.R. (d$_6$-DMSO, δ): 1.06 (9H, s), 3.50 (2H, broad s), 3.80 (3H, s), 4.83 (2H, AB$_q$, J=13 Hz), 5.13 (1H, d, J=5 Hz), 5.76 (1H, d,d, J=5 and 8 Hz), 6.75 (1H, s), 9.58 (1H, d, J=8 Hz).

(5) 7-[2-Methoxyimino-2-(2-aminothiazol-4-yl)acetamido]-3-(2-thenoyl)oxymethyl-3-cephem-4-carboxylic acid (syn isomer).

I.R. (Nujol): 3250, 1780, 1710, 1680, 1635, 1530 cm$^{-1}$.

N.M.R. (d$_6$-DMSO, δ): 3.70 (2H, broad s), 3.92 (3H, s), 5.15 (2H, AB$_q$, J=13 Hz), 5.22 (1H, d, J=5 Hz), 5.83 (1H, d,d, J=5 and 8 Hz), 6.85 (1H, s), 7.27 (1H, m), 7.83~8.12 (2H, m), 9.72 (1H, d, J=8 Hz).

(6) 7-[2-Methoxyimino-2-(2-aminothiazol-4-yl)acetamido]-3-(4-aminobenzoyloxymethyl)-3-cephem-4-carboxylic acid (syn isomer).

I.R. (Nujol): 3350, 1780, 1680, 1605, 1540 cm$^{-1}$.

N.M.R. (d$_6$-DMSO, δ): 3.72 (2H, broad s), 3.87 (3H, s), 5.08 (2H, AB$_q$, J=13 Hz), 5.20 (1H, d, J=5 Hz), 5.83 (1H, d,d, J=5 and 8 Hz), 6.77 (1H, s), 6.88 (2H, d, J=9 Hz), 7.80 (2H, d, J=9 Hz), 9.67 (1H, d, J=8 Hz).

EXAMPLE 71

Platinic oxide (0.4 g.) was added to a solution of benzhydryl 7-[2-methoxyimino-2-(2-aminothiazol-4-yl)acetamido]-3-(4-nitrobenzoyloxymethyl)-3-cephem-4-carboxylate (syn isomer) (4.3 g.) in a mixture of ethanol (50 ml.) and tetrahydrofuran (50 ml.), and the suspension was subjected to catalytic reduction at ambient temperature under ordinary pressure for 3 hours. After removing the catalyst from the resultant mixture by filtration, the filtrate was evaporated under reduced pressure. The residue was dissolved in ethyl acetate and the solution was washed with a saturated aqueous solution of sodium chloride, dried over magnesium sulfate and evaporated in vacuo. The residue was pulverized with diethyl ether to give benzhydryl 7-[2-methoxyimino-2-(2-aminothiazol-4-yl)acetamido]-3-(4-aminobenzoyl-oxymethyl)-3-cephem-4-carboxylate (syn isomer) (3.0 g.).

I.R. (Nujol): 3280, 1780, 1710, 1670, 1605, 1520 cm$^{-1}$.

N.M.R. (d$_6$-DMSO, δ): 3.76 (2H, broad s), 3.88 (3H, s), 5.02 (2H, AB$_q$, J=13 Hz), 5.26 (1H, d, J=5 Hz), 5.96 (1H, d,d, J=5 and 8 Hz), 6.82 (1H, s), 6.90 (2H, d, J=9 Hz), 6.98 (1H, s), 7.04~7.66 (10H, m), 7.82 (2H, d, J=9 Hz), 9.72 (1H, d, J=8 Hz).

Preparation 33

(1) Ethyl 2-hydroxyimino-3-oxybutyrate (syn isomer, 40.0 g.), 4-fluorobenzyl chloride (43.6 g.), N,N-dimethylformamide (60.0 ml), potassium carbonate (52.0 g.) and ethyl acetate (60.0 ml.) were treated in a conventional manner to give ethyl 2-(4-fluorobenzoyloxyimino)-3-oxybutyrate (syn isomer, 64.4 g.).

I.R. (Film): 3000, 2940, 1730, 1690, 1600 cm$^{-1}$.

N.M.R. (DMSO-d$_6$, δ): 1.21 (3H, t, J=7.0 Hz), 2.34 (3H, s), 4.26 (2H, q, J=7.0 Hz), 5.32 (2H, s), 6.97-7.73 (4H, m).

(2) Ethyl 2-(4-fluorobenzyloxyimino)-3-oxobutyrate (syn isomer), 64.0 g.) and sulfuryl chloride (35.6 g.) and acetic acid (70.0 ml.) were treated in a similar manner to that of Preparation 14-(1) to give ethyl 2-(4-fluorobenzyloxyimino)-3-oxo-4-chlorobutyrate (syn isomer, 29.55 g.).

I.R. (Film): 1720, 1600 cm$^{-1}$.

N.M.R. (DMSO-d$_6$, δ): 1.20 (3H, t, J=7.0 Hz), 4.28 (2H, q, J=7.0 Hz), 4.87 (2H, s), 5.36 (2H, s), 7.00–7.75 (4H, m).

(3) Ethyl 2-(4-fluorobenzyloxyimino)-3-oxo-4-chlorobutyrate (syn isomer, 29.0 g.), thiourea (8.8 g.), sodium acetate (7.9 g.), water (72.5 ml.), tetrahydrofuran (60 ml.) and ethanol (72.5 ml.) were treated in a similar manner to that of Preparation 14-(2) to give ethyl 2-(4-fluorobenzyloxyimino)-2-(2-aminothiazol-4-yl)acetate (syn isomer, 28.0 g.).

I.R. (Nujol): 3450, 3150, 3100, 1710, 1620 cm$^{-1}$.

N.M.R. (DMSO-d$_6$, δ): 1.23 (3H, t, J=7.0 Hz), 4.30 (2H, q, J=7 Hz), 5.15 (2H, s), 6.90 (1H, s), 6.95–7.60 (4H, m).

(4) Ethyl 2-(4-fluorobenzyloxyimino)-2-(2-aminothiazol-4-yl)acetate (syn isomer, 25.5 g), 1-methylimidazole (1.3 g), 1N sodium hydroxide solution (118.3 ml.), methanol (250 ml.) and tetrahydrofuran (200 ml.) were treated in a similar manner to that of Preparation 14-(3) to give 2-(4-fluorobenzyloxyimino)-2-(2-aminothiazol-4-yl)acetic acid (syn isomer, 22.11 g.).

I.R. (Nujol): 3650, 3450, 3300, 3150, 1630 cm$^{-1}$.

N.M.R. (DMSO-d$_6$, δ): 5.16 (2H, s), 6.88 (1H, s), 7.04–7.66 (4H, m).

(5) 2-(4-Fluorobenzyloxyimino)-2-(2-aminothiazol-4-yl)acetic acid (syn isomer, 23.4 g.), bis(trimethylsilyl)acetamide (32.2 g.), 2,2,2-trifluoroacetic anhydride (49.9 g.) and dry ethyl acetate (234 ml.) were treated in a similar manner to that of Preparation 12 to give 2-(4-fluorobenzyloxyimino)-2-[2-(2,2,2-trifluoroacetamido)thiazol-4-yl]acetic acid (syn isomer, 18.9 g.), mp. 180° to 182° C.

I.R. (Nujol): 3200, 3150, 1730 cm$^{-1}$.

N.M.R. (DMSO-d$_6$, δ): 5.25 (2H, s), 7.02–7.60 (4H, m), 7.72 (1H, s).

Preparation 34

(1) The following compounds were obtained by reacting ethyl 2-hydroxyimino-3-oxobutyrate (syn isomer) with cyclopentyl bromide or 3,4-dichlorobenzyl chloride, respectively, in a conventional manner.

(i) Ethyl 2-cyclopentyloxyimino-3-oxobutyrate (syn isomer), oil.

I.R. (Film): 1740, 1670, 1495, 1430 cm$^{-1}$.

N.M.R. (CCl$_4$, δ): 1.32 (3H, t, J=7 Hz), 1.4–2.2 (8H, m), 2.33 (H, s), 4.27 (2H, q, J=7 Hz), 4.87 (1H, m).

(ii) Ethyl 2-(3,4-dichlorobenzyloxyimino)-3-oxobutyrate (syn isomer), oil.

I.R. (Film): 1730, 1690, 1600, 1470, 1400, 1370, 1310, 1240, 1130, 1080, 1010 cm$^{-1}$.

N.M.R. (CCl$_4$, δ): 1.30 (3H, t, J=6 Hz), 2.30 (3H, s), 4.30 (2H, q, J=6 Hz), 4.47 (2H, s), 7.00–7.53 (3H, m).

(2) The following compounds were obtained according to a similar manner to that of Preparation 14-(1).

(i) Ethyl 2-cyclopentyloxyimino-3-oxo-4-chlorobutyrate (syn isomer), oil.

I.R. (Film): 1750, 1735, 1465, 1435 cm$^{-1}$.

N.M.R. (CCl$_4$, δ): 1.33 (3H, t, J=7 Hz), 1.3–2.4 (8H, m), 4.28 (2H, q, J=7 Hz), 4.46 (2H, s), 4.86 (1H, m).

(ii) Ethyl 2-(3,4-dichlorobenzyloxyimino)-3-oxo-4-chlorobutyrate (syn isomer), oil.

I.R. (Film): 1740, 1710, 1590, 1470, 1400, 1370, 1320, 1260, 1200, 1130, 1010 cm$^{-1}$.

N.M.R. (CCl$_4$, δ): 1.37 (3H, t, J=6 Hz), 4.23 (2H, q, J=6 Hz), 4.43 (2H, s), 5.27 (2H, s), 7.10–7.60 (3H, m).

(3) The following compounds were obtained according to a similar manner to that of Preparation 14-(2).

(i) Ethyl 2-cyclopentyloxyimino-2-(2-aminothiazol-4-yl)acetate (syn isomer), mp 134° to 136° C.

I.R. (Nujol): 3490, 3450, 3250, 3120, 1735, 1540, 1460 cm$^{-1}$.

N.M.R. (DMSO-d$_6$, δ): 1.25 (3H, t, J=7 Hz), 1.62 (8H, broad s), 4.27 (2H, q, J=7 Hz), 4.70 (1H, m), 6.85 (1H, s), 7.20 (2H, s).

(ii) Ethyl 2-(3,4-dichlorobenzyloxyimino)-2-(2-aminothiazol-4-yl)acetate (syn isomer).

I.R. (Nujol): 3460, 1720, 1600, 1540, 1460, 1390, 1260, 1180, 1020, 1010, 880, 810 cm$^{-1}$.

N.M.R. (DMSO-d$_6$, δ): 1.25 (3H, t, J=7 Hz), 4.30 (2H, q, J=7 Hz), 5.17 (2H, s), 6.93 (1H, s), 7.27–7.73 (3H, m).

(4) The following compounds were obtained according to a similar manner to that of Preparation 14-(3).

(i) 2-Cyclopentyloxyimino-2-(2-aminothiazol-4-yl)acetic acid (syn isomer), mp 186° C. (dec.).

I.R. (Nujol): 3330, 3120, 1635, 1450 cm$^{-1}$.

N.M.R. (DMSO-d$_6$, δ): 1.1–2.2 (8H, m), 4.68 (1H, m), 6.81 (1H, s), 7.18 (2H, broad s).

(ii) 2-(3,4-Dichlorobenzyloxyimino)-2-(2-aminothiazol-4-yl)acetic acid (syn isomer).

I.R. (Nujol): 3430, 1660, 1590, 1400, 1010 cm$^{-1}$.

N.M.R. (DMSO-d$_6$, δ): 5.23 (2H, s), 6.93 (1H, s), 7.30–7.77 (3H, m).

(5) The following compounds were obtained according to a similar manner to that of Preparation 12.

(i) 2-Cyclopentyloxyimino-2-[2-(2,2,2-trifluoroacetamido)thiazol-4-yl]acetic acid (syn isomer).

I.R. (Nujol): 3200, 3130, 1720, 1590, 1580 cm$^{-1}$.

N.M.R. (DMSO-d$_6$, δ): 1.34–2.22 (8H, m), 4.81 (1H, m), 7.71 (1H, s).

(ii) 2-(3,4-Dichlorobenzyloxyimino)-2-[2-(2,2,2-trifluoroacetamido)thiazol-4-yl]acetic acid (syn isomer).

I.R. (Nujol): 1720, 1580, 1300, 1260, 1200, 1160, 1150 cm$^{-1}$.

N.M.R. (DMSO-d$_6$, δ): 5.40 (2H, s), 7.47–7.93 (4H, m).

Preparation 35

The solution of 4-bromo-3-hydroxybenzyloxyamine phosphate (17.4 g.) in water (200 ml.) and ethanol (200 ml.) was stirred at room temperature and adjusted to pH 7.0 with sodium bicarbonate. 2-(2-Formamidothiazol-4-yl)glyoxylic acid (10.0 g.) was added to the solution and the resulting suspension was adjusted to pH 4.0 to 4.5. After stirring the solution at room temperature for 2 hours, ethanol was removed from the resultant solution in vacuo. Ethyl acetate was added to aqueous residue and adjusted to pH 2.5 with 10% hydrochloric acid. The ethyl acetate layer was separated, washed with water and dried over magnesium sulfate. The solution was concentrated in vacuo to give 2-(2-formamidothiazol-4-yl)-2-(4-bromo-3-hydroxybenzyloxyimino)acetic acid (syn isomer, 14.8 g.).

I.R. $\nu_{max}^{Nujol}$: 3350, 3150, 1720, 1680, 1570 cm$^{-1}$.

N.M.R. δ (DMSO-d$_6$, ppm): 5.13 (2H, m), 6.8 (1H, dd, J=8 Hz, 2 Hz), 7.02 (1H, d, J=2 Hz), 7.5 (1H, d, J=8 Hz), 7.58 (1H, s), 8.58 (1H, s), 10.35 (1H, broad s), 12.7 (1H, broad s).

Preparation 36

(1) A mixture of 1,4-bis(chloromethyl)benzene (25 g.), N-hydroxyphthalimide (23.4 g.) and triethylamine (14.5 g.) in acetonitrile (200 ml.) was heated under reflux for 1.5 hours. The reaction mixture was poured into ice-water (1 l.) and the precipitates were collected by filtration. The precipitates were washed with ethanol and dried to give N-(4-chloromethylbenzyloxy)phthalimide (25.5 g.).

I.R. $\nu_{max}^{Nujol}$: 1780, 1740 cm$^{-1}$.

N.M.R. $\delta$ (DMSO-d$_6$, ppm): 4.8 (2H, s), 5.23 (2H, s), 7.22 (4H, s), 7.9 (4H, s).

(2) A mixture of N-(4-chloromethylbenzyloxy)phthalimide (18.5 g.) and potassium phthalimide (15.4 g.) in N,N-dimethylformamide (180 ml.) was stirred at 60° C. for 5 hours. The mixture was poured into ice-water and the precipitates were collected by filtration. The precipitate were washed with water and acetone in turn to give N-(4-phthalimidomethylbenzyloxy)phthalimide (21.0 g.).

I.R. $\nu_{max}^{Nujol}$: 1780, 1760, 1740, 1720, 1610 cm$^{-1}$.

N.M.R. $\delta$ (DMSO-d$_6$, ppm): 4.78 (2H, s), 5.13 (2H, s), 7.38 (4H, m), 7.83 (8H, m).

(3) 100% Hydrazine hydrate (2.4 g.) was added to a suspension of N-(4-phthalimidomethylbenzyloxy)phthalimide (16.4 g.) in ethanol (160 ml.) at 60° C. and stirred at the same temperature for an hour. Conc.hydrochloric acid (12 ml.) and water (120 ml.) were added to the resultant mixture under ice-cooling. After filtration of the insoluble substance, the filtrate was concentrated in vacuo. The residue was adjusted to pH 7.0 with 10% sodium hydroxide solution and washed with ethyl acetate. To the aqueous solution containing 4-aminomethylbenzyloxyamine were added 2-(2-formamidothiazol-4-yl)glyoxylic acid (5.3 g.) and ethanol (150 ml.), and the solution was stirred at pH 4.0 to 4.5 for 2.5 hours. The precipitates were collected by filtration and washed with water. The precipitates containing 2-(2-formamidothiazol-4-yl)-2-(4-aminomethylbenzyloxyimino)acetic acid (syn isomer) were added to a mixture of water (100 ml.) and dioxane (100 ml.) and adjusted to pH 8.0 with 10% sodium hydroxide. Triethylamine (3.2 g.) and 2-tert-butoxycarbonyloxyimino-2-phenylacetonitrile (4.7 g.) were added to the mixture and stirred at room temperature for 6 hours.

Dioxane was removed in vacuo, and the aqueous residue was washed with diethyl ether. Diethyl ether was added to the aqueous solution and adjusted to pH 3.0 with 10% hydrochloric acid. After removing diethyl ether from the mixture, the residue was washed with a sodium chloride saturated solution, dried over magnesium sulfate and evaporated in vacuo to give 2-(2-formamidothiazol-4-yl)-2-(4-tert-butoxycarbonylaminomethylbenzyloxyimino)acetic acid (syn isomer, 3.8 g.).

I.R. $\nu_{max}^{Nujol}$: 3300, 3150, 1710, 1690, 1620, 1560 cm$^{-1}$.

N.M.R. $\delta$ (DMSO-d$_6$, ppm): 1.38 (9H, s), 4.15 (2H, d, J=6 Hz), 5.22 (2H, s), 7.6 (1H, s), 7.68 (4H, s), 8.62 (1H, s), 12.8 (1H, broad s).

Preparation 37

To a suspension of N-(cinnamyloxy)phthalimide (21.0 g) in ethanol (200 ml) was added hydrazine hydrate (8.3 g) at 60° C. and the mixture was stirred for 1.5 hours at the same temperature. To the mixture were added conc. hydrochloric acid (22 ml) and water (220 ml) and the resulting mixture was filtered. The filtrate was concentrated to give precipitates, which were filtered off. The filtrate was adjusted to pH 7.0 and to the solution containing O-cinnamyl hydroxylamine were added ethanol (300 ml) and 2-(2-formamidothiazol-4-yl)glyoxylic acid (10.0 g). The mixture was stirred for 2 hours at pH 4.0 to 4.5. The reaction mixture was concentrated and adjusted to pH 2.0 after addition of ethyl acetate. The organic layer was washed with an aqueous solution of sodium chloride, dried over magnesium sulfate and evaporated to give 2-cinnamyloxyimino-2-(2-formamidothiazol-4-yl)-acetic acid (syn isomer) (8.6 g).

I.R. (Nujol): 3400–3100, 1700, 1550 cm$^{-1}$.

N.M.R. (DMSO-d$_6$, $\delta$): 4.85 (2H, d, J=5 Hz), 6.2–6.93 (2H, m), 7.2–7.72 (5H, m), 7.6 (1H, s), 8.57 (1H, s), 12.7 (1H, broad s).

EXAMPLE 72

The Vilsmeier reagent was prepared from dry dimethylformamide (2.6 g.), phosphorus oxychloride (5.4 g.) and dry ethyl acetate (10.4 ml) by the conventional method. Dry ethyl acetate (100 ml) was added thereto and then 2-cyclopentyloxyimino-2-[2-(2,2,2-trifluoroacetamido)thiazol-4-yl]acetic acid (syn isomer) (10.4 g.) was added thereto at 0° C. The mixture was stirred for 30 minutes at the same temperature. The resulting mixture was added under −10° C. to a stirred solution of 7-amino-3-(1-allyl-1H-tetrazol-5-yl)thiomethyl-3-cephem-4-carboxylic acid (9.6 g) and trimethylsilylacetamide (24.8 g) in dry ethyl acetate (192 ml), and the mixture was stirred for 30 minutes at the same temperature. To the reaction mixture was added water. The ethyl acetate layer was separated and extracted with aqueous solution of sodium bicarbonate (pH 7.5). The aqueous layer was washed twice with ethyl acetate and adjusted to pH 2.0 with 10% hydrochloric acid after addition of ethyl acetate and tetrahydrofuran. The organic layer was separated, washed with water, dried over magnesium sulfate, treated with an activated charcoal and concentrated to dryness. The residue was pulverized with diethyl ether and the powder was collected by filtration and washed with diethyl ether to give 7-[2-cyclopentyloxyimino-2-{2-(2,2,2-trifluoroacetamido)thiazol-4-yl}acetamido]-3-(1-allyl-1H-tetrazol-5-yl)thiomethyl-3-cephem-4-carboxylic acid (syn isomer) (18.18 g).

N.M.R. (DMSO-d$_6$, $\delta$): 1.28–2.26 (8H, m), 3.73 (2H, m), 4.39 (2H, Abq, J=14 Hz), 4.77 (1H, m), 4.88–5.47 (5H, m), 5.70–6.52 (2H, m), 7.50 (1H, s), 9.67 (1H, d, J=8.0 Hz).

EXAMPLE 73

7-[2-Cyclopentyloxyimino-2-{2-(2,2,2-trifluoroacetamido)thiazol-4-yl}acetamido]-3-(1-allyl-1H-tetrazol-5-yl)thiomethyl-3-cephem-4-carboxylic acid (syn isomer)(18.0 g) and tetrahydrofuran (36 ml) were added to a stirred solution of sodium acetate trihydrate (35.6 g) in water (360 ml). The mixture was stirred for 18 hours at ambient temperature and then tetrahydrofuran was distilled off from the reaction mixture. The remaining solution was adjusted to pH 3.0 with 15% hydrochloric acid and precipitates were collected by filtration, washed with water and dried to give crude 7-[2-cyclopentyloxyimino-2-(2-aminothiazol-4-yl)acetamido]-3-(1-allyl-1H-tetrazol-5-yl)thiomethyl-3-cephem-4-carboxylic acid (syn isomer)(20 g). The crude substance was purified by column chromatography on aluminum oxide (60 ml) using a 3-5% aqueous solution of sodium acetate as an eluent to give pure object compound (8.31 g), mp 140° to 145° C. (dec.).

I.R. (Nujol): 3300, 1770, 1660, 1620 cm$^{-1}$.

N.M.R. (DMSO-d$_6$, δ): 1.16-2.26 (8H, m), 3.73 (2H, m), 4.41 (2H, ABq, J=14 Hz), 4.68 (1H, m), 4.89-5.52 (5H, m), 5.62-6.43 (2H, m), 6.73 (1H, s), 9.51 (1H, d, J=8 Hz).

EXAMPLE 74

To a stirred solution of sodium acetate (2.7 g) in water (46 ml) was added 7-[2-(4-fluorobenzyloxyimino)-2-{2-(2,2,2-trifluoroacetamido)thiazol-4-yl}-acetamido]-3-(1,3,4-thiadiazol-2-yl)-thiomethyl-3-cephem-4-carboxylic acid (syn isomer) (2.3 g) and the mixture was stirred for 20.5 hours at ambient temperature. The reaction mixture was adjusted to pH 5.0 with 10% hydrochloric acid after addition of ethyl acetate and the resulting mixture was shaken. The aqueous layer was separated, washed twice with ethyl acetate and adjusted to pH 3.0 with 10% hydrochloric acid. Precipitates were collected by filtration, washed with water and dried to give 7-[2-(4-fluorobenzyloxyimino)-2-(2-aminothiazol-4-yl)acetamido]-3-(1,3,4-thiadiazol-2-yl)thiomethyl-3-cephem-4-carboxylic acid (syn isomer) (1.82 g), mp 145° to 149° C. (dec.).

I.R. (Nujol): 3250, 1765, 1650 cm$^{-1}$.

N.M.R. (DMSO-d$_6$, δ): 3.73 (2H, ABq, J=18 Hz), 4.48 (2H, ABq, J=14 Hz), 5.01-5.39 (3H, m), 5.85 (1H, dd, J=4 and 8 Hz), 6.83 (1H, s), 7.02-7.75 (4H, m), 9.63 (1H, s), 9.75 (1H, d, J=8 Hz).

EXAMPLE 75

The following compounds were obtained according to similar manners to those of the aforementioned Examples.

(1) 7-[2-(4-Fluorobenzyloxyimino)-2-{2-(2,2,2-trifluoroacetamido)thiazol-4-yl}-acetamido]-3-(1-allyl-1H-tetrazol-5-yl)thiomethyl-3-cephem-4-carboxylic acid (syn isomer).

I.R. (Nujol): 3250, 3170, 1780, 1720, 1650 cm$^{-1}$.

N.M.R. (DMSO-d$_6$, δ): 3.64 (2H, m), 4.34 (2H, ABq, J=14 Hz), 4.79-5.44 (7H, m), 5.65-6.27 (2H, m), 6.95-7.61 (4H, m), 7.51 (1H, s), 9.83 (1H, d, J=8 Hz).

(2) 7-[2-(4-Fluorobenzyloxyimino)-2-(2-aminothiazol-4-yl)acetamido]-3-(1-allyl-1H-tetrazol-5-yl)thiomethyl-3-cephem-4-carboxylic acid (syn isomer), mp 157° to 161° C. (dec.).

I.R. (Nujol): 3500, 1770, 1660, 1630, 1600 cm$^{-1}$.

N.M.R. (DMSO-d$_6$, δ): 3.69 (2H, m), 4.39 (2H, ABq, J=14 Hz), 4.75-5.48 (7H, m), 5.63-6.57 (2H, m), 6.76 (1H, s), 6.86-7.76 (4H, m), 9.67 (1H, d, J=8 Hz).

(3) 7-[2-(3,4-Dichlorobenzyloxyimino)-2-(2-aminothiazol-4-yl)acetamido]-3-(1-allyl-1H-tetrazol-5-yl)thiomethyl-3-cephem-4-carboxylic acid (syn isomer), mp 155° to 175° C. (dec.).

I.R. (Nujol): 1770, 1660-1620, 1450 cm$^{-1}$.

N.M.R. (DMSO-d$_6$, δ): 3.63 (2H, m), 4.33 (2H, m), 4.93-5.37 (7H, m), 5.67-6.40 (2H, m), 6.73 (1H, s), 7.10-7.70 (3H, m), 9.73 (1H, d, J=8 Hz).

(4) 7-[2-(3,4-Dichlorobenzyloxyimino)-2-{2-(2,2,2-trifluoroacetamido)thiazol-4-yl}acetamido]-3-(1-allyl-1H-tetrazol-5-yl)thiomethyl-3-cephem-4-carboxylic acid (syn isomer).

I.R. (Nujol): 1770, 1650 cm$^{-1}$.

N.M.R. (DMSO-d$_6$, δ): 3.72 (2H, m), 4.40 (2H, m), 5.00-5.43 (7H, m), 5.73-6.60 (2H, m), 7.30-7.77 (4H, m), 9.90 (1H, d, J=8 Hz).

(5) 7-[2-(4-t-Butoxycarbonylaminomethylbenzyloxyimino)-2-(2-formamidothiazol-4-yl)acetamido]-3-(1,3,4-thiadiazol-2-yl)thiomethyl-3-cephem-4-carboxylic acid (syn isomer).

I.R. (Nujol): 3300-3150, 1790, 1690, 1550 cm$^{-1}$.

N.M.R. (DMSO-d$_6$, δ): 1.33 (9H, s), 3.6 (2H, m), 4.08 (2H, d, J=5 Hz), 4.4 (2H, ABq, J=14 Hz), 5.11 (1H, d, J=5 Hz), 5.13 (2H, m), 5.78 (1H, dd, J=5 and 8 Hz), 7.25 (4H, m), 7.33 (1H, s), 8.47 (1H, s), 9.68 (1H, d, J=8 Hz), 12.5 (1H, broad s).

(6) 7-[2-(t-Butoxycarbonylmethoxyimino)-2-(2-formamidothiazol-4-yl)acetamido]-3-(1H-tetrazol-5-yl)thiomethyl-3-cephem-4-carboxylic acid (syn isomer).

I.R. (Nujol): 3170, 1770, 1720, 1670 cm$^{-1}$.

N.M.R. (DMSO-d$_6$, δ): 1.44 (9H, s), 3.68 (2H, m), 4.33 (2H, ABq, J=12.0 Hz), 4.63 (2H, s), 5.16 (1H, d, J=5.0 Hz), 5.82 (1H, dd, J=5.0 and 8.0 Hz), 7.43 (1H, s), 8.51 (1H, s), 9.56 (1H, d, J=8.0 Hz).

(7) 7-[2-(4-Fluorobenzyloxyimino)-2-{2-(2,2,2-trifluoroacetamido)thiazol-4-yl}acetamido]-3-(1-methyl-1H-tetrazol-5-yl)-thiomethyl-3-cephem-4-carboxylic acid (syn isomer).

I.R. (Nujol): 3370, 3180, 1760, 1710, 1680, 1650 cm$^{-1}$.

N.M.R. (DMSO-d$_6$, δ): 3.68 (2H, m), 3.92 (3H, s), 4.32 (2H, m), 5.03-5.35 (3H, m), 5.83 (1H, dd, J=5 and 8 Hz), 6.99-7.70 (4H, m), 7.54 (1H, s), 9.87 (1H, d, J=8 Hz).

(8) 7-[2-Ethoxycarbonylmethoxyimino-2-(2-formamidothiazol-4-yl)acetamido]-3-(1H-tetrazol-5-yl)thiomethyl-3-cephem-4-carboxylic acid (syn isomer), mp 112° to 125° C. (dec.).

I.R. (Nujol): 3250, 1770, 1730, 1680 cm$^{-1}$.

N.M.R. (DMSO-d$_6$, δ): 1.20 (3H, t, J=8 Hz), 3.71 (2H, m), 4.07 (2H, q, J=8 Hz), 4.36 (2H, m), 4.77 (2H, m), 5.20 (1H, d, J=5 Hz), 5.88 (1H, dd, J=5 and 8 Hz), 7.50 (1H, s), 8.57 (1H, s), 9.67 (1H, d, J=8 Hz), 12.38 (1H, broad s).

(9) 7-[2-Benzyloxyimino-2-(2-aminothiazol-4-yl)acetamido]-3-(1H-tetrazol-5-yl)thiomethyl-3-cephem-4-carboxylic acid (syn isomer), mp 172° to 174° C. (dec.).

I.R. (Nujol): 3250, 3150, 1770, 1620 cm$^{-1}$.

N.M.R. (DMSO-d$_6$, δ): 3.67 (2H, m), 4.33 (2H, m), 5.08-5.36 (3H, m), 5.83 (1H, dd, J=4 and 8 Hz), 6.88 (1H, s), 7.39 (5H, s), 9.73 (1H, d, J=8 Hz).

(10) 7-[2-(4-Fluorobenzyloxyimino)-2-{2-(2,2,2-trifluoroacetamido)thiazol-4-yl}acetamido]-3-(1,3,4-thiadiazol-2-yl)thiomethyl-3-cephem-4-carboxylic acid (syn isomer).

I.R. (Nujol): 3200, 1770, 1720, 1650 cm$^{-1}$.

N.M.R. (DMSO-d$_6$, δ): 3.73 (2H, ABq, J=18 Hz), 4.49 (2H, ABq, J=14 Hz), 5.03-5.46 (3H, m), 5.88 (1H, dd, J=4 and 8 Hz), 7.03-7.84 (4H, m), 7.59 (1H, s), 9.60 (1H, s), 9.88 (1H, d, J=8 Hz).

(11) 7-[2-Cinnamyloxyimino-2-(2-formamidothiazol-4-yl)acetamido]-3-(1,3,4-thiadiazol-2-yl)thiomethyl-3-cephem-4-carboxylic acid (syn isomer).

I.R. (Nujol): 3400-3100, 1780, 1680, 1540 cm$^{-1}$.

N.M.R. (DMSO-d$_6$, δ): 3.67 (2H, m), 4.45 (2H, ABq, J=14 Hz), 4.83 (2H, d, J=5 Hz), 5.18 (1H, d, J=5 Hz), 5.87 (1H, dd, J=5 and 8 Hz), 6.65 (1H, s), 6.12-7.0 (2H, m), 7.1–7.7 (5H, m), 8.53 (1H, s), 9.57 (1H, s), 9.73 (1H, d, J=8 Hz), 12.6 (1H, broad s).

(12) 7-[2-(4-Fluorobenzyloxyimino)-2-{2-(2,2,2-trifluoroacetamido)thiazol-4-yl}acetamido]-3-(1H-tetrazol-5-yl)thiomethyl-3-cephem-4-carboxylic acid (syn isomer).

I.R. (Nujol): 3200, 1780, 1730, 1660 cm$^{-1}$.

(13) 7-[2-(4-Fluorobenzyloxyimino)-2-{2-(2,2,2-trifluoroacetamido)thiazol-4-yl}acetamido]-cephalosporanic acid (syn isomer).

I.R. (Nujol): 3250, 1780, 1730, 1660, 1630 cm$^{-1}$.

N.M.R. (DMSO-d$_6$, δ): 2.07 (3H, s), 3.59 (2H, m), 4.90 (2H, ABq, J=14 Hz), 5.13–5.46 (3H, m), 5.90 (1H, dd, J=5 and 8 Hz), 7.30–7.77 (4H, m), 7.58 (1H, s), 9.68 (1H, d, J=4.0 Hz).

(14) 7-[2-(3,4-Dichlorobenzyloxyimino)-2-{2-(2,2,2-trifluoroacetamido)thiazol-4-yl}acetamido]-cephalosporanic acid (syn isomer).

I.R. (Nujol): 1780, 1730, 1650 cm$^{-1}$.

N.M.R. (DMSO-d$_6$, δ): 2.03 (3H, s), 3.57 (2H, m), 4.87 (2H, ABq, J=12 Hz), 5.17–5.23 (3H, m), 5.87 (1H, dd, J=6 and 8 Hz), 7.33–7.73 (4H, m), 9.87 (1H, d, J=8 Hz).

(15) 7-[2-(3-Hydroxy-4-bromobenzyloxyimino)-2-(2-formamidothiazol-4-yl)acetamido]-3-(1,3,4-thiadiazol-2-yl)thiomethyl-3-cephem-4-carboxylic acid (syn isomer).

I.R. (Nujol): 3400–3100, 1780, 1680, 1540 cm$^{-1}$.

N.M.R. (DMSO-d$_6$, δ): 3.7 (2H, broad s), 4.45 (2H, ABq, J=13 Hz), 5.13 (1H, d, J=5 Hz), 5.18 (2H, s), 5.82 (1H, dd, J=5 and 8 Hz), 6.97 (1H, d, J=2 Hz), 7.4 (1H, s), 7.45 (1H, d, J=8 Hz), 8.5 (1H, s), 9.68 (1H, d, J=8 Hz), 12.6 (1H, broad s).

(16) 7-[2-t-Butoxycarbonylmethoxyimino-2-(2-formamidothiazol-4-yl)acetamido]-3-[tetrazolo[1,5-b]pyridazin-6-yl]thiomethyl-3-cephem-4-carboxylic acid (syn isomer).

I.R. (Nujol): 3150, 1780, 1720, 1670 cm$^{-1}$.

N.M.R. (DMSO-d$_6$, δ): 1.42 (9H, s), 3.73 (2H, m), 4.25–4.85 (4H, m), 5.17 (1H, d, J=4 Hz), 5.84 (1H, dd, J=4 and 8 Hz), 7.43 (1H, s), 7.72 (1H, d, J=10 Hz), 8.50 (1H, s), 8.56 (1H, d, J=10 Hz), 9.56 (1H, d, J=8 Hz).

(17) 7-[2-(4-Aminomethylbenzyloxyimino)-2-(2-aminothiazol-4-yl)acetamido]-3-(1,3,4-thiadiazol-2-yl)thiomethyl-3-cephem-4-carboxylic acid dihydrochloride (syn isomer).

I.R. (Nujol): 3400–3100, 1770, 1660, 1620, 1540 cm$^{-1}$.

N.M.R. (DMSO-d$_6$, δ): 3.68 (2H, broad s), 3.97 (2H, d, J=6 Hz), 4.43 (2H, ABq, J=13 Hz), 5.12 (1H, d, J=5 Hz), 5.12 (2H, s), 5.72 (1H, dd, J=5 and 7 Hz), 6.88 (1H, s), 7.43 (4H, s), 9.5 (1H, s), 9.8 (1H, d, J=7 Hz).

(18) 7-[2-(t-Butoxycarbonylmethoxyimino)-2-(2-aminothiazol-4-yl)acetamido]-3-(1H-tetrazol-5-yl)thiomethyl-3-cephem-4-carboxylic acid (syn isomer).

I.R. (Nujol): 3280, 3200, 1770, 1670, 1630 cm$^{-1}$.

(19) 7-[2-(4-Fluorobenzyloxyimino)-2-(2-aminothiazol-4-yl)acetamido]-3-(1-methyl-1H-tetrazol-5-yl)-thiomethyl-3-cephem-4-carboxylic acid (syn isomer).

I.R. (Nujol): 3300, 3200, 1770, 1660, 1620, 1600 cm$^{-1}$.

N.M.R. (DMSO-d$_6$, δ): 3.67 (2H, m), 3.94 (3H, s), 4.32 (2H, m), 4.98–5.36 (3H, m), 5.78 (1H, dd, J=5 and 8 Hz), 6.72 (1H, s), 6.95–7.65 (4H, m), 9.65 (1H, d, J=8 Hz).

(20) 7-[2-Ethoxycarbonylmethoxyimino-2-(2-aminothiazol-4-yl)acetamido]-3-(1H-tetrazol-5-yl)thiomethyl-3-cephem-4-carboxylic acid (syn isomer), mp 168° to 185° C. (dec.).

I.R. (Nujol): 3250, 1765, 1670, 1625 cm$^{-1}$.

N.M.R. (DMSO-d$_6$, δ): 1.21 (3H, t, J=7 Hz), 3.70 (2H, broad s), 4.18 (2H, q, J=7 Hz), 4.31 (2H, m), 4.72 (2H, broad s), 5.17 (1H, d, J=4 Hz), 5.82 (1H, dd, J=4 and 7 Hz), 6.83 (1H, s), 7.17 (2H, broad s), 9.57 (1H, d, J=7 Hz).

(21) 7-[2-(4-Fluorobenzyloxyimino)-2-(2-aminothiazol-4-yl)acetamido]-3-(1,3,4-thiadiazol-2-yl)thiomethyl-3-cephem-4-carboxylic acid (syn isomer), mp 145° to 149° C. (dec.).

I.R. (Nujol): 3250, 1765, 1650 cm$^{-1}$.

(22) 7-[2-Cinnamyloxyimino-2-(2-aminothiazol-4-yl)acetamido]-3-(1,3,4-thiadiazol-2-yl)thiomethyl-3-cephem-4-carboxylic acid (syn isomer).

I.R. (Nujol): 3350–3100, 1760, 1650, 1620, 1520 cm$^{-1}$.

N.M.R. (DMSO-d$_6$, δ): 3.47–3.97 (2H, m), 4.47 (2H, ABq, J=14 Hz), 4.8 (2H, d, J=5 Hz), 5.18 (1H, d, J=5 Hz), 5.83 (1H, dd, J=5 and 8 Hz), 6.83 (1H, s), 6.1–7.0 (2H, m), 7.08–7.72 (5H, m), 9.6 (1H, s), 9.72 (1H, d, J=8 Hz).

(23) 7-[2-(4-Fluorobenzyloxyimino)-2-(2-aminothiazol-4-yl)acetamido]-3-(1H-tetrazol-5-yl)thiomethyl-3-cephem-4-carboxylic acid (syn isomer).

I.R. (Nujol): 3300, 3200, 1770, 1660, 1630, 1600 cm$^{-1}$.

N.M.R. (DMSO-d$_6$, δ): 3.69 (2H, ABq, J=18 Hz), 4.35 (2H, ABq, J=15 Hz), 4.93–5.43 (3H, m), 5.81 (1H, dd, J=5 and 8 Hz), 6.80 (1H, s), 6.96–7.70 (4H, m), 9.73 (1H, d, J=8 Hz).

(24) 7-[2-(4-Fluorobenzyloxyimino)-2-(2-aminothiazol-4-yl)acetamido]cephalosporanic acid (syn isomer), mp 185° to 192° C. (dec.).

I.R. (Nujol): 3380, 3250, 1780, 1700, 1650 cm$^{-1}$.

N.M.R. (DMSO-d$_6$, δ): 2.02 (3H, s), 3.53 (2H, m), 4.84 (2H, ABq, J=13 Hz), 5.13 (2H, s), 5.40 (1H, d, J=4 Hz), 5.79 (1H, dd, J=4 and 8 Hz), 6.73 (1H, s), 6.96–7.63 (4H, m), 9.62 (1H, d, J=8 Hz).

(25) 7-[2-(3,4-Dichlorobenzyloxyimino)-2-(2-aminothiazol-4-yl)acetamido]cephalosporanic acid (syn isomer), mp 200° to 205° C. (dec.).

I.R. (Nujol): 1730, 1640, 1600, 1230, 1020 cm$^{-1}$.

N.M.R. (DMSO-d$_6$, δ): 2.00 (3H, s), 3.30 (2H, ABq, J=18 Hz), 4.68–5.12 (5H, m), 5.60 (1H, dd, J=6 and 8 Hz), 6.72 (1H, s), 7.32–7.64 (3H, m), 9.60 (1H, d, J=8 Hz).

(26) 7-[2-(3-Hydroxy-4-bromobenzyloxyimino)-2-(2-aminothiazol-4-yl)acetamido]-3-(1,3,4-thiadiazol-2-yl)thiomethyl-3-cephem-4-carboxylic acid (syn isomer).

I.R. (Nujol): 3400–3100, 1760, 1660, 1620, 1520 cm$^{-1}$.

N.M.R. (DMSO-d$_6$, δ): 3.72 (2H, broad s), 4.47 (2H, ABq, J=14 Hz), 5.1 (1H, d, J=5 Hz), 5.22 (2H, s), 5.83 (1H, dd, J=5 and 8 Hz), 6.85 (1H, s), 6.87 (1H, dd, J=2 and 8 Hz), 7.08 (1H, d, J=2 Hz), 7.52 (1H, d, J=8 Hz), 9.67 (1H, s), 9.77 (1H, d, J=8 Hz).

(27) 7-[2-Carboxymethoxyimino-2-(2-aminothiazol-4-yl)acetamido]-3-(1H-tetrazol-5-yl)thiomethyl-3-cephem-4-carboxylic acid (syn isomer), mp 178° to 180° C. (dec.).

I.R. (Nujol): 3300, 3280, 1770, 1670, 1630 cm$^{-1}$.

N.M.R. (DMSO-d$_6$, δ): 3.69 (2H, m), 4.32(2H, ABq, J=14 Hz), 4.60(2H, m), 5.14(1H, d, J=5 Hz), 5.79(1H, d d, J=5 and 8 Hz), 6.79 (1H, s), 9.47(1H, d, J=8 Hz).

(28) 7-[2-Carboxymethoxyimino-2-(2-aminothiazol-4-yl)acetamido]-3-[tetrazolo[1,5-b]pyridazin-6-yl]thiomethyl-3-cephem-4-carboxylic acid (syn isomer).

I.R. (Nujol): 3270, 3170, 1765, 1670, 1620 cm$^{-1}$.

N.M.R. (DMSO-d$_6$, δ): 3.77(2H, ABq, J=18 Hz), 4.45 (2H, ABq, J=14 Hz), 4.63(2H, s), 5.20 (1H, d, J=4 Hz), 5.86(1H, d d, J=4 and 8 Hz), 6.84(1H, s), 7.78(1H, d, J=10 Hz), 8.61(1H, d, J=10 Hz), 9.54(1H, d, J=8 Hz).

(29) 7-[2-(t-Butoxycarbonylmethoxyimino)-2-(2-aminothiazol-4-yl)acetamido]-3-[tetrazolo[1,5-b]pyridazin-6-yl]thiomethyl-3-cephem-4-carboxylic acid (syn isomer).

I.R. (Nujol): 3300, 1770, 1670, 1620 cm$^{-1}$.

N.M.R. (DMSO-d$_6$, δ): 1.41 (9H, s), 3.72 (2H, m), 4.42 (2H, ABq, J=14 Hz), 4.55 (2H, s), 5.16 (1H, d, J=4 Hz), 5.80 (1H, dd, J=4 and 8 Hz), 6.79 (1H, s), 7.74 (1H, d, J=10 Hz), 8.57 (1H, d, J=10 Hz), 9.48 (1H, d, J=8 Hz).

What we claim is:

1. Syn-isomer of 3,7-disubstituted-3-cephem-4-carboxylic acid compounds of the formula:

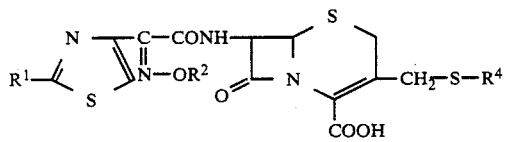

wherein

R$^1$ is amino or a protected amino,

R$^2$ is ethyl, cyclopentyl, carboxymethyl or 3-isoxazolylmethyl;

R$^4$ is 1-allyl-1H-tetrazol-5-yl, and pharmaceutically acceptable salts thereof.

2. A compound of claim 1, which is 7-[2-ethoxyimino-2-(2-aminothiazol-4-yl)acetamido]-3-(1-allyl-1H-tetrazol-5-yl)thiomethyl-3-cephem-4-carboxylic acid (syn isomer).

3. A compound of claim 1, which is 7-[2-cyclopentyloxyimino-2-(2-aminothiazol-4-yl)acetamido]-3-(1-allyl-1H-tetrazol-5-yl)-thiomethyl-3-cephem-4-carboxylic acid (syn isomer).

4. A compound of claim 1, which is 7-[2-carboxymethoxyimino-2-(2-aminothiazol-4-yl)acetamido]-3-(1-allyl-1H-tetrazol-5-yl)-thiomethyl-3-cephem-4-carboxylic acid (syn isomer).

5. A compound of claim 1, which is 7-[2-(3-isoxazolylmethoxyimino)-2-(2-aminothiazol-4-yl)acetamido]-3-(1-allyl-1H-tetrazol-5-yl)-thiomethyl-3-cephem-4-carboxylic acid (syn isomer).

6. A compound, which is 7-[2-methoxyimino-2-(2-aminothiazol-4-yl)acetamido]-3-(4-allyl-4H-1,2,4-triazol-3-yl)thiomethyl-3-cephem-4-carboxylic acid (syn isomer).

7. An antibacterial composition comprising an effective amount of a compound of claim 1 or pharmaceutically acceptable salt thereof in association with a pharmaceutically acceptable, substantially non-toxic carrier or excipient.

* * * * *